United States Patent
Jurischka et al.

(10) Patent No.: US 11,236,401 B2
(45) Date of Patent: Feb. 1, 2022

(54) SENSORS FOR DETECTION AND QUANTIFICATION OF MICROBIOLOGICAL PROTEIN SECRETION

(71) Applicant: SenseUp GmbH, Jülich (DE)

(72) Inventors: Sarah-Kristin Jurischka, Merzenich (DE); Georg Schaumann, Düsseldorf (DE); Stephan Binder, Eschweiler (DE); Britta Kleine, Gevelsberg (DE); Roland Freudl, Merzenich (DE)

(73) Assignee: SenseUp GmbH, Jülich (DE)

( * ) Notice: Subject to any disclaimer, the term of this patent is extended or adjusted under 35 U.S.C. 154(b) by 220 days.

(21) Appl. No.: 15/561,502

(22) PCT Filed: Mar. 23, 2016

(86) PCT No.: PCT/EP2016/056464
§ 371 (c)(1),
(2) Date: Sep. 25, 2017

(87) PCT Pub. No.: WO2016/151054
PCT Pub. Date: Sep. 29, 2016

(65) Prior Publication Data
US 2019/0284645 A1 Sep. 19, 2019

(30) Foreign Application Priority Data
Mar. 25, 2015 (EP) ..................................... 15160897

(51) Int. Cl.
| | |
|---|---|
| *C12Q 1/6897* | (2018.01) |
| *C12N 15/77* | (2006.01) |
| *C12Q 1/18* | (2006.01) |
| *C12Q 1/04* | (2006.01) |
| *C12N 9/28* | (2006.01) |
| *G01N 21/64* | (2006.01) |
| *C12N 15/63* | (2006.01) |

(52) U.S. Cl.
CPC ......... *C12Q 1/6897* (2013.01); *C12N 9/2417* (2013.01); *C12N 15/63* (2013.01); *C12N 15/77* (2013.01); *C12Q 1/04* (2013.01); *C12Q 1/18* (2013.01); *C12Y 302/01001* (2013.01); *G01N 21/6486* (2013.01)

(58) Field of Classification Search
None
See application file for complete search history.

(56) References Cited

U.S. PATENT DOCUMENTS

| | | |
|---|---|---|
| 2005/0153402 A1 | 7/2005 | Pompejus et al. |
| 2009/0209007 A1* | 8/2009 | Meima .................. C07K 14/32 435/91.1 |
| 2011/0129894 A1 | 6/2011 | Scheele et al. |
| 2013/0310458 A1 | 11/2013 | Eggeling et al. |

OTHER PUBLICATIONS

S. Binder et al., "A High-Throughput Approach to Identify Genomic Variants of Bacterial Metabolite Producers at the Single-Cell Level." Genome Biology, vol. 13, No. 5, R40, pp. 1-12, 2012.
B.C. Marciniak et al., "Comparative Transcriptional Analysis of Bacillus Subtilis Cells Overproducing Either Secreted Proteins, Lipoproteins or Membrane Proteins." Microbial Cell Factories, vol. 11, No. 1,66, pp. 1-13, 2012.
S.L. Rusch et al., "Interactions That Drive Sec-Dependent Bacterial Protein Transport." Biochemistry, vol. 46, No. 34, pp. 9665-9673, 2007.
A.A. Toymentseva et al., "The LIKE System, a Novel Protein Expression Toolbox for Bacillus Subtilis Based on the Lial Promoter." Microbial Cell Factories, vol. 11, No. 1, 143, pp. 1-13, 2012.
P. Natale et al., "Sec- and Tat-Mediated Protein Secretion Across the Bacterial Cytoplasmic Membrane—Distinct Translocases and Mechanisms." Biochimica et Biophysica Acta, vol. 1778, pp. 1735-1756, 2008.
F. Lausberg et al., "A Tetracycline Inducible Expression Vector for Corynebacterium Glutamicum Allowing tightly Regulable Gene Expression." Plasmid, vol. 68, pp. 142-147, 2012.
H. Trip et al., "A Novel Screening System for Secretion of Heterologous Proteins in Bacillus Subtilis." Microbial Biotechnology, vol. 4, No. 5, pp. 673-682, 2011.

(Continued)

*Primary Examiner* — Channing S Mahatan
(74) *Attorney, Agent, or Firm* — Marshall, Gerstein & Borun LLP

(57) ABSTRACT

The present invention relates to a cell which is genetically modified with respect to its wild type and which comprises a gene sequence coding for a fluorescent protein, wherein the expression of the fluorescent protein depends on the amount of protein that is secreted across the cytoplasmic membrane into the extracytosolic space. The present invention also relates to a method for the identification of a cell having an increased secretion of protein across the cytoplasmic membrane into the extracytosolic space, a method for the identification of a culture medium composition that is optimized for the recombinant production of protein, a method for the identification of culture conditions that are optimized for the recombinant production of protein, a method for the identification of a compound that is characterized by an antibiotic activity due to its property to damage the membrane of a bacterial cell or to analyse the effect of such a compound on a population of genetically different bacterial cells or genetically identical cells in different physiological states or different growths phases, a method for the production of a cell which is genetically modified with respect to its wild type with optimized secretion of protein across the cytoplasmic membrane into the extracytosolic space, a cell obtained by this method, a method for the production of proteins and a method for the preparation of a mixture.

14 Claims, 8 Drawing Sheets
Specification includes a Sequence Listing.

(56) References Cited

OTHER PUBLICATIONS

T. Drepper et al., "Flavin Mononucleotide-Based Fluorescent Reporter Proteins Outperform Green Fluorescent Protein-Like Proteins as Quantitative In Vivo Real-Time Reporters," Applied and Environmental Microbiology, Sep. 2010, vol. 76, No. 17, pp. 5990-5994.

* cited by examiner

SEQUENCE LISTING

<160> NUMBER OF SEQ ID NOS: 55

<210> SEQ ID NO 1
<211> LENGTH: 201
<212> TYPE: DNA
<213> ORGANISM: Corynebacterium
<220> FEATURE:
<221> NAME/KEY: misc_feature
<223> OTHER INFORMATION: DNA-sequence of the cg0706-promoter

<400> SEQUENCE: 1
gcgggtctgc cacatttgct gaaaagtacc agttgcaagg tgtggtgttg gagcttcata      60
accaggttgg gcaaaaggga tgaatccctg gttgtggtgg ggctcctgaa agtactcat     120 agactctatt gtggagtgtt gaggctgata agtgaatggg ggaaagccct gaaaaggtgg    180
cgttcagggt cttccctgat g                                              201

<210> SEQ ID NO 2
<211> LENGTH: 194
<212> TYPE: DNA
<213> ORGANISM: Corynebacterium
<220> FEATURE:
<221> NAME/KEY: misc_feature
<223> OTHER INFORMATION: DNA-sequence of thecg0996-promoter

<400> SEQUENCE: 2
accttaaatt catcgcctac aacctttgt aggtaagaat ttaacaagag ccagttatct       60
tctcttaaaa tgaggaggta actggcttct ttatgcttaa gaggtgttag cataagtgaa    120
atatgttcca acgcgtggac gtcttaattg ggaggaagtc tgtcacggac tggaagacga    180
aaagggtatc gatg                                                      194

<210> SEQ ID NO 3
<211> LENGTH: 118
<212> TYPE: DNA
<213> ORGANISM: Corynebacterium
<220> FEATURE:
<221> NAME/KEY: misc_feature
<223> OTHER INFORMATION: DNA-sequence of the g0998-promoter

<400> SEQUENCE: 3 gggaaccccat tcgcagcggg ttcgaaaatg tcgatgatta aaccactaaa gagctcacag     60

```
gaagtgttca gactacttag agtgacgccc cagccacagg gttcataatc aaatcatg      118
```

<210> SEQ ID NO 4
<211> LENGTH: 216
<212> TYPE: DNA
<213> ORGANISM: Corynebacterium
<220> FEATURE:
<221> NAME/KEY: misc_feature
<223> OTHER INFORMATION: DNA-sequence of the cg1325-promoter

<400> SEQUENCE: 4

```
accagcgacg ccgccgatcc atttgtcggt ggtgcttcgg gcgagtcgtc gagattgtgc      60
tgggaaagtc atcgggatca agctccttta tggctgattg agttttttctt tcttcttcaa    120 tcatcgccaa taagaaccta gagcacatcg gggatttccc ctctcctaac ccctaaaaac    180
ccctgagaaa acgctccaag taaacccttta cagctc                               216
```

<210> SEQ ID NO 5
<211> LENGTH: 693
<212> TYPE: DNA
<213> ORGANISM: Corynebacterium
<220> FEATURE:
<221> NAME/KEY: misc_feature
<223> OTHER INFORMATION: DNA-sequence of the cg0706-cg1325-regulator

<400> SEQUENCE: 5

```
atggttgatg tgttttttggt cgatgaccac tccgtgtttc gctccggcgt caaagcagaa      60
ctaggcaacg ccgtcacagt agtcggcgaa gcagggacgg tggccgacgc cgtagccggc    120
atcaaggcaa gcaaaccaga ggtagtgctt ctcgacgtcc acatgcccga cggcggcggc    180
ctcgcagtgc tccagcagat caacgactcc gatgtggaca ccattttctt ggcactcagt    240
gtctctgatg ctgcggaaga tgtcatcgcc atcatccgtg gcggtgccag gggatacgtg    300
accaaatcaa tctccggtga agaactcatc gaagccatca accgcgtgaa atccggcgac    360
gcattcttct caccacgcct ggcaggcttc gtcctgacg ccttcgccgc cccgattcc      420 gcagctggcg caggcattgt cgacgcaccc gaaaaagacg ccgccgtaga atccggaaaa    480
atcctcgacg acccagttgt cgacgccctc acccgccgcg aactcgaagt cctccgccta    540
ctagcccgcg gctacaccta caaagaaatc ggcaaagaac tgttcatttc cgtcaaaacc    600
gtggaaaccc acgcctcaaa cattctgcgg aaaaaccaac aatccaaccg ccacgcgttg    660
acccggtggg ctcactcgag ggatcttgac taa                                  693
```

<210> SEQ ID NO 6
<211> LENGTH: 768
<212> TYPE: DNA
<213> ORGANISM: Corynebacterium
<220> FEATURE:
<221> NAME/KEY: misc_feature
<223> OTHER INFORMATION: DNA-sequence of the cg0996-cg0998-regulator

<400> SEQUENCE: 6

```
atgttccaac gcgtggacgt cttaattggg aggaagtctg tcacggactg gaagacgaaa      60
agggtatcga tgaaaatttt agttgttgat gacgagcaag ctgtacgtga ctccttgcga    120
cgttcccttt cgttcaacgg atacaacgtt gttctcgcag aagacggcat ccaagcacta    180
gagatgattg acaaggaaca gcctgctttg gtgatcctcg atgtcatgat gcctggtatg    240
gacggacttg aggtctgtcg ccaccttcgc agcgaaggcg atgatcggcc aattcttatt    300
cttactgccc gcgataatgt ttctgatcgt gttggtggcc tcgatgcagg cgcagatgac    360
```

```
tatttggcta aaccatttgc tcttgaagag ctgttggcgc gcgtccgttc actggtgcgt      420
cgctctgcag tggaatcaaa tcagagttcc agcattgaac aggctctatt atcttgtggc      480
gatttgacgc ttgacccaga aagtcgagat gtctaccgca acggacgcgc catcagcctt      540
actcgaacag agttcgcgct cctgcaattg ctcctcaaaa accaaaggaa agtgctcact      600
cgcgcccaga ttttggaaga ggtatggggc tgcgatttcc ccacttcagg caatgccctc      660
gaggtctaca ttgataacct tcgacgcaag actgaattgg aaggagaaga ccgcctgatc      720
catacagtac gaggagtcgg atacgtcctg cgagagaccg ctccgtga                    768

<210> SEQ ID NO 7
<211> LENGTH: 1350
<212> TYPE: DNA
<213> ORGANISM: Bacillus
<220> FEATURE:
<221> NAME/KEY: misc_feature
<223> OTHER INFORMATION: DNA-sequence of the htrA-promoter

<400> SEQUENCE: 7
atggataact atcgtgatga aaacagaacg aaaggtaatg agaatgaggt cttttaacg       60 aaagagaacg atcagagcgc ctcctactcg gcccgcaatg tcattcatga tcaggagaag     120
aaaaaacgag gattcggatg gttcagaccg ttgcttggcg gagtgatcgg cggcagtctt     180
gctcttggca tttacacgtt taccgctt ggtgaccatg attctcagga cactgcaaaa        240
caatcatcca gccagcagca aacgcaatct gttacagcaa caagcacctc ctctgaatct     300
aaaaaaagct caagcagctc atctgcattc aagagcgagg actcttctaa aatctcagat     360
atggtagaag acctttcacc agcgattgtc ggtattacaa atcttcaggc acaatcaaac     420
agctctttgt tcggctctag ttcttctgat tccagcgaag atacagaaag cggttcaggg     480
tcaggtgtca ttttcaaaaa agagaatggc aaggcttata tcattacaaa taaccacgtc    540
gtagaagggg catcatcact gaaggtatct ttatatgacg gcactgaggt tactgcaaag    600
ctggtaggca gtgactcgtt aactgattta gccgtcctcc aaatcagtga tgaccacgtc    660
acaaaagtgg caaacttcgg tgattcatct gatcttagaa caggcgagac cgttattgcg    720
attggggatc cgcttggaaa agacctgtcc cgcacagtaa cacaaggaat tgtaagcggc    780
gtggacagaa cggtttcaat gtctacatca gccggcgaaa cgagcattaa cgtcattcag    840
acagacgcag caattaatcc aggtaacagc ggcggtcctt tgttaaatac agacggcaaa    900
attgtcggca ttaacagtat gaaaatcagt gaggatgatg ttgagggtat cggattcgcc    960
attccaagca atgacgtaaa accgattgct gaagaattgc tgtctaaagg acaaattgaa   1020
cgtccatata tcggtgtcag catgcttgat ctagagcaag tgccgcaaaa ttaccaagaa   1080
ggcacactcg gcctgttcgg cagccagctg aataaaggcg tttacatccg tgaggtcgct   1140
tcaggctctc ctgctgaaaa ggccggatta aaagcggagg atattatcat cggcctaaaa   1200
ggtaaagaaa ttgatacagg cagtgaattg cgcaatatct tatataaaga cgcaaagatc   1260
ggtgataccg ttgaagtgaa aattctccga aacggcaaag aaatgacgaa aaaaattaaa   1320
ctggatcaaa aagaagagaa aacttcgtaa                                    1350

<210> SEQ ID NO 8
<211> LENGTH: 678
<212> TYPE: DNA
<213> ORGANISM: Bacillus
<220> FEATURE:
<221> NAME/KEY: misc_feature
<223> OTHER INFORMATION: DNA-sequence of the Css-regulator
```

<400> SEQUENCE: 8

```
ttgtcataca ccatttatct agttgaagat gaggataacc tgaatgaact gctgacgaag      60
tatttagaga atgagggctg gaacattaca tcttttacga aaggtgaaga cgccagaaag     120
aaaatgacac cgtctcccca cctatggatt ctcgatatca tgctgccgga taccgacggc     180
tatacattaa taaaagaaat caaggcgaaa gatcctgacg tgccggtcat ttttatttcc     240
gcccgagatg cggatattga cagagtgctt ggcttagagc ttggcagcaa tgactacatt     300
tcaaagccgt ttttgccgcg ggagctgatt atccgtgtgc aaaagctgct gcagctcgta     360
tataaggaag ctcctcctgt ccaaaaaaat gaaattgccg tctcctcgta tcgggtcgct     420
gaagacgccc gcgaggtcta tgacgaaaac gggaatatca tcaatttgac gtcaaaggaa     480
tttgatctgc tgctattatt tatccatcat aaagggcatc catactctcg tgaggatatc     540
ctcctaaaag tgtggggaca tgactacttc ggaacagacc gggtcgttga tgatctcgtc     600
cggagactgc gcagaaagat gcctgaattg aaggtggaga cgatttacgg tttcggctac     660
aggatgatgt catcatga                                                   678
```

<210> SEQ ID NO 9
<211> LENGTH: 113
<212> TYPE: DNA
<213> ORGANISM: Bacillus
<220> FEATURE:
<221> NAME/KEY: misc_feature
<223> OTHER INFORMATION: DNA-sequence of the liaL-promoter

<400> SEQUENCE: 9

```
tccggtgcga gatacgactc cggtcttata taaaaatcaa tctctgattc gttttgcata      60
tcttccaact tgtataagat gaagacaagg aaaacgaaag gaggatctgc atg           113
```

<210> SEQ ID NO 10
<211> LENGTH: 636
<212> TYPE: DNA
<213> ORGANISM: Bacillus
<220> FEATURE:
<221> NAME/KEY: misc_feature
<223> OTHER INFORMATION: DNA-sequence coding for the LiaR-regulator

<400> SEQUENCE: 10

```
gtgattcgag tattattgat tgatgatcat gaaatggtca gaatgggggct cgcggctttt     60
ttggaggcgc agcccgatat tgaagtcatc ggcgaagcat cggacggcag cgaaggtgtt    120
cggcttgctg tggaactgtc gcctgatgtc atttaatgg accttgtcat ggagggcatg    180
gatggcattg aagctacaaa gcaaatttgc cgggagcttt ccgacccgaa aattattgtg    240
ctcactagct tcattgatga tgacaaagtg tacccggtta ttgaagctgg cgcgctcagc    300
tatctgttga aaacctcaaa agcggcagaa atcgccgatg ccatccgcgc cgcaagcaag    360
ggagagccga agctggagtc aaaagtggcg ggaaaagtat tatccaggct gcgccactca    420
ggtgaaaacg cgctcccgca tgaatcgctt acaaaacggg agctcgaaat actctgcctg    480
atcgcagaag gaaagacaaa caagaaaata ggcgaggaac tgtttattac gattaaaaca    540
gtcaaaacac atattacgaa tatttttatca aagctggatg tcagtgaccg gacgcaggcg    600
gcggtgtacg cacaccgaaa tcatctcgtg aattag                              636
```

<210> SEQ ID NO 11
<211> LENGTH: 726
<212> TYPE: DNA

<213> ORGANISM: Bacillus
<220> FEATURE:
<221> NAME/KEY: misc_feature
<223> OTHER INFORMATION: DNA-sequence coding for the LiaF-protein

<400> SEQUENCE: 11

```
atgacaaaaa aacagcttct cggattgatc attgctttat tcggcatcag tatgttttg      60
caaattatcg aataggcga tctgctgttt tggccgctct tttttctgat tgccggctat     120
ttccttaaaa aatattcccg tgattggctt ggctccgtca tgtatatctt tgccgcgttt   180
ctatttttga aaaacctctt cagcatcacc tttaatttat tcggctatgc gtttgccgca   240
tttctgattt acgccggcta caggcttatc aaagggaagc cgatatttga accgaatgag   300
aaacaggtca atctcaataa aaagaacat catgagccgc aaaagatgt aaaacatccc    360
gacatgcgca gctttttat cggtgagctg caaatgatga agcagccgtt tgacctgaac    420
gatttaaatg tctctggttt tatcggtgat atcaaaatcg atttatctaa gcgatgatt    480
cccgagggag aaagtacaat cgtcattagc ggagtcattg gtaacgttga tatttatgta   540
ccatcggacc ttgaagtggc tgtcagctcg gctgttttta taggagacat taatctgatc   600
ggctcgaaga aaagcggatt aagcacgaag gtatatgccg cgtcaactga ttttagcgag   660
tcaaagcgcc gggtaaaagt gtccgtttcc ttatttatcg gtgatgtgga tgtgaagtac   720
gtatga                                                              726
```

<210> SEQ ID NO 12
<211> LENGTH: 1083
<212> TYPE: DNA
<213> ORGANISM: Bacillus
<220> FEATURE:
<221> NAME/KEY: misc_feature
<223> OTHER INFORMATION: DNA-sequence coding for the LiaS-protein

<400> SEQUENCE: 12

```
atgagaaaaa aatgcttgc cagcctccaa tggcgcgcca tccgcatgac aacgggaatc    60
agcctgctcc ttttttgttg cctgatttcc tttatgatgt tttactatcg gctcgatccg   120
cttgttttgc tgtcatcaag ctggttcgga attccgttta tcctgatttt gcttctgatc   180
agcgtgaccg tcggtttcgc ctcagggtat atgtacggca accggttgaa gacaaggatt   240
gatacattaa ttgaatccat tttaaccttt gaaaacggca atttcgctta tcggataccg   300
ccgctcggtg atgatgaaat cggcctggct gctgatcagc tgaacgaaat ggcgaagcgc   360
gtggagcttc aagtcgcatc cctccagaaa ctttccaatg aacgtgcgga atggcaggct   420
caaatgaaga agtcggttat ctcagaagaa cgccagcgat tggccagaga tcttcatgat   480
gcggtcagcc agcagctctt tgccatatcg atgatgacat cagccgtgct ggaacatgtc   540
aaggatgctg atgacaaaac agtcaagcgg atcaggatgg tcgagcatat ggcaggcgaa   600
gcccaaaatg agatgaggg gctgctgctc catttacggc ctgttaccct tgaaggaaaa   660
gggctgaagg agggccttac ggagcttttg gacgagttcc gaaaaaagca gccgattgat   720
attgagtggg atatacagga cacagcgata tccaagggtg ttgaagacca cttgttcaga   780
atcgtgcagg aggccctttc aaacgtattt agacattcaa aagcgtcaaa gtaaccgtg    840
attctgggca taagaacag ccagctccgt ctgaaggtga ttgataatgg aaaaggcttt    900
aaaatggacc aggtgaaagc ctcctcatac ggcttgaatt ctatgaaaga acgtgcaagt   960
gaaatcggcg gtgtcgccga agtgatttca gtagaaggaa aaggcactca aatcgaagtg  1020
aaggtcccga ttttccgga agaaaaagga gagaacgaac gtgattcgag tattattgat  1080
``` tga                                                          1083

<210> SEQ ID NO 13
<211> LENGTH: 116
<212> TYPE: DNA
<213> ORGANISM: Mycobakterium
<220> FEATURE:
<221> NAME/KEY: misc_feature
<223> OTHER INFORMATION: DNA-sequence of the mprA-promoter

<400> SEQUENCE: 13
ggacatcgag aactctcggg gttcggcgaa cgttatctca gtggaatctc agtccacgcg    60
cgcaacctag ttgtgcagtt actgttgaaa gccacaccca tgccagtcca cgcatg      116

<210> SEQ ID NO 14
<211> LENGTH: 1515
<212> TYPE: DNA
<213> ORGANISM: Mycobakterium
<220> FEATURE:
<221> NAME/KEY: misc_feature
<223> OTHER INFORMATION: DNA-sequence of the MprB-regulator

<400> SEQUENCE: 14
atgtggtggt tccgccgccg agaccgggcg ccgctgcgcg ccaccagctc attatccctg    60
cggtggcggg tcatgctgct ggcgatgtcc atggtcgcga tggtggttgt gctgatgtcg   120
ttcgccgtct atgcggtgat ctcggccgcg ctctacagcg acatcgacaa ccaactgcag   180
agccgggcgc aactgctcat cgccagtggc tcgctggcag ctgatccggg taaggcaatc   240
gagggtaccg cctattcgga tgtcaacgcg atgctggtca ccccggcca gtccatctac    300 accgctcaac agccgggcca gacgctgccg gtcggtgctg ccgagaaggc ggtgatccgt   360
ggcgagttgt tcatgtcgcg gcgcaccacc gccgaccaac gggtgcttgc catccgtctg   420
accaacggta gttcgctgct gatctccaaa agtctcaagc ccaccgaagc agtcatgaac   480
aagctgcgtt gggtgctatt gatcgtgggt gggatcgggg tggcggtcgc cgcggtggcc   540 gggggatgg tcacccgggc cgggctgagg ccggtgggcc gcctcaccga agcggccgag   600
cgggtggcgc gaaccgacga cctgcggccc atccccgtct tcggcagcga cgaattggcc   660
aggctgacag aggcattcaa tttaatgctg cgggcgctgg ccgagtcacg gaacggcag    720 gcaaggctgg ttaccgacgc cggacatgaa ttgcgtaccc cgctaacgtc gctgcgcacc   780
aatgtcgaac tcttgatggc ctcgatggcc ccggggctc cgcggctacc caagcaggag   840
atggtcgacc tgcgtgccga tgtgctggct caaatcgagg aattgtccac actggtaggc   900
gatttggtgg acctgtcccg aggcgacgcc ggagaagtgg tgcacgagcc ggtcgacatg   960
gctgacgtcg tcgaccgcag cctggagcgg tcaggcggc ggcgcaacga tatcctttttc   1020 gacgtcgagg tgattgggtg gcaggtttat ggcgataccg ctggattgtc gcggatggcg   1080
cttaacctga tggacaacgc cgcgaagtgg agcccgccgg gcggcacgt gggtgtcagg   1140 ctgagccagc tcgacgcgtc gcacgctgag ctggtggttt ccgaccgcgg cccgggcatt   1200
cccgtgcagg agcgccgtct ggtgtttgaa cggttttacc ggtcggcatc ggcacgggcg   1260
ttgccgggtt cgggcctcgg gttggcgatc gtcaaacagg tggtgctcaa ccacggcgga   1320
ttgctgcgca tcgaagacac cgacccaggc ggccagcccc ctggaacgtc gatttacgtg   1380
ctgctccccg gccgtcggat gccgattccg cagcttcccg gtgcgacggc tggcgctcgg   1440
agcacggaca tcgagaactc tcggggttcg gcgaacgtta tctcagtgga atctcagtcc   1500

```
acgcgcgcaa cctag                                              1515

<210> SEQ ID NO 15
<211> LENGTH: 774
<212> TYPE: DNA
<213> ORGANISM: Mycobakterium
<220> FEATURE:
<221> NAME/KEY: misc_feature
<223> OTHER INFORMATION: DNA-sequence of the sigma factor (SigE)

<400> SEQUENCE: 15
atggaactcc tcggcggacc ccggggttggg aatacggaat cgcaactttg cgttgccgac    60
ggtgacgact tgccaactta ttgcagtgca aattcggagg atctcaatat cacgaccatc   120
acgaccttga gtccgaccag catgtctcat ccccaacagg tccgcgatga ccagtgggtg   180
gagccgtctg accaattgca gggcaccgcc gtattcgacg ccaccgggga caaggccacc   240
atgccgtcct gggatgagct ggtccgtcag cacgccgatc gggtgtaccg gctggcttat   300
cggctctccg gcaaccagca cgatgccgaa gacctgaccc aggagacctt tatcagggtg   360
ttccggtcgg tccagaatta ccagccgggc accttcgaag gctggctaca ccgcatcacc   420
accaacttgt tcctggacat ggtccgccgc cgggctcgca tccggatgga ggcgttaccc   480
gaggactacg accgggtgcc cgccgatgag cccaaccccg agcagatcta ccacgacgca   540
cggctgggac ctgacctgca ggctgccttg gcctcgctgc cgccggagtt tcgtgccgcg   600
gtggtgctgt gtgacatcga gggtctgtcg tacgaggaga tcggcgccac actgggcgtg   660
aagctcggga cggtacgtag ccggatacac cgcggacgcc aggcactgcg ggactacctg   720
gcagcgcacc ccgaacatgg cgagtgcgca gttcacgtca acccagttcg ctga         774

<210> SEQ ID NO 16
<211> LENGTH: 272
<212> TYPE: DNA
<213> ORGANISM: Escherichia
<220> FEATURE:
<221> NAME/KEY: misc_feature
<223> OTHER INFORMATION: DNA-sequence of the htrA-promoter

<400> SEQUENCE: 16
gtaaattacc gtcagattct cctgagtttc cgctatggga atattattac cgttgccgcc    60
tgctgcagga ttatatcagc ggtatgaccg acctctatgc gtgggatgaa taccgacgtc   120
tgatggccgt agaacaataa ccaggctttt gtaaagacga acaataaatt tttacctttt   180
gcagaaactt tagttcggaa cttcaggcta taaaacgaat ctgaagaaca cagcaatttt   240
gcgttatctg ttaatcgaga ctgaaataca tg                                 272

<210> SEQ ID NO 17
<211> LENGTH: 699
<212> TYPE: DNA
<213> ORGANISM: Escherichia
<220> FEATURE:
<221> NAME/KEY: misc_feature
<223> OTHER INFORMATION: DNA-sequence of the CpxR-regulator

<400> SEQUENCE: 17
atgaataaaa tcctgttagt tgatgatgac cgagagctga cttccctatt aaaggagctg    60
ctcgagatgg aaggcttcaa cgtgattgtt gcccacgatg gggaacaggc gcttgatctt   120
ctggacgaca gcattgattt acttttgctt gacgtaatga tgccgaagaa aaatggtatc   180
gacacattaa aagcacttcg ccagacacac cagacgcctg tcattatgtt gacggcgcgc   240
```

```
ggcagtgaac ttgatcgcgt tctcggcctt gagctgggcg cagatgacta tctcccgaaa      300
ccgtttaatg atcgtgagct ggtggcacgt attcgcgcga tcctgcgccg ttcgcactgg      360
agcgagcaac agcaaaacaa cgacaacggt tcaccgacac tggaagttga tgccttagtg      420
ctgaatccag gccgtcagga agccagcttc gacgggcaaa cgctggagtt aaccggtact      480
gagtttaccc tgctctattt gctggcacag catctgggtc aggtggtttc ccgtgaacat      540
ttaagccagg aagtgttggg caaacgcctg acgcctttcg accgcgctat tgatatgcac      600
atttccaacc tgcgtcgtaa actgccggat cgtaaagatg gtcacccgtg gtttaaaacc      660
ttgcgtggtc gcggctatct gatggtttct gcttcatga                            699

<210> SEQ ID NO 18
<211> LENGTH: 720
<212> TYPE: DNA
<213> ORGANISM: Artificial sequence
<220> FEATURE:
<223> OTHER INFORMATION: enhanced yellow fluorescens protein (eyfp)

<400> SEQUENCE: 18
gtgagcaagg gcgaggagct gttcaccggg gtggtgccca tcctggtcga gctggacggc       60
gacgtaaacg gccacaagtt cagcgtgtcc ggcgagggcg agggcgatgc cacctacggc      120
aagctgaccc tgaagttcat ctgcaccacc ggcaagctgc ccgtgccctg gcccaccctc      180
gtgaccacct tcggctacgg cctgcagtgc ttcgcccgct accccgacca catgaagcag      240
cacgacttct tcaagtccgc catgcccgaa ggctacgtcc aggagcgcac catcttcttc      300
aaggacgacg gcaactacaa gacccgcgcc gaggtgaagt tcgagggcga caccctggtg      360
aaccgcatcg agctgaaggg catcaacttc aaggaggacg gcaacatcct ggggcacaag      420
ctggagtaca actacaacag ccacaacgtc tatatcatgg ccgacaagca gaagaacggc      480
atcaaggtga acttcaagat ccgccacaac atcgagggcg gcagcgtgca gctcgccgac      540
cactaccagc agaacacccc catcggcgac ggccccgtgc tgctgcccga caaccactac      600
ctgagctacc agtccgccct gagcaaagac cccaacgaga gcgcgatca catggtcctg      660 ctggagttcg tgaccgccgc cgggatcact ctcggcatgg acgagctgta caagtaataa      720

<210> SEQ ID NO 19
<211> LENGTH: 238
<212> TYPE: PRT
<213> ORGANISM: Artificial sequence
<220> FEATURE:
<223> OTHER INFORMATION: protein sequence of the eYFP

<400> SEQUENCE: 19

Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Gly Tyr Gly Leu Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
```

```
              100                 105                 110
Lys Phe Glu Gly Asp Thr Leu Val Asn Arg Ile Glu Leu Lys Gly Ile
        115                 120                 125

Asn Phe Lys Glu Asp Gly Asn Ile Leu Gly His Lys Leu Glu Tyr Asn
130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Gly Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Tyr Gln Ser Ala Leu Ser
        195                 200                 205

Lys Asp Pro Asn Glu Lys Arg Asp His Met Val Leu Leu Glu Phe Val
210                 215                 220

Thr Ala Ala Gly Ile Thr Leu Gly Met Asp Glu Leu Tyr Lys
225                 230                 235
```

<210> SEQ ID NO 20
<211> LENGTH: 29
<212> TYPE: DNA
<213> ORGANISM: Artificial sequence
<220> FEATURE:
<223> OTHER INFORMATION: Primer 0706-Sal-fII

<400> SEQUENCE: 20
gcggtcgacg ggtaaacgtg ggatataaa                                    29

<210> SEQ ID NO 21
<211> LENGTH: 46
<212> TYPE: DNA
<213> ORGANISM: Artificial sequence
<220> FEATURE:
<223> OTHER INFORMATION: Primer 0706-RBSNde_r

<400> SEQUENCE: 21
gcgcatatga tatctccttc ttctagcggg tctgccacat ttgctg                 46

<210> SEQ ID NO 22
<211> LENGTH: 37
<212> TYPE: DNA
<213> ORGANISM: Artificial sequence
<220> FEATURE:
<223> OTHER INFORMATION: Primer Spc SacII-f

<400> SEQUENCE: 22
gcgccgcgga ctaataacgt aacgtgactg gcaagag                           37

<210> SEQ ID NO 23
<211> LENGTH: 37
<212> TYPE: DNA
<213> ORGANISM: Artificial sequence
<220> FEATURE:
<223> OTHER INFORMATION: Primer Spc Bgl-r

<400> SEQUENCE: 23
gcgagatctt ctgcctcgtg aagaaggtgt tgctgac                           37

<210> SEQ ID NO 24
<211> LENGTH: 25
<212> TYPE: DNA
<213> ORGANISM: Artificial sequence

```
<220> FEATURE:
<223> OTHER INFORMATION: Primer SenCas-fw

<400> SEQUENCE: 24
gtcgccgtcc agctcgacca ggatg                                         25

<210> SEQ ID NO 25
<211> LENGTH: 24
<212> TYPE: DNA
<213> ORGANISM: Artificial sequence
<220> FEATURE:
<223> OTHER INFORMATION: Primer TKP-seq-rv

<400> SEQUENCE: 25
cgggaagcta gagtaagtag ttcg                                          24

<210> SEQ ID NO 26
<211> LENGTH: 29
<212> TYPE: DNA
<213> ORGANISM: Artificial sequence
<220> FEATURE:
<223> OTHER INFORMATION: Primer 1325-Sal-f

<400> SEQUENCE: 26
gcggtcgacg agctgtaagg gtttacttg                                     29

<210> SEQ ID NO 27
<211> LENGTH: 45
<212> TYPE: DNA
<213> ORGANISM: Artificial sequence
<220> FEATURE:
<223> OTHER INFORMATION: Primer 1325-RBSNde-r

<400> SEQUENCE: 27
gcgcatatga tatctccttc ttctaaccag cgacgccgcc gatcc                   45

<210> SEQ ID NO 28
<211> LENGTH: 570
<212> TYPE: DNA
<213> ORGANISM: Artificial sequence
<220> FEATURE:
<223> OTHER INFORMATION: Synthetic DNA-fragement for pSen0996_8

<400> SEQUENCE: 28
gaatttaaca agagccagtt atcttctctt aaaatgagga ggtaactggc ttctttatgc    60
ttaagaggtg ttagcataag tgaaatatgt tccaacgcgt ggacgtctta attgggagga   120
agtctgtcac ggactggaag acgaaaaggg tatcgatgaa aatttttagtt gttgatgacg  180 agcaagctgt acgttaatct atcgcgccgt cagctcccgt tccatgccgg gatcgggatt   240
aggtcttgcc atcgtgaatc aggttgtgaa tcggcatggt ggccaactcg ttgtgggtga   300
atcagatgat ggcggaacga gaatcactat tgatttgcca ggggaaccca ttcgcagcgg   360
gttcgaaaat gtcgatgatt aaggtaccac cactaaagag ctcacaggaa gtgttcagac   420
tacttagagt gacgccccag ccacagggtt cataatcaaa tcatgacaaa tcaattcccc   480
acaaacaacg gtgagaaccc ggaccgtgca tcggaaactc catcagaaac caactccggt   540
acctgaactt aagaaggag atatcatatg                                    570

<210> SEQ ID NO 29
<211> LENGTH: 281
<212> TYPE: DNA
<213> ORGANISM: Artificial sequence
<220> FEATURE:
```

<223> OTHER INFORMATION: Synthetic DNA-fragment for pSen0996_8c

<400> SEQUENCE: 29

```
caatttaaca agagccagtt atcttctctt aaaatgagga ggtaactggc ttctttatgc    60
ttaagaggtg ttagcataag tgaaatatgt tccaacgcgt ggacgtctta attgggagga  120
agtctgtcac ggactggaag acgaaaaggg tatcgatgtg aacccattcg cagcgggttc  180
gaaaatgtcg atgattaagg taccaccact aaagagctca caggaagtgt tcagactact  240
tagagtgacg ccccagccac agggttcata atcaaatcat g                      281
```

<210> SEQ ID NO 30
<211> LENGTH: 2471
<212> TYPE: DNA
<213> ORGANISM: Artificial sequence
<220> FEATURE:
<223> OTHER INFORMATION: Synthetic DNA-fragement for pSen0996_8e

<400> SEQUENCE: 30

```
aatttaacaa gagccagtta tcttctctta aaatgaggag gtaactggct tctttatgct    60
taagaggtgt tagcataagt gaaatatgtt ccaacgcgtg gacgtcttaa ttgggaggaa  120
gtctgtcacg gactggaaga cgaaaagggt atcgatgaaa attttagttg ttgatgacga  180
gcaagctgta cgtgactcct tgcgacgttc cctttcgttc aacggataca acgttgttct  240
cgcagaaagac ggcatccaag cactagagat gattgacaag aacagcctg ctttggtgat  300
cctcgatgtc atgatgcctg gtatggacgg acttgaggtc tgtcgccacc ttcgcagcga  360
aggcgatgat cggccaattc ttattcttac tgcccgcgat aatgtttctg atcgtgttgg  420
tggcctcgat gcaggcgcag atgactattt ggctaaacca tttgctcttg aagagctgtt  480
ggcgcgcgtc cgttcactgg tgcgtcgctc tgcagtggaa tcaaatcaga gttccagcat  540
tgaacaggct ctattatctt gtggcgattt gacgcttgac ccagaaagtc gagatgtcta  600
ccgcaacgga cgcgccatca gccttactcg aacagagttc gcgctcctgc aattgctcct  660
caaaaaccaa aggaaagtgc tcactcgcgc ccagattttg gaagaggtat ggggctgcga  720
tttcccccact tcaggcaatg ccctcgaggt ctacattgga taccttcgac gcaagactga  780
attggaagga gaagaccgcc tgatccatac agtacgagga gtcggatacg tcctgcgaga  840
gaccgctccg tgacattaag gcgaatcgg gcaggggaaa atgggcctgc cctaccgaa    900
agtgatgact ccgacggttc aatgtcgttg cgttggcgct tggctttgct gagcgccact  960
ttggtagctt cgccgttgg tgttattact gttgctgcat attggtctgt ctccagctat  1020
gtcaccaact caatcgatcg tgatctggaa aaacaagcgg atgcaatgct ggacgagcc  1080
agtgaagcgg gattctatgc aaccgcagaa accgaaattg ctctgttagg tgaatatgcc  1140
agtgacactc gaatcgcctt aatcccacct gggtgggaat acgtcatcgg tgaatccata  1200
tcactgcctg attcagattt ccttaagagt aaagaagcgg ggaaacagat cctcgtaaca  1260
agtgctgagc gcattctcat gaaacgagat agctcgggca cagtggtggt ttttgctaaa  1320
gatatggtgg ataccgatcg gcagctcacg gtgcttggcg tcattctctt gatcattggc  1380
ggcagtggtt ttttggcgtc gattctgctt ggtttcatca ttgcgaagga ggggctgaaa  1440
ccactgtcaa agctgcagcg tgccgtcgaa gagatcgaac gaactgatga gcttcgtgcg  1500
attcccgtgg tgggaaatga tgagttcgct aagttgactc gtagtttcaa tgacatgctc  1560
aaggcactgc gggagtctcg tacccggcaa tctcagttgg tggcagatgc aggacacgag  1620
ctgaaaactc cactgaccctc aatgcggaca atattgaat tgctgttgat ggcaaccaac  1680
```

```
agtggaggat cgggaatccc caaggaagaa ttggatggcc ttcagcgtga tgtattggcg   1740
cagatgaccg aaatgtctga tttgattggt gatcttgttg atcttgcgcg tgaagaaacc   1800
gccgaaacgt caagcattgt agatctcaac caagtgttgg aaattgcgct tgaccgaatg   1860
gaaagccgtc gcatgacggt gcggatagat gtttccgaga ctgtggattg aaactgctg    1920 ggcgatgatt tttccttaac cagggcatta gtaaatgttt tggataatgc cattaaatgg   1980
tcgcctgaga atggcattgt tcgagtgtcg atgtcacaga tcgacaaagc aacggtccgc   2040
attgttattg atgattcagg gcctggaatt gctgaaaaag aacgaggatt agttttggaa   2100
cggttctatc gcgccgtcag ctcccgttcc atgccgggat cgggattagg tcttgccatc   2160
gtgaatcagg ttgtgaatcg gcatggtggc caactcgttg tgggtgaatc agatgatggc   2220
ggaacgagaa tcactattga tttgccaggg gaacccattc gcagcgggtt cgaaaatgtc   2280
gatgattaaa ccactaaaga gctcacagga agtgttcaga ctacttagag tgacgcccca   2340
gccacagggt tcataatcaa atcatgacaa atcaattccc cacaaacaac ggtgagaacc   2400
cggaccgtgc atcggaaact ccatcagaaa ccaactccgg tacctgaact ttaagaagga   2460
gatatcatat g                                                        2471

<210> SEQ ID NO 31
<211> LENGTH: 20
<212> TYPE: DNA
<213> ORGANISM: Artificial sequence
<220> FEATURE:
<223> OTHER INFORMATION: Primer JPS0003

<400> SEQUENCE: 31
ctgaacttgt ggccgtttac                                               20

<210> SEQ ID NO 32
<211> LENGTH: 20
<212> TYPE: DNA
<213> ORGANISM: Artificial sequence
<220> FEATURE:
<223> OTHER INFORMATION: Primer JPS0004

<400> SEQUENCE: 32
ttgttgccgg gaagctagag                                               20

<210> SEQ ID NO 33
<211> LENGTH: 34
<212> TYPE: DNA
<213> ORGANISM: Artificial sequence
<220> FEATURE:
<223> OTHER INFORMATION: Primer AmyE-HpaI-f

<400> SEQUENCE: 33
gcgcgttaac cgaaggagat atagatatgt ttgc                               34

<210> SEQ ID NO 34
<211> LENGTH: 22
<212> TYPE: DNA
<213> ORGANISM: Artificial sequence
<220> FEATURE:
<223> OTHER INFORMATION: Primer AmyE-SacI-r

<400> SEQUENCE: 34
cagtgaattc gagctcctag tg                                            22

<210> SEQ ID NO 35
```

<211> LENGTH: 7153
<212> TYPE: DNA
<213> ORGANISM: Artificial sequence
<220> FEATURE:
<223> OTHER INFORMATION: DNA-sequence of plasmid pSen0706

<400> SEQUENCE: 35

| | |
|---|---|
| ggatccttat tacttgtaca gctcgtccat gccgagagtg atcccggcgg cggtcacgaa | 60 |
| ctccagcagg accatgtgat cgcgcttctc gttggggtct ttgctcaggg cggactggta | 120 |
| gctcaggtag tggttgtcgg gcagcagcac ggggccgtcg ccgatggggg tgttctgctg | 180 |
| gtagtggtcg gcgagctgca cgctgccgcc ctcgatgttg tggcggatct tgaagttcac | 240 |
| cttgatgccg ttcttctgct tgtcggccat gatatagacg ttgtggctgt tgtagttgta | 300 |
| ctccagcttg tgccccagga tgttgccgtc ctccttgaag ttgatgccct tcagctcgat | 360 |
| gcggttcacc agggtgtcgc cctcgaactt cacctcggcg cgggtcttgt agttgccgtc | 420 |
| gtccttgaag aagatggtgc gctcctggac gtagccttcg ggcatggcgg acttgaagaa | 480 |
| gtcgtgctgc ttcatgtggt cggggtagcg ggcgaagcac tgcaggccgt agccgaaggt | 540 |
| ggtcacgagg gtgggccagg gcacgggcag cttgccggtg gtgcagatga acttcagggt | 600 |
| cagcttgccg taggtggcat cgccctcgcc ctcgccggac acgctgaact gtggccgtt | 660 |
| tacgtcgccg tccagctcga ccaggatggg caccaccccg gtgaacagct cctcgccctt | 720 |
| gctcaccata tgatatctcc ttcttctagc gggtctgcca catttgctga aaagtaccag | 780 |
| ttgcaaggtg tggtgttgga gcttcataac caggttgggc aaaagggatg aatccctggt | 840 |
| tgtggtgggg ctcctgaaaa gtactcatag actctattgt ggagtgttga ggctgataag | 900 |
| tgaatggggg aaagccctga aaggtggcg ttcagggtct tccctgatgg tttggtgtcg | 960 |
| caggggcatg acatgatcga agatatgagt aacacacctg cgccttatac cccgcagcct | 1020 |
| gcggggcaag cggtgccttt atatcccacg tttacccgtc gacctgcagc aatggcaaca | 1080 |
| acgttgcgca aactattaac tggcgaacta cttactctag cttcccggca acaattaata | 1140 |
| gactggatgg aggcggataa agttgcagga ccacttctgc gctcggccct tccggctggc | 1200 |
| tggtttattg ctgataaatc tggagccggt gagcgtgggt ctcgcggtat cattgcagca | 1260 |
| ctggggccag atggtaagcc ctcccgtatc gtagttatct acacgacggg gagtcaggca | 1320 |
| actatggatg aacgaaatag acagatcgct gagataggtg cctcactgat taagcattgg | 1380 |
| taactgtcag accaagttta ctcatatata ctttagattg atttaaaact tcatttttaa | 1440 |
| tttaaaagga tctaggtgaa gatcctttt gataatctca tgaccaaaat cccttaacgt | 1500 |
| gagttttcgt tccactgagc gtcagacccc ttaataagat gatcttcttg agatcgtttt | 1560 |
| ggtctgcgcg taatctcttg ctctgaaaac gaaaaaaccg ccttgcaggg cggttttcg | 1620 |
| aaggttctct gagctaccaa ctctttgaac cgaggtaact ggcttggagg agcgcagtca | 1680 |
| ccaaaacttg tccttcagt ttagccttaa ccggcgcatg acttcaagac taactcctct | 1740 |
| aaatcaatta ccagtggctg ctgccagtgg tgcttttgca tgtctttccg ggttggactc | 1800 |
| aagacgatag ttaccggata aggcgcagcg gtcggactga acgggggtt cgtgcataca | 1860 |
| gtccagcttg gagcgaactg cctacccgga actgagtgtc aggcgtggaa tgagacaaac | 1920 |
| gcggccataa cagcggaatg acaccggtaa accgaaaggc aggaacagga gagcgcacga | 1980 |
| gggagccgcc aggggaaac gcctggtatc tttatagtcc tgtcgggttt cgccaccact | 2040 |
| gatttgagcg tcagatttcg tgatgcttgt caggggggcg gagcctatgg aaaaacggct | 2100 |
| ttgccgcggc cctctcactt ccctgttaag tatcttcctg gcatcttcca ggaaatctcc | 2160 |

```
gccccgttcg taagccattt ccgctcgccg cagtcgaacg accgagcgta gcgagtcagt    2220
gagcgaggaa gcggaatata tcctgtatca catattctgc tgacgcaccg gtgcagcctt    2280
ttttctcctg ccacatgaag cacttcactg acaccctcat cagtgccaac atagtaagcc    2340
agtatacact ccgctagcgc tgaggtctgc ctcgtgaaga aggtgttgct gactcatacc    2400
aggcctgaat cgccccatca tccagccaga aagtgaggga gccacggttg atgagagctt    2460
tgttgtaggt ggaccagttg gtgattttga acttttgctt tgccacggaa cggtctgcgt    2520
tgtcgggaag atgcgtgatc tgatccttca actcagcaaa agttcgattt attcaacaaa    2580
gccacgttgt gtctcaaaat ctctgatgtt acattgcaca agataaaaat atatcatcat    2640
gaacaataaa actgtctgct tacataaaca gtaatacaag gggtgttatg agccatattc    2700
aacgggaaac gtcttgctcg aggccgcgat taaattccaa catggatgct gatttatatg    2760
ggtataaatg ggctcgcgat aatgtcgggc aatcaggtgc gacaatctat cgattgtatg    2820
ggaagcccga tgcgccagag ttgtttctga acatggcaa aggtagcgtt gccaatgatg    2880
ttacagatga gatggtcaga ctaaactggc tgacggaatt tatgcctctt ccgaccatca    2940
agcattttat ccgtactcct gatgatgcat ggttactcac cactgcgatc cccgggaaaa    3000
cagcattcca ggtattagaa gaatatcctg attcaggtga aaatattgtt gatgcgctgg    3060
cagtgttcct gcgccggttg cattcgattc ctgtttgtaa ttgtcctttt aacagcgatc    3120
gcgtatttcg tctcgctcag gcgcaatcac gaatgaataa cggtttggtt gatgcgagtg    3180
attttgatga cgagcgtaat ggctggcctg ttgaacaagt ctggaaagaa atgcataagc    3240
ttttgccatt ctcaccggat tcagtcgtca ctcatggtga tttctcactt gataacctta    3300 ttttgacga gggaaatta ataggttgta ttgatgttgg acgagtcgga atcgcagacc    3360
gataccagga tcttgccatc ctatggaact gcctcggtga gttttctcct tcattacaga    3420
aacggctttt tcaaaaatat ggtattgata atcctgatat gaataaattg cagtttcatt    3480
tgatgctcga tgagttttc taatcagaat tggttaattg gttgtaacac tggcagagca    3540
ttacgctgac ttgacgggac ggcggctttg ttgaataaat cgaacttttg ctgagttgaa    3600
ggatcagatc acgcatcttc ccgacaacgc agaccgttcc gtggcaaagc aaaagttcaa    3660
aatcaccaac tggtccacct acaacaaagc tctcatcaac cgtggctccc tcactttctg    3720
gctggatgat ggggcgattc aggcctggta tgagtcagca acaccttctt cacgaggcag    3780
acctcagcgc tcaaagatgc aggggtaaaa gctaaccgca tctttaccga caaggcatcc    3840
ggcagttcaa cagatcggga agggctggat ttgctgagga tgaaggtgga ggaaggtgat    3900
gtcattctgg tgaagaagct cgaccgtctt ggccgcgaca ccgccgacat gatccaactg    3960
ataaaagagt ttgatgctca gggtgtagcg gttcggttta ttgacgacgg gatcagtacc    4020
gacggtgata tggggcaaat ggtggtcacc atcctgtcgg ctgtggcaca ggctgaacgc    4080
cggaggatca agtcggtcaa gccaagcgca accagcggca ccgccgcgag caacgtcgca    4140
agggcgatca ggggacgatt tttgcgaaga atttccacgg taagaatcca atctctcgaa    4200
tttagggtga aagaagcttg gcataggggt gtgcacgaac tcggtggagg aaatttccgc    4260
ggggcaaggc ttcgcgaagc ggagtcgcgg cagtggcttt gaagatcttt gggagcagtc    4320
cttgtgcgct tacgaggtga gccggtgggg aaccgttatc tgcctatggt gtgagccccc    4380
ctagagagct tcaagagcaa tcagcccgac ctagaaagga ggccaagaga gagaccccta    4440 cgggggggaac cgttttctgc ctacgagatg gcacatttac tgggaagctt tacggcgtcc    4500
```

```
tcgtggaagt tcaatgcccg cagacttaag tgctctattc acggtctgac gtgacacgct    4560
aaattcagac atagcttcat tgattgtcgg ccacgagcca gtctctccct caacagtcat    4620
aaaccaacct gcaatggtca agcgatttcc tttagctttc ctagcttgtc gttgactgga    4680
cttagctagt ttttctcgct gtgctcgggc gtactcactg tttgggtctt ccagcgttc     4740 tgcggccttt ttaccgccac gtcttcccat agtggccaga gcttttcgcc ctcggctgct    4800
ctgcgtctct gtctgacgag cagggacgac tggctggcct ttagcgacgt agccgcgcac    4860
acgtcgcgcc atcgtctggc ggtcacgcat cggcggcaga tcaggctcac ggccgtctgc    4920
tccgaccgcc tgagcgacgg tgtaggcacg ctcgtaggcg tcgatgatct tggtgtcttt    4980
taggcgctca ccagccgctt ttaactggta tcccacagtc aaagcgtggc gaaaagccgt    5040
ctcatcacgg gcggcacgcc ctggagcagt ccagaggaca cggacgccgt cgatcagctc    5100
tccagacgct tcagcggcgc tcggcaggct tgcttcaagc gtggcaagtg cttttgcttc    5160
cgcagtggct tttcttgccg cttcgatacg tgcccgtccg ctagaaaact cctgctcata    5220
gcgtttttta ggttttctg tgcctgagat catgcgagca acctccataa gatcagctag     5280
gcgatccacg cgattgtgct gggcatgcca gcggtacgcg gtgggatcgt cggagacgtg    5340
cagtggccac cggctcagcc tatgtgaaaa agcctggtca gcgccgaaaa cgcgggtcat    5400
ttcctcggtc gttgcagcca gcaggcgcat attcgggctg ctcatgcctg ctgcggcata    5460
caccggatca atgagccaga tgagctgcca tttcccgctc agtggattca cgccgatcca    5520
agctggcgct ttttccaggc gtgcccagcg ctccaaaatc gcgtagacct cggggtttac    5580
gtgctcgatt ttcccgccgg cctggtggct cggcacatca atgtccagga caagcacggc    5640
tgcgtgctgc gcgtgcgtca gagcaacata ctggcaccgg gcaagcgatt tgaaccaac     5700 tcggtataac ttcggctgtg tttctcccgt gtccgggtct ttgatccaag cgctggcgaa    5760
gtcgcgggtc ttgctgccct ggaaattttc tctgcccagg tgagcgagga attcgcggcg    5820
gtcttcgctc gtccagccac gtgatcgcag gcgagctcg ggatgggtgt cgaacagatc     5880
agcggaaaat ttccaggccg gtgtgtcaat gtctcgtgaa tccgctagag tcattttga     5940 gcgctttctc ccaggtttgg actggggtt agccgacgcc ctgtgagtta ccgctcacgg     6000
ggcgttcaac attttttcagg tattcgtgca gcttatcgct tcttgccgcc tgtgcgcttt    6060
ttcgacgcgc gacgctgctg ccgattcggt gcaggtggtg gcggcgctga cacgtcctgg    6120
gcggccacgg ccacacgaaa cgcggcattt acgatgtttg tcatgcctgc gggcaccgcg    6180
ccacgatcgc ggataattct cgctgccgct tccagctctg tgacgaccat ggccaaaatt    6240
tcgctcgggg gacgcacttc cagcgccatt tgcgacctag ccgcctccag ctcctcggcg    6300
tggcgtttgt tggcgcgctc gcggctggct gcggcacgac acgcatctga gcaatatttt    6360
gcgcgccgtc ctcgcgggtc aggccgggga ggaatcaggc caccgcagta ggcgcaactg    6420
attcgatcct ccactactgt gcgtcctcct ggcgctgccg agcacgcagc tcgtcagcca    6480
gctcctcaag atccgccacg agagtttcta ggtcgctcgc ggcactggcc cagtctcgtg    6540
atgctggcgc gtccgtcgta tcgagagctc ggaaaaatcc gatcaccgtt tttaaatcga    6600
cggcagcatc gagcgcgtcg gactccacgc cgacatcaga gagatccata gctgatgatt    6660
cgggccaatt ttggtacttc gtcgtgaagg tcatgacacc attataacga acgttcgtta    6720 aagttttttgg cggaaaatca cgcggcacga aaattttcac gaagcgggac tttgcgcagc    6780
tcaggggtgc taaaaatttt gtatcgcact tgattttcc gaaagacaga ttatctgcaa     6840
acggtgtgtc gtatttctgg cttggttttt aaaaaatctg gaatcgaaaa tttgcgggc     6900
```

| gaccgagaag | ttttttacaa | aaggcaaaaa | cttttcgggg | atcgacagaa | ataaaacgat | 6960 |
| gacggtacg | caacaaaaaa | gcgtcaggat | cgccgtagag | cgattgaaga | ccgtcaacca | 7020 |
| aaggggaagc | ctccaatcga | cgcgacgcgc | gctctacggc | gatcctgacg | cagatttta | 7080 |
| gctatctgtc | gcagcgccct | cagggacaag | ccacccgcac | aacgtcgcga | gggcgatcag | 7140 |
| cgacgccgca | ggg | | | | | 7153 |

<210> SEQ ID NO 36
<211> LENGTH: 7060
<212> TYPE: DNA
<213> ORGANISM: Artificial sequence
<220> FEATURE:
<223> OTHER INFORMATION: DNA-sequence of plasmid pSen1325

<400> SEQUENCE: 36

| ggatccttat | tacttgtaca | gctcgtccat | gccgagagtg | atcccggcgg | cggtcacgaa | 60 |
| ctccagcagg | accatgtgat | cgcgcttctc | gttggggtct | ttgctcaggg | cggactggta | 120 |
| gctcaggtag | tggttgtcgg | gcagcagcac | ggggccgtcg | ccgatggggg | tgttctgctg | 180 |
| gtagtggtcg | gcgagctgca | cgctgccgcc | ctcgatgttg | tggcggatct | tgaagttcac | 240 |
| cttgatgccg | ttcttctgct | tgtcggccat | gatatagacg | ttgtggctgt | tgtagttgta | 300 |
| ctccagcttg | tgccccagga | tgttgccgtc | ctccttgaag | ttgatgccct | tcagctcgat | 360 |
| gcggttcacc | agggtgtcgc | cctcgaactt | cacctcggcg | cgggtcttgt | agttgccgtc | 420 |
| gtccttgaag | aagatggtgc | gctcctggac | gtagccttcg | ggcatggcgg | acttgaagaa | 480 |
| gtcgtgctgc | ttcatgtggt | cggggtagcg | ggcgaagcac | tgcaggccgt | agccgaaggt | 540 |
| ggtcacgagg | gtgggccagg | gcacgggcag | cttgccggtg | gtgcagatga | acttcagggt | 600 |
| cagcttgccg | taggtggcat | cgccctcgcc | ctcgccggac | acgctgaact | gtggccgtt | 660 |
| tacgtcgccg | tccagctcga | ccaggatggg | caccacccg | gtgaacagct | cctcgccctt | 720 |
| gctcaccata | tgatatctcc | ttcttctaac | cagcgacgcc | gccgatccat | tgtcggtgg | 780 |
| tgcttcgggc | gagtcgtcga | gattgtgctg | ggaaagtcat | cgggatcaag | ctcctttatg | 840 |
| gctgattgag | ttttctttc | ttcttcaatc | atcgccaata | agaacctaga | gcacatcggg | 900 |
| gatttcccct | ctcctaaccc | ctaaaaaccc | ctgagaaaac | gctccaagta | aacccttaca | 960 |
| gctcgtcgac | ctgcagcaat | ggcaacaacg | ttgcgcaaac | tattaactgg | cgaactactt | 1020 |
| actctagctt | cccggcaaca | attaatagac | tggatggagg | cggataaagt | tgcaggacca | 1080 |
| cttctgcgct | cggcccttcc | ggctggctgg | tttattgctg | ataaatctgg | agccggtgag | 1140 |
| cgtgggtctc | gcggtatcat | tgcagcactg | gggccagatg | gtaagccctc | ccgtatcgta | 1200 |
| gttatctaca | cgacggggag | tcaggcaact | atggatgaac | gaaatagaca | gatcgctgag | 1260 |
| ataggtgcct | cactgattaa | gcattggtaa | ctgtcagacc | aagtttactc | atatatactt | 1320 |
| tagattgatt | taaaacttca | ttttaattt | aaaaggatct | aggtgaagat | ccttttgat | 1380 |
| aatctcatga | ccaaaatccc | ttaacgtgag | ttttcgttcc | actgagcgtc | agacccctta | 1440 |
| ataagatgat | cttcttgaga | tcgttttggt | ctgcgcgtaa | tctcttgctc | tgaaaacgaa | 1500 |
| aaaaccgcct | tgcagggcgg | ttttcgaag | gttctctgag | ctaccaactc | tttgaaccga | 1560 |
| ggtaactggc | ttggaggagc | gcagtcacca | aaacttgtcc | tttcagttta | gccttaaccg | 1620 |
| gcgcatgact | tcaagactaa | ctcctctaaa | tcaattacca | gtggctgctg | ccagtggtgc | 1680 |
| ttttgcatgt | ctttccgggt | tggactcaag | acgatagtta | ccggataagg | cgcagcggtc | 1740 |

```
ggactgaacg gggggttcgt gcatacagtc cagcttggag cgaactgcct acccggaact   1800
gagtgtcagg cgtggaatga gacaaacgcg gccataacag cggaatgaca ccggtaaacc   1860
gaaaggcagg aacaggagag cgcacgaggg agccgccagg gggaaacgcc tggtatcttt   1920
atagtcctgt cgggtttcgc caccactgat ttgagcgtca gatttcgtga tgcttgtcag   1980
gggggcggag cctatggaaa aacggctttg ccgcggccct ctcacttccc tgttaagtat   2040
cttcctggca tcttccagga aatctccgcc ccgttcgtaa gccatttccg ctcgccgcag   2100
tcgaacgacc gagcgtagcg agtcagtgag cgaggaagcg gaatatatcc tgtatcacat   2160
attctgctga cgcaccggtg cagccttttt tctcctgcca catgaagcac ttcactgaca   2220
ccctcatcag tgccaacata gtaagccagt atacactccg ctagcgctga ggtctgcctc   2280
gtgaagaagg tgttgctgac tcataccagg cctgaatcgc cccatcatcc agccagaaag   2340
tgagggagcc acggttgatg agagctttgt tgtaggtgga ccagttggtg attttgaact   2400
tttgctttgc cacggaacgg tctgcgttgt cgggaagatg cgtgatctga tccttcaact   2460
cagcaaaagt tcgatttatt caacaaagcc acgttgtgtc tcaaaatctc tgatgttaca   2520
ttgcacaaga taaaaatata tcatcatgaa cataaaaact gtctgcttac ataaacagta   2580
atacaagggg tgttatgagc catattcaac gggaaacgtc ttgctcgagg ccgcgattaa   2640
attccaacat ggatgctgat ttatatgggt ataaatgggc tcgcgataat gtcgggcaat   2700
caggtgcgac aatctatcga ttgtatggga agcccgatgc gccagagttg tttctgaaac   2760
atggcaaagg tagcgttgcc aatgatgtta cagatgagat ggtcagacta aactggctga   2820
cggaatttat gcctcttccg accatcaagc attttatccg tactcctgat gatgcatggt   2880
tactcaccac tgcgatcccc gggaaaacag cattccaggt attagaagaa tatcctgatt   2940
caggtgaaaa tattgttgat gcgctggcag tgttcctgcg ccggttgcat cgattcctg   3000
tttgtaattg tccttttaac agcgatcgcg tatttcgtct cgctcaggcg caatcacgaa   3060
tgaataacgg tttggttgat gcgagtgatt ttgatgacga gcgtaatggc tggcctgttg   3120
aacaagtctg gaaagaaatg cataagcttt tgccattctc accggattca gtcgtcactc   3180
atggtgattt ctcacttgat aaccttattt ttgacgaggg gaaattaata ggttgtattg   3240
atgttggacg agtcggaatc gcagaccgat accaggatct tgccatccta tggaactgcc   3300
tcggtgagtt ttctccttca ttacagaaac ggcttttca aaaatatggt attgataatc   3360
ctgatatgaa taaattgcag tttcatttga tgctcgatga gttttctaa tcagaattgg   3420
ttaattggtt gtaacactgg cagagcatta cgctgacttg acgggacggc ggctttgttg   3480
aataaatcga acttttgctg agttgaagga tcagatcacg catcttcccg acaacgcaga   3540
ccgttccgtg gcaaagcaaa agttcaaaat caccaactgg tccacctaca acaaagctct   3600
catcaaccgt ggctccctca ctttctggct ggatgatggg gcgattcagg cctggtatga   3660
gtcagcaaca ccttcttcac gaggcagacc tcagcgctca agatgcagg ggtaaaagct   3720
aaccgcatct ttaccgacaa ggcatccggc agttcaacag atcgggaagg ctggatttg   3780
ctgaggatga aggtggagga aggtgatgtc attctggtga agaagctcga ccgtcttggc   3840
cgcgacaccg ccgacatgat ccaactgata aaagagtttg atgctcaggg tgtagcggtt   3900
cggtttattg acgacgggat cagtaccgac ggtgatatgg ggcaaatggt ggtcaccatc   3960
ctgtcggctg tggcacaggc tgaacgccgg aggatcaagt cggtcaagcc aagcgcaacc   4020
agcggcaccg ccgcgagcaa cgtcgcaagg gcgatcaggg gacgatttt gcgaagaatt   4080
tccacggtaa gaatccaatc tctcgaattt agggtgaaag aagcttggca tagggggtgtg   4140
```

```
cacgaactcg gtggaggaaa tttccgcggg gcaaggcttc gcgaagcgga gtcgcggcag      4200
tggctttgaa gatctttggg agcagtcctt gtgcgcttac gaggtgagcc ggtggggaac      4260
cgttatctgc ctatggtgtg agccccccta gagagcttca agagcaatca gcccgaccta      4320
gaaaggaggc caagagagag accccctacgg ggggaaccgt tttctgccta cgagatggca      4380
catttactgg gaagctttac ggcgtcctcg tggaagttca atgcccgcag acttaagtgc      4440
tctattcacg gtctgacgtg acacgctaaa ttcagacata gcttcattga ttgtcggcca      4500
cgagccagtc tctccctcaa cagtcataaa ccaacctgca atggtcaagc gatttccttt      4560
agcttcccta gcttgtcgtt gactggactt agctagtttt tctcgctgtg ctcgggcgta      4620
ctcactgttt gggtctttcc agcgttctgc ggcctttta ccgccacgtc ttcccatagt       4680
ggccagagct tttcgccctc ggctgctctg cgtctctgtc tgacgagcag ggacgactgg      4740
ctggccttta gcgacgtagc cgcgcacacg tcgcgccatc gtctggcggt cacgcatcgg      4800
cggcagatca ggctcacggc cgtctgctcc gaccgcctga gcgacggtgt aggcacgctc      4860
gtaggcgtcg atgatcttgg tgtctttag gcgctcacca gccgctttta actggtatcc       4920
cacagtcaaa gcgtggcgaa aagccgtctc atcacgggcg gcacgccctg gagcagtcca      4980
gaggacacgg acgccgtcga tcagctctcc agacgcttca gcggcgctcg gcaggcttgc      5040
ttcaagcgtg gcaagtgctt ttgcttccgc agtggctttt cttgccgctt cgatacgtgc      5100
ccgtccgcta gaaaactcct gctcatagcg ttttttaggt ttttctgtgc ctgagatcat      5160
gcgagcaacc tccataagat cagctaggcg atccacgcga ttgtgctggg catgccagcg      5220
gtacgcggtg ggatcgtcgg agacgtgcag tggccaccgg ctcagcctat gtgaaaaagc      5280
ctggtcagcg ccgaaaacgc gggtcatttc ctcggtcgtt gcagccagca ggcgcatatt      5340
cgggctgctc atgcctgctg cggcatacac cggatcaatg agccagatga gctggcattt      5400
cccgctcagt ggattcacgc cgatccaagc tggcgctttt tccaggcgtg cccagcgctc      5460
caaaatcgcg tagacctcgg ggtttacgtg ctcgattttc ccgccggcct ggtggctcgg      5520
cacatcaatg tccaggacaa gcacggctgc gtgctgcgcg tgcgtcagag caacatactg      5580
gcaccgggca agcgattttg aaccaactcg gtataacttc ggctgtgttt ctcccgtgtc      5640
cgggtctttg atccaagcgc tggcgaagtc gcgggtcttg ctgccctgga aattttctct      5700
gcccaggtga gcgaggaatt cgcggcggtc ttcgctcgtc cagccacgtg atcgcagcgc      5760
gagctcggga tgggtgtcga acagatcagc ggaaaatttc caggccggtg tgtcaatgtc      5820
tcgtgaatcc gctagagtca tttttgagcg ctttctccca ggtttggact gggggttagc      5880
cgacgccctg tgagttaccg ctcacggggc gttcaacatt tttcaggtat tcgtgcagct      5940
tatcgcttct tgccgcctgt gcgctttttc gacgcgcgac gctgctgccg attcggtgca      6000
ggtggtggcg gcgctgacac gtcctgggcg gccacggcca cacgaaacgc ggcatttacg      6060
atgtttgtca tgcctgcggg caccgcgcca cgatcgcgga taattctcgc tgccgcttcc      6120
agctctgtga cgaccatggc caaaatttcg ctcggggac gcacttccag cgccatttgc       6180
gacctagccg cctccagctc ctcggcgtgg cgtttgttgg cgcgctcgcg gctggctgcg      6240
gcacgacacg catctgagca atattttgcg cgccgtcctc gcgggtcagg ccggggagga      6300
atcaggccac cgcagtaggc gcaactgatt cgatcctcca ctactgtgcg tcctcctggc      6360
gctgccgagc acgcagctcg tcagccagct cctcaagatc cgccacgaga gtttctaggt      6420
cgctcgcggc actggcccag tctcgtgatg ctggcgcgtc cgtcgtatcg agagctcgga      6480
```

```
aaaatccgat caccgttttt aaatcgacgg cagcatcgag cgcgtcggac tccagcgcga    6540
catcagagag atccatagct gatgattcgg gccaattttg gtacttcgtc gtgaaggtca    6600
tgacaccatt ataacgaacg ttcgttaaag ttttttggcgg aaaatcacgc ggcacgaaaa    6660
ttttcacgaa gcgggacttt gcgcagctca ggggtgctaa aaattttgta tcgcacttga    6720
tttttccgaa agacagatta tctgcaaacg gtgtgtcgta tttctggctt ggttttaaa     6780 aaatctggaa tcgaaaattt gcggggcgac cgagaagttt tttacaaaag gcaaaaactt    6840
tttcgggatc gacagaaata aaacgatcga cggtacgcaa caaaaaagcg tcaggatcgc    6900
cgtagagcga ttgaagaccg tcaaccaaag gggaagcctc caatcgacgc gacgcgcgct    6960
ctacggcgat cctgacgcag atttttagct atctgtcgca gcgccctcag ggacaagcca    7020
cccgcacaac gtcgcgaggg cgatcagcga cgccgcaggg                          7060
```

<210> SEQ ID NO 37
<211> LENGTH: 7561
<212> TYPE: DNA
<213> ORGANISM: Artificial sequence
<220> FEATURE:
<223> OTHER INFORMATION: DNA-sequence of plasmid pSen0996_8

<400> SEQUENCE: 37

```
ccctgcggcg tcgctgatcg ccctcgcgac gttgtgcggg tggcttgtcc ctgagggcgc      60
tgcgacagat agctaaaaat ctgcgtcagg atcgccgtag agcgcgcgtc gcgtcgattg     120
gaggcttccc ctttggttga cggtcttcaa tcgctctacg gcgatcctga cgcttttttg     180
ttgcgtaccg tcgatcgttt tatttctgtc gatcccgaaa aagttttgc cttttgtaaa     240 aaacttctcg gtcgccccgc aaattttcga ttccagattt tttaaaaacc aagccagaaa    300
tacgacacac cgtttgcaga taatctgtct ttcggaaaaa tcaagtgcga tacaaaattt    360
ttagcacccc tgagctgcgc aaagtcccgc ttcgtgaaaa ttttcgtgcc gcgtgatttt    420
ccgccaaaaa ctttaacgaa cgttcgttat aatggtgtca tgaccttcac gacgaagtac    480
caaaattggc ccgaatcatc agctatggat ctctctgatg tcgcgctgga gtccgacgcg    540
ctcgatgctg ccgtcgattt aaaaacggtg atcggatttt tccgagctct cgatacgacg    600
gacgcgccag catcacgaga ctgggccagt gccgcgagcg acctagaaac tctcgtggcg    660
gatcttgagg agctggctga cgagctgcgt gctcggcagc gccaggagga cgcacagtag    720
tggaggatcg aatcagttgc gcctactgcg gtggcctgat tcctcccgg cctgacccgc     780 gaggacggcg cgcaaaatat tgctcagatg cgtgtcgtgc cgcagccagc cgcgagcgcg    840
ccaacaaacg ccacgccgag gagctggagg cggctaggtc gcaaatggcg ctggaagtgc    900
gtcccccgag cgaaattttg gccatggtcg tcacagagct ggaagcggca gcgagaatta    960
tccgcgatcg tggcgcggtg cccgcaggca tgacaaacat cgtaaatgcc gcgtttcgtg   1020
tggccgtggc cgcccaggac gtgtcagcgc cgccaccacc tgcaccgaat cggcagcagc   1080
gtcgcgcgtc gaaaaagcgc acaggcggca agaagcgata agctgcacga ataccctgaaa   1140 aatgttgaac gccccgtgag cggtaactca cagggcgtcg gctaaccccc agtccaaacc   1200
tgggagaaag cgctcaaaaa tgactctagc ggattcacga acattgaca caccggcctg    1260 gaaattttcc gctgatctgt tcgacaccca tcccgagctc gcgctgcgat cacgtggctg   1320
gacgagcgaa gaccgccgcg aattcctcgc tcacctgggc agagaaaatt tccagggcag   1380
caagacccgc gacttcgcca gcgcttggat caaagacccg gacacgggag aaacacagcc   1440
gaagttatac cgagttggtt caaaatcgct tgcccggtgc cagtatgttg ctctgacgca   1500
```

```
cgcgcagcac gcagccgtgc ttgtcctgga cattgatgtg ccgagccacc aggccggcgg    1560
gaaaatcgag cacgtaaacc ccgaggtcta cgcgattttg gagcgctggg cacgcctgga    1620
aaaagcgcca gcttggatcg gcgtgaatcc actgagcggg aaatgccagc tcatctggct    1680
cattgatccg gtgtatgccg cagcaggcat gagcagcccg aatatgcgcc tgctggctgc    1740
aacgaccgag gaaatgaccc gcgttttcgg cgctgaccag gcttttcac ataggctgag     1800 ccggtggcca ctgcacgtct ccgacgatcc caccgcgtac cgctggcatg cccagcacaa    1860
tcgcgtggat cgcctagctg atcttatgga ggttgctcgc atgatctcag gcacagaaaa    1920
acctaaaaaa cgctatgagc aggagttttc tagcggacgg gcacgtatcg aagcggcaag    1980
aaaagccact gcggaagcaa agcacttgc cacgcttgaa gcaagcctgc cgagcgccgc     2040
tgaagcgtct ggagagctga tcgacggcgt ccgtgtcctc tggactgctc cagggcgtgc    2100
cgcccgtgat gagacggctt ttcgccacgc tttgactgtg ggataccagt taaaagcggc    2160
tggtgagcgc ctaaaagaca ccaagatcat cgacgcctac gagcgtgcct acaccgtcgc    2220
tcaggcggtc ggagcagacg gccgtgagcc tgatctgccg ccgatgcgtg accgccagac    2280
gatggcgcga cgtgtgcgcg gctacgtcgc taaaggccag ccagtcgtcc ctgctcgtca    2340
gacagagacg cagagcagcc gagggcgaaa agctctggcc actatgggaa gacgtggcgg    2400
taaaaaggcc gcagaacgct ggaaagaccc aaacagtgag tacgcccgag cacagcgaga    2460
aaaactagct aagtccagtc aacgacaagc taggaaagct aaaggaaatc gcttgaccat    2520
tgcaggttgg tttatgactg ttgagggaga gactggctcg tggccgacaa tcaatgaagc    2580
tatgtctgaa tttagcgtgt cacgtcagac cgtgaataga gcacttaagt ctgcgggcat    2640
tgaacttcca cgaggacgcc gtaaagcttc ccagtaaatg tgccatctcg taggcagaaa    2700
acggttcccc ccgtaggggt ctctctcttg gcctcctttc taggtcgggc tgattgctct    2760
tgaagctctc taggggggct cacaccatag gcagataacg gttccccacc ggctcacctc    2820
gtaagcgcac aaggactgct cccaaagatc ttcaaagcca ctgccgcgac tccgcttcgc    2880 gaagcctgc cccgcggaaa tttcctccac cgagttcgtg cacacccta tgccaagctt      2940 ctttcaccct aaattcgaga gattggattc ttaccgtgga aattcttcgc aaaaatcgtc    3000
ccctgatcgc ccttgcgacg ttgctcgcgg cggtgccgct ggttgcgctt ggcttgaccg    3060
acttgatcct ccggcgttca gcctgtgcca cagccgacag gatggtgacc accatttgcc    3120
ccatatcacc gtcggtactg atcccgtcgt caataaaccg aaccgctaca ccctgagcat    3180
caaactcttt tatcagttgg atcatgtcgg cggtgtcgcg gccaagacgg tcgagcttct    3240
tcaccagaat gacatcacct tcctccacct tcatcctcag caaatccagc ccttcccgat    3300
ctgttgaact gccggatgcc ttgtcggtaa agatgcggtt agcttttacc cctgcatctt    3360
tgagcgctga ggtctgcctc gtgaagaagg tgttgctgac tcataccagg cctgaatcgc    3420
cccatcatcc agccagaaag tgagggagcc acgttgatg agagctttgt tgtaggtgga    3480
ccagttggtg attttgaact tttgctttgc cacggaacgg tctgcgttgt cgggaagatg    3540
cgtgatctga tccttcaact cagcaaaagt tcgatttatt caacaaagcc gccgtcccgt    3600
caagtcagcg taatgctctg ccagtgttac aaccaattaa ccaattctga ttagaaaaac    3660
tcatcgagca tcaaatgaaa ctgcaattta ttcatatcag gattatcaat accatatttt    3720
tgaaaaagcc gtttctgtaa tgaaggagaa aactcaccga gcagttcca taggatggca     3780 agatcctggt atcggtctgc gattccgact cgtccaacat caatacaacc tattaatttc    3840
```

| | | | | | |
|---|---|---|---|---|---|
| ccctcgtcaa | aaataaggtt | atcaagtgag | aaatcaccat | gagtgacgac | tgaatccggt | 3900 |
| gagaatggca | aaagcttatg | catttctttc | cagacttgtt | caacaggcca | gccattacgc | 3960 |
| tcgtcatcaa | aatcactcgc | atcaaccaaa | ccgttattca | ttcgtgattg | cgcctgagcg | 4020 |
| agacgaaata | cgcgatcgct | gttaaaagga | caattacaaa | caggaatcga | atgcaaccgg | 4080 |
| cgcaggaaca | ctgccagcgc | atcaacaata | ttttcacctg | aatcaggata | ttcttctaat | 4140 |
| acctggaatg | ctgtttccc | ggggatcgca | gtggtgagta | accatgcatc | atcaggagta | 4200 |
| cggataaaat | gcttgatggt | cggaagaggc | ataaattccg | tcagccagtt | tagtctgacc | 4260 |
| atctcatctg | taacatcatt | ggcaacgcta | cctttgccat | gtttcagaaa | caactctggc | 4320 |
| gcatcgggct | tcccatacaa | tcgatagatt | gtcgcacctg | attgcccgac | attatcgcga | 4380 |
| gcccatttat | acccatataa | atcagcatcc | atgttggaat | ttaatcgcgg | cctcgagcaa | 4440 |
| gacgtttccc | gttgaatatg | gctcataaca | ccccttgtat | tactgtttat | gtaagcagac | 4500 |
| agttttattg | ttcatgatga | tatatttta | tcttgtgcaa | tgtaacatca | gagattttga | 4560 |
| gacacaacgt | ggctttgttg | aataaatcga | acttttgctg | agttgaagga | tcagatcacg | 4620 |
| catcttcccg | acaacgcaga | ccgttccgtg | gcaaagcaaa | agttcaaaat | caccaactgg | 4680 |
| tccacctaca | acaaagctct | catcaaccgt | ggctccctca | ctttctggct | ggatgatggg | 4740 |
| gcgattcagg | cctggtatga | gtcagcaaca | ccttcttcac | gaggcagacc | tcagcgctag | 4800 |
| cggagtgtat | actggcttac | tatgttggca | ctgatgaggg | tgtcagtgaa | gtgcttcatg | 4860 |
| tggcaggaga | aaaaaggctg | caccggtgcg | tcagcagaat | atgtgataca | ggatatattc | 4920 |
| cgcttcctcg | ctcactgact | cgctacgctc | ggtcgttcga | ctgcggcgag | cggaaatggc | 4980 |
| ttacgaacgg | ggcggagatt | tcctggaaga | tgccaggaag | atacttaaca | gggaagtgag | 5040 |
| agggccgcgg | caaagccgtt | tttccatagg | ctccgccccc | ctgacaagca | tcacgaaatc | 5100 |
| tgacgctcaa | atcagtggtg | gcgaaacccg | acaggactat | aaagatacca | ggcgtttccc | 5160 |
| cctggcggct | ccctcgtgcg | ctctcctgtt | cctgcctttc | ggtttaccgg | tgtcattccg | 5220 |
| ctgttatggc | cgcgtttgtc | tcattccacg | cctgacactc | agttccgggt | aggcagttcg | 5280 |
| ctccaagctg | gactgtatgc | acgaaccccc | cgttcagtcc | gaccgctgcg | ccttatccgg | 5340 |
| taactatcgt | cttgagtcca | acccggaaag | acatgcaaaa | gcaccactgg | cagcagccac | 5400 |
| tggtaattga | tttagaggag | ttagtcttga | agtcatgcgc | cggttaaggc | taaactgaaa | 5460 |
| ggacaagttt | tggtgactgc | gctcctccaa | gccagttacc | tcggttcaaa | gagttggtag | 5520 |
| ctcagagaac | cttcgaaaaa | ccgccctgca | aggcggtttt | ttcgttttca | gagcaagaga | 5580 |
| ttacgcgcag | accaaaacga | tctcaagaag | atcatcttat | taagggggtct | gacgctcagt | 5640 |
| ggaacgaaaa | ctcacgttaa | gggattttgg | tcatgagatt | atcaaaaagg | atcttcacct | 5700 |
| agatcctttt | aaattaaaaa | tgaagtttta | aatcaatcta | aagtatatat | gagtaaactt | 5760 |
| ggtctgacag | ttaccaatgc | ttaatcagtg | aggcacctat | ctcagcgatc | tgtctatttc | 5820 |
| gttcatccat | agttgcctga | ctccccgtcg | tgtagataac | tacgatacgg | gagggcttac | 5880 |
| catctggccc | cagtgctgca | atgataccgc | gagacccacg | ctcaccggct | ccagatttat | 5940 |
| cagcaataaa | ccagccagcc | ggaagggccg | agcgcagaag | tggtcctgca | actttatccg | 6000 |
| cctccatcca | gtctattaat | tgttgccggg | aagctagagt | aagtagttcg | ccagttaata | 6060 |
| gtttgcgcaa | cgttgttgcc | attgctgcag | gtcgaccatg | cgccgttccc | agtggaaggc | 6120 |
| cgacaatgtc | gcccttcagg | aggtcaagat | cgacggtcag | accgtcgcca | tcccacgccg | 6180 |
| tctggttaag | gcagcacagc | tcggtctcgt | ggacgtagag | cagttctaaa | ccttaaattc | 6240 |

```
atcgcctaca accttttgta ggtaagaatt taacaagagc cagttatctt ctcttaaaat      6300
gaggaggtaa ctggcttctt tatgcttaag aggtgttagc ataagtgaaa tatgttccaa      6360
cgcgtggacg tcttaattgg gaggaagtct gtcacggact ggaagacgaa aagggtatcg      6420
atgaaaattt tagttgttga tgacgagcaa gctgtacgtt aatctatcgc gccgtcagct      6480
cccgttccat gccgggatcg ggattaggtc ttgccatcgt gaatcaggtt gtgaatcggc      6540
atggtggcca actcgttgtg ggtgaatcag atgatggcgg aacgagaatc actattgatt      6600
tgccagggga acccattcgc agcgggttcg aaaatgtcga tgattaaggt accaccacta      6660
aagagctcac aggaagtgtt cagactactt agagtgacgc cccagccaca gggttcataa      6720
tcaaatcatg acaaatcaat tccccacaaa caacggtgag aacccggacc gtgcatcgga      6780
aactccatca gaaaccaact ccggtacctg aactttaaga aggagatatc atatggtgag      6840
caagggcgag gagctgttca ccggggtggt gcccatcctg gtcgagctgg acggcgacgt      6900
aaacggccac aagttcagcg tgtccggcga gggcgagggc gatgccacct acggcaagct      6960
gaccctgaag ttcatctgca ccaccggcaa gctgcccgtg ccctggccca ccctcgtgac      7020
caccttcggc tacggcctgc agtgcttcgc ccgctacccc gaccacatga agcagcacga      7080
cttcttcaag tccgccatgc ccgaaggcta cgtccaggag cgcaccatct tcttcaagga      7140
cgacggcaac tacaagaccc gcgccgaggt gaagttcgag ggcgacaccc tggtgaaccg      7200
catcgagctg aagggcatca acttcaagga ggacggcaac atcctggggc acaagctgga      7260
gtacaactac aacagccaca acgtctatat catggccgac aagcagaaga acggcatcaa      7320
ggtgaacttc aagatccgcc acaacatcga gggcggcagc gtgcagctcg ccgaccacta      7380
ccagcagaac ccccatcg cgacggccc cgtgctgctg cccgacaacc actacctgag      7440
ctaccagtcc gccctgagca agaccccaa cgagaagcgc gatcacatgg tcctgctgga      7500
gttcgtgacc gccgccggga tcactctcgg catggacgag ctgtacaagt aataaggatc      7560
c                                                                    7561
```

<210> SEQ ID NO 38
<211> LENGTH: 7102
<212> TYPE: DNA
<213> ORGANISM: Artificial sequence
<220> FEATURE:
<223> OTHER INFORMATION: DNA-sequence of plasmid pSen0996_8c

<400> SEQUENCE: 38

```
ccctgcggcg tcgctgatcg ccctcgcgac gttgtgcggg tggcttgtcc ctgagggcgc        60
tgcgacagat agctaaaaat ctgcgtcagg atcgccgtag agcgcgcgtc gcgtcgattg       120
gaggcttccc ctttggttga cggtcttcaa tcgctctacg gcgatcctga cgcttttttg       180
ttgcgtaccg tcgatcgttt tatttctgtc gatcccgaaa aagttttgc cttttgtaaa       240 aaacttctcg gtcgccccgc aaattttcga ttccagattt tttaaaaacc aagccagaaa       300
tacgacacac cgtttgcaga taatctgtct ttcggaaaaa tcaagtgcga tacaaaattt       360
ttagcacccc tgagctgcgc aaagtcccgc ttcgtgaaaa ttttcgtgcc gcgtgatttt       420
ccgccaaaaa ctttaacgaa cgttcgttat aatggtgtca tgaccttcac gacgaagtac       480
caaaattggc ccgaatcatc agctatggat ctctctgatg tcgcgctgga gtccgacgcg       540
ctcgatgctg ccgtcgattt aaaaacggtg atcggatttt ccgagctct cgatacgacg       600 gacgcgccag catcacgaga ctgggccagt gccgcgagcg acctagaaac tctcgtggcg       660
```

```
gatcttgagg agctggctga cgagctgcgt gctcggcagc gccaggagga cgcacagtag    720
tggaggatcg aatcagttgc gcctactgcg gtggcctgat tcctcccgg cctgacccgc    780
gaggacggcg cgcaaaatat tgctcagatg cgtgtcgtgc cgcagccagc cgcgagcgcg    840
ccaacaaacg ccacgccgag gagctggagg cggctaggtc gcaaatggcg ctggaagtgc    900
gtcccccgag cgaaattttg gccatggtcg tcacagagct ggaagcggca gcgagaatta    960
tccgcgatcg tggcgcggtg cccgcaggca tgacaaacat cgtaaatgcc gcgtttcgtg   1020
tggccgtggc cgcccaggac gtgtcagcgc cgccaccacc tgcaccgaat cggcagcagc   1080
gtcgcgcgtc gaaaaagcgc acaggcggca agaagcgata agctgcacga atacctgaaa   1140
aatgttgaac gccccgtgag cggtaactca cagggcgtcg gctaaccccc agtccaaacc   1200
tgggagaaag cgctcaaaaa tgactctagc ggattcacga cacattgaca caccggcctg   1260
gaaattttcc gctgatctgt tcgacaccca tcccgagctc gcgctgcgat cacgtggctg   1320
gacgagcgaa gaccgccgcg aattcctcgc tcacctgggc agagaaaatt tccagggcag   1380
caagacccgc gacttcgcca gcgcttggat caaagacccg gacacgggag aaacacagcc   1440
gaagttatac cgagttggtt caaaatcgct tgcccggtgc cagtatgttg ctctgacgca   1500
cgcgcagcac gcagccgtgc ttgtcctgga cattgatgtg ccgagccacc aggccggcgg   1560
gaaaatcgag cacgtaaacc ccgaggtcta cgcgattttg gagcgctggg cacgcctgga   1620
aaaagcgcca gcttggatcg gcgtgaatcc actgagcggg aaatgccagc tcatctggct   1680
cattgatccg gtgtatgccg cagcaggcat gagcagcccg aatatgcgcc tgctggctgc   1740
aacgaccgag gaaatgaccc gcgttttcgg cgctgaccag gcttttcac ataggctgag   1800
ccggtggcca ctgcacgtct ccgacgatcc caccgcgtac cgctggcatg cccagcacaa   1860
tcgcgtggat cgcctagctg atcttatgga ggttgctcgc atgatctcag gcacagaaaa   1920
acctaaaaaa cgctatgagc aggagttttc tagcggacgg gcacgtatcg aagcggcaag   1980
aaaagccact gcgaagcaa aagcacttgc cacgcttgaa gcaagcctgc cgagcgccgc   2040
tgaagcgtct ggagagctga tcgacggcgt ccgtgtcctc tggactgctc cagggcgtgc   2100
cgcccgtgat gagacggctt ttcgccacgc tttgactgtg ggataccagt taaaagcggc   2160
tggtgagcgc ctaaaagaca ccaagatcat cgacgcctac gagcgtgcct acaccgtcgc   2220
tcaggcggtc ggagcagacg gccgtgagcc tgatctgccg ccgatgcgtg accgccagac   2280
gatggcgcga cgtgtgcgcg gctacgtcgc taaaggccag ccagtcgtcc ctgctcgtca   2340
gacagagacg cagagcagcc gagggcgaaa agctctggcc actatgggaa gacgtggcgg   2400
taaaaaggcc gcagaacgct ggaaagaccc aaacagtgag tacgcccgag cacagcgaga   2460
aaaactagct aagtccagtc aacgacaagc taggaaagct aaaggaaatc gcttgaccat   2520
tgcaggttgg tttatgactg ttgagggaga gactggctcg tggccgacaa tcaatgaagc   2580
tatgtctgaa tttagcgtgt cacgtcagac cgtgaataga gcacttaagt ctgcgggcat   2640
tgaacttcca cgaggacgcc gtaaagcttc ccagtaaatg tgccatctcg taggcagaaa   2700
acggttcccc ccgtaggggt ctctctcttg gcctcctttc taggtcgggc tgattgctct   2760
tgaagctctc tagggggct cacaccatag gcagataacg gttccccacc ggctcacctc   2820
gtaagcgcac aaggactgct cccaaagatc ttcaaagcca ctgccgcgac tccgcttcgc   2880
gaagccttgc cccgcggaaa tttcctccac cgagttcgtg cacacccta tgccaagctt   2940
ctttcacccct aaattcgaga gattggattc ttaccgtgga aattcttcgc aaaaatcgtc   3000
ccctgatcgc ccttgcgacg ttgctcgcgg cggtgccgct ggttgcgctt ggcttgaccg   3060
```

```
acttgatcct ccggcgttca gcctgtgcca cagccgacag gatggtgacc accatttgcc    3120
ccatatcacc gtcggtactg atcccgtcgt caataaaccg aaccgctaca ccctgagcat    3180
caaactcttt tatcagttgg atcatgtcgg cggtgtcgcg gccaagacgg tcgagcttct    3240
tcaccagaat gacatcacct tcctccacct tcatcctcag caaatccagc ccttcccgat    3300
ctgttgaact gccggatgcc ttgtcggtaa agatgcggtt agcttttacc cctgcatctt    3360
tgagcgctga ggtctgcctc gtgaagaagg tgttgctgac tcataccagg cctgaatcgc    3420
cccatcatcc agccagaaag tgagggagcc acggttgatg agagctttgt tgtaggtgga    3480
ccagttggtg attttgaact tttgctttgc cacggaacgg tctgcgttgt cgggaagatg    3540
cgtgatctga tccttcaact cagcaaaagt tcgatttatt caacaaagcc gccgtcccgt    3600
caagtcagcg taatgctctg ccagtgttac aaccaattaa ccaattctga ttagaaaaac    3660
tcatcgagca tcaaatgaaa ctgcaattta ttcatatcag gattatcaat accatatttt    3720
tgaaaaagcc gtttctgtaa tgaaggagaa aactcaccga ggcagttcca taggatggca    3780
agatcctggt atcggtctgc gattccgact cgtccaacat caatacaacc tattaatttc    3840
ccctcgtcaa aataaggtt atcaagtgag aaatcaccat gagtgacgac tgaatccggt    3900
gagaatggca aaagcttatg catttctttc cagacttgtt caacaggcca gccattacgc    3960
tcgtcatcaa aatcactcgc atcaaccaaa ccgttattca ttcgtgattg cgcctgagcg    4020
agacgaaata cgcgatcgct gttaaaagga caattacaaa caggaatcga atgcaaccgg    4080
cgcaggaaca ctgccagcgc atcaacaata ttttcacctg aatcaggata ttcttctaat    4140
acctggaatg ctgttttccc ggggatcgca gtggtgagta accatgcatc atcaggagta    4200
cggataaaat gcttgatggt cggaagaggc ataaattccg tcagccagtt tagtctgacc    4260
atctcatctg taacatcatt ggcaacgcta cctttgccat gtttcagaaa caactctggc    4320
gcatcgggct tcccatacaa tcgatagatt gtcgcacctg attgcccgac attatcgcga    4380
gcccatttat acccatataa atcagcatcc atgttggaat ttaatcgcgg cctcgagcaa    4440
gacgtttccc gttgaatatg gctcataaca ccccttgtat tactgtttat gtaagcagac    4500
agttttattg ttcatgatga tatatttta tcttgtgcaa tgtaacatca gagatttga    4560 gacacaacgt ggctttgttg aataaatcga acttttgctg agttgaagga tcagatcacg    4620
catcttcccg acaacgcaga ccgttccgtg caaagcaaa agttcaaaat caccaactgg    4680
tccacctaca caaagctct catcaaccgt ggctccctca ctttctggct ggatgatggg    4740
gcgattcagg cctggtatga gtcagcaaca ccttcttcac gaggcagacc tcagcgctag    4800
cggagtgtat actggcttac tatgttggca ctgatgaggg tgtcagtgaa gtgcttcatg    4860
tggcaggaga aaaaggctg caccggtgcg tcagcagaat atgtgataca ggatatattc    4920
cgcttcctcg ctcactgact cgctacgctc ggtcgttcga ctgcggcgag cggaaatggc    4980
ttacgaacgg gcggagatt tcctggaaga tgccaggaag atacttaaca gggaagtgag    5040
agggccgcgg caaagccgtt tttccatagg ctccgccccc ctgacaagca tcacgaaatc    5100
tgacgctcaa atcagtggtg gcgaaacccg acaggactat aaagatacca ggcgtttccc    5160
cctggcggct cctcgtgcg ctctcctgtt cctgcctttc ggtttaccgg tgtcattccg    5220
ctgttatggc cgcgtttgtc tcattccacg cctgacactc agttccgggt aggcagttcg    5280
ctccaagctg gactgtatgc acgaaccccc cgttcagtcc gaccgctgcg ccttatccgg    5340
taactatcgt cttgagtcca acccggaaag acatgcaaaa gcaccactgg cagcagccac    5400
```

-continued

| | |
|---|---|
| tggtaattga tttagaggag ttagtcttga agtcatgcgc cggttaaggc taaactgaaa | 5460 |
| ggacaagttt tggtgactgc gctcctccaa gccagttacc tcggttcaaa gagttggtag | 5520 |
| ctcagagaac cttcgaaaaa ccgccctgca aggcggtttt ttcgttttca gagcaagaga | 5580 |
| ttacgcgcag accaaaacga tctcaagaag atcatcttat taaggggtct gacgctcagt | 5640 |
| ggaacgaaaa ctcacgttaa gggattttgg tcatgagatt atcaaaaagg atcttcacct | 5700 |
| agatcctttt aaattaaaaa tgaagtttta aatcaatcta agtatatat gagtaaactt | 5760 |
| ggtctgacag ttaccaatgc ttaatcagtg aggcacctat ctcagcgatc tgtctatttc | 5820 |
| gttcatccat agttgcctga ctccccgtcg tgtagataac tacgatacgg agggcttac | 5880 |
| catctggccc cagtgctgca atgataccgc gagacccacg ctcaccggct ccagatttat | 5940 |
| cagcaataaa ccagccagcc ggaagggcc agcgcagaag tggtcctgca actttatccg | 6000 |
| cctccatcca gtctattaat tgttgccggg aagctagagt aagtagttcg ccagttaata | 6060 |
| gtttgcgcaa cgttgttgcc attgctgcag gtcgacaatt taacaagagc cagttatctt | 6120 |
| ctcttaaaat gaggaggtaa ctggcttctt tatgcttaag aggtgttagc ataagtgaaa | 6180 |
| tatgttccaa cgcgtggacg tcttaattgg gaggaagtct gtcacggact ggaagacgaa | 6240 |
| aagggtatcg atgtgaaccc attcgcagcg ggttcgaaaa tgtcgatgat taaggtacca | 6300 |
| ccactaaaga gctcacagga agtgttcaga ctacttagag tgacgcccca gccacagggt | 6360 |
| tcataatcaa atcatggtga gcaagggcga ggagctgttc accggggtgg tgcccatcct | 6420 |
| ggtcgagctg gacggcgacg taaacggcca caagttcagc gtgtccggcg agggcgaggg | 6480 |
| cgatgccacc tacggcaagc tgaccctgaa gttcatctgc accaccggca agctgcccgt | 6540 |
| gccctggccc accctcgtga ccaccttcgg ctacggcctg cagtgcttcg cccgctaccc | 6600 |
| cgaccacatg aagcagcacg acttcttcaa gtccgccatg cccgaaggct acgtccagga | 6660 |
| gcgcaccatc ttcttcaagg acgacggcaa ctacaagacc cgcgccgagg tgaagttcga | 6720 |
| gggcgacacc ctggtgaacc gcatcgagct gaagggcatc aacttcaagg aggacggcaa | 6780 |
| catcctgggg cacaagctgg agtacaacta caacagccac aacgtctata tcatggccga | 6840 |
| caagcagaag aacggcatca aggtgaactt caagatccgc cacaacatcg agggcggcag | 6900 |
| cgtgcagctc gccgaccact accagcagaa cacccccatc ggcgacggcc ccgtgctgct | 6960 |
| gcccgacaac cactacctga gctaccagtc cgccctgagc aaagaccca acgagaagcg | 7020 |
| cgatcacatg gtcctgctgg agttcgtgac cgccgccggg atcactctcg gcatggacga | 7080 |
| gctgtacaag taataaggat cc | 7102 |

<210> SEQ ID NO 39
<211> LENGTH: 9463
<212> TYPE: DNA
<213> ORGANISM: Artificial sequence
<220> FEATURE:
<223> OTHER INFORMATION: DNA-sequence of plasmid pSen0996_8e

<400> SEQUENCE: 39

| | |
|---|---|
| ccctgcggcg tcgctgatcg ccctcgcgac gttgtgcggg tggcttgtcc ctgagggcgc | 60 |
| tgcgacagat agctaaaaat ctgcgtcagg atcgccgtag agcgcgcgtc gcgtcgattg | 120 |
| gaggcttccc ctttggttga cggtcttcaa tcgctctacg gcgatcctga cgcttttttg | 180 |
| ttgcgtaccg tcgatcgttt tatttctgtc gatcccgaaa aagttttgc cttttgtaaa | 240 |
| aaacttctcg gtcgccccgc aaattttcga ttccagattt tttaaaaacc aagccagaaa | 300 |
| tacgacacac cgtttgcaga taatctgtct ttcggaaaaa tcaagtgcga tacaaaattt | 360 |

```
ttagcacccc tgagctgcgc aaagtcccgc ttcgtgaaaa ttttcgtgcc gcgtgatttt    420
ccgccaaaaa ctttaacgaa cgttcgttat aatggtgtca tgaccttcac gacgaagtac    480
caaaattggc ccgaatcatc agctatggat ctctctgatg tcgcgctgga gtccgacgcg    540
ctcgatgctg ccgtcgattt aaaaacggtg atcggatttt tccgagctct cgatacgacg    600
gacgcgccag catcacgaga ctgggccagt gccgcgagcg acctagaaac tctcgtggcg    660
gatcttgagg agctggctga cgagctgcgt gctcggcagc gccaggagga cgcacagtag    720
tggaggatcg aatcagttgc gcctactgcg gtggcctgat tcctcccgg cctgacccgc     780 gaggacggcg cgcaaaatat tgctcagatg cgtgtcgtgc cgcagccagc cgcgagcgcg    840
ccaacaaacg ccacgccgag gagctggagg cggctaggtc gcaaatggcg ctggaagtgc    900
gtcccccgag cgaaattttg gccatggtcg tcacagagct ggaagcggca gcgagaatta    960
tccgcgatcg tggcgcggtg cccgcaggca tgacaaacat cgtaaatgcc gcgtttcgtg   1020
tggccgtggc cgcccaggac gtgtcagcgc cgccaccacc tgcaccgaat cggcagcagc   1080
gtcgcgcgtc gaaaaagcgc acaggcggca agaagcgata agctgcacga atacctgaaa   1140
aatgttgaac gccccgtgag cggtaactca cagggcgtcg gctaacccc agtccaaacc    1200 tgggagaaag cgctcaaaaa tgactctagc ggattcacga gacattgaca caccggcctg   1260
gaaattttcc gctgatctgt tcgacaccca tcccgagctc gcgctgcgat cacgtggctg   1320
gacgagcgaa gaccgccgcg aattcctcgc tcacctgggc agagaaaatt tccagggcag   1380
caagacccgc gacttcgcca gcgcttggat caaagacccg gacacgggag aaacacagcc   1440
gaagttatac cgagttggtt caaaatcgct tgcccggtgc cagtatgttg ctctgacgca   1500
cgcgcagcac gcagccgtgc ttgtcctgga cattgatgtg ccgagccacc aggccggcgg   1560
gaaaatcgag cacgtaaacc ccgaggtcta cgcgattttg gagcgctggg cacgcctgga   1620
aaaagcgcca gcttggatcg gcgtgaatcc actgagcggg aaatgccagc tcatctggct   1680
cattgatccg gtgtatgccg cagcaggcat gagcagcccg aatatgcgcc tgctggctgc   1740
aacgaccgag gaaatgaccc gcgttttcgg cgctgaccag gcttttcac ataggctgag    1800 ccggtggcca ctgcacgtct ccgacgatcc caccgcgtac cgctggcatg cccagcacaa   1860
tcgcgtggat cgcctagctg atcttatgga ggttgctcgc atgatctcag gcacagaaaa   1920
acctaaaaaa cgctatgagc aggagttttc tagcggacgg gcacgtatcg aagcggcaag   1980
aaaagccact gcggaagcaa aagcacttgc cacgcttgaa gcaagcctgc cgagcgccgc   2040
tgaacgtctc ggagagctga tcgacggcgt ccgtgtcctc tggactgctc cagggcgtgc   2100
cgcccgtgat gagacggctt ttcgccacgc tttgactgtg ggataccagt taaaagcggc   2160
tggtgagcgc ctaaaagaca ccaagatcat cgacgcctac gagcgtgcct acaccgtcgc   2220
tcaggcggtc ggagcagacg gccgtgagcc tgatctgccg ccgatgcgtg accgccagac   2280
gatggcgcga cgtgtgcgcg gctacgtcgc taaaggccag ccagtcgtcc ctgctcgtca   2340
gacagagacg cagagcagcc gagggcgaaa agctctggcc actatgggaa gacgtggcgg   2400
taaaaaggcc gcagaacgct ggaaagaccc aaacagtgag tacgcccgag cacagcgaga   2460
aaaactagct aagtccagtc aacgacaagc taggaaagct aaaggaaatc gcttgaccat   2520
tgcaggttgg tttatgactg ttgagggaga gactggctcg tggccgacaa tcaatgaagc   2580
tatgtctgaa tttagcgtgt cacgtcagac cgtgaataga gcacttaagt ctgcgggcat   2640
tgaacttcca cgaggacgcc gtaaagcttc ccagtaaatg tgccatctcg taggcagaaa   2700
```

```
acggttcccc ccgtaggggt ctctctcttg gcctcctttc taggtcgggc tgattgctct    2760
tgaagctctc taggggggct cacaccatag gcagataacg gttccccacc ggctcacctc    2820
gtaagcgcac aaggactgct cccaaagatc ttcaaagcca ctgccgcgac tccgcttcgc    2880
gaagccttgc cccgcggaaa tttcctccac cgagttcgtg cacacccta tgccaagctt     2940 ctttcaccct aaattcgaga gattggattc ttaccgtgga aattcttcgc aaaaatcgtc    3000
ccctgatcgc ccttgcgacg ttgctcgcgg cggtgccgct ggttgcgctt ggcttgaccg    3060
acttgatcct ccggcgttca gcctgtgcca cagccgacag gatggtgacc accatttgcc    3120
ccatatcacc gtcggtactg atcccgtcgt caataaaccg aaccgctaca ccctgagcat    3180
caaactcttt tatcagttgg atcatgtcgg cggtgtcgcg gccaagacgg tcgagcttct    3240
tcaccagaat gacatcacct tcctccacct tcatcctcag caaatccagc ccttcccgat    3300
ctgttgaact gccggatgcc ttgtcggtaa agatgcggtt agcttttacc cctgcatctt    3360
tgagcgctga ggtctgcctc gtgaagaagg tgttgctgac tcataccagg cctgaatcgc    3420
cccatcatcc agccagaaag tgagggagcc acggttgatg agagctttgt tgtaggtgga    3480
ccagttggtg attttgaact tttgctttgc cacggaacgg tctgcgttgt cgggaagatg    3540
cgtgatctga tccttcaact cagcaaaagt tcgatttatt caacaaagcc gccgtcccgt    3600
caagtcagcg taatgctctg ccagtgttac aaccaattaa ccaattctga ttagaaaaac    3660
tcatcgagca tcaaatgaaa ctgcaattta ttcatatcag gattatcaat accatatttt    3720
tgaaaaagcc gtttctgtaa tgaaggagaa aactcaccga ggcagttcca taggatggca    3780
agatcctggt atcggtctgc gattccgact cgtccaacat caatacaacc tattaatttc    3840
ccctcgtcaa aaataaggtt atcaagtgag aaatcaccat gagtgacgac tgaatccggt    3900
gagaatggca aaagcttatg catttctttc cagacttgtt caacaggcca gccattacgc    3960
tcgtcatcaa aatcactcgc atcaaccaaa ccgttattca ttcgtgattg cgcctgagcg    4020
agacgaaata cgcgatcgct gttaaaagga caattacaaa caggaatcga atgcaaccgg    4080
cgcaggaaca ctgccagcgc atcaacaata ttttcacctg aatcaggata ttcttctaat    4140
acctggaatg ctgttttccc ggggatcgca gtggtgagta accatgcatc atcaggagta    4200
cggataaaat gcttgatggt cggaagaggc ataaattccg tcagccagtt tagtctgacc    4260
atctcatctg taacatcatt ggcaacgcta ccttttgccat gtttcagaaa caactctggc    4320
gcatcgggct tcccatacaa tcgatagatt gtcgcacctg attgcccgac attatcgcga    4380
gcccatttat acccatataa atcagcatcc atgttggaat ttaatcgcgg cctcgagcaa    4440
gacgtttccc gttgaatatg gctcataaca ccccttgtat tactgtttat gtaagcagac    4500
agttttattg ttcatgatga tatattttta tcttgtgcaa tgtaacatca gagattttga    4560
gacacaacgt ggctttgttg aataaatcga acttttgctg agttgaagga tcagatcacg    4620
catcttcccg acaacgcaga ccgttccgtg caaagcaaa agttcaaaat caccaactgg    4680
tccacctaca acaaagctct catcaaccgt ggctccctca ctttctggct ggatgatggg    4740
gcgattcagg cctggtatga gtcagcaaca ccttcttcac gaggcagacc tcagcgctag    4800
cggagtgtat actggcttac tatgttggca ctgatgaggg tgtcagtgaa gtgcttcatg    4860
tggcaggaga aaaaaggctg caccggtgcg tcagcagaat atgtgataca ggatatattc    4920
cgcttcctcg ctcactgact cgctacgctc ggtcgttcga ctgcggcgag cggaaatggc    4980
ttacgaacgg ggcggagatt tcctggaaga tgccaggaag atacttaaca gggaagtgag    5040
agggccgcgg caaagccgtt tttccatagg ctccgccccc ctgacaagca tcacgaaatc    5100
```

```
tgacgctcaa atcagtggtg gcgaaacccg acaggactat aaagatacca ggcgtttccc   5160
cctggcggct ccctcgtgcg ctctcctgtt cctgcctttc ggtttaccgg tgtcattccg   5220
ctgttatggc cgcgtttgtc tcattccacg cctgacactc agttccgggt aggcagttcg   5280
ctccaagctg gactgtatgc acgaaccccc cgttcagtcc gaccgctgcg ccttatccgg   5340
taactatcgt cttgagtcca acccggaaag acatgcaaaa gcaccactgg cagcagccac   5400
tggtaattga tttagaggag ttagtcttga agtcatgcgc cggttaaggc taaactgaaa   5460
ggacaagttt tggtgactgc gctcctccaa gccagttacc tcggttcaaa gagttggtag   5520
ctcagagaac cttcgaaaaa ccgccctgca aggcggtttt ttcgttttca gagcaagaga   5580
ttacgcgcag accaaaacga tctcaagaag atcatcttat taagggtct gacgctcagt    5640
ggaacgaaaa ctcacgttaa gggatttggg tcatgagatt atcaaaaagg atcttcacct   5700
agatcctttt aaattaaaaa tgaagtttta atcaatcta agtatatat gagtaaactt      5760
ggtctgacga ttaccaatgc ttaatcagtg aggcacctat ctcagcgatc tgtctatttc   5820
gttcatccat agttgcctga ctccccgtcg tgtagataac tacgatacgg gagggcttac   5880
catctggccc cagtgctgca atgataccgc gagacccacg ctcaccggct ccagatttat   5940
cagcaataaa ccagccagcc ggaagggccg agcgcagaag tggtcctgca actttatccg   6000
cctccatcca gtctattaat tgttgccggg aagctagagt aagtagttcg ccagttaata   6060
gtttgcgcaa cgttgttgcc attgctgcag gtcgaccatg cgccgttccc agtggaaggc   6120
cgacaatgtc gcccttcagg aggtcaagat cgacggtcag accgttcgca tcccacgccg   6180
tctggttaag gcagcacagc tcggtctcgt ggacgtagag cagttctaaa ccttaaattc   6240
atcgcctaca acctttgta ggtaagaatt taacaagagc cagttatctt ctcttaaaat    6300
gaggaggtaa ctggcttctt tatgcttaag aggtgttagc ataagtgaaa tatgttccaa   6360
cgcgtggacg tcttaattgg gaggaagtct gtcacggact ggaagacgaa aagggtatcg   6420
atgaaatttt tagttgttga tgacgagcaa gctgtacgtg actccttgcg acgttccctt   6480
tcgttcaacg gatacaacgt tgttctcgca gaagacggca tccaagcact agagatgatt   6540
gacaaggaac agcctgcttt ggtgatcctc gatgtcatga tgcctggtat ggacggactt   6600
gaggtctgtc gccaccttcg cagcgaaggc gatgatcggc caattcttat tcttactgcc   6660
cgcgataatg tttctgatcg tgttggtggc ctcgatgcag gcgcagatga ctatttggct   6720
aaaccatttg ctcttgaaga gctgttggcg cgcgtccgtt cactggtgcg tcgctctgca   6780
gtggaatcaa atcagagttc cagcattgaa caggctctat tatcttgtgg cgatttgacg   6840
cttgacccag aaagtcgaga tgtctaccgc aacggacgcg ccatcagcct tactcgaaca   6900
gagttcgcgc tcctgcaatt gctcctcaaa aaccaaagga agtgctcac tcgcgcccag    6960
attttggaag aggtatgggg ctgcgatttc cccacttcag gcaatgccct cgaggtctac   7020
attggatacc ttcgacgcaa gactgaattg gaaggagaag accgcctgat ccatacagta   7080
cgaggagtcg gatacgtcct gcgagagacc gctccgtgac attaaggcga atcggcgcag   7140
gggaaaatgg gcctgcccct accgaaagtg atgactccga cggttcaatg tcgttgcgtt   7200
ggcgcttggc tttgctgagc gccacttggg tagctttcgc cgttggtgtt attactgttg   7260
ctgcatattg gtctgtctcc agctatgtca ccaactcaat cgatcgtgat ctggaaaaac   7320
aagcggatgc aatgcttgga cgagccagtg aagcgggatt ctatgcaacc gcagaaaccg   7380
aaattgctct gttaggtgaa tatgccagtg acactcgaat cgccttaatc ccacctgggt   7440
```

-continued

```
gggaatacgt catcggtgaa tccatatcac tgcctgattc agatttcctt aagagtaaag    7500
aagcggggaa acagatcctc gtaacaagtg ctgagcgcat tctcatgaaa cgagatagct    7560
cgggcacagt ggtggttttt gctaaagata tggtggatac cgatcggcag ctcacggtgc    7620
ttggcgtcat tctcttgatc attggcggca gtggtgtttt ggcgtcgatt ctgcttggtt    7680
tcatcattgc gaaggagggg ctgaaaccac tgtcaaagct gcagcgtgcc gtcgaagaga    7740
tcgaacgaac tgatgagctt cgtgcgattc ccgtggtggg aaatgatgag ttcgctaagt    7800
tgactcgtag tttcaatgac atgctcaagg cactgcggga gtctcgtacc cggcaatctc    7860
agttggtggc agatgcagga cacgagctga aaactccact gacctcaatg cggacaaata    7920
ttgaattgct gttgatggca accaacagtg gaggatcggg aatccccaag gaagaattgg    7980
atggccttca gcgtgatgta ttggcgcaga tgaccgaaat gtctgatttg attggtgatc    8040
ttgttgatct tgcgcgtgaa gaaaccgccg aaacgtcaag cattgtagat ctcaaccaag    8100
tgttggaaat tgcgcttgac cgaatggaaa gccgtcgcat gacggtgcgg atagatgttt    8160
ccgagactgt ggattggaaa ctgctgggcg atgattttc cttaaccagg gcattagtaa    8220
atgttttgga taatgccatt aaatggtcgc ctgagaatgg cattgttcga gtgtcgatgt    8280
cacagatcga caaagcaacg gtccgcattg ttattgatga ttcagggcct ggaattgctg    8340
aaaaagaacg aggattagtt ttggaacggt tctatcgcgc cgtcagctcc cgttccatgc    8400
cgggatcgga ttaggtctt gccatcgtga atcaggttgt gaatcggcat ggtggccaac    8460
tcgttgtggg tgaatcagat gatggcggaa cgagaatcac tattgatttg caggggaac    8520 ccattcgcag cgggttcgaa aatgtcgatg attaaaccac taaagagctc acaggaagtg    8580
ttcagactac ttagagtgac gccccagcca cagggttcat aatcaaatca tgacaaatca    8640 attcccaca acaacggtg agaacccgga ccgtgcatcg gaaactccat cagaaaccaa     8700
ctccggtacc tgaactttaa gaaggagata tcatatggtg agcaagggcg aggagctgtt    8760
caccggggtg gtgcccatcc tggtcgagct ggacggcgac gtaaacggcc acaagttcag    8820
cgtgtccggc gagggcgagg gcgatgccac ctacggcaag ctgaccctga gttcatctg    8880 caccaccggc aagctgcccg tgccctggcc caccctcgtg accaccttcg gctacggcct    8940
gcagtgcttc gcccgctacc ccgaccacat gaagcagcac gacttcttca gtccgccat    9000 gcccgaaggc tacgtccagg agcgcaccat cttcttcaag gacgacggca actacaagac    9060
ccgcgccgag gtgaagttcg agggcgacac cctggtgaac cgcatcgagc tgaagggcat    9120
caacttcaag gaggacggca acatcctggg gcacaagctg gagtacaact acaacagcca    9180
caacgtctat atcatggccg acaagcagaa gaacggcatc aaggtgaact tcaagatccg    9240
ccacaacatc gagggcggca gcgtgcagct cgccgaccac taccagcaga acaccccat    9300 cggcgacggc cccgtgctgc tgcccgacaa ccactacctg agctaccagt ccgccctgag    9360
caaagacccc aacgagaagc gcgatcacat ggtcctgctg gagttcgtga ccgccgccgg    9420
gatcactctc ggcatggacg agctgtacaa gtaataagga tcc                     9463
```

<210> SEQ ID NO 40
<211> LENGTH: 49
<212> TYPE: DNA
<213> ORGANISM: Artificial sequence
<220> FEATURE:
<223> OTHER INFORMATION: Primer AmyA-BamHI-f

<400> SEQUENCE: 40

```
cgcggatcca aggagaatga cgatgagaaa acgtaaaaat ggattaatc               49
```

<210> SEQ ID NO 41
<211> LENGTH: 40
<212> TYPE: DNA
<213> ORGANISM: Artificial Sequence
<220> FEATURE:
<223> OTHER INFORMATION: Primer AmyA-SacI-r

<400> SEQUENCE: 41
gcggagctct aattatttac ccatatagat acagacccac                                40

<210> SEQ ID NO 42
<211> LENGTH: 24
<212> TYPE: DNA
<213> ORGANISM: Artificial sequence
<220> FEATURE:
<223> OTHER INFORMATION: Primer 0998up-f

<400> SEQUENCE: 42
gaagaaaccg ccgaaacgtc aagc                                                 24

<210> SEQ ID NO 43
<211> LENGTH: 21
<212> TYPE: DNA
<213> ORGANISM: Artificial sequence
<220> FEATURE:
<223> OTHER INFORMATION: Primer 0998up-r

<400> SEQUENCE: 43
cgatgcacgg tccgggttct c                                                    21

<210> SEQ ID NO 44
<211> LENGTH: 36
<212> TYPE: DNA
<213> ORGANISM: Artificial sequence
<220> FEATURE:
<223> OTHER INFORMATION: Primer 0998dw-f

<400> SEQUENCE: 44
gtttaaaaga gttaatctgc atctaatcaa gtagcc                                    36

<210> SEQ ID NO 45
<211> LENGTH: 23
<212> TYPE: DNA
<213> ORGANISM: Artificial sequence
<220> FEATURE:
<223> OTHER INFORMATION: Primer 0998dw-r

<400> SEQUENCE: 45
gccatcacga attgccgaac gag                                                  23

<210> SEQ ID NO 46
<211> LENGTH: 44
<212> TYPE: DNA
<213> ORGANISM: Artificial sequence
<220> FEATURE:
<223> OTHER INFORMATION: Primer eyfp-ol-f

<400> SEQUENCE: 46
gagaacccgg accgtgcatc gtagaagaag gagatatcat atgg                           44

<210> SEQ ID NO 47
<211> LENGTH: 48
<212> TYPE: DNA
<213> ORGANISM: Artificial sequence
<220> FEATURE:

<223> OTHER INFORMATION: Primer eyfp-ol-r

<400> SEQUENCE: 47
gcagattaac tcttttaaac ttattacttg tacagctcgt ccatgccg                48

<210> SEQ ID NO 48
<211> LENGTH: 5722
<212> TYPE: DNA
<213> ORGANISM: Artificial sequence
<220> FEATURE:
<223> OTHER INFORMATION: Plasmid pK19

<400> SEQUENCE: 48

```
attaggcacc ccaggcttta cactttatgc ttccggctcg tatgttgtgt ggaattgtga     60
gcggataaca atttcacaca ggaaacagct atgaccatga ttacgccaag cttgcatgcc    120
tgcaggtcga ctctagagga tccccgggta ccgagctcga attcactggc cgtcgtttta    180
caacgtcgtg actgggaaaa ccctggcgtt acccaactta atcgccttgc agcacatccc    240
cctttcgcca gctggcgtaa tagcgaagag gcccgcaccg atcgcccttc ccaacagttg    300
cgcagcctga atggcgaatg gcgcgataag ctagcttcac gctgccgcaa gcactcaggg    360
cgcaagggct gctaaaggaa gcggaacacg tagaaagcca gtccgcagaa acggtgctga    420
ccccggatga atgtcagcta ctgggctatc tggacaaggg aaaacgcaag cgcaaagaga    480
aagcaggtag cttgcagtgg gcttacatgg cgatagctag actgggcggt tttatggaca    540
gcaagcgaac cggaattgcc agctggggcg ccctctggta aggttgggaa gccctgcaaa    600
gtaaactgga tggctttctt gccgccaagg atctgatggc gcagggatc aagatctgat    660
caagagacag gatgaggatc gtttcgcatg attgaacaag atggattgca cgcaggttct    720
ccggccgctt gggtggagag gctattcggc tatgactggg cacaacagac aatcggctgc    780
tctgatgccg ccgtgttccg gctgtcagcg caggggcgcc cggttctttt tgtcaagacc    840
gacctgtccg gtgccctgaa tgaactccaa gacgaggcag cgcggctatc gtggctggcc    900
acgacgggcg ttccttgcgc agctgtgctc gacgttgtca ctgaagcggg aagggactgg    960
ctgctattgg gcgaagtgcc ggggcaggat ctcctgtcat ctcaccttgc tcctgccgag   1020
aaagtatcca tcatggctga tgcaatgcgg cggctgcata cgcttgatcc ggctacctgc   1080
ccattcgacc accaagcgaa acatcgcatc gagcgagcac gtactcggat ggaagccggt   1140
cttgtcgatc aggatgatct ggacgaagag catcaggggc tcgcgccagc cgaactgttc   1200
gccaggctca aggcgcggat gcccgacggc gaggatctcg tcgtgaccca tggcgatgcc   1260
tgcttgccga atatcatggt ggaaaatggc cgcttttctg gattcatcga ctgtggccgg   1320
ctgggtgtgg cggaccgcta tcaggacata gcgttggcta cccgtgatat tgctgaagag   1380
cttggcggcg aatgggctga ccgcttcctc gtgctttacg gtatcgccgc tcccgattcg   1440
cagcgcatcg ccttctatcg ccttcttgac gagttcttct gagcgggact ctggggttcg   1500
ctagaggatc gatccttttt aacccatcac atatacctgc cgttcactat tatttagtga   1560
aatgagatat tatgatattt tctgaattgt gattaaaaag gcaactttat gcccatgcaa   1620
cagaaactat aaaaaataca gagaatgaaa agaaacagat agattttta gttctttagg   1680
cccgtagtct gcaaatcctt ttatgatttt ctatcaaaca aagaggaaa atagaccagt   1740
tgcaatccaa acgagagtct aatagaatga ggtcgaaaag taaatcgcgc gggtttgtta   1800
ctgataaagc aggcaagacc taaaatgtgt aaagggcaaa gtgtatactt tggcgtcacc   1860
ccttacatat tttaggtctt ttttattgt gcgtaactaa cttgccatct tcaaacagga   1920
```

```
gggctggaag aagcagaccg ctaacacagt acataaaaaa ggagacatga acgatgaaca   1980
tcaaaaagtt tgcaaaacaa gcaacagtat taaccttac taccgcactg ctggcaggag   2040
gcgcaactca agcgtttgcg aaagaaacga accaaaagcc atataaggaa acatacggca   2100
tttcccatat tacacgccat gatatgctgc aaatccctga acagcaaaaa aatgaaaaat   2160
atcaagtttc tgaatttgat tcgtccacaa ttaaaatat ctcttctgca aaaggcctgg    2220
acgtttggga cagctggcca ttacaaaacg ctgacggcac tgtcgcaaac tatcacggct   2280
accacatcgt ctttgcatta gccggagatc ctaaaaatgc ggatgacaca tcgatttaca   2340
tgttctatca aaaagtcggc gaaacttcta ttgacagctg gaaaaacgct ggccgcgtct   2400
ttaaagacag cgacaaattc gatgcaaatg attctatcct aaaagaccaa acacaagaat   2460
ggtcaggttc agccacattt acatctgacg gaaaaatccg tttattctac actgatttct   2520
ccggtaaaca ttacggcaaa caaacactga caactgcaca agttaacgta tcagcatcag   2580
acagctcttt gaacatcaac ggtgtagagg attataaatc aatctttgac ggtgacggaa   2640
aaacgtatca aaatgtacag cagttcatcg atgaaggcaa ctacagctca ggcgacaacc   2700
atacgctgag agatcctcac tacgtagaag ataaaggcca caaatactta gtatttgaag   2760
caaacactgg aactgaagat ggctaccaag gcgaagaatc tttatttaac aaagcatact   2820
atggcaaaag cacatcattc ttccgtcaag aaagtcaaaa acttctgcaa gcgataaaa    2880 aacgcacggc tgagttagca aacggcgctc tcggtatgat tgagctaaac gatgattaca   2940
cactgaaaaa agtgatgaaa ccgctgattg catctaacac agtaacagat gaaattgaac   3000
gcgcgaacgt ctttaaaatg aacggcaaat ggtacctgtt cactgactcc cgcggatcaa   3060
aaatgacgat tgacggcatt acgtctaacg atatttacat gcttggttat gtttctaatt   3120 cttaactgg cccatacaag ccgctgaaca aaactggcct tgtgttaaaa atggatcttg    3180
atcctaacga tgtaaccttt acttactcac acttcgctgt acctcaagcg aaaggaaaca   3240
atgtcgtgat tacaagctat atgacaaaca gaggattcta cgcagacaaa caatcaacgt   3300
ttgcgccgag cttcctgctg aacatcaaag gcaagaaaac atctgttgtc aaagacagca   3360
tccttgaaca aggacaatta acagttaaca ataaaaacg caaagaaaa tgccgatggg     3420 taccgagcga aatgaccgac caagcgacgc ccaacctgcc atcacgagat tcgattcca    3480 ccgccgcctt ctatgaaagg ttgggcttcg gaatcgtttt ccgggacgcc ctcgcggacg   3540
tgctcatagt ccacgacgcc cgtgattttg tagccctggc cgacggccag caggtaggcc   3600
gacaggctca tgccggccgc cgccgccttt cctcaatcg ctcttcgttc gtctggaagg    3660
cagtacacct tgataggtgg gctgcccttc ctggttggct tggtttcatc agccatccgc   3720
ttgccctcat ctgttacgcc ggcggtagcc ggccagcctc gcagagcagg attcccgttg   3780
agcaccgcca ggtgcgaata agggacagtg aagaaggaac accgctcgc gggtgggcct    3840 acttcaccta tcctgccccg ctgacgccgt tggatacacc aaggaaagtc tacacgaacc   3900
ctttggcaaa atcctgtata tcgtgcgaaa aaggatggat ataccgaaaa atcgctata    3960 atgaccccga agcagggtta tgcagcggaa aagcgctgct tccctgctgt tttgtggaat   4020
atctaccgac tggaaacagg caaatgcagg aaattactga actgaggga caggcgagag    4080 acgatgccaa agagctcctg aaaatctcga taactcaaaa aatacgcccg gtagtgatct   4140
tatttcatta tggtgaaagt tggaacctct acgtgccga tcaacgtctc attttcgcca    4200
aaagttggcc cagggcttcc cggtatcaac agggacacca ggatttattt attctgcgaa   4260
```

```
gtgatcttcc gtcacaggta tttattcggc gcaaagtgcg tcgggtgatg ctgccaactt   4320
actgatttag tgtatgatgg tgtttttgag gtgctccagt ggcttctgtt tctatcagct   4380
cctgaaaatc tcgataactc aaaaaatacg cccggtagtg atcttatttc attatggtga   4440
aagttggaac ctcttacgtg ccgatcaacg tctcattttc gccaaaagtt ggcccagggc   4500
ttcccggtat caacagggac accaggattt atttattctg cgaagtgatc ttccgtcaca   4560
ggtatttatt cggcgcaaag tgcgtcgggt gatgctgcca acttactgat ttagtgtatg   4620
atggtgtttt tgaggtgctc cagtggcttc tgtttctatc agggctggat gatcctccag   4680
cgcggggatc tcatgctgga gttcttcgcc caccccaaaa ggatctaggt gaagatcctt   4740
tttgataatc tcatgaccaa aatcccttaa cgtgagtttt cgttccactg agcgtcagac   4800
cccgtagaaa agatcaaagg atcttcttga gatcctttt ttctgcgcgt aatctgctgc   4860
ttgcaaacaa aaaaccacc gctaccagcg gtggtttgtt tgccggatca agagctacca   4920
actctttttc cgaaggtaac tggcttcagc agagcgcaga taccaaatac tgtccttcta   4980
gtgtagccgt agttaggcca ccacttcaag aactctgtag caccgcctac atacctcgct   5040
ctgctaatcc tgttaccagt ggctgctgcc agtggcgata gtcgtgtct taccgggttg   5100 gactcaagac gatagttacc ggataaggcg cagcggtcgg gctgaacggg gggttcgtgc   5160
acacagccca gcttggagcg aacgacctac accgaactga gatacctaca gcgtgagcat   5220
tgagaaagcg ccacgcttcc cgaagggaga aaggcggaca ggtatccggt aagcggcagg   5280
gtcggaacag gagagcgcac gagggagctt caggggggaa acgcctggta tctttatagt   5340
cctgtcgggt ttcgccacct ctgacttgag cgtcgatttt tgtgatgctc gtcaggggg   5400 cggagcctat ggaaaaacgc cagcaacgcg gcctttttac ggttcctggc cttttgctgg   5460
ccttttgctc acatgttctt tcctgcgtta tcccctgatt ctgtggataa ccgtattacc   5520
gcctttgagt gagctgatac cgctcgccgc agccgaacga ccgagcgcag cgagtcagtg   5580
agcgaggaag cggaagagcg cccaatacgc aaaccgcctc tccccgcgcg ttggccgatt   5640
cattaatgca gctggcacga caggtttccc gactggaaag cgggcagtga gcgcaacgca   5700
attaatgtga gttagctcac tc                                           5722
```

<210> SEQ ID NO 49
<211> LENGTH: 23
<212> TYPE: DNA
<213> ORGANISM: Artificial sequence
<220> FEATURE:
<223> OTHER INFORMATION: Primer M13uni(-43)

<400> SEQUENCE: 49

```
agggttttcc cagtcacgac gtt                                            23
```

<210> SEQ ID NO 50
<211> LENGTH: 24
<212> TYPE: DNA
<213> ORGANISM: Artificial sequence
<220> FEATURE:
<223> OTHER INFORMATION: Primer M13rev(-49)

<400> SEQUENCE: 50

```
gagcggataa caatttcaca cagg                                           24
```

<210> SEQ ID NO 51
<211> LENGTH: 7666
<212> TYPE: DNA
<213> ORGANISM: Artificial sequence
<220> FEATURE:
<223> OTHER INFORMATION: Plasmid pK19-pSen0996_8e

<400> SEQUENCE: 51

```
cgataagcta gcttcacgct gccgcaagca ctcagggcgc aagggctgct aaaggaagcg      60
gaacacgtag aaagccagtc cgcagaaacg gtgctgaccc cggatgaatg tcagctactg     120
ggctatctgg acaagggaaa acgcaagcgc aaagagaaag caggtagctt gcagtgggct     180
tacatggcga tagctagact gggcggtttt atggacagca agcgaaccgg aattgccagc     240
tggggcgccc tctggtaagg ttgggaagcc ctgcaaagta aactggatgg ctttcttgcc     300
gccaaggatc tgatggcgca ggggatcaag atctgatcaa gagacaggat gaggatcgtt     360
tcgcatgatt gaacaagatg gattgcacgc aggttctccg gccgcttggg tggagaggct     420
attcggctat gactgggcac aacagacaat cggctgctct gatgccgccg tgttccggct     480
gtcagcgcag gggcgcccgg ttcttttttgt caagaccgac ctgtccggtg ccctgaatga     540
actccaagac gaggcagcgc ggctatcgtg gctggccacg acgggcgttc cttgcgcagc     600
tgtgctcgac gttgtcactg aagcgggaag ggactggctg ctattgggcg aagtgccggg     660
gcaggatctc ctgtcatctc accttgctcc tgccgagaaa gtatccatca tggctgatgc     720
aatgcggcgg ctgcatacgc ttgatccggc tacctgccca ttcgaccacc aagcgaaaca     780
tcgcatcgag cgagcacgta ctcggatgga agccggtctt gtcgatcagg atgatctgga     840
cgaagagcat caggggctcg cgccagccga actgttcgcc aggctcaagg cgcggatgcc     900
cgacggcgag gatctcgtcg tgacccatgg cgatgcctgc ttgccgaata tcatggtgga     960
aaatggccgc ttttctggat tcatcgactg tggccggctg ggtgtggcgg accgctatca    1020
ggacatagcg ttggctaccc gtgatattgc tgaagagctt ggcggcgaat gggctgaccg    1080
cttcctcgtg ctttacggta tcgccgctcc cgattcgcag cgcatcgcct tctatcgcct    1140
tcttgacgag ttcttctgag cgggactctg gggttcgcta gaggatcgat ccttttaac    1200
ccatcacata tacctgccgt tcactattat ttagtgaaat gagatattat gatattttct    1260
gaattgtgat taaaaaggca actttatgcc catgcaacag aaactataaa aaatacagag    1320
aatgaaaaga aacagataga ttttttagtt ctttaggccc gtagtctgca aatccttttta    1380
tgattttcta tcaaacaaaa gaggaaaata gaccagttgc aatccaaacg agagtctaat    1440
agaatgaggt cgaaaagtaa atcgcgcggg tttgttactg ataaagcagg caagacctaa    1500
aatgtgtaaa gggcaaagtg tatactttgg cgtcaccccct tacatatttt aggtctttttt    1560
ttattgtgcg taactaactt gccatcttca aacaggaggg ctggaagaag cagaccgcta    1620
acacagtaca taaaaaagga gacatgaacg atgaacatca aaagtttgc aaaacaagca    1680
acagtattaa cctttactac cgcactgctg gcaggaggcg caactcaagc gtttgcgaaa    1740
gaaacgaacc aaaagccata taggaaaaca tacggcattt cccatattac acgccatgat    1800
atgctgcaaa tccctgaaca gcaaaaaaat gaaaaatatc aagtttctga atttgattcg    1860
tccacaatta aaaatatctc ttctgcaaaa ggcctggacg tttgggacag ctggccatta    1920
caaaacgctg acggcactgt cgcaaactat cacggctacc acatcgtctt tgcattagcc    1980
ggagatccta aaaatgcgga tgacacatcg atttacatgt tctatcaaaa agtcggcgaa    2040
acttctattg acagctggaa aaacgctggc gcgtctttaa agacagcga caaattcgat    2100
gcaaatgatt ctatcctaaa agaccaaaca caagaatggt caggttcagc cacatttaca    2160
tctgacggaa aaatccgttt attctacact gatttctccg gtaaacatta cggcaaacaa    2220
```

```
acactgacaa ctgcacaagt taacgtatca gcatcagaca gctctttgaa catcaacggt    2280
gtagaggatt ataaatcaat ctttgacggt gacggaaaaa cgtatcaaaa tgtacagcag    2340
ttcatcgatg aaggcaacta cagctcaggc gacaaccata cgctgagaga tcctcactac    2400
gtagaagata aaggccacaa atacttagta tttgaagcaa acactggaac tgaagatggc    2460
taccaaggcg aagaatcttt atttaacaaa gcatactatg gcaaaagcac atcattcttc    2520
cgtcaagaaa gtcaaaaact tctgcaaagc gataaaaaac gcacggctga gttagcaaac    2580
ggcgctctcg gtatgattga gctaaacgat gattacacac tgaaaaaagt gatgaaaccg    2640
ctgattgcat ctaacacagt aacagatgaa attgaacgcg cgaacgtctt taaaatgaac    2700
ggcaaatggt acctgttcac tgactcccgc ggatcaaaaa tgacgattga cggcattacg    2760
tctaacgata tttacatgct tggttatgtt tctaattctt taactggccc atacaagccg    2820
ctgaacaaaa ctggccttgt gttaaaaatg gatcttgatc taacgatgt aacctttact    2880 tactcacact tcgctgtacc tcaagcgaaa ggaaacaatg tcgtgattac aagctatatg    2940
acaaacagag gattctacgc agacaaacaa tcaacgtttg cgccgagctt cctgctgaac    3000
atcaaaggca agaaaacatc tgttgtcaaa gacagcatcc ttgaacaagg acaattaaca    3060
gttaacaaat aaaaacgcaa aagaaaatgc cgatgggtac cgagcgaaat gaccgaccaa    3120
gcgacgccca acctgccatc acgagatttc gattccaccg ccgccttcta tgaaaggttg    3180
ggcttcggaa tcgttttccg ggacgccctc gcggacgtgc tcatagtcca cgacgcccgt    3240
gattttgtag ccctggccga cggccagcag gtaggccgac aggctcatgc cggccgccgc    3300 cgcctttttcc tcaatcgctc ttcgttcgtc tggaaggcag tacaccttga taggtgggct    3360
gcccttcctg gttggcttgg tttcatcagc catccgcttg ccctcatctg ttacgccggc    3420
ggtagccggc cagcctcgca gagcaggatt cccgttgagc accgccaggt gcgaataagg    3480
gacagtgaag aaggaacacc cgctcgcggg tgggcctact tcacctatcc tgccccgctg    3540
acgccgttgg atacaccaag gaaagtctac acgaaccctt tggcaaaatc ctgtatatcg    3600
tgcgaaaaag gatggatata ccgaaaaaat cgctataatg accccgaagc agggttatgc    3660
agcggaaaag cgctgcttcc ctgctgtttt gtggaatatc taccgactgg aaacaggcaa    3720
atgcaggaaa ttactgaact gagggagcag gcgagagacg atgccaaaga gctcctgaaa    3780
atctcgataa ctcaaaaaat acgcccggta gtgatcttat ttcattatgg tgaaagttgg    3840
aacctcttac gtgccgatca acgtctcatt ttcgccaaaa gttggcccag gcttccccgg    3900
tatcaacagg gacaccagga tttatttatt ctgcgaagtg atcttccgtc acaggtattt    3960
attcggcgca aagtgcgtcg ggtgatgctg ccaacttact gatttagtgt atgatggtgt    4020
ttttgaggtg ctccagtggc ttctgttttct atcagctcct gaaatctcg ataactcaaa    4080 aaatacgccc ggtagtgatc ttatttcatt atggtgaaag ttggaacctc ttacgtgccg    4140
atcaacgtct cattttcgcc aaaagttggc ccagggcttc ccggtatcaa cagggacacc    4200
aggatttatt tattctgcga agtgatcttc cgtcacaggt atttattcgg cgcaaagtgc    4260
gtcgggtgat gctgccaact tactgattta gtgtatgatg gtgtttttga ggtgctccag    4320
tggcttctgt ttctatcagg gctggatgat cctccagcgc ggggatctca tgctggagtt    4380
cttcgcccac cccaaaagga tctaggtgaa gatccttttt gataatctca tgaccaaaat    4440
cccttaacgt gagttttcgt tccactgagc gtcagacccc gtagaaaaga tcaaaggatc    4500
ttcttgagat cctttttttc tgcgcgtaat ctgctgcttg caaacaaaaa aaccaccgct    4560
accagcggtg gtttgtttgc cggatcaaga gctaccaact cttttttccga aggtaactgg    4620
```

```
cttcagcaga gcgcagatac caaatactgt ccttctagtg tagccgtagt taggccacca   4680
cttcaagaac tctgtagcac cgcctacata cctcgctctg ctaatcctgt taccagtggc   4740
tgctgccagt ggcgataagt cgtgtcttac cgggttggac tcaagacgat agttaccgga   4800
taaggcgcag cggtcgggct gaacgggggg ttcgtgcaca cagcccagct tggagcgaac   4860
gacctacacc gaactgagat acctacagcg tgagcattga aaagcgcca cgcttcccga    4920 agggagaaag gcggacaggt atccggtaag cggcagggtc ggaacaggag agcgcacgag   4980
ggagcttcca gggggaaacg cctggtatct ttatagtcct gtcgggtttc gccacctctg   5040
acttgagcgt cgattttgt gatgctcgtc agggggggcgg agcctatgga aaaacgccag    5100
caacgcggcc ttttacggt tcctggcctt ttgctggcct tttgctcaca tgttctttcc    5160
tgcgttatcc cctgattctg tggataaccg tattaccgcc tttgagtgag ctgataccgc   5220
tcgccgcagc cgaacgaccg agcgcagcga gtcagtgagc gaggaagcgg aagagcgccc   5280
aatacgcaaa ccgcctctcc ccgcgcgttg gccgattcat taatgcagct ggcacgacag   5340
gtttcccgac tggaaagcgg gcagtgagcg caacgcaatt aatgtgagtt agctcactca   5400
ttaggcaccc caggctttac actttatgct tccggctcgt atgttgtgtg gaattgtgag   5460
cggataacaa tttcacacag gaaacagcta tgaccatgat tacgccaagc ttgcatgcct   5520
gcaggtcgac tctagaggat ccccgaagaa accgccgaaa cgtcaagcat tgtagatctc   5580
aaccaagtgt tggaaattgc gcttgaccga atggaaagcc gtcgcatgac ggtgcggata   5640
gatgtttccg agactgtgga ttggaaactg ctgggcgatg atttttcctt aaccagggca   5700
ttagtaaatg ttttggataa tgccattaaa tggtcgcctg agaatggcat tgttcgagtg   5760
tcgatgtcac agatcgacaa agcaacggtc cgcattgtta ttgatgattc agggcctgga   5820
attgctgaaa agaacgagg attagttttg gaacggttct atcgcgccgt cagctcccgt    5880
tccatgccgg gatcgggatt aggtcttgcc atcgtgaatc aggttgtgaa tcggcatggt   5940
ggccaactcg ttgtgggtga atcagatgat ggcggaacga gaatcactat tgatttgcca   6000
ggggaaccca ttcgcagcgg gttcgaaaat gtcgatgatt aaaccactaa agagctcaca   6060
ggaagtgttc agactactta gagtgacgcc ccagccacag ggttcataat caaatcatga   6120
caaatcaatt ccccacaaac aacggtgaga acccggaccg tgcatcgtag aagaaggaga   6180
tatcatatgg tgagcaaggg cgaggagctg ttcaccgggg tggtgcccat cctggtcgag   6240
ctggacggcg acgtaaacgg ccacaagttc agcgtgtccg gcgagggcga gggcgatgcc   6300
acctacggca agctgaccct gaagttcatc tgcaccaccg gcaagctgcc cgtgccctgg   6360
cccaccctcg tgaccacctt cggctacggc ctgcagtgct tcgcccgcta ccccgaccac   6420
atgaagcagc acgacttctt caagtccgcc atgcccgaag gctacgtcca ggagcgcacc   6480
atcttcttca aggacgacgg caactacaag acccgcgccg aggtgaagtt cgagggcgac   6540
accctggtga accgcatcga gctgaagggc atcaacttca aggaggacgg caacatcctg   6600
gggcacaagc tggagtacaa ctacaacagc cacaacgtct atatcatggc cgacaagcag   6660
aagaacggca tcaaggtgaa cttcaagatc cgccacaaca tcgagggcgg cagcgtgcag   6720
ctcgccgacc actaccagca gaacacccc atcggcgacg ccccgtgct gctgcccgac    6780 aaccactacc tgagctacca gtccgccctg agcaaagacc ccaacgagaa gcgcgatcac   6840
atggtcctgc tggagttcgt gaccgccgcc gggatcactc tcggcatgga cgagctgtac   6900
aagtaataag tttaaaagag ttaatctgca tctaatcaag tagccaagta tgagtgagga   6960
```

```
acaatgagca aggatccatt gggaagtctt accgatgttg tagacacacg agttccgctt    7020
ccggatgttg aaccggatcc ggagttcctg aaggctacgg aaaaagaatt ccacatggca    7080
tcccagaagc gcgctcttgt tgtcctggtg ggcgatcatg tcgctgaggc agatgggact    7140
ggccgtttgg ttacggagct gctcttagag tctggcttca acgtggacgc tgtggtcagc    7200
gtgaagtcta agaagtctca gattaggcaa gctattgaaa ccgcagttgt tggcggcgct    7260
gaccttgtgc tgaccatcgg cggagtgggc gttggtcctc gggataaaac tcctgaggca    7320
accagcgctg tgttggacca ggacgtccca ggaatcgcgc aggcgcttcg ttcctccggt    7380
ttggcctgtg cgcgcggtgga tgcaagtgtt cccgaggcg tagcgggcgt atccggctca    7440
accgtggtgg tcaacctcgc tgagtctcgt tcggcaattc gtgatggcgg gtaccgagct    7500
cgaattcact ggccgtcgtt ttacaacgtc gtgactggga aaaccctggc gttacccaac    7560
ttaatcgcct tgcagcacat ccccctttcg ccagctggcg taatagcgaa gaggcccgca    7620
ccgatcgccc ttcccaacag ttgcgcagcc tgaatggcga atggcg                  7666

<210> SEQ ID NO 52
<211> LENGTH: 27
<212> TYPE: PRT
<213> ORGANISM: Artificial sequence
<220> FEATURE:
<223> OTHER INFORMATION: NprE signal sequence

<400> SEQUENCE: 52

Met Gly Leu Gly Lys Lys Leu Ser Val Ala Val Ala Ala Ser Phe Met
1               5                   10                  15

Ser Leu Ser Ile Ser Leu Pro Gly Val Gln Ala
            20                  25

<210> SEQ ID NO 53
<211> LENGTH: 23
<212> TYPE: PRT
<213> ORGANISM: Artificial sequence
<220> FEATURE:
<223> OTHER INFORMATION: Ywmc signal sequence

<400> SEQUENCE: 53

Met Lys Lys Arg Phe Ser Leu Ile Met Met Thr Gly Leu Leu Phe Gly
1               5                   10                  15

Leu Thr Ser Pro Ala Phe Ala
            20

<210> SEQ ID NO 54
<211> LENGTH: 21
<212> TYPE: DNA
<213> ORGANISM: Artificial sequence
<220> FEATURE:
<223> OTHER INFORMATION: Primer pEKEx2-fw
```

```
<400> SEQUENCE: 54
ctcgtataat gtgtggaatt g                                              21

<210> SEQ ID NO 55
<211> LENGTH: 18
<212> TYPE: DNA
<213> ORGANISM: Artificial sequence
<220> FEATURE:
<223> OTHER INFORMATION: Primer pEKEx2-rv

<400> SEQUENCE: 55
cagaccgctt ctgcgttc                                                  18
```

SENSORS FOR DETECTION AND QUANTIFICATION OF MICROBIOLOGICAL PROTEIN SECRETION

CROSS REFERENCE TO RELATED APPLICATIONS

This application is the U.S. national stage application of International (PCT) Patent Application Serial No. PCT/EP2016/056464, filed Mar. 23, 2016, which claims the benefit of EP Application No. 15160897.3, filed Mar. 25, 2015. The disclosures of these two applications are hereby incorporated by reference herein in their entirety.

REFERENCE TO AN ELECTRONIC SEQUENCE LISTING

The contents of the Sequence Listing that we have submitted herewith (Name: Revised.txt, Size: 96.142 bytes, Date of Creation: May 22, 2019) is hereby incorporated by reference in its entirety.

The present invention relates to a cell which is genetically modified with respect to its wild type, a method for the identification of a cell which are characterized by an increased secretion of protein across the cytoplasmic membrane into the extracytosolic space, a method for the identification of a culture medium composition that is optimized for the recombinant production of protein, a method for the identification of culture conditions that are optimized for the recombinant production of protein, a method for the identification of a compound that is characterized by an antibiotic activity due to its property to damage the membrane of a bacterial cell or to analyse the effect of such a compound on a population of genetically different bacterial cells, a method for the production of a cell which is genetically modified with respect to its wild type with optimized secretion of protein across the cytoplasmic membrane into the extracytosolic space, a cell obtained by this method, a method for the production of proteins and a method for the preparation of a mixture.

Proteins are of great economic interest. Enzymes, for example, are used as biocatalysts in chemical synthesis of various compounds, in particular in enantioselective synthesis, in detergents or in human or animal food. Other proteins, such as antibodies, hormones and immune modulators, can be found in medicinal compositions.

A preferred method for preparing such proteins is the biotechnological production using recombinant microorganisms. In fermentation processes these microorganisms are cultivated such that they produce the desired protein through cellular protein synthesis. By means of this biosynthetic production route the natural proteins can be directly obtained and simple and inexpensive raw materials can be used. As microorganisms, for example, *Bacillus subtilis, Pichia, pastoris, Escherichia coli, Corynebacterium glutamicum* or related bacteria are frequently used for that purpose.

Biological and procedural parameters are crucial for the efficiency and cost-effectiveness with which proteins can be produced in biotechnological processes. These parameters, for example, comprise the host microorganism, the strain/vector-combination, the codon usage of the protein-coding gene, the signal peptides that are necessary for the transport of the protein through the cell wall (secretory signal peptides), the expression level, the induction time, the temperature, the composition of the medium, the growth rate etc.

For the development of efficient biotechnological processes for the production of proteins these parameters have to be varied and optimized. The problem, however, is that not only each of the above mentioned parameter is variable over a wide range, but that furthermore the different parameters also influence each other, which results in a huge number of possible parameter combinations that have to be evaluated. As according to the current state of the art a mere theoretical prediction of optimized parameters or parameter combinations is not possible and as furthermore for each specific protein different parameters and parameter combinations are considered as ideal, a lot of different parameter combinations have to be tested for each production process.

For the generation of different properties in a certain strain that is intended to be used for the recombinant production of a desired protein conventional chemical or physical mutagenesis steps are applied (e. g MNNG or UV), by means of which random mutations are induced in the genome of the strain (undirected mutagenesis). For producing mutants with an altered secretion of the protein, for example, libraries of a protein-encoding gene are generated, in which the protein-encoding gene sequence is fused with different secretion signal peptide-encoding sequences. For analyzing the effect of different culture conditions or different media compositions on the protein secretion strains that secrete the specific protein are cultured under these different conditions and/or in these different culture media.

The search for genetic modifications and optimized culture parameters and culture media that lead to an increased yield, efficiency or economy of the biotechnological process for the production of the desired protein is commonly referred to as "screening". The problem in such a screening process, however, has to be seen in the fact that in a cell suspension comprising a plurality of genetically different cells or in an experimental set up in which various parameters have been adjusted (or in which only one parameter has ben varied that nevertheless also effects other parameters) it is nearly impossible to clearly identify which genetic modification or which parameter was responsible for an eventually observed increase of the production of a desired protein. The screening methods that are necessary for such an evaluation are not only very time consuming and expensive, they are also highly specific for each individual protein and they are thus not generally applicable. Furthermore, these screening methods are dependent from the availability of a practical screening assay for the desired protein as the amount of the production or secretion of the desired protein in a given experimental setup can only be determined by the detection of the catalytic activity of the protein in the culture medium or within the cells.

The present invention was based on the object of overcoming the disadvantages arising in connection with the detection of genetically modified cells that secrete a particular protein.

In particular, the present invention was based on the object of providing a genetically modified cell in which, after a genetic modification or after a change of a parameter relating to the cultivation conditions or after a change of the composition of the culture medium, those variants can be identified in a simple manner which are characterized by an increased secretion of a specific protein, wherein it is also possible to easily separate these cells from a plurality of different cells. Also, the identification of cells that are characterized by an increased secretion of a specific protein should not be dependent from the nature of the desired protein and should thus be applicable for all proteins that can be recombinantly produced in a fermentation process.

The present invention was also based on the object of providing a method for identifying a cell that is characterized by an increased secretion of a specific protein within a plurality of genetically different cells in a simple, fast and cost-effective manner and to specifically separate these cells from the plurality of genetically different cells.

The present invention was also based on the object of providing a method for identifying a cell that is—when being cultured under certain culture conditions or in a certain culture medium—characterized by an increased secretion of a specific protein, compared to the same cell that has been cultured under different culture conditions or in a different culture medium, thereby allowing the determination of optimized culture conditions and/or optimized culture media in a simple, fast and cost-effective manner.

The present invention was also based on the object of providing a genetically modified cell with an optimized secretion of a specific protein, in which genes or mutations, in particular genes for secretion signal peptides or mutations in these genes, are selectively introduced which have been identified as suitable by means of the above mentioned screening process for increasing the secretion of the specific protein or the concentration of the specific protein on the trans-side of the cytoplasmic membrane.

A contribution to achieving at least one of the above described objects is made by the subject matter of the category forming claims of the present invention. A further contribution is made by the subject matter of the dependent claims which represent specific embodiments of the invention.

EMBODIMENTS

|1| A cell which is genetically modified with respect to its wild type and which comprises a gene sequence coding for a fluorescent protein, wherein the expression of the fluorescent protein depends on the amount of protein that is secreted across the cytoplasmic membrane into the extracytosolic space.

|2| The cell according to embodiment |1|, wherein the gene sequence coding for the fluorescent protein is under the control of at least one heterologous promoter which, in the wild type of the cell, controls the expression of a gene of which the expression in the wild-type cell depends on the mount of protein that is secreted across the cytoplasmic membrane into the extracytosolic space.

|3| The cell according to embodiment |1| or |2|, wherein the cell is a cell of the genus *Corynebacterium, Escherichia, Bacillus* or *Mycobakterium*.

|4| The cell according to one of the preceding embodiments, wherein the promotor is selected from the group consisting of the cg0706-promoter, the cg0996-promoter, the cg0998-promoter, the cg1325-promoter, the htrA-promoter, the liaI-promoter, the mprA-promoter or the pepD-promoter.

|5| The cell according to one of embodiments |1| to |4|, wherein the cell is a cell of the genus *Corynebacterium* and wherein the promotor is the cg0706-promoter, the cg0996-promoter, the cg0998-promoter or the cg1325-promoter.

|6| The cell according to embodiment |5|, wherein the gene sequence coding for the fluorescent protein is under the control of a combination of the cg0996-promoter and the cg0998-promoter, in which the cg0996-promoter is located upstream from the cg0998-promoter.

|7| The cell according to one of embodiments |1| to |4|, wherein the cell is a cell of the genus *Bacillus* and wherein the promotor is the htrA-promoter or the liaI-promoter.

|8| The cell according to one of embodiments |1| to |4|, wherein the cell is a cell of the genus *Mycobakterium* and wherein the promotor is the mprA-promoter or the pepD-promoter.

|9| The cell according to one of embodiments |1| to |4|, wherein the cell is a cell of the genus *Escherichia* and wherein the promotor is the htrA-promoter.

|10| The cell according to one of the preceding embodiments, wherein the fluorescent protein is green fluorescent protein (GFP) or a variant of this protein.

|11| A method for the identification of a cell that is characterized by an increased secretion of protein across the cytoplasmic membrane into the extracytosolic space in a cell suspension, comprising the method steps:
  α1) provision of a cell suspension comprising cells according to one of embodiments |1| to |10|;
  α2) genetic modification of the cells to obtain a cell suspension in which the cells differ with respect to the amount of protein that is secreted across the cytoplasmic membrane into the extracytosolic space;
  α3) identification of individual cells in the cell suspension having an increased secretion of protein across the cytoplasmic membrane into the extracytosolic space.

|12| The method according to embodiment |11|, wherein the genetic modification in method step α2) is carried out by non-targeted mutagenesis or by metabolic engineering.

|13| The method according to embodiment |11| or |12|, furthermore comprising the method step:
  α4) separating off of the identified cells from the cell suspension.

|14| The method according to embodiment |13|, wherein the separating off is carried out by means of flow cytometry.

|15| A method for the identification of a cell that is characterized by a high secretion of protein across the cytoplasmic membrane into the extracytosolic space in a cell suspension or for the identification of a cell suspension comprising cells that are characterized by a high secretion of protein across the cytoplasmic membrane into the extracytosolic space, comprising the method steps:
  β1) provision of
    a cell suspension comprising a plurality of cells according to one of embodiments |1| to |10|, wherein the cells in the cell suspension differ from each other with respect to the amount of protein that is secreted across the cytoplasmic membrane into the extracytosolic space, or
    a plurality of cell suspensions, each cell suspension comprising cells according to one of embodiments |1| to |10|, wherein the cell suspensions differ from each other with respect to the amount of protein that is secreted by the cells across the cytoplasmic membrane into the extracytosolic space;
  β2) cultivation of different cells in the cell suspension or of the different cell suspensions;
  β3) identification of individual cells in the cell suspension having a high secretion of protein across the cytoplasmic membrane into the extracytosolic space or identification of individual cell suspensions comprising cells having a high secretion of protein across the cytoplasmic membrane into the extracytosolic space.

|16| A method for the identification of a culture medium composition that is optimized for the recombinant production of a protein, comprising the method steps:
  γ1) provision of a plurality of culture media which differ from each other with respect to the composition of the culture medium;

γ2) cultivation of cells according to one of embodiments |1| to |10| in the different culture media, thereby obtaining a plurality of cell suspensions in which the cells of the cell suspensions, due to the difference in the composition of the culture media, differ from each other with respect to the amount of secretion of protein that is secreted across the cytoplasmic membrane into the extracytosolic space;

γ3) identification of those cell suspensions that comprise cells having a high secretion of protein across the cytoplasmic membrane into the extracytosolic space.

|17| A method for the identification of culture conditions that are optimized for the recombinant production of a protein, comprising the method steps:

δ1) provision of a plurality of cell suspensions comprising cells according to one of embodiments |1| to |10|;

δ2) cultivation of the cells in these cell suspensions under different culture conditions such that the cells in the different cell suspensions, due to the difference in the culture conditions, differ from each other with respect to the amount of protein that is secreted across the cytoplasmic membrane into the extracytosolic space;

δ3) identification of those cell suspensions that comprise cells having a high secretion of protein across the cytoplasmic membrane into the extracytosolic space.

|18| A method for the identification of a compound that is characterized by an antibiotic activity due to its property to damage the membrane of a bacterial cell or to analyse the effect of such a compound on a population of genetically different bacterial cells or genetically identical cells in different physiological states or different growths phases, comprising the method steps:

ε1) provision of a cell suspension comprising the cells according to one of embodiments |1| to |10|;

ε2) cultivation of the cells in the suspension in the presence of the compound;

ε3) determination of the antibiotic activity and concentration-dependent antibiotic activity of the compound by detection of the intracellular fluorescence activity.

|19| A method for the production of a cell which is genetically modified with respect to its wild type with optimized secretion of protein across the cytoplasmic membrane into the extracytosolic space, comprising the method steps:

I) provision of a cell suspension comprising cells according to one of embodiments |1| to |10|;

II) genetic modification of the cells to obtain a cell suspension in which the cells differ with respect to the amount of protein that is secreted across the cytoplasmic membrane into the extracytosolic space;

III) identification of individual cells in the cell suspension having an increased secretion of protein across the cytoplasmic membrane into the extracytosolic space;

IV) separating off of the identified cells from the cell suspension;

V) identification of those genetically modified genes $G_1$ to $G_n$ or those mutations $M_1$ to $M_m$ in the cells identified and separated off which are responsible for the increased secretion of protein across the cytoplasmic membrane into the extracytosolic space;

VI) production of a cell which is genetically modified with respect to its wild type with optimized secretion of protein across the cytoplasmic membrane into the extracytosolic space, of which the genome comprises at least one of the genes $G_1$ to $G_n$ and/or at least one of the mutations $M_1$ to $M_m$.

|20| The method according to embodiment |19|, wherein the genetic modification in method step II) is carried out by non-targeted mutagenesis or by metabolic engineering.

|21| Cell obtained by a method according to embodiment |19| or |20|.

|22| A method for the production of a protein, comprising the method steps:

(a) production of a cell which is genetically modified with respect to its wild type with optimized secretion of protein across the cytoplasmic membrane into the extracytosolic space by a method according to embodiment |19| to |20|;

(b) cultivation of the cell in a culture medium comprising nutrients under conditions under which the cell produces protein from the nutrients.

|23| The method according to embodiment |22|, wherein the protein is a hormone, a toxine, an antibody, a structural protein, an enzyme, a transport protein, a storage protein, a channel-protein, a regulating protein, a fluorescent protein or a protein with selective binding-, polymerizing-, coating-, stabilizing-, repairing-, isoalting-capacities.

|24| Method for the preparation of a mixture, comprising the method steps:

(A) production of a protein by the method according to one of embodiments |22| or |23|;

(B) mixing of the protein with a mixture component which differs from the protein.

|25| Method according to embodiment |24|, wherein the mixture is a foodstuff, an animal feed, a pharmaceutical composition, a composition for food production, a gluing-composition, a textile-finishing composition or a lignocellulolytic composition.

The present invention relates to a cell which is genetically modified with respect to its wild type and which comprises a gene sequence coding for a fluorescent protein, wherein the expression of the fluorescent protein depends on the amount of protein that is secreted across the cytoplasmic membrane into the extracytosolic space.

This extracytosolic space is separated from the cytosolic space (cytoplasm) by the cytoplasmic membrane. The expression "extracytosolic space" as used herein generally encompasses any volume element in and beyond the cytoplasmic membrane (when seen from the cytosolic space), including the peptidoglycan layer as well as the periplasm and the bacterial outer membrane (in the case of gram-negative bacteria and diderm gram-positive bacteria or gram-positive bacteria that possess an outer membrane). Also encompassed by the expression "extracytosolic space" is the area that is farer away from the immediate surrounding of the cytoplasmic membrane, including the total volume of the culture supernatant.

A "wild type" of a cell is preferably understood as meaning a cell of which the genome is present in a state such as has formed naturally by evolution. The term is used both for the entire cell and for individual genes. In particular, those cells or those genes of which the gene sequences have been modified at least partly by humans by means of recombinant methods therefore do not fall under the term "wild type".

The modified cell according to the present invention is preferably a cell that secretes a certain protein across the cytoplasmic membrane into the extracytosolic space. The term "protein" as used herein has to be understood in its broadest sense as a compound comprising two or more amino acids that are connected via a peptide bond, the compound being the product of the cellular protein biosynthesis. The expression "protein" therefore not only encompasses proteins of higher molecular weight (i. e. proteins having a molecular weight of larger than 10,000 Da), but also dipeptides, tripeptides, tetrapeptides, pentapeptides, oligopeptides comprising up to 10 amino acids, polypeptides comprising 10 to 100 amino acids and macropeptides comprising more than 100 amino acids. Furthermore, depending on the nature of the protein the protein may comprise, besides the polymerized amino acids, further components such as sugar residues resulting from co- or post-translational glycosylation.

The protein can, for example, be a hormone, a toxine, an antibody, a structural protein (such as collagen), an enzyme, a transport protein or a regulating protein. Suitable proteins can be selected from the group consisting of a growth hormone including human growth hormone, des-N-methionyl human growth hormone and bovine growth hormone; growth hormone releasing factor; parathyroid hormone; thyroid stimulating hormone; thyroxine; lipoproteins; α1-antitrypsin; insulin A-chain; insulin B-chain; proinsulin; follicle stimulating hormone; calcitonin; leutinizing hormone; glucagon; clotting factors such as factor VIIIC, factor IX, tissue factor, and von Willebrands factor; anti-clotting factors such as Protein C; atrial naturietic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; a serum albumin such as human serum albumin; mullerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor; receptors for hormones or growth factors; integrin; thrombopoietin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); insulin-like growth factor binding proteins; CD proteins such as CD-3, CD-4, CD-8, and CD-19; erythropoietin; osteoinductive factors; immunotoxins; a bone morphogenetic protein (BMP); somatotropins; an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; antibodies; and fragments of any of the above-listed polypeptides. Suitable enzymes include transglutaminases, dehydrogenases (such as alcohol dehydrogenases), monooxygenases, lipases, proteases, cellulases, glycosidases (such as amylases, xylanases, sucrases, maltases, arabinases, isomaltases or fructases), nukleases (such as ribonucleases, desoxyribonucleases, exonucleases, endonucleases, topoisomerases or ligases), phosphatases (such as phytases or akaline phosphatases), polymerases (such as DNA-polymerases or RNA-Polymerases) as well as lyases.

Cells which are particularly preferred according to the invention are those of the genera *Corynebacterium*, *Brevibacterium*, *Bacillus*, *Lactobacillus*, *Lactococcus*, *Candida*, *Pichia*, *Kluveromyces*, *Saccharomyces*, *Escherichia*, *Zymomonas*, *Yarrowia*, *Mycobacterium*, *Methylobacterium*, *Ralstonia Clostridium* and *Pseudomonas*, where *Brevibacterium flavum*, *Brevibacterium lactofermentum*, *Escherichia coli*, *Saccharomyces cerevisiae*, *Kluveromyces lactis*, *Candida blankii*, *Candida rugosa*, *Corynebacterium glutamicum*, *Corynebacterium efficiens*, *Zymonomas mobilis*, *Yarrowia lipolytica*, *Methylobacterium extorquens*, *Ralstonia eutropha* and *Pichia pastoris* are particularly preferred. Cells which are most preferred according to the invention are those of the genus *Corynebacterium*, *Bacillus*, *Mycobacterium*, *Escherichia*, *Saccharomyces* and *Pichia*, where *Corynebacterium glutamicum*, *Bacillus subtilis* and *Escherichia coli* are very particularly preferred bacterial strains.

Particularly suitable are also cells chosen from the group consisting of *Corynebacterium glutamicum* ATCC13032, *Corynebacterium acetoglutamicum* ATCC15806, *Corynebacterium acetoacidophilum* ATCC13870, *Corynebacterium melassecola* ATCC17965, *Corynebacterium thermoaminogenes* FERM BP-1539, *Brevibacterium flavum* ATCC14067, *Brevibacterium lactofermentum* ATCC13869 and *Brevibacterium divaricatum* ATCC14020, and mutants and strains produced therefrom which secrete proteins.

The cells according to the present invention which are genetically modified with respect to their wild type are characterized in that they comprise a gene sequence coding for a fluorescent protein, wherein the expression of the fluorescent protein depends on the amount of protein that is secreted across the cytoplasmic membrane into the extracytosolic space.

All gene sequences known to the person skilled in the art which code for a fluorescent protein are possible as a gene sequence coding for a fluorescent protein. Gene sequences which code for autofluorescent proteins of the genus Aequora, such as green fluorescent protein (GFP), and variants thereof which are fluorescent in a different wavelength range (e.g. yellow fluorescent protein, YFP; blue fluorescent protein, BFP; cyan fluorescent protein, CFP) or of which the fluorescence is enhanced (enhanced GFP or EGFP, or EYFP, EBFP or ECFP), are particularly suitable. However, gene sequences which code for other fluorescent proteins, e.g., DsRed, HcRed, AsRed, AmCyan, ZsGreen, AcGFP, ZsYellow, such as are known from BD Biosciences, Franklin Lakes, USA, can also be used. Also suitable are gene sequences which code for fluorescent proteins such as the Flavin mononucleotide-based fluorescent protein (FbFP) which can be obtained from the evocatal GmbH, Monheim, Germany.

The feature according to which the expression of the fluorescent protein depends on the amount of protein that is secreted across the cytoplasmic membrane into the extracytosolic space and can therefore be controlled by the cell as a function of this protein secretion can be realized according to the invention at the transcription level. Depending on the amount of protein that is secreted across the cytoplasmic membrane into the extracytosolic space more or less mRNA which can be translated in the ribosomes to form the fluorescent proteins is consequently formed.

In this connection the control of the expression at the translation level can be effected by the gene sequence coding for the fluorescent protein being under the control of at least one heterologous promoter which, in the wild type of the cell, controls the expression of a gene of which the expression in the wild-type cell depends on the amount of protein that is secreted across the cytoplasmic membrane into the extracytosolic space. A DNA sequence coding for a fluorescent protein and being under the control of such a promoter is subsequently referred to as a "sensor".

The wording "under the control of at least one heterologous promoter" indicates that the promoter in the natural manner, in particular in the source cell from which the at least one promoter has been isolated and optionally genetically modified to further increase the promoter efficiency, does not regulate the expression of a gene sequence coding for the fluorescent protein. In this connection, the wording "which is derived from such a promoter" means that the at least one promoter which is contained in the genetically modified cell according to the present invention (i. e. the cell comprising the sensor) and which regulates the expression of the gene sequence coding for the fluorescent protein does not have to be a promoter which must be contained with an identical nucleic acid sequence in a source cell. Rather, for the purpose of increasing the promoter efficiency, this promoter sequence can have been modified, for example, by insertion, deletion or exchange of individual bases, for example by palindromization of individual nucleic acid sequences. The at least one promoter which regulates the expression of the gene sequence coding for the fluorescent protein also does not necessarily have to be a promoter or derived from a promoter which is contained in the genome of the genetically modified cell itself (i. e. in the genome of the cell according to the present invention that comprises the sensor). Nevertheless, it may prove to be entirely advantageous if the at least one promoter is a promoter or is derived from a promoter which is contained in the genome of the genetically modified cell itself and in the genetically modified cell controls there the expression of a gene the expression of which depends on the amount of protein that is secreted across the cytoplasmic membrane into the extracytosolic space.

In the cell according to the present invention the gene sequence coding for the fluorescent protein is under the control of at least one promoter. The term "under the control of at least one promoter" in this context is preferably to be understood as meaning that the gene sequence coding for the fluorescent protein is functionally linked to the at least one promoter. The at least one promoter and the gene sequence coding for the fluorescent protein are functionally linked if these two sequences and optionally further regulative elements, such as, for example, a terminator, are arranged sequentially such that each of the regulative elements can fulfil its function in the transgenic expression of the nucleic acid sequence. For this, a direct linking in the chemical sense is not absolutely necessary. Genetic control sequences, such as, for example, enhancer sequences, can also exert their function on the target sequence from further removed positions or even from other DNA molecules. Arrangements in which the gene sequence coding for the fluorescent protein is positioned after the promoter sequence (i.e. at the 3' end), so that the two sequences are bonded covalently to one another, are preferred. It is also possible for the gene sequence coding for the fluorescent protein and the promoter to be linked functionally to one another such that there is still a part sequence of the homologous gene (that is to say that gene of which the expression in the wild-type cell is regulated by the promoter) between these two gene sequences. In the expression of such a DNA construct, a fusion protein from the fluorescent protein and the amino acid sequence which is coded by the corresponding part sequence of the homologous gene is obtained. The lengths of such part sequences of the homologous gene are not critical as long as the functional capacity of the fluorescent protein, that is to say its property of being fluorescent when excited with light of a particular wavelength, is not noticeably impaired.

In addition to the at least one promoter and the gene sequence coding for the fluorescent protein, according to this particular embodiment the cell according to the present invention can also comprise a gene sequence coding for a regulator, wherein the regulator is preferably a protein which interacts in any manner directly or indirectly with a protein that is to be secreted across the cytoplasmic membrane into the extracytosolic space or with a variant of such a protein, in particular with a misfolded version of the protein. This direct or indirect interaction between the regulator and the protein, which influences the bonding affinity of the promoter sequence to the RNA polymerase, is dependent from the amount of protein that is secreted across the cytoplasmic membrane into the extracytosolic space. In this context the regulator can in principle be an activator or a repressor.

According to the invention, possible promoters are in principle all promoters which usually control, via a functional linking, the expression of a gene of which the expression depends on the amount of protein that is secreted across the cytoplasmic membrane into the extracytosolic space. The protein coded by such a gene preferably belongs to the group comprising proteases, peptidases, heat-shock proteins, phage-shock proteins, sigma factors, anti-sigma factors, two-component-signal-transduction systems, three-component-signal-transduction systems, ABC-transporters, membrane associated proteins, periplasmic proteins, putative secreted proteins, regulatory proteins (that by themselves regulate further proteins), proteins involved in cell wall biogenesis, proteins involved in teichoic acid biogenesis, penicillin-binding proteins, proteins involved in outer membrane biogenesis, membrane-associated chaperones, periplasmic chaperones, proteins responsive to cell wall antibiotics (such as bacitracin, vancomycin), proteins responsive to alkaline shock, proteins responsive to detergents, proteins responsive to phenol, proteins responsive to organic solvents, proteins involved in osmoprotection or proteins of unknown function that respond to Sec-dependent protein secretion, cell wall antibotics, alkaline shock, detergents, phenol or organic solvents etc.

The promoters can furthermore be those promoters which in the case of an increased secretion of protein across the cytoplasmic membrane into the extracytosolic space interact with particular activators and in this way cause expression of the gene sequence coding for the fluorescent protein, or promoters which are inhibited by a repressor, the repressor diffusing away from the promoter in the case of an increased secretion of protein across the cytoplasmic membrane into the extracytosolic space, as a result of which the inhibition is eliminated and the expression of the gene sequence coding for the fluorescent protein is effected.

Suitable examples of cells according to the present invention will now be described in more detail in the following. However, it is to be emphasized at this point that the present invention is not limited to the following examples.

The genetically modified cell may be a genetically modified a *Corynebacterium* cell comprising a sequence encoding a fluorescent protein under the control of the cg0706-promoter (Pcg0706) or a variant thereof, the cg0996-promoter (Pcg0996) or a variant thereof, the cg0998-promoter (Pcg0998) or a variant thereof, the cg1325-promoter (Pcg1325) or a variant thereof or combinations of these promoters or variants, in particular combinations of the cg0996-promoter (Pcg0996) or a variant thereof and the cg0998-promoter (Pcg0998) or a variant thereof, in which the cg0996-promoter (Pcg0996) or the variant thereof is located upstream from the cg0998-promoter (Pcg0998) or the variant thereof, which itself is fused to a sequence encoding a fluorescent protein gene sequence. If the sequence encoding a fluorescent protein is under the control of a combination of the cg0996-promoter (Pcg0996) or the variant thereof and the cg0998-promoter (Pcg0998) or the variant thereof, in which the cg0996-promoter (Pcg0996) or the variant thereof is located upstream from the cg0998-promoter (Pcg0998) or the variant thereof, the sequence of the cg0998-promoter or the variant thereof can be directly connected to the cg0996-promoter or to the variant thereof or can be separated from the cg0996-promoter or from the variant thereof by up to 2500 base pairs, preferably up to 1000 base pairs and more preferably by up to 200 base pairs.

In this case an increased secretion of protein across the cytoplasmic membrane into the extracytosolic space leads to an expression of the fluorescent protein. In case of the cg0706-promoter, the cg0998-promoter, the cg1325-promoter or a variant of these promoters such a cell can, besides the promoter and the sequence of the fluorescent protein being under the control of the promoter, further comprise a gene sequence coding for the cg0706-cg1325-regulator or a variant of this sequence or the cg0996-cg0998-regulator or a variant of this sequence. The DNA sequence of the cg0706-promoter corresponds to SEQ ID No. 01, the DNA sequence of the cg0996-promoter corresponds to SEQ ID No. 02, the DNA sequence of the cg0998-promoter corresponds to SEQ ID No. 03 and the DNA sequence of the cg1325-promoter corresponds to SEQ ID No. 04. The DNA sequence coding for the cg0706-cg1325-regulator corresponds to SEQ ID No. 05, the DNA sequence coding for the cg0996-cg0998-regulator corresponds to SEQ ID No. 06.

The genetically modified cell may also be a genetically modified *Bacillus* cell comprising a sequence encoding a fluorescent protein under the control of the htrA-promoter (PhtrA) or a variant thereof. In this case an increased secretion of protein across the cytoplasmic membrane into the extracytosolic space also leads to an expression of the fluorescent protein. In case of the htrA-promoter such a cell can, besides the promoter and the sequence of the fluorescent protein being under the control the promoter, further comprise a gene sequence coding for the Css-regulator or a variant of this sequence. The DNA sequence of the htrA-promoter that is regulated by the Css-regulator corresponds to SEQ ID No. 07 and the DNA sequence coding for the Css-regulator corresponds to SEQ ID No. 08.

The genetically modified cell may be a genetically modified *Bacillus* cell comprising a sequence encoding a fluorescent protein under the control of the liaL-promoter (PliaL) or a variant thereof. In this case an increased secretion of protein across the cytoplasmic membrane into the extracytosolic space again leads to an expression of the fluorescent protein. In case of the liaL-promoter such a cell can, besides the promoter and the sequence of the fluorescent protein being under the control of the promoter, further comprise a gene sequence coding for the LiaR-regulator or a variant of this sequence, a gene sequence coding for the LiaF-protein or a variant of this sequence, a gene sequence coding for the LiaS-protein or a variant of this sequence or a combination of two or more of these sequences. The DNA sequence of the liaL-promoter that is regulated by the LiaR-regulator corresponds to SEQ ID No. 09, the DNA sequence coding for the LiaR-regulator corresponds to SEQ ID No. 10, the DNA sequence coding for the LiaF-protein corresponds to SEQ ID No. 11 and the DNA sequence coding for the LiaS-protein corresponds to SEQ ID No. 12.

The genetically modified cell may be a genetically modified *Mycobakterium* cell comprising a sequence encoding a fluorescent protein under the control of the mprA-promoter (PmprA) or a variant thereof. In this case an increased secretion of protein across the cytoplasmic membrane into the extracytosolic space again leads to an expression of the fluorescent protein. In case of the mprA-promoter such a cell can, besides the promoter and the sequence of the fluorescent protein being under the control of the promoter, further comprise a gene sequence coding for the MprB-regulator or a variant of this sequence, a gene sequence coding for the sigma factor aE (SigE) or a variant of this sequence or a combination of both sequences. The DNA sequence of the mprA-promoter that is regulated by the MprB-regulator by means of sigma factor σrE (SigE) corresponds to SEQ ID No. 13, the DNA sequence coding for the MprB-regulator corresponds to SEQ ID No. 14 and the DNA sequence coding for the sigma factor σrE (SigE) corresponds to SEQ ID No. 15.

The genetically modified cell may also be a genetically modified *Escherichia* cell comprising a sequence encoding a fluorescent protein under the control of the htrA-promoter or a variant thereof. In this case an increased secretion of protein across the cytoplasmic membrane into the extracytosolic space also leads to an expression of the fluorescent protein. In case of the htrA-promoter such a cell can, besides the promoter and the sequence of the fluorescent protein being under the control of the promoter, further comprise a gene sequence coding for the CpxR-regulator or a variant of this sequence. The DNA sequence of the htrA-promoter that is regulated by the CpxR-regulator corresponds to SEQ ID No. 16 and the DNA sequence coding for the CpxR-regulator corresponds to SEQ ID No. 17.

The term "variant" as used above when describing a certain promotor X or the gene sequence Y coding for a certain regulator comprises (1) all nucleic acids which are at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to gene sequences X and Y, respectively, the identity being the identity over the total length of the corresponding nucleic acid;

(2) in case of a gene sequence Y coding for a certain regulator all nucleic acids encoding an amino acid sequence which is at least 70%, at least 80%, at least 85%, at least 90%, at least 95%, at least 96%, at least 97%, at least 98%, at least 99%, at least 99.5%, at least 99.6%, at least 99.7%, at least 99.8% or at least 99.9%, most preferably 100% identical to the amino acid sequence of the corresponding regulator;

(3) in case of a gene sequence Y coding for a regulator all nucleic acids encoding the same regulator, but differing from gene sequence Y due to the degeneracy of the genetic code.

(4) all nucleic acids capable of hybridizing under stringent conditions with a complementary sequence of sequences X and Y, respectively.

The term "hybridization" as used herein includes "any process by which a strand of nucleic acid molecule joins with a complementary strand through base pairing" (J. Coombs (1994) Dictionary of Biotechnology, Stockton Press, New York). Hybridization and the strength of hybridization (i.e., the strength of the association between the nucleic acid molecules) is impacted by such factors as the degree of complementarity between the nucleic acid molecules, stringency of the conditions involved, the Tm of the formed hybrid, and the G:C ratio within the nucleic acid molecules.

As used herein, the term "Tm" is used in reference to the "melting temperature". The melting temperature is the temperature at which a population of double-stranded nucleic acid molecules becomes half dissociated into single strands. The equation for calculating the Tm of nucleic acid molecules is well known in the art. As indicated by standard references, a simple estimate of the Tm value may be calculated by the equation: Tm=81.5+0.41(% G+C), when a nucleic acid molecule is in aqueous solution at 1 M NaCl (see e.g., Anderson and Young, Quantitative Filter Hybridization, in Nucleic Acid Hybridization (1985)). Other references include more sophisticated computations, which take structural as well as sequence characteristics into account for the calculation of Tm. Stringent conditions, are known to those skilled in the art and can be found in Current Protocols in Molecular Biology, John Wiley & Sons, N.Y. (1989), 6.3.1-6.3.6.

In particular, the term "stringency conditions" refers to conditions, wherein 100 contiguous nucleotides or more, 150 contiguous nucleotides or more, 200 contiguous nucleotides or more or 250 contiguous nucleotides or more which are a fragment or identical to the complementary nucleic acid molecule (DNA, RNA, ssDNA or ssRNA) hybridizes under conditions equivalent to hybridization in 7% sodium dodecyl sulfate (SDS), 0.5 M NaPO4, 1 mM EDTA at 50° C. with washing in 2×SSC, 0.1% SDS at 50° C. or 65° C., preferably at 65° C., with a specific nucleic acid molecule (DNA; RNA, ssDNA or ssRNA). Preferably, the hybridizing conditions are equivalent to hybridization in 7% sodium dodecyl sulfate (SDS), 0.5 M NaPO4, 1 mM EDTA at 50° C. with washing in 1×SSC, 0.1% SDS at 50° C. or 65° C., preferably 65° C., more preferably the hybridizing conditions are equivalent to hybridization in 7% sodium dodecyl sulfate (SDS), 0.5 M NaPO4, 1 mM EDTA at 50° C. with washing in 0.1×SSC, 0.1% SDS at 50° C. or 65° C., preferably 65° C. Preferably, the complementary nucleotides hybridize with a fragment or the whole fruA nucleic acids. Alternatively, preferred hybridization conditions encompass hybridisation at 65° C. in 1×SSC or at 42° C. in 1×SSC and 50% formamide, followed by washing at 65° C. in 0.3×SSC or by bridisation at 50° C. in 4×SSC or at 40° C. in 6×SSC and 50% formamide, followed by washing at 50° C. in 2×SSC. Further preferred hybridization conditions are 0.1% SDS, 0.1 SSD and 65° C.

In principle there are thus various possibilities for producing a cell according to the invention comprising a promoter described above and a nucleic acid which codes for a fluorescent protein and is under the control of this promoter.

A first possibility consists of, for example, starting from a cell of which the genome already comprises one of the promoters described above and preferably a gene sequence coding for the corresponding regulator, and then introducing into the genome of the cell a gene sequence coding for a fluorescent protein such that this gene sequence is under the control of the promoter. If appropriate, the nucleic acid sequence of the promoter itself can be modified, before or after the integration of the gene sequence coding for the fluorescent protein into the genome, by one or more nucleotide exchanges, nucleotide deletions or nucleotide insertions for the purpose of increasing the promoter efficiency.

A second possibility consists, for example, of introducing into the cell one or more nucleic acid constructs comprising the promoter sequence and the gene sequence which codes for the fluorescent protein and is under the control of the promoter, it also being possible here to modify the nucleic acid sequence of the promoter itself by one or more nucleotide exchanges, nucleotide deletions or nucleotide insertions for the purpose of increasing the promoter efficiency. The insertion of the nucleic acid construct can take place chromosomally or extrachromosomally, for example on an extrachromosomally replicating vector. Suitable vectors are those which are replicated in the particular bacteria strains. Numerous known plasmid vectors, such as e.g. pZ1 (Merkel et al., Applied and Environmental Microbiology (1989) 64: 549-554), pEKEx1(Eikmanns et al., Gene 102: 93-98 (1991)) or pHS2-1 (Sonnen et al., Gene 107: 69-74 (1991)) are based on the cryptic plasmids pHM1519, pBL1 or pGA1. Other plasmid vectors, such as e.g. those which are based on pCG4 (U.S. Pat. No. 4,489,160), or pNG2 (Serwold-Davis et al., FEMS Microbiology Letters 66, 119-124 (1990)), or pAG1 (U.S. Pat. No. 5,158,891), can be used in the same manner. However, this list is not limiting for the present invention.

Instructions for the production of gene constructs comprising a promoter and a gene sequence under the control of this promoter and the integration of such a construct into the chromosome of a cell or the transfer of an extrachromosomally replicating vector comprising this gene construct into a cell are sufficiently known to the person skilled in the art, for example from Martin et al. (Bio/Technology 5, 137-146 (1987)), from Guerrero et al. (Gene 138, 35-41 (1994)), from Tsuchiya and Morinaga (Bio/Technology 6, 428-430 (1988)), from Eikmanns et al. (Gene 102, 93-98 (1991)), from EP-A-0 472 869, from U.S. Pat. No. 4,601,893, from Schwarzer and Pühler (Bio/Technology 9, 84-87 (1991), from Remscheid et al. (Applied and Environmental Microbiology 60, 126-132 (1994)), from LaBarre et al. (Journal of Bacteriology 175, 1001-1007 (1993)), from WO-A-96/15246, from Malumbres et al. (Gene 134, 15-24 (1993), from JP-A-10-229891, from Jensen and Hammer (Biotechnology and Bioengineering 58, 191-195 (1998)) and from known textbooks of genetics and molecular biology.

The present invention also relates to a method for the identification of a cell that is characterized by an increased secretion of protein across the cytoplasmic membrane into the extracytosolic space in a cell suspension, comprising the method steps:

α1) provision of a cell suspension comprising the cells according to the present invention which are genetically modified with respect to their wild type and which comprises a gene sequence coding for a fluorescent protein, wherein the expression of the fluorescent protein depends on the amount of protein that is secreted across the cytoplasmic membrane into the extracytosolic space;

α2) genetic modification of the cells to obtain a cell suspension in which the cells differ with respect to the amount of protein that is secreted across the cytoplasmic membrane into the extracytosolic space;

α3) identification of individual cells in the cell suspension having an increased secretion of protein across the cytoplasmic membrane into the extracytosolic space;

α4) optionally separating off of the identified cells from the cell suspension.

In step α1) of the method according to the invention, a cell suspension comprising a nutrient medium and a large number of the genetically modified cells described above is first provided.

In step α2) of the method according to the invention one or more of the cells in the cell suspension is or are then genetically modified in order to obtain a cell suspension in which the cells differ with respect to the amount of protein that is secreted across the cytoplasmic membrane into the extracytosolic space.

The genetic modification of the cell suspension can be carried out by targeted or non-targeted mutagenesis or by metabolic engineering, non-targeted mutagenesis being particularly preferred.

In targeted mutagenesis, mutations in particular genes of the cell are generated in a controlled manner. Possible mutations are transitions, transversions, insertions and deletions. Depending on the effect of the amino acid exchange on the enzyme activity, "missense mutations" or "nonsense mutations" are referred to. Insertions or deletions of at least one base pair in a gene lead to "frame shift mutations", as a consequence of which incorrect amino acid are incorporated or the translation is discontinued prematurely. Deletions of several codons typically lead to a complete loss of the enzyme activity. Instructions for generating such mutations belong to the prior art and can be found in known textbooks of genetics and molecular biology, such as e.g. the textbook by Knippers ("*Molekulare Genetik*", 6th edition, Georg Thieme-Verlag, Stuttgart, Germany, 1995), that by Winnacker ("*Gene and Klone*", VCH Verlagsgesellschaft, Weinheim, Germany, 1990) or that by Hagemann ("*Allgemeine Genetik*", Gustav Fischer-Verlag, Stuttgart, 1986). Details, in particular helpful literature references relating to these methods of targeted mutagenesis, can be found, for example, in DE-A-102 24 088.

However, it is particularly preferable according to the invention if the genetic modification in method step a2) is carried out by non-targeted mutagenesis. An example of such a non-targeted mutagenesis is treatment of the cells with chemicals such as e.g. N-methyl-N-nitro-N-nitrosoguanidine or irradiation of the cells with UV light. Such methods for inducing mutations are generally known and can be looked up, inter alia, in Miller ("*A Short Course in Bactenial Genetics, A Laboratory Manual and Handbook for Escherichia coli and Related Bacteria*" (Cold Spring Harbor Laboratory Press, 1992)) or in the handbook "*Manual of Methods for General Bacteriology*" of the American Society for Bacteriology (Washington D.C., USA, 1981).

According to a further embodiment of the process according to the present invention it is also possible if in method step α2) the genetic modification is achieved by metabolic engineering. The term "metabolic engineering" as used herein refers to targeted genetic modification of genetic cellular information. This modification includes the introduction of genes into a species that do not belong to the species (i. e. heterologous genes), the duplication of native genes (i. e. homologous genes), the deletion of genes, the rearrangement of homologous or heterologous genes or the introduction of regulatory sequences such as signal sequences, attenuators, promoters or terminators. Methods for performing metabolic engineering are known in the art and can be derived from known textbooks of genetics and molecular biology, such as the textbook by Mülhardt ("*The experimenter: molecular biology/genomics*", 6th edition, Spektrum Akademischer Verlag, Heidelberg, Germany, 2009), by Wink ("*Molecular Biotechnology: Concepts, Methods and Applications*", 2nd Edition, Wiley-VCH Verlag GmbH & Co. KGaA, Weinheim, Germany, 2011).

An example of metabolic engineering is the introduction of regulatory sequences that encode for the Sec-signal peptides and, when directly or indirectly fused with a gene encoding a protein sequence, cause the secretion of the fusion protein from the cell (Rusch and Kendall, 2007, "*Interactions that drive Sec-dependent bacterial protein transport*", Biochemistry 46, 9665e9673; Bendtsen et al., 2004: "*Improved prediction of signal peptides: SignalP 3.0*", J. Mol. Biol. 340, 783e795; Nielsen et al., 1997: "*Identification of prokaryotic and eukaryotic signal peptides and prediction of their cleavage sites*", Protein Eng. 10, 1e6; von Heijne and Abrahmsen, 1989: "*The structure of signal peptides from bacterial lipoproteins*", Protein Eng. 2, 531e534; von Heijne, 1989: "*Species-specific variation in signal peptide design: Implications for protein secretion in foreign hosts*", FEBS Lett. 244, 439e446; Dalbey et al., 2012: "*Membrane proteases in the bacterial protein secretion and quality control pathway*", Microbiol. Mol. Biol. Rev. 76, 311e350). Other examples of metabolic engineering are the variation of the codon usage of the protein-coding gene, the variation of the promoter under the control of which the protein-coding gene is or the variation of the ribosome binding site in the upstream region of the protein-coding gene.

By the genetic modification of the cell in method step α2), depending on the nature of the mutation which has taken place in the cell, in a particular cell, for example as a consequence of an increased or reduced enzyme activity, an increased or reduced expression of a particular enzyme, an increased or reduced activity of a particular transporter protein, an increased or reduced expression of a particular transporter protein, a mutation in a regulator protein, a mutation in a regulatory sequence, a mutation in a structural protein, a mutation in an RNA control element, the introduction of a new (heterologous) enzymatic activity, the introduction of a new (heterologous) regulator protein, the introduction of a new (heterologous or synthetic) regulatory sequence, the introduction of a new (heterologous) structural protein or the introduction of a new (heterologous) RNA control element, there may be an increase of the secretion of protein across the cytoplasmic membrane into the extracytosolic space which has an influence on the expression of the fluorescent protein by interaction with a corresponding regulator protein via the promoter. A cell in which the secretion of protein across the cytoplasmic membrane into the extracytosolic space is increased as a consequence of the mutation is therefore distinguished in that the fluorescent protein is formed in this cell. The gene for the fluorescent protein thus acts as a reporter gene for an increased secretion of protein across the cytoplasmic membrane into the extracytosolic space.

In method step α3) of the method according to the invention, individual cells in the cell suspension having an increased secretion of protein across the cytoplasmic membrane into the extracytosolic space are therefore identified by detection of the intracellular fluorescence activity. For this, the cell suspension is exposed to electromagnetic radiation in that frequency which excites the fluorescent proteins to emission of light.

According to a particular configuration of the method according to the invention, after, preferably directly after the identification of the cells in method step α3), a further method step α4) is carried out, in which the cells identified are separated off from the cell suspension, this separating off preferably being carried out by means of flow cytometry (FACS=fluorescence activated cell sorting), very particularly preferably by means of high performance flow cytometry (HT-FACS=high throughput fluorescence activated cell sorting). Details on the analysis of cell suspensions by means of flow cytometry can be found, for example, in Sack U, Tarnok A, Rothe G (eds.): Zelluläre Diagnostik. Grundlagen, Methoden and klinische Anwendungen der Durchflusszytometrie, Basel, Karger, 2007, pages 27-70.

By means of the method according to the invention, in a cell suspension in which targeted or non-targeted mutations have been generated in the cells or in which the genetic information has been altered by metabolic engineering it is therefore possible to isolate in a targeted manner, without influencing the vitality of the cells, those cells in which the mutation has led to an increased secretion of protein across the cytoplasmic membrane into the extracytosolic space.

The sensor according to the present invention cannot only be used to identify genetic modifications that lead to an increased secretion of protein across the cytoplasmic membrane into the extracytosolic space as described above, the sensor can also be used

- to identify cells that are characterized by a particularly high secretion of protein across the cytoplasmic membrane into the extracytosolic space in a cell suspension comprising a plurality of genetically different cells,
- to optimize the cell culture conditions for the secretion of protein across the cytoplasmic membrane into the extracytosolic space,
- to optimize the culture medium for the secretion of protein across the cytoplasmic membrane into the extracytosolic space, or
- to identify a compound that is characterized by an antibiotic activity due to its property to damage the membrane of a bacterial cell or to analyse the effect of such a compound on a population of genetically different bacterial cells. as described in the following methods comprising method steps β1) to β3), γ1) to γ3), δ1) to δ3) or ε1) to ε3).

The present invention also relates to a method for the identification of a cell that is characterized by a high secretion of protein across the cytoplasmic membrane into the extracytosolic space in a cell suspension or for the identification of a cell suspension comprising cells that are characterized by a high secretion of protein across the cytoplasmic membrane into the extracytosolic space, comprising the method steps:

β1) provision of
a cell suspension comprising a plurality of cells according to the present invention which are genetically modified with respect to their wild type and which comprise a gene sequence coding for a fluorescent protein, wherein the expression of the fluorescent protein depends on the amount of protein that is secreted across the cytoplasmic membrane into the extracytosolic space, wherein the cells in the cell suspension differ from each other with respect to the amount of protein that is secreted across the cytoplasmic membrane into the extracytosolic space,
or
a plurality of cell suspensions, each cell suspension comprising cells according to the present invention which are genetically modified with respect to their wild type and which comprise a gene sequence coding for a fluorescent protein, wherein the expression of the fluorescent protein depends on the amount of protein that is secreted across the cytoplasmic membrane into the extracytosolic space, wherein the cell suspensions differ from each other with respect to the amount of protein that is secreted by the cells across the cytoplasmic membrane into the extracytosolic space;

β2) cultivation of different cells in the cell suspension or of the different cell suspensions;

β3) identification of individual cells in the cell suspension having a high secretion of protein across the cytoplasmic membrane into the extracytosolic space or identification of individual cell suspensions comprising cells having a high secretion of protein across the cytoplasmic membrane into the extracytosolic space.

The expression "cells having a high secretion of protein across the cytoplasmic membrane into the extracytosolic space" as used in connection with this particular process refers to those cells or cell suspensions which, compared to the other cells in the cell suspension or compared to the other cell suspensions, are characterized by a particularly high amount of protein that is secreted across the cytoplasmic membrane into the extracytosolic space.

The present invention also relates to a method for the identification of a culture medium composition that is optimized for the recombinant production of protein, comprising the method steps:

γ1) provision of a plurality of culture media which differ from each other with respect to the composition of the culture medium;

γ2) cultivation of cells according to the present invention which are genetically modified with respect to their wild type and which comprise a gene sequence coding for a fluorescent protein, wherein the expression of the fluorescent protein depends on the amount of protein that is secreted across the cytoplasmic membrane into the extracytosolic space in the different culture media, thereby obtaining a plurality of cell suspensions in which the cells of the cell suspensions, due to the difference in the composition of the culture media, differ from each other with respect to the amount of protein that is secreted across the cytoplasmic membrane into the extracytosolic space;

γ3) identification of those cell suspensions comprising cells having a high secretion of protein across the cytoplasmic membrane into the extracytosolic space.

The expression "cells having a high secretion of protein across the cytoplasmic membrane into the extracytosolic space" as used in connection with this particular process refers to those cell suspensions which, compared to the other cell suspensions, are characterized by a particularly high amount of protein that is secreted across the cytoplasmic membrane into the extracytosolic space. A high amount of protein secretion across the cytoplasmic membrane into the extracytosolic space in this cell suspension therefore indicates that the culture medium used in this particular cell suspension is particularly advantageous for the cultivation of cells that are intended to secrete high amounts of protein across the cytoplasmic membrane into the extracytosolic space.

The culture media that are provided in process step γ1) can differ from each other with respect to the kind and amount of the carbon source, the kind and amount of the nitrogen source, the kind and amount of the phosphate source, the kind and amount of trace elements, the kind and amount of salts, the kind and amount of detergents, the kind and amount of vitamins, the kind and amount of buffers etc.

The present invention also relates to a method for the identification of culture conditions that are optimized for the recombinant production of protein, comprising the method steps:

δ1) provision of a plurality of cell suspensions comprising cells according to the present invention which are genetically modified with respect to their wild type and which comprise a gene sequence coding for a fluorescent protein, wherein the expression of the fluorescent protein depends on the amount of protein that is secreted across the cytoplasmic membrane into the extracytosolic space;

δ2) cultivation of the cells in these cell suspensions under different culture conditions such that the cells in the different cell suspensions, due to the difference in the culture conditions, differ from each other with respect to the amount of protein that is secreted across the cytoplasmic membrane into the extracytosolic space;

δ3) identification of those cell suspensions comprising cells having a high secretion of protein across the cytoplasmic membrane into the extracytosolic space.

The expression "cells having a high secretion of protein across the cytoplasmic membrane into the extracytosolic space" as used in connection with this particular process refers to those cell suspensions which, compared to the other cell suspensions, are characterized by a particularly high amount of protein that is secreted across the cytoplasmic membrane into the extracytosolic space. A high amount of protein that is secreted across the cytoplasmic membrane into the extracytosolic space in this cell suspension therefore indicates that the culture conditions that have been selected in this experimental set up are particularly advantageous for the cultivation of cells that are intended to secrete high amounts of protein across the cytoplasmic membrane into the extracytosolic space.

The variation of the culture conditions in process step 62) can, for example, concern the temperature, the stirring rate, the oxygen supply, the feed rate, the time point of adding an inducer, the culture period and way of performing the cell culture (batch process, continuous fermentation etc.).

The present invention also relates to a method for the identification of a compound that is characterized by an antibiotic activity due to its property to damage the membrane of a bacterial cell or to analyse the effect of such a compound on a population of genetically different bacterial cells or genetically identical cells in different physiological states or different growths phases, comprising the method steps:

ε1) provision of a cell suspension comprising the cells according to the present invention which are genetically modified with respect to their wild type and which comprises a gene sequence coding for a fluorescent protein, wherein the expression of the fluorescent protein depends on the amount of protein that is secreted across the cytoplasmic membrane into the extracytosolic space;

ε2) cultivation of the cells in these cell suspensions in the presence of the compound;

ε3) determination of the antibiotic activity of the compound by detection of the intracellular fluorescence activity.

It has surprisingly been discovered that the sensor according to the present invention can also be used for the identification of a compound that is characterized by an antibiotic activity due to its property to damage the membrane of a bacterial cell. If such a compound damages the membrane of a cell that comprises the sensor according to the present invention, an increased expression of the fluorescent protein within the cells is observed.

Cells comprising the sensor according to the present invention can therefore be used, for example, to determine whether a given compound has the ability to damage the membrane of a bacterial cell or in which concentration a given compound has the ability to damage the membrane of a bacterial cell. For this purpose the compound is added in one or different concentrations to a suspension of cells comprising the sensor according to the present invention and the cells are incubated in the presence of this compound to determine—via detection of the intracellular fluorescence activity—if the compound damages the cell membrane and in which concentration the compound damages the cell membrane.

Cells comprising the sensor according to the present invention can also be used, for example, to determine which cells in a cell suspension comprising a plurality of genetically different cells or genetically identical cells in different physiological states or different growths phases are susceptible to a certain compound that is known do damage the cell membrane of bacterial cells. For this purpose the compound is added to a suspension of genetically different cells (for example cells of a different species) or genetically identical cells in different physiological states or different growths phases, each cell comprising the sensor according to the present invention, and the cells are incubated in the presence of this compound to determine—via detection of the intracellular fluorescence activity—which cells are susceptible for the compound.

The present invention also relates to a method for the production of a cell which is genetically modified with respect to its wild type with optimized secretion of protein across the cytoplasmic membrane into the extracytosolic space, comprising the method steps:

I) provision of a cell suspension comprising cells according to the present invention which are genetically modified with respect to their wild type and which comprises a gene sequence coding for a fluorescent protein, wherein the expression of the fluorescent protein depends on the amount of protein that is secreted across the cytoplasmic membrane into the extracytosolic space;

II) genetic modification of the cells to obtain a cell suspension in which the cells differ with respect to the amount of protein that is secreted across the cytoplasmic membrane into the extracytosolic space;

III) identification of individual cells in the cell suspension having an increased secretion of protein across the cytoplasmic membrane into the extracytosolic space;

IV) separating off of the identified cells from the cell suspension;

V) identification of those genetically modified genes $G_1$ to $G_n$ or those mutations $M_1$ to $M_m$ in the cells identified and separated off which are responsible for the increased secretion of protein across the cytoplasmic membrane into the extracytosolic space;

VI) production of a cell which is genetically modified with respect to its wild type with optimized secretion of protein across the cytoplasmic membrane into the extracytosolic space, of which the genome comprises at least one of the genes $G_1$ to $G_n$ and/or at least one of the mutations $M_1$ to $M_m$.

According to method steps I) to IV), cells having an increased secretion of protein across the cytoplasmic membrane into the extracytosolic space are first generated by mutagenesis or by metabolic engineering and are separated off from a cell suspension. For details concerning these process steps reference is made to process steps i) to iv) as described above.

In method step V), in the cells identified and separated off, those genetically modified genes $G_1$ to $G_n$ or those mutations $M_1$ to $M_m$ which are responsible for the increased secretion of protein across the cytoplasmic membrane into the extracytosolic space are then identified by means of genetic methods known to the person skilled in the art, the numerical value of n and m depending on the number of modified genes observed and, respectively of mutations observed in the cell identified and separated off. Preferably, the procedure in this context is such that the sequence of those genes or promoter sequences in the cells which are known to stimulate the secretion of protein across the cytoplasmic membrane into the extracytosolic space is first analysed. If no mutation is recognized in any of these genes, the entire genome of the cell identified and separated off is analysed in order to identify, where appropriate, further modified genes $G_i$ or further mutations M. Advantageous modified gene sequences $G_i$ or advantageous mutations $M_i$ which lead to an increased secretion of protein across the cytoplasmic membrane into the extracytosolic space can be identified in this manner.

In a further method step VI), a cell which is genetically modified with respect to its wild type with optimized secretion of protein across the cytoplasmic membrane into the extracytosolic space, of which the genome comprises at least one of the genes $G_1$ to $G_n$ and/or at least one of the mutations $M_1$ to $M_m$ can then be produced. For this, one or more of the advantageous modified genes G and/or modified mutations M observed in method step V) are introduced into a cell in a targeted manner. This targeted introduction of particular mutations can be carried out, for example, by means of "gene replacement". In this method, a mutation, such as e.g. a deletion, insertion or base exchange, is produced in vitro in the gene of interest. The allele produced is in turn cloned into a vector which is non-replicative for the target host and this is then transferred into the target host by transformation or conjugation. After homologous recombination by means of a first "cross-over" event effecting integration and a suitable second "cross-over" event effecting an excision in the target gene or in the target sequence, the incorporation of the mutation or the allele is achieved.

The present invention also relates to a cell with optimized secretion of protein across the cytoplasmic membrane into the extracytosolic space which has been obtained by the method described above.

The present invention also relates to a process for the production of protein, comprising the method steps:
(a) production of a cell which is genetically modified with respect to its wild type with optimized secretion of protein across the cytoplasmic membrane into the extracytosolic space by the method described above;
(b) cultivation of the cell in a culture medium comprising nutrients under conditions under which the cell produces protein from the nutrients.

Suitable proteins that can be prepared by this method comprise a hormone, a toxine, an antibody, a structural protein, an enzyme, a transport protein or a regulating protein. Particular suitable are those proteins that have already been mentioned in connection with the cell according to the present invention.

The genetically modified cells according to the invention with optimized secretion of protein across the cytoplasmic membrane into the extracytosolic space which are produced in method step (a) can be cultivated in the nutrient medium in method step (b) continuously or discontinuously in the batch method (batch cultivation) or in the fed batch method (feed method) or repeated fed batch method (repetitive feed method) for the purpose of production of the protein. A semi-continuous method such as is described in GB-A-1009370 is also conceivable. A summary of known cultivation methods is described in the textbook by Chmiel ("*Bioprozesstechnik l. Einführung in die Bioverfahrenstechnik*", Gustav Fischer Verlag, Stuttgart, 1991) or in the textbook by Storhas ("*Bioreaktoren and periphere Einrichtungen*", Vieweg Verlag, Braunschweig/Wiesbaden, 1994).

The nutrient medium to be used must meet the requirements of the particular strains in a suitable manner. Descriptions of culture media of various microorganisms are contained in the handbook "*Manual of Methods for General Bacteriology*" of the American Society for Bacteriology (Washington D.C., USA, 1981).

The nutrient medium can comprise carbohydrates, such as e.g. glucose, sucrose, lactose, fructose, maltose, molasses, starch and cellulose, oils and fats, such as e.g. soya oil, sunflower oil, groundnut oil and coconut fat, fatty acids, such as e.g. palmitic acid, stearic acid and linoleic acid, alcohols, such as e.g. glycerol and methanol, hydrocarbons, such as methane, amino acids, such as L-glutamate or L-valine, or organic acids, such as e.g. acetic acid, as a source of carbon. These substances can be used individually or as a mixture.

The nutrient medium can comprise organic nitrogen-containing compounds, such as peptones, yeast extract, meat extract, malt extract, corn steep liquor, soya bean flour and urea, or inorganic compounds, such as ammonium sulphate, ammonium chloride, ammonium phosphate, ammonium carbonate and ammonium nitrate, as a source of nitrogen. The sources of nitrogen can be used individually or as a mixture.

The nutrient medium can comprise phosphoric acid, potassium dihydrogen phosphate or dipotassium hydrogen phosphate or the corresponding sodium-containing salts as a source of phosphorus. The nutrient medium must furthermore comprise salts of metals, such as e.g. magnesium sulphate or iron sulphate, which are necessary for growth. Finally, essential growth substances, such as amino acids and vitamins, can be employed in addition to the above-mentioned substances. Suitable precursors can moreover be added to the nutrient medium. The starting substances mentioned can be added to the culture in the form of a one-off batch or can be fed in during the cultivation in a suitable manner.

Basic compounds, such as sodium hydroxide, potassium hydroxide, ammonia or aqueous ammonia, or acidic compounds, such as phosphoric acid or sulphuric acid, are employed in a suitable manner to control the pH of the culture. Antifoam agents, such as e.g. fatty acid polyglycol esters, can be employed to control the development of foam. Suitable substances having a selective action, such as e.g. antibiotics, can be added to the medium to maintain the stability of plasmids. Oxygen or oxygen-containing gas mixtures, such as e.g. air, are introduced into the culture in order to maintain aerobic conditions. The temperature of the culture is usually 15° C. to 45° C., and preferably 25° C. to 40° C.

The present invention also relates to a method for the preparation of a mixture comprising the method steps:
(A) production of a protein by the method described above;
(B) mixing of the protein with a mixture component which differs from the protein.

The mixture can be a foodstuff, an animal feed, a pharmaceutical composition, a composition for food production, for example a mixture comprising amylolytic enzymes and lipolytic enzymes that are used as enzymatic monoglyceride replacer to achieve crumb texture profiles in yeast-raised baked good, a gluing-composition, a textile-finishing composition or a lignocellulolytic composition.

The invention is now explained in more detail with the aid of figures and non-limiting examples.

EXAMPLE 1

Figure 1:
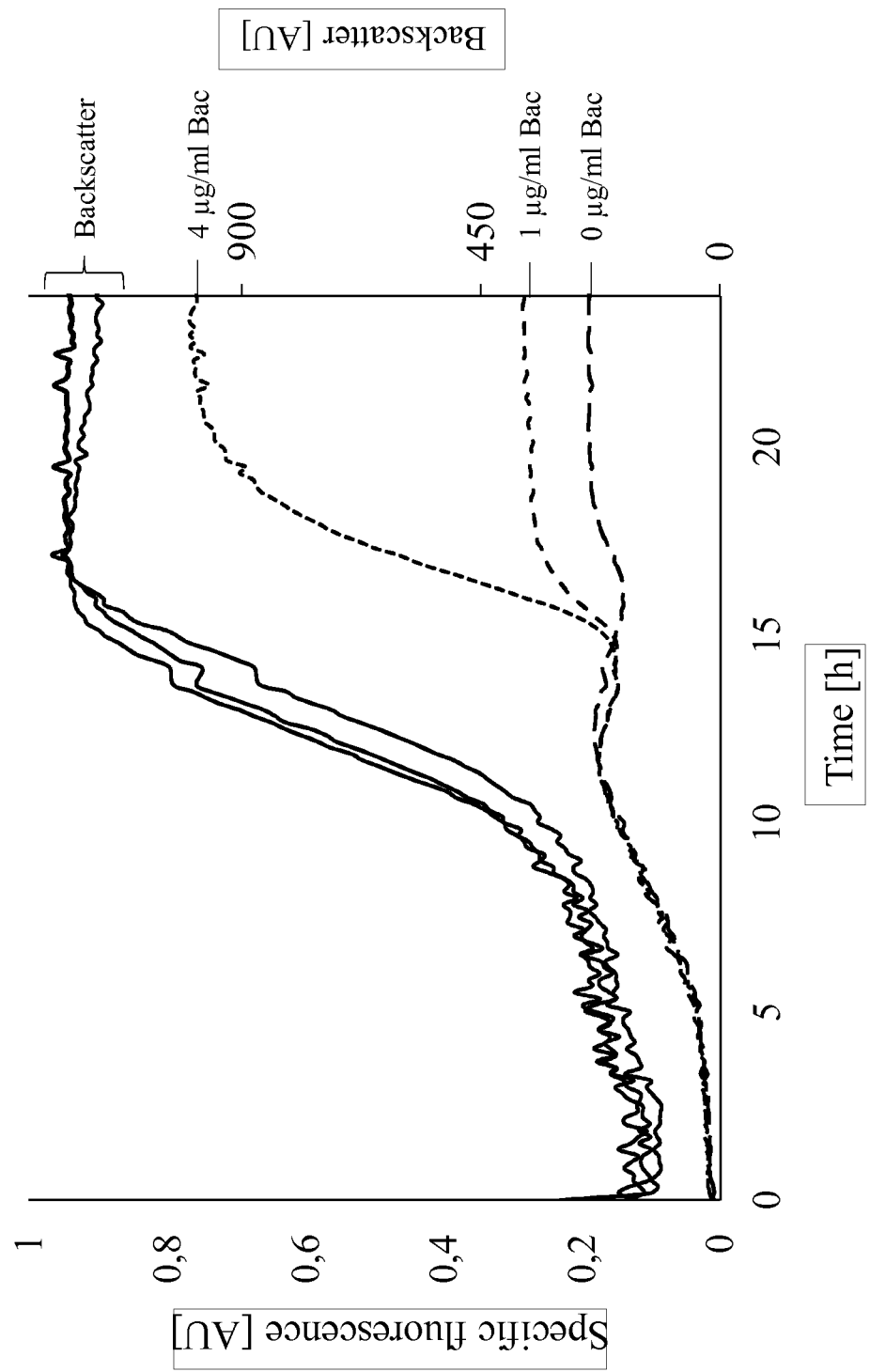
FIG. 1 shows the detection of the fluorescence as a function of the concentration of a Bacitracine (Bac) in strain ATCC 13032 pSen0706 (see Example 1c).

Production of a cell according to the invention according to the first embodiment by the example of a cell in which a gene sequence coding for a fluorescent protein is under the control of the cg0706 promoter and in which the expression of the fluorescent protein depends on the presence and concentration of a compound that is characterized by an antibiotic activity due to its property to damage the membrane of a bacterial cell or on the concentration of α-Amylase (AmyE) on the trans-side of the cytoplasmic membrane.

a) Construction of the vectors pSen0706 and pSen0706S

The construction of the fusion of promoter P(cg0706) with the reporter gene eyfp (SEQ ID No. 18; protein sequence of the eYFP: SEQ ID No. 19) was achieved by PCR-amplification of the promoter sequence and subsequent cloning into the vector pSenLys (Binder et al.: "A high-throughput approach to identify genomic variants of bacterial metabolite producers at the single-cell level"; Genome Biology 13(5), R40, 2012). Genomic DNA of Corynebacterium glutamicum ATCC13032 served as a template and oligonucleotides 0706-Sal-flu (SEQ ID No. 20) and 0706-RBSNde-r (SEQ ID No. 21) served as primers. pSenLys already comprises the sequence coding for eyfp.

```
0706-RBSNde_r:
GCGCATATGATATCTCCTTCTTCTAGCGGGTCTGCCACATTTGCTG

0706-Sal-fii:
GCGGTCGACGGGTAAACGTGGGATATAAA
```

After purification of the amplified fragment from a 0.8% agarose gel the fragment was digested with the restriction enzymes SalI and NdeI and after purification of the reaction mixture the fragment was ligated into vector pSenLys that has also been opened with SalI and NdeI and dephosphorylated. The ligation mixture was used directly to transform E. coli XL1-blue, and the selection of transformants was carried out on LB plates containing 50 μg/ml kanamycin. 32 colonies which grew on these plates and were therefore resistant to kanamycin were used for colony PCR. The colony PCR was performed with primers SenCas-fw (SEQ ID No. 24) and TKP-seq-ry (SEQ ID No. 25), to check whether the promoter fragment was inserted into vector pSenLys. The analysis of colony PCR in an agarose gel showed the expected PCR product with a size of 343 bp in the samples that has been analyzed, whereupon four colonies were cultured for plasmid preparations in a larger scale. After 16 h of cultivation these cultures were collected by centrifugation and the plasmid DNA was prepared. Two of these plasmid preparations were sequenced with the primers used in the colony PCR and sequence of the inserts showed 100% identity with the expected sequence. The resulting plasmid was named pSen0706 (SEQ ID No. 35).

The plasmid pSen0706S, a variant of pSen0706 that conveys a spectinomycin resistance instead of the kanamycin resistance was obtained by amplification of the spectinomycin resistance-mediating sequence by PCR and subsequent cloning of the PCR product into the vector pSen0706. Plasmid pEKEx3 served as a template for PCR and oligonucleotides Spc SacII-f (SEQ ID No. 22) and Spc Bgl-r (SEQ ID No. 23) served as primers.

```
Spc SacII-f:
GCGCCGCGGACTAATAACGTAACGTGACTGGCAAGAG

Spc Bgl-r:
GCGAGATCTTCTGCCTCGTGAAGAAGGTGTTGCTGAC
```

After purification of the amplified fragment from a 0.8% agarose gel the fragment was digested with the restriction enzymes SacII and BglII and after purification of the reaction mixture the fragment was ligated into vector pSen0706 that has also been digested with SacII and BglII and dephosphorylated. The ligation mixture was used directly to transform E. coli XL1-blue, and the selection of transformants was carried out on LB plates containing 100 μg/ml spectinomycin. 4 colonies which grew on these plates and therefore were spectinomycin-resistant were used to inoculate liquid cultures (5 ml LB medium containing 100 μg/ml spectinomycin). After 16 h of cultivation these cultures were centrifuged and the plasmid DNA was prepared. 2 of these plasmid preparations were sequenced with primers SenCas-fw (SEQ ID No. 24) and TKP-seq-ry (SEQ ID No. 25) and the sequence of the insert showed 100% identity with the expected sequence. The resulting plasmid was named pSen0706S.

```
SenCas-fw:
GTCGCCGTCCAGCTCGACCAGGATG
```

-continued

TKP-seq-rv:
CGGGAAGCTAGAGTAAGTAGTTCG b) Transformation of *Corynebacterium glutamicum* with pSen0706

Competent cells of the *C. glutamicum* strain ATCC 13032 were prepared as described by Tauch et al., 2002 (*Curr Microbiol.* 45(5) (2002), pages 362-7. These cells were transformed by electroporation with pSen0706 as described by Tauch et al. The selection of the transformants was carried out on BHIS plates with 25 µg/ml of kanamycin. Clones thus obtained were named ATCC 13032 pSen0706.

c) Detection of the fluorescence as a function of the concentration of a compound that is characterized by an antibiotic activity due to its property to damage the membrane of a bacterial cell.

Figure 2:
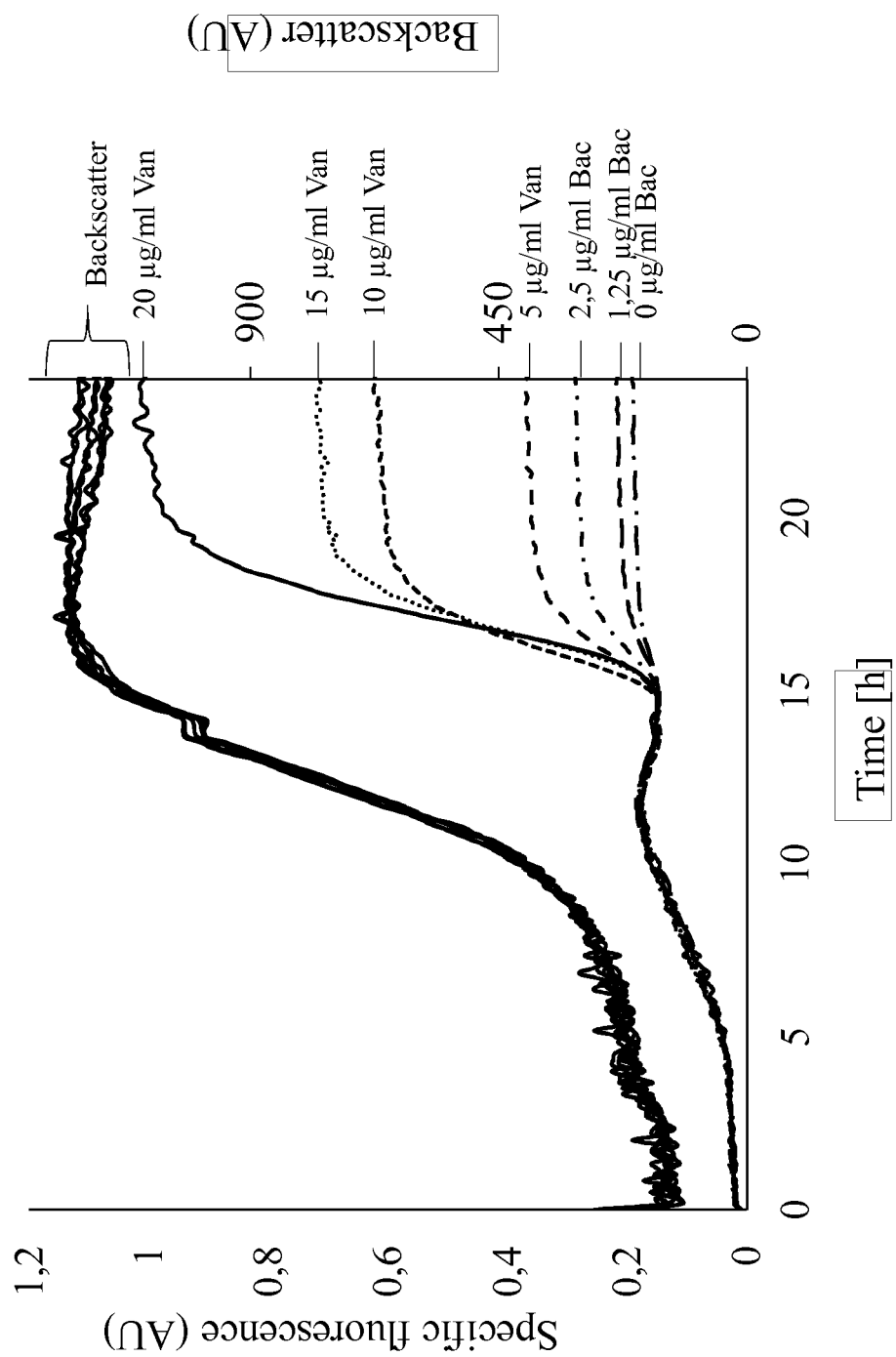
FIG. 2 shows the detection of the fluorescence as a function of the concentration of a Vancomycine (Van) in strain ATCC 13032 pSen0706 (see Example 1c).

The examination of in vivo fluorescence emission was carried out by culturing the cells of strain ATCC 13032 pSen0706 with 0.8 ml CGXII medium (Keilhauer et al, 1993, *J. Bacteriol.* 175: 5595-603) in microtiter dimension (Flowerplate® MTP-48-B) in the BioLector system (m2p-labs GmbH, 52499 Baesweiler, Germany). This system allows for the parallel cultivation of 48 cultures and regular and automated optical measurements of the culture growth as well as the fluorescence. 10 cultures with cells of strain ATCC 13032 pSen0706 were inoculated to an OD of 0.1 and cultured for 24 hours. After 4 hours the antibiotic substances Vancomycine or Bacitracine were added to the cultures. Vancomycine-concentrations were adjusted to 0; 1.25; 2.5; 5; 10; 15; 20 µg/ml and Bacitracin-concentrations were adjusted to 0; 1; 4 µg/ml. Every 10 minutes the cell densities of cultures and the fluorescence were measured. The fluorescence was excited with light of wavelength 485 nm, the fluorescence emission measurement of EYFP was carried out at 520/10 nm. The fluorescence of the cultures has been digitally recorded by means of the BioLection V.2.4.1.0 software. It was observed that the fluorescence emissions of cultures with different Vancomycine or Bacitracine concentrations also differs (FIGS. 1 and 2).

d) Transformation of ATCC 13032 pSen0706 with pCLTON2-AmyE

Competent cells of the *C. glutamicum* strain ATCC 13032 pSen0706 as described above were transformed by electroporation with vector pCLTON2-AmyE as described above. This vector comprises a nucleic acid sequence coding for the amylolytic enzyme α-Amylase (AmyE) from *Bacillus subtilis* and the Sec-specific native signal peptide in order to enable the export of the protein over the Sec path of *Corynebacterium glutamicum*. pCLTON2-AmyE was prepared by amplification of the AmyE encoding sequence from chromosomal DNA of *Bacillus subtilis* with primers AmyE-HpaI-f (SEQ ID No. 33) and AmyE-SacI-r (SEQ ID No. 34), restriction with HpaI and SacI and ligation in SmaI/SacI cutted pCLTON2-vector, a spectinomycin-resistance conferring derivative of pCLTON1 (A tetracycline inducible expression vector for *Corynebacterium glutamicum* allowing tightly regulable gene expression. Lausberg F, Chattopadhyay A R, Heyer A, Eggeling L, Freudl R. Plasmid. 2012 68(2): 142-7). Clones thus obtained were named ATCC 13032 pSen0706 pCLTON2-AmyE.

AmyE-Hpa-f:
GCGCGTTAACCGAAGGAGATATAGATATGTTTGC

-continued

AmyE-Sac-r:
CAGTGAATTCGAGCTCCTAGTG e) Detection of the fluorescence as a function of the level of secretion of AmyE or the concentration of AmyE on the trans side of the cytoplasmic membrane (parameter variation)

Figure 3:
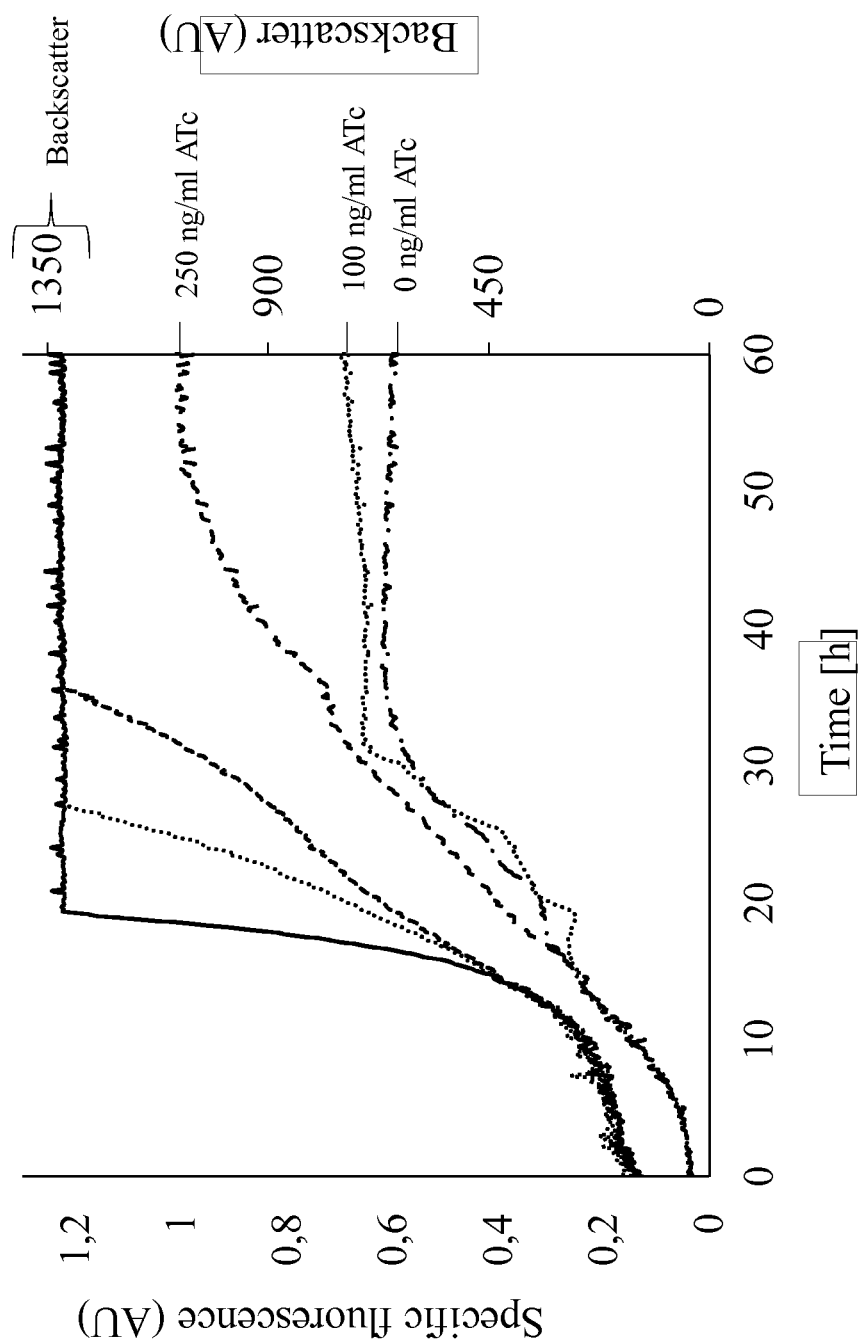
FIG. 3 shows the detection of the fluorescence as a function of the level of secretion of AmyE or the concentration of AmyE on the trans side of the cytoplasmic membrane in strain ATCC 13032 pSen0706 pCLTON2-AmyE (see Example 1c).

The examination of in vivo fluorescence emission was carried out by culturing the cells of strain ATCC 13032 pSen0706 pCLTON2-AmyE with 0.8 ml CGXII medium (Keilhauer et al, 1993, *J. Bacteriol.* 175: 5595-603) in microtiter dimension (Flowerplate® MTP-48-B) in the BioLector system (m2p-labs GmbH, 52499 Baesweiler, Germany). 3 cultures with cells of strain ATCC 13032 pSen0706 pCLTON2-AmyE were inoculated to an OD of 0.1 and cultured for 24 hours. After 4 hours the expression of AmyE was induced by the addition of Anhydrotetracycline (ATc). ATc-concentrations were adjusted to 0, 100, 250 ng/ml to cause different expression intensities. Every 10 minutes the cell densities of cultures and the fluorescence were measured. The fluorescence was excited with light of wavelength 485 nm, the fluorescence emission measurement of EYFP was carried out at 520/10 nm. The fluorescence of the cultures has been digitally recorded by means of the BioLection V.2.4.1.0 software. It was observed that the fluorescence emissions of cultures that have been induced differently also differs (FIG. 3). After 24 hours the cultures in the Flowerplate were centrifuged to pellet the cells and to obtain cell-free culture supernatants. 20 µl of each culture supernatant were used to quantify the enzymatic activity of the secreted AmyE by means of an Amylase-assay (Phadebas Amylase Test, Magle A B, Lund, Sweden). It was observed that higher activities of Amylase in the culture supernatant induced by ATc concentrations which under these chosen culture conditions have to be considered as optimal correlate with higher fluorescence emissions.

f) Transformation of *C. glutamicum* ATCC 13032 pSen0706S with pEKEx2-AmyA

Competent cells of strain *C. glutamicum* ATCC 13032 pSen0706S as described above were transformed by electroporation with vector pEKEx2-AmyA as described above. This vector comprises a nucleic acid sequence coding for the amylolytic enzyme α-Amylase (AmyA) from *Bacillus* and the Sec-specific native signal peptide in order to enable the export of the protein over the Sec path of *C. glutamicum*. pEKEx2-AmyA was prepared by amplification of the AmyA encoding sequence from chromosomal DNA of *Bacillus* with primers AmyA-BamHI-f (SEQ ID No. 40), and AmyA-SacI-r (SEQ ID No. 41), restriction with BamHI and SacI and ligation in BamHI/SacI cut pEKEx2-vector (Eikmanns et al., Gene 102: 93-98 (1991)). Clones thus obtained were named ATCC 13032 pSen0706S pEKEx2-AmyA.

AmyA-BamHI-f:
CGCGGATCCAAGGAGAATGACGATGAGAAAACGTAAAAATGGATTAATC

AmyA-SacI-r:
GCGGAGCTCTAATTATTTACCCATATAGATACAGACCCAC g) Detection of the fluorescence as a function of the level of secretion of AmyA or the concentration of AmyA on the trans-side of the cytoplasmic membrane as an example for the variation of the nutrient mediums with resepct to the sorbitol content.

The examination of in vivo fluorescence emission was carried out by culturing the cells of strain *C. glutamicum*

Figure 5:
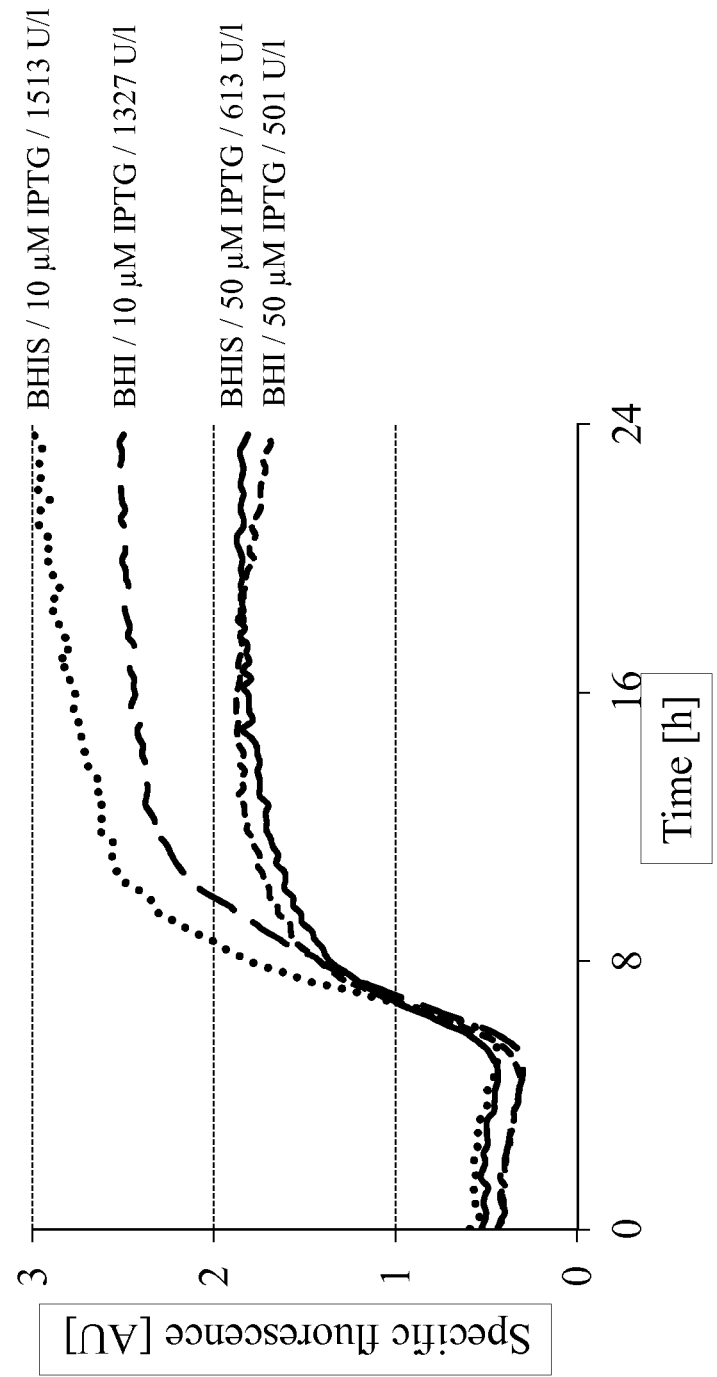
FIG. 5 shows the in vivo fluorescence of cells of strain C. glutamicum ATCC 13032 pSen0706S pEKEx2-AmyA as a function of the level of secretion of AmyA, wherein the cells have been cultivated in a nutrient medium with or without sorbitol (Example 1g)).

ATCC 13032 pSen0706S pEKEx2-AmyA with 0.8 ml "Difco Brain Heart Infusion" medium (Difco, Becton Dikinson BD, 1 Becton Drive, Franklin Lakes, N.J. USA) with or without addition of 91 g/l sorbitol in microtiter dimension (Flowerplate® MTP-48-B) in the BioLector system (m2p-labs GmbH, 52499 Baesweiler, Germany). 4 cultures with cells of strain ATCC 13032 pSen0706S pEKEx2-AmyA were inoculated to an OD of 0.1 and cultured for 24 hours. After 4 hours the expression of AmyA was induced by the addition of Isopropyl-β-D-thiogalactopyranosid (IPTG). IPTG-concentrations were adjusted to 10 or 50 µM to cause different expression intensities. Every 10 minutes the cell densities of cultures and the fluorescence were measured. The fluorescence was excited with light of wavelength 485 nm, the fluorescence emission measurement of EYFP was carried out at 520/10 nm. The fluorescence of the cultures has been digitally recorded by means of the BioLection V.2.4.1.0 software. It was observed that the fluorescence emissions of cultures that have been induced differently also differ and that the fluorescence emissions of cultures grown in nutrient medium with or without sorbitol differ (FIG. 5). After 24 hours the cultures in the Flowerplate were centrifuged to pellet the cells and to obtain cell-free culture supernatants. 20 µl of each culture supernatant were used to quantify the enzymatic activity of the secreted AmyA by means of an Amylase-assay (Phadebas Amylase Test, Magle A B, Lund, Sweden). It was observed that higher activities of Amylase in the culture supernatant correlate with higher fluorescence emissions.

EXAMPLE 2

Production of a cell according to the invention according to the first embodiment by the example of a cell in which a gene sequence coding for a fluorescent protein is under the control of the cg1325 promoter and in which the expression of the fluorescent protein depends on the presence and concentration of a compound that is characterized by an antibiotic activity due to its property to damage the membrane of a bacterial cell or on the concentration of a certain protein on the trans-side of the cytoplasmic membrane.

a) Construction of the vector pSen1325

The construction of the fusion of promoter P(cg1235) with the reporter gene eyfp (SEQ ID No. 18; protein sequence of the eYFP: SEQ ID No. 19) was achieved by PCR-amplification of the promoter sequence and subsequent cloning into the vector pSenLys (Binder et al.: "A high-throughput approach to identify genomic variants of bacterial metabolite producers at the single-cell level"; Genome Biology 13(5), R40, 2012). Genomic DNA of Corynebacterium glutamicum ATCC13032 served as a template and oligonucleotides 1325-Sal-f (SEQ ID No. 26) and 1325-RBSNde-r (SEQ ID No. 27) served as primers. pSenLys already comprises the sequence coding for eyfp.

```
1325-Sal-f:
GCGGTCGACGAGCTGTAAGGGTTTACTTG

1325-RBSNde-r:
GCGCATATGATATCTCCTTCTTCTAACCAGCGACGCCGCCGATCC
```

After purification of the amplified fragment from a 1% agarose gel the fragment was digested with the restriction enzymes SalI and NdeI and after purification of the reaction mixture the fragment was ligated into vector pSenLys that has also been digested with SalI and NdeI and dephosphorylated. The ligation mixture was used directly to transform E. coli XL1-blue, and the selection of transformants was carried out on LB plates containing 50 µg/ml kanamycin. 48 colonies which grew on these plates and were therefore resistant to kanamycin were used for colony PCR. The colony PCR was performed with primers SenCas-fw (SEQ ID No. 24) and TKP-seq-ry (SEQ ID No. 25) to check whether the promoter fragment was inserted into vector pSenLys. The analysis of colony PCR in an agarose gel showed the expected PCR product with a size of 250 bp in the samples that has been analyzed, whereupon four colonies were cultured for plasmid preparations in a larger scale. After 16 h of cultivation these cultures were collected by centrifugation and the plasmid DNA was prepared. Two of these plasmid preparations were sequenced with the primers used in the colony PCR and sequence of the inserts showed 100% identity with the expected sequence. The resulting plasmid was named pSen1325 (SEQ ID No. 36).

b) Transformation of Corynebacterium glutamicum with pSen1325

Competent cells of the C. glutamicum strain ATCC 13032 were prepared as described by Tauch et al., 2002 (Curr Microbiol. 45(5) (2002), pages 362-7. These cells were transformed by electroporation with pSen1325 as described by Tauch et al. The selection of the transformants was carried out on BHIS plates with 50 µg/ml of kanamycin. Clones thus obtained were named ATCC 13032 pSen1325.

c) Detection of the fluorescence as a function of the concentration of a compound that is characterized by an antibiotic activity due to its property to damage the membrane of a bacterial cell.

The examination of in vivo fluorescence emission was carried out by culturing the cells of strain ATCC 13032 pSen1325 with 0.8 ml CGXII medium (Keilhauer et al, 1993, J. Bacteriol. 175: 5595-603) in microtiter dimension (Flowerplate® MTP-48-B) in the BioLector system (m2p-labs GmbH, 52499 Baesweiler, Germany). 13 cultures with cells of strain ATCC 13032 pSen1325 were inoculated to an OD of 0.1 and cultured for 24 hours. After 4 hours the antibiotic substances Vancomycine or Bacitracine were added to the cultures. Vancomycine-concentrations were adjusted to 0; 1.25; 2.5; 5; 10; 15; 20 µg/ml and Bacitracin-concentrations were adjusted to 0; 0.25; 0.5; 1; 2; 4 µg/ml. Every 10 minutes the cell densities of cultures and the fluorescence were measured. The fluorescence was excited with light of wavelength 485 nm, the fluorescence emission measurement of EYFP was carried out at 520/10 nm. The fluorescence of the cultures has been digitally recorded by means of the BioLection V.2.4.1.0 software. It was observed that the fluorescence emissions of cultures with different Vancomycine or Bacitracine concentrations also differs.

EXAMPLE 3

Production of a cell according to the invention according to the first embodiment by the example of a cell in which a gene sequence coding for a fluorescent protein is under the common control of the cg0996 promoter and the cg0998 promoter and in which the expression of the fluorescent protein depends on the concentration of a certain protein on the trans-side of the cytoplasmic membrane.

a) Construction of vectors pSen0996_8, pSen0996_8c and pSen0996_8e

The constructions of the fusions of promoters P(cg0996) and P(cg0998) with the reporter gene eyfp (SEQ ID No. 18; protein sequence of the eYFP: SEQ ID No. 19) were achieved by means of chemical synthesis of synthetic DNA-fragments (SEQ ID No. 28 for pSen0996_8, SEQ ID No. 29 for pSen0996_8c and SEQ ID No. 30 for pSen0996_8e) and their ligation into vector pSenLys (Binder et al.: "A high-throughput approach to identify genomicgenomic variants of bacterial metabolite producers at the single-cell level"; Genome Biology 13(5), R40, 2012). pSenLys already comprises the sequence coding for eyfp.

After cleavage of the synthesized DNA fragments with the restriction enzymes SalI and NdeI and subsequent purification of the reaction mixture the DNA fragments that had been cut out were used in individual ligation reactions with vector pSenLys that has also been digested with SalI/NdeI and dephosphorylated. The ligation mixtures were used directly to separately transform E. coli XL1-blue, and the selections of transformants were carried out on LB plates containing 50 µg/ml kanamycin. 8 colonies that grew on each of these plates and therefore were kanamycin-resistant were used for colony PCRs. Colony PCRs were performed using primers SenCas-fw (SEQ ID No. 24) and TKP-seq-ry (SEQ ID No. 25) in order to verify that the synthesized DNA fragments were inserted into pSenLys.

The analysis of colony PCRs in an agarose gel showed the expected PCR products with a size of 872 bp in case of pSen0996_8, a size of 413 bp in case of pSen0996_8c and a size of 2774 bp in case of pSen0996_8e in the samples that has been analyzed, whereupon eight colonies were cultured each for plasmid preparations in a larger scale. After 16 h of cultivation these cultures were collected by centrifugation and the plasmid DNA was prepared. One of each of these plasmid preparations was sequenced with primers JPS0003 (SEQ ID No. 31) and JPS0004 (SEQ ID No. 32) and sequence of the inserts showed 100% identity with the expected sequence. The resulting plasmids were named pSen0996_8 (SEQ ID No. 37), pSen0996_8c (SEQ ID No. 38) and pSen0996_8e (SEQ ID No. 39).

```
JPS0003:
CTGAACTTGTGGCCGTTTAC

JPS0004:
TTGTTGCCGGGAAGCTAGAG
``` b) Transformation of Corynebacterium glutamicum with pSen0996_8, pSen0996_8c and pSen0996_8e Competent cells of the C. glutamicum strain ATCC 13032 were prepared as described by Tauch et al., 2002 (Curr Microbiol. 45(5) (2002), pages 362-7. These cells were transformed by electroporation with either pSen0996_8 or pSen0996_8c or pSen0996_8e as described by Tauch et al.

c) Transformation of ATCC 13032 pSen0996_8 or ATCC 13032 pSen0996_8c or ATCC 13032 pSen0996_8e with pCLTON2-FsCut Competent cells of the C. glutamicum strain ATCC 13032 pSen0996_8 or ATCC 13032 pSen0996_8c or ATCC 13032 pSen0996_8e as described above were transformed by electroporation with vector pCLTON2-FsCut as described above. This vector comprises a nucleic acid sequence coding for the lipase enzyme Cutinase (FsCut) from Fusarium solani pisi and the Sec-specific signal peptide NprE in order to enable the export of the protein over the Sec path of Corynebacterium glutamicum. pCLTON2-FsCut was achieved by means of chemical synthesis of a synthetic DNA-fragment (SEQ ID No. 33), restriction of the synthetic DNA fragment with PstII SacI and ligation of the restricted fragment into equally digested vector pCLTON2, a spectinomycin-resistance conferring derivative of pCLTON1 (A tetracycline inducible expression vector for Corynebacterium glutamicum allowing tightly regulable gene expression. Lausberg F, Chattopadhyay A R, Heyer A, Eggeling L, Freudl R. Plasmid. 2012 68(2): 142-7). Clones thus obtained were named ATCC 13032 pSen0996_8 pCLTON2-FsCut, ATCC 13032 pSen0996_8c pCLTON2-FsCut or ATCC 13032 pSen0996_8e pCLTON2-FsCut.

d) Detection of the fluorescence as a function of the level of secretion of Cutinase or the concentration of Cutinase on the trans-side of the cytoplasmic membrane (parameter variation)

Figure 4:
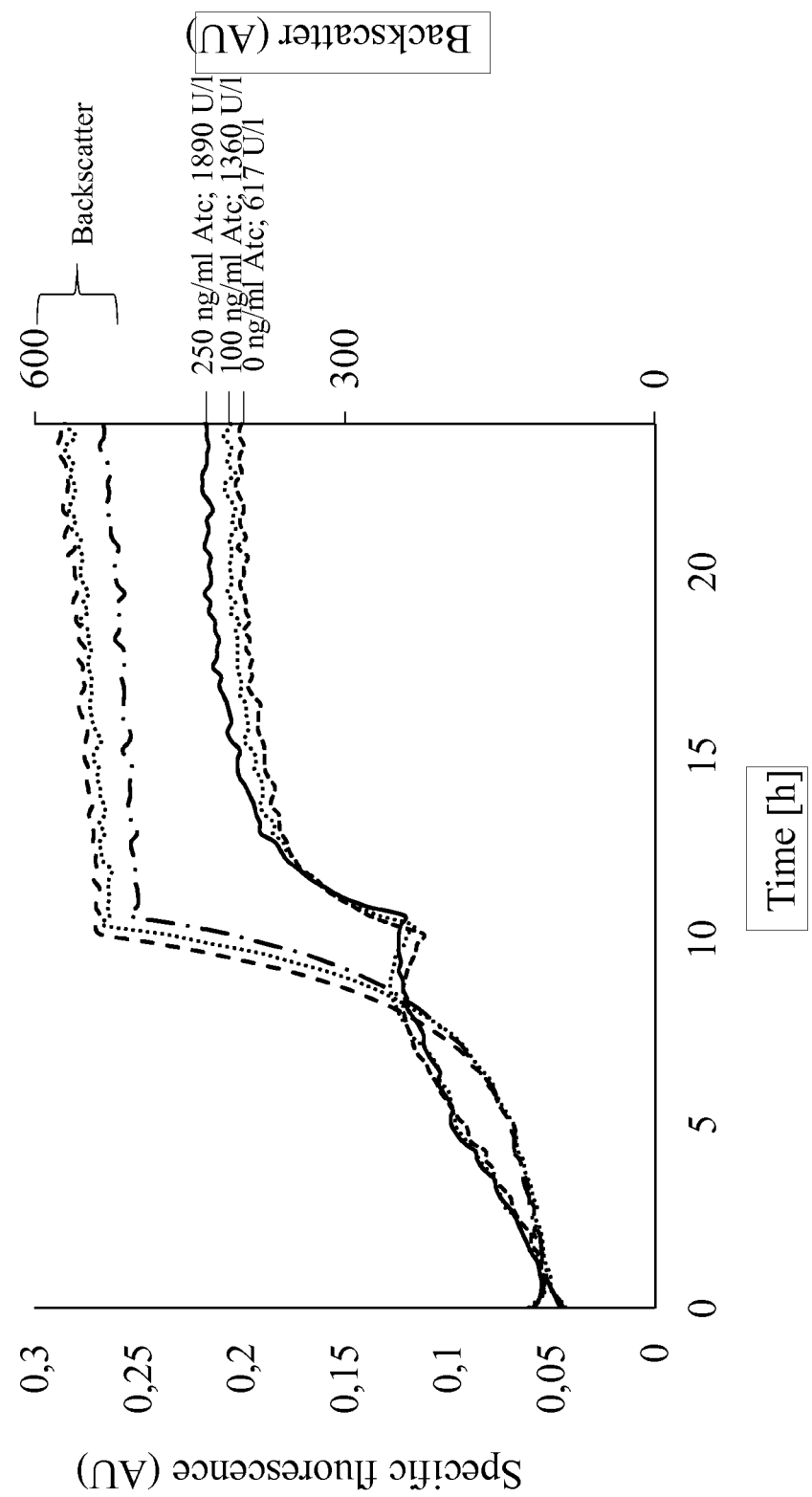
FIG. 4 shows the detection of the fluorescence as a function of the level of secretion of Cutinase or the concentration of Cutinase on the trans side of the cytoplasmic membrane in strain ATCC 13032 pSen0996_8 pCLTON2 (Example 3d)

The examination of in vivo fluorescence emission was carried out by culturing the cells of strain ATCC 13032 pSen0996_8 pCLTON2-FsCut with 0.8 ml CGXII medium (Keilhauer et al, 1993, J. Bacteriol. 175: 5595-603) in microtiter dimension (Flowerplate® MTP-48-B) in the Bio-Lector system (m2p-labs GmbH, 52499 Baesweiler, Germany). 3 cultures with cells of strain ATCC 13032 pSen0996_8 pCLTON2-FsCut were inoculated to an OD of 0.1 and cultured for 24 hours. After 4 hours the expression of Cutinase was induced by the addition of Anhydrotetracycline (ATc). ATc-concentrations were adjusted to 0, 100, 250 mM to cause different expression intensities. Every 10 minutes the cell densities of cultures and the fluorescence were measured. The fluorescence was excited with light of wavelength 485 nm, the fluorescence emission measurement of EYFP was carried out at 520/10 nm. The fluorescence of the cultures has been digitally recorded by means of the BioLection V.2.4.1.0 software. It was observed that the fluorescence emissions of cultures that have been induced differently also differs (FIG. 4). After 24 hours the cultures in the Flowerplate were centrifuged to pellet the cells and to obtain cell-free culture supernatants. 20 µl of each culture supernatant were used to quantify the enzymatic activity of the secreted Cutinase by means of a p-nitrophenylpalmitate (pNPP) assay. It was observed that higher activities of Cutinase in the culture supernatant induced by ATc concentrations which under these chosen culture conditions have to be considered as optimal correlate with higher fluorescence emissions.

e) Construction of vector pK19-pS en0996_8e pK19-pSen0996_8e was prepared by amplification of the cg0998-upstream region with genomic DNA of C. glutamicum ATCC13032 as template and primers 0998up-f (SEQ ID No. 42) and 0998up-r (SEQ ID No. 43), amplification of the cg0998-downstream region with genomic DNA of C. glutamicum ATCC13032 as template and primers 0998dw-f (SEQ ID No. 44) and 0998dw-r (SEQ ID No. 45), amplification of eyfp encoding sequence with pSen0996_8e as template and primers eyfp-ol-f (SEQ ID No. 46) and eyfp-ol-r (SEQ ID No. 47), subsequent overlap-extension PCR with PCR products of aforementioned PCR reactions as template and primers 0998up-f and 0998dw-r. Finally the product of overlap-extension PCR was phosphorylated with T4-polynucleotid kinase and ligated into SmaI cut plasmid pK19 (SEQ ID No. 48).

```
0998up-f:
GAAGAAACCGCCGAAACGTCAAGC

0998up-r:
CGATGCACGGTCCGGGTTCTC

0998dw-f:
GTTTAAAAGAGTTAATCTGCATCTAATCAAGTAGCC

0998dw-r:
GCCATCACGAATTGCCGAACGAG
```

-continued
eyfp-ol-f:
GAGAACCCGGACCGTGCATCGTAGAAGAAGGAGATATCATATGG eyfp-ol-r:
GCAGATTAACTCTTTTAAACTTATTACTTGTACAGCTCGTCCATGCCG The ligation mixture was used directly to transform *E. coli* XL1-blue and the selection of transformants was carried out on LB plates containing 50 µg/ml kanamycin and 100 µg/ml Xgal (5-Brom-4-chlor-3-indoxyl-(3-D-galactopyranosid) via blue/white sceening. 4 colonies were cultured each for plasmid preparations in a larger scale. After 16 h of cultivation these cultures were collected by centrifugation, the plasmid DNA was prepared and used for sequencing with primers M13uni(-43) (SEQ ID No. 49) and M13rev(-49) (SEQ ID No. 50). The sequence of the inserts showed 100% identity with the expected sequence. The resulting plasmid was named pK19-pSen0996_8e (SEQ ID No. 51).

M13uni(-43): AGGGTTTTCCCAGTCACGACGTT

M13rev(-49): GAGCGGATAACAATTTCACACAGG f) Construction of strains *C. glutamicum* ATCC 13032 gSen0996_8 and *C. glutamicum* MB001 gSen0996_8.

Competent cells of *C. glutamicum* strain ATCC 13032 and *C. glutamicum* MB001 gSen0996_8 were prepared as described by Tauch et al., 2002 (*Curr Microbiol.* 45(5) (2002), pages 362-7). These cells were transformed by electroporation with vector pK19-pSen0996_8e as described above. Because this vector cannot be replicated in *C. glutamicum*, colonies on kanamycin containing agar plates can only grow from those cells, which integrated the vector containing the pSen0996_8e sequence into their chromosome via homologous recombination. In a second homologous recombination the vector can be removed from the chromosome again, leaving solely the introduced pSen0996_8e sequence in the genome. To select on those cells, colonies grown on kanamycin containing agar plates are selected, cultivated in complex medium and plated on agar plates containing 10% saccharose. The vector pK19 contains a modified variant of the gene sacB from *Bacillus subtilis* encoding a levansucrase, which catalyzes reaction of saccharose to levan, the latter one being toxic for *C. glutamicum*. Thus colonies on saccharose containing agar can only grow from those cells, in which a second homologous recombination removed the integrated vector sequences, leaving solely the introduced pSen0996_8e sequence in the genome. Clones thus obtained were named ATCC 13032 gSen0996_8 and MB001 gSen0996_8. (Schäfer, A., Tauch, A., Jäger, W., Kalinowski, J., Thierbach, G., Pühler, A. (1994), Small mobilizable multipurpose cloning vectors derived from the *Escherichia coli* plasmids pK18 and pK19: selection of defined deletions in the chromosome of *Corynebacterium glutamicum*, Gene 145: 69-73).

g) Transformation of *C. glutamicum* ATCC 13032 gSen0996_8 and MB001 gSen0996_8 with pCLTON2-FsCut as an example of the variation of the genetic background of the bacterial strain.

Competent cells of the *C. glutamicum* strains ATCC 13032 gSen0996_8 and MB001 gSen0996_8 were prepared as described by Tauch et al., 2002 (*Curr Microbiol.* 45(5) (2002), pages 362-7). These cells were transformed by electroporation with vector pCL-TON2-FsCut as described above. Clones thus obtained were named ATCC 13032 gSen0996_8 pCLTON2-FsCut and MB001 gSen0996_8 pCLTON2-FsCut.

h) Detection of the fluorescence as a function of the level of secretion of Cutinase or the concentration of Cutinase on the trans-side of the cytoplasmic membrane.

Figure 6:
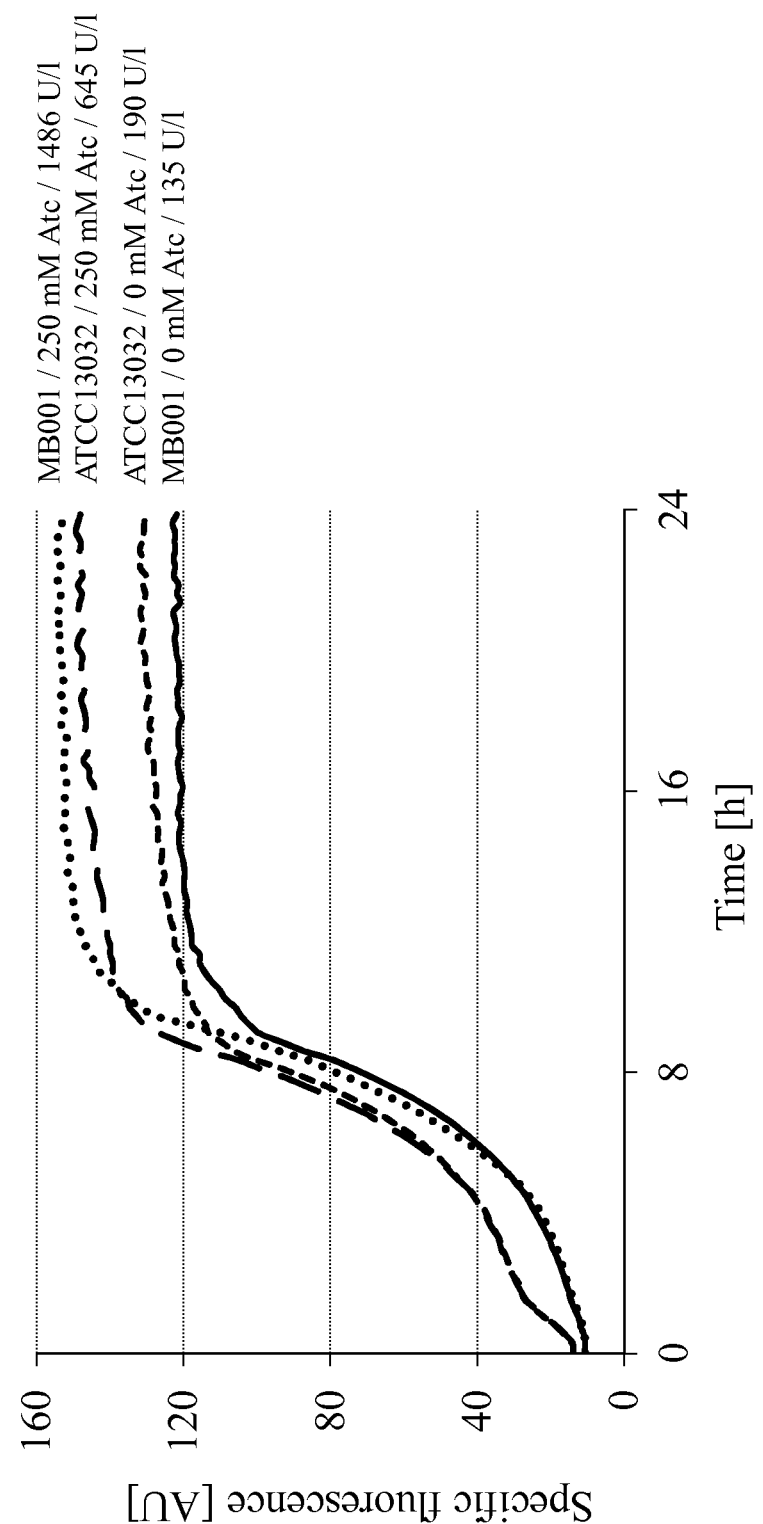
FIG. 6 shows the in vivo fluorescence as a function of the level of secretion of Cutinase or the concentration of Cutinase on the trans-side of the cytoplasmic membrane, wherein strains with a different genetic background (ATCC 13032 gSen0996_8 and MB001 gSen0996_8) have been used (Example 3f)).

The examination of in vivo fluorescence emission was carried out by culturing the cells of strains *C. glutamicum* ATCC 13032 pSen0996_8 pCLTON2-FsCut and MB001 gSen0996_8 pCLTON2-FsCut in 0.8 ml CGXII medium (Keilhauer et al, 1993, *J. Bacteriol.* 175: 5595-603) in microtiter dimension (Flowerplate® MTP-48-B) in the BioLector system (m2p-labs GmbH, 52499 Baesweiler, Germany). 3 cultures with cells of strain ATCC 13032 pSen0996_8 pCLTON2-FsCut and 3 cultures of strain MB001 gSen0996_8 pCLTON2-FsCut were inoculated to an OD of 0.1 and cultured for 24 hours. After 4 hours the expression of Cutinase was induced by the addition of Anhydrotetracycline (ATc). ATc-concentrations were adjusted to 0 and 250 mM to cause different expression intensities. Every 10 minutes the cell densities of cultures and the fluorescence were measured. The fluorescence was excited with light of wavelength 485 nm, the fluorescence emission measurement of EYFP was carried out at 520/10 nm. The fluorescence of the cultures has been digitally recorded by means of the BioLection V.2.4.1.0 software. It was observed that the fluorescence emissions of cultures that have been induced differently also differ and that the fluorescence emissions of cultures of different strains differ (FIG. 6). After 24 hours the cultures in the Flowerplate were centrifuged to pellet the cells and to obtain cell-free culture supernatants. 20 µl of each culture supernatant were used to quantify the enzymatic activity of the secreted Cutinase by means of a p-nitrophenylpalmitate (pNPP) assay. It was observed that higher activities of Cutinase in the culture supernatant correlate with higher fluorescence emissions, enabling differentiation of strains with different levels of secretion of Cutinase or different concentrations of Cutinase on the trans-side of the cytoplasmic membrane by optical analysis of the sensor signal.

i) Transformation of *C. glutamicum* ATCC 13032 gSen0996_8 with pCLTON2-FsCut(NprE) and pCLTON2-FsCut(Ywmc) as an example of the variation of the secretion-signal peptide.

Competent cells of the *C. glutamicum* strain ATCC 13032 gSen0996_8 were prepared as described by Tauch et al., 2002 (*Curr Microbial.* 45(5) (2002), pages 362-7). These cells were transformed by electroporation with vectors pCL-TON2-FsCut(NprE) and pCL-TON2-FsCut(Ywmc) as described above. These vectors are variants of pCLTON2-FsCut as described above, replacing the native secretion signal sequence of Cutinase by NprE- or Ywmc-signal sequences (SEQ ID No. 52, SEQ ID No. 53). Clones thus obtained were named ATCC 13032 gSen0996_8 pCLTON2-FsCut(NprE) and ATCC 13032 gSen0996_8 pCLTON2-FsCut(Ywmc).

j) Detection of the fluorescence as a function of the level of secretion of Cutinase or the concentration of Cutinase on the trans-side of the cytoplasmic membrane.

Figure 7:
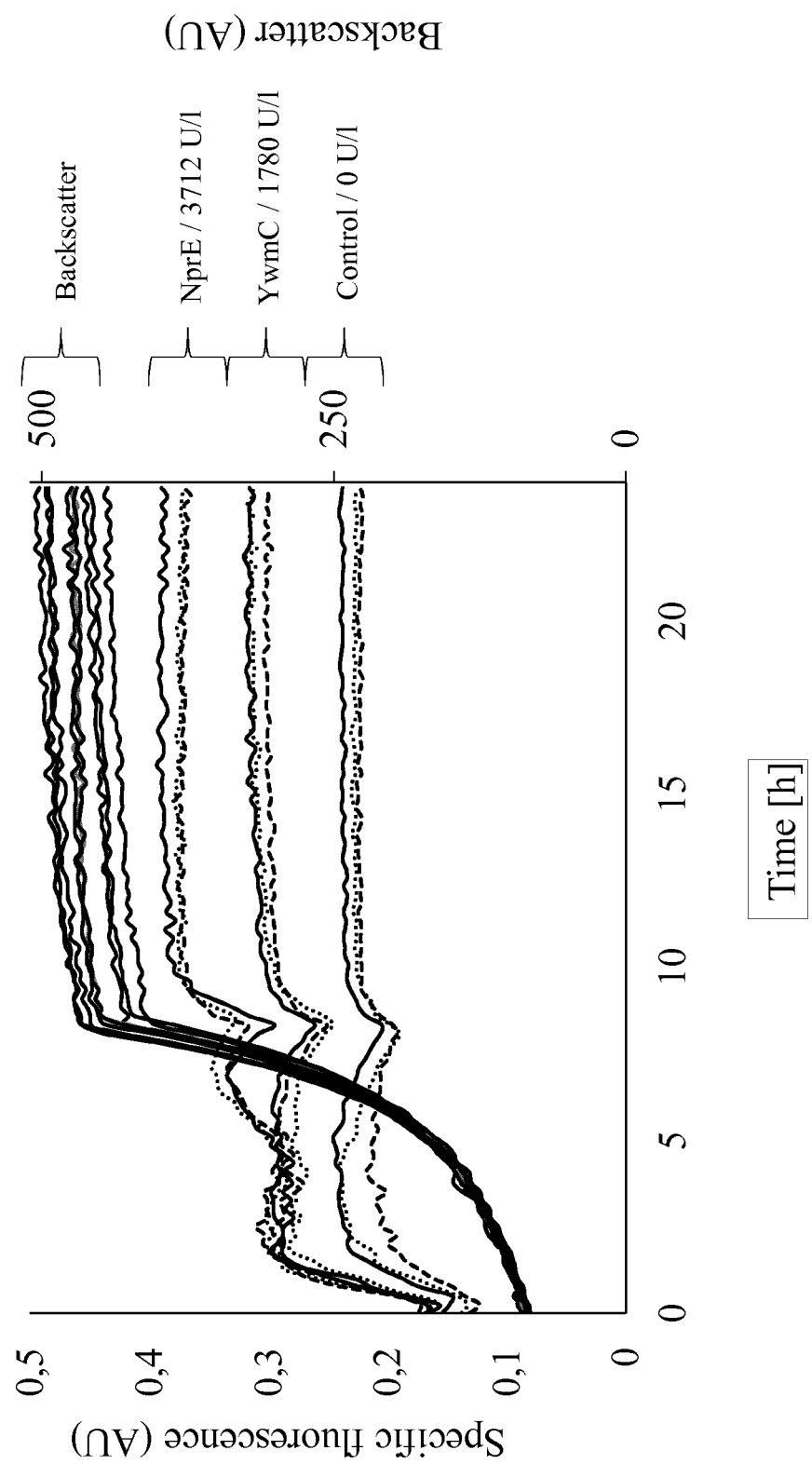
FIG. 7 show the in vivo fluorescence as a function of the level of secretion of Cutinase or the concentration of Cutinase on the trans-side of the cytoplasmic membrane, wherein different secretion-signal peptides have been used (Example 3i)).
Figure 8:
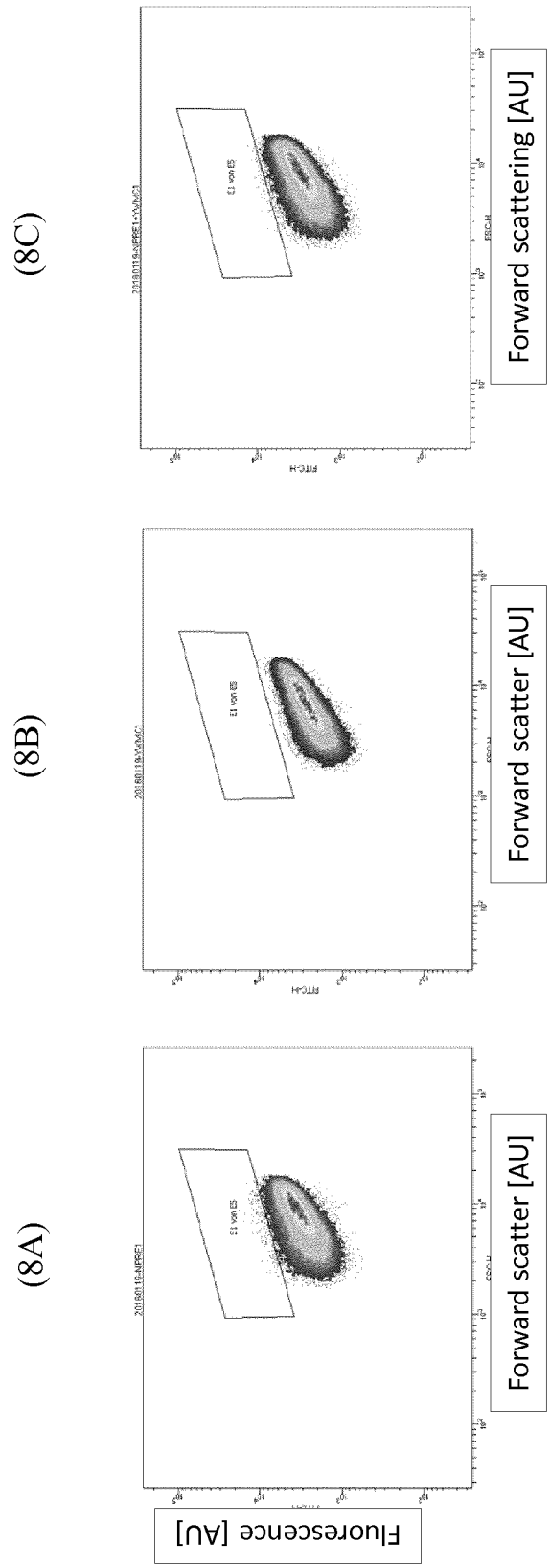
FIG. 8 shows the examination of the in vivo fluorescence emission carried out by fluorescence activated cell sorting (FACS) for strain C. glutamicum ATCC 13032 pSen0996_8 pCL-TON2-FsCut(NprE) (FIG. 8A), strain C. glutamicum ATCC 13032 pSen0996_8 pCLTON2-FsCut(Ywmc) (FIG. 8B) and a mixed culture containing both strains in a ratio of 1:1 (FIG. 8C) (Example 3k)).

The examination of in vivo fluorescence emission was carried out by culturing the cells of strains *C. glutamicum* ATCC 13032 pSen0996_8 pCLTON2-FsCut(NprE) and ATCC 13032 pSen0996_8 pCLTON2-FsCut(Ywmc) in 0.8 ml CGXII medium (Keilhauer et al, 1993, *J. Bacteriol.* 175: 5595-603) in microtiter dimension (Flowerplate® MTP-48-B) in the BioLector system (m2p-labs GmbH, 52499 Baesweiler, Germany). 3 cultures with cells of strain ATCC 13032 pSen0996_8 pCLTON2-FsCut(NprE) and 3 cultures with cells of strain ATCC 13032 pSen0996_8 pCLTON2-FsCut(Ywmc) were inoculated to an OD of 0.1 and cultured for 24 hours. After 4 hours the expression of Cutinase was induced by the addition of 250 mM Anhydrotetracycline (ATc). Every 10 minutes the cell densities of cultures and the fluorescence were measured. The fluorescence was excited with light of wavelength 485 nm, the fluorescence emission measurement of EYFP was carried out at 520/10 nm. The fluorescence of the cultures has been digitally recorded by means of the BioLection V.2.4.1.0 software. It was observed that the fluorescence emissions of strains expressing Cutinase fused to different secretion-signal peptides also differ (FIG. 7). After 24 hours the cultures in the Flowerplate were centrifuged to pellet the cells and to obtain cell-free culture supernatants. 20 µl of each culture supernatant were used to quantify the enzymatic activity of the secreted Cutinase by means of a p-nitrophenylpalmitate (pNPP) assay. It was observed that higher activities of Cutinase in the culture supernatant correlate with higher fluorescence emissions.

k) Additionally, the examination of in vivo fluorescence emission was carried out by fluorescence activated cell sorting (FACS). Cultures of strain C. glutamicum ATCC 13032 pSen0996_8 pCLTON2-FsCut(NprE), strain C. glutamicum ATCC 13032 pSen0996_8 pCLTON2-FsCut (Ywmc) and mixed cultures containing both strains in a ratio of 1:1 and 1:100 (NprE:Ywmc) were inoculated in 0.8 ml CGXII medium (Keilhauer et al, 1993, J. Bacteriol. 175: 5595-603) and cultivated in microtiter dimension (Flowerplate® MTP-48-B) in the BioLector system (m2p-labs GmbH, 52499 Baesweiler, Germany). After 4 hours expression of Cutinase was induced by the addition of 250 mM Anhydrotetracycline (ATc). After further incubation for 10 hours the optical properties of all cultures were analyzed. It was observed that the fluorescence emissions of strains expressing Cutinase fused to different secretion-signal peptides also differ (FIGS. 8A and 8B). The mixed cultures containing cells of both strains ATCC 13032 pSen0996_8 pCL-TON2-FsCut(NprE) and ATCC 13032 pSen0996_8 pCLTON2-FsCut(Ywmc) (FIG. 8C) were used to sort cells with a FACS Aria cell sorter III from Becton Dickinson (Becton Dikinson BD, 1 Becton Drive, Franklin Lakes, N.J. USA). The FACS settings were 200 as threshold limits for the "forward scatter" and "side scatter" in an electronic gain of 16 mV for the "forward scatter" (ND Filter 1.0) and 269 mV for the "side scatter". Excitation of EYFP was carried out at a wavelength of 488 nm and detection by means of "parameter gain" PMT at 400 mV with an emission band path filter 530/30 nm connected upstream. 44 cells of each mixed culture were sorted out with respect to the EYFP fluorescence and stored in 96-well microtiter plates (each well containing 200 µl CGXII medium) using the FACS Aria cell sorter III (FIG. 8C). After 16 h of cultivation these cultures were collected by centrifugation and the plasmid DNA was prepared. The plasmid preparations were sequenced with primers pEKEx2-fw (SEQ ID No. 54) and pEKEx2-ry (SEQ ID No. 55). In case of the 1:1 mixed culture it was observed that 44 of 46 sorted cells were ATCC 13032 pSen0996_8 pCLTON2-FsCut(NprE) and 2 of 46 cells were ATCC 13032 pSen0996_8 pCLTON2-FsCut (Ywmc). In case of the 1:100 mixed culture it was observed that 16 of 46 sorted cells were ATCC 13032 pSen0996_8 pCLTON2-FsCut(NprE) and 30 of 46 cells were ATCC 13032 pSen0996_8 pCLTON2-FsCut(Ywmc).

pEKEx2-fw: CTCGTATAATGTGTGGAATTG pEKEx2-rv: CAGACCGCTTCTGCGTTC

1) Mutagenesis of C. glutamicum ATCC 13032 pSen0996_8 pCLTON2-FsCut(NprE) Strain C. glutamicum ATCC 13032 pSen0996_8 pCLTON2-FsCut(NprE) was grown overnight in "Difco Brain Heart Infusion" medium (Difco, Becton Dikinson B D, 1 Becton Drive, Franklin Lakes, N.J. USA) at 30° C. and 5 ml of this culture were combined with 0.1 ml of a solution of 0.5 mg of N-methyl-N-nitroso-N'-nitroguanidine dissolved in 1 ml dimethyl sulfoxide. This culture was shaken at 30° C. for 15 minutes. Subsequently, the cells were centrifuged at 4° C. and 2,500×g and were resuspended in 5 ml of 0.9% NaCl. The centrifugation step and the resuspension step were repeated. 7.5 ml of 80% glycerol were added to the cell suspension thus obtained and aliquots of this mutant cell suspension were stored at −20° C. 200 µl of this cell suspension were used to inoculate 0.8 ml CGXII medium (Keilhauer et al, 1993, J. Bacteriol. 175: 5595-603). Incubation was done in microtiter dimension (Flowerplate® MTP-48-B) at 30° C. and 1000 rpm. After 4 hours expression of Cutinase was induced by the addition of 250 mM Anhydrotetracycline (ATc). After further incubation for 10 hours the optical properties of all cultures were analyzed by FACS as described above. 8,000,000 cells were analyzed with an analysis speed of 10,000 particles per second and 384 cells were sorted out with respect to the EYFP fluorescence and stored in 96-well microtiter plates (each well containing 200 µl CGXII medium) using the FACS Aria cell sorter III. The plates were cultured for 16 h at 1000 rpm and 30° C. 336 of the 384 cells that have been deposited grew to cultures. These were used to inoculate fresh CGXII medium and cultured for 24 h at 1,000 rpm and 30° C. After 4 hours expression of Cutinase was induced by the addition of 250 mM Anhydrotetracycline (ATc). After 24 hours the cultures were centrifuged to pellet the cells and to obtain cell-free culture supernatants. 20 µl of each culture supernatant were used to quantify the enzymatic activity of the secreted Cutinase by means of a p-nitrophenylpalmitate (pNPP) assay. It was observed that compared to ATCC 13032 pSen0996_8 pCLTON2-FsCut(NprE) as the starting and control strain, enhanced enzymatic activity of secreted Cutinase was measured in the culture supernatants of the isolated strains.

| Sequences |
|---|
| SEQ ID No. 01 |
| gcgggtctgc cacatttgct gaaaagtacc agttgcaagg tgtggtgttg gagcttcata    60 |
| accaggttgg gcaaaaggga tgaatccctg gttgtggtgg ggctcctgaa aagtactcat   120 |
| agactctatt gtggagtgtt gaggctgata agtgaatggg ggaaagccct gaaaaggtgg   180 |
| cgttcagggt cttccctgat g                                             201 |
|  |
| SEQ ID No. 02 |
| accttaaatt catcgcctac aaccttttgt aggtaagaat ttaacaagag ccagttatct    60 |
| tctcttaaaa tgaggaggta actggcttct ttatgcttaa gaggtgttag cataagtgaa   120 |
| atatgttcca acgcgtggac gtcttaattg ggaggaagtc tgtcacggac tggaagacga   180 |
| aaagggtatc gatg                                                     194 |

-continued

| Sequences | |
|---|---|
| SEQ ID No. 03 | |
| gggaacccat tcgcagcggg ttcgaaaatg tcgatgatta aaccactaaa gagctcacag | 60 |
| gaagtgttca gactacttag agtgacgccc cagccacagg gttcataatc aaatcatg | 118 |
| | |
| SEQ ID No. 04 | |
| accagcgacg ccgccgatcc atttgtcggt ggtgcttcgg gcgagtcgtc gagattgtgc | 60 |
| tgggaaagtc atcgggatca agctccttta tggctgattg agttttttctt tcttcttcaa | 120 |
| tcatcgccaa taagaaccta gagcacatcg gggatttccc ctctcctaac ccctaaaaac | 180 |
| ccctgagaaa acgctccaag taaacccttta cagctc | 216 |
| | |
| SEQ ID No. 05 | |
| atggttgatg tgttttttggt cgatgaccac tccgtgtttc gctccggcgt caaagcagaa | 60 |
| ctaggcaacg ccgtcacagt agtcggcgaa gcagggacgg tggccgacgc cgtagccggc | 120 |
| atcaaggcaa gcaaaccaga ggtagtgctt ctcgacgtcc acatgcccga cggcggcggc | 180 |
| ctcgcagtgc tccagcagat caacgactcc gatgtggaca ccattttctt ggcactcagt | 240 |
| gtctctgatg ctgcggaaga tgtcatcgcc atcatccgtg gcggtgccag gggatacgtt | 300 |
| accaaatcaa tctccggtga agaactcatc gaagccatca accgcgtgaa atccggcgac | 360 |
| gcattcttct caccacgcct ggcaggcttc gtcctcgacg ccttcgccgc cccgattcc | 420 |
| gcagctggcg caggcattgt cgacgcaccc gaaaaagacg ccgccgtaga atccggaaaa | 480 |
| atcctcgacg acccagttgt cgacgccctc acccgccgcg aactcgaagt cctccgccta | 540 |
| ctagcccgcg gctacaccta caaagaaatc ggcaaagaac tgttcatttc cgtcaaaacc | 600 |
| gtggaaaccc acgcctcaaa cattctgcgg aaacccaac aatccaaccg ccacgcgttg | 660 |
| acccggtggg ctcactcgag ggatcttgac taa | 693 |
| | |
| SEQ ID No. 06 | |
| atgttccaac gcgtggacgt cttaattggg aggaagtctg tcacggactg gaagacgaaa | 60 |
| agggtatcga tgaaaatttt agttgttgat gacgagcaag ctgtacgtga ctccttgcga | 120 |
| cgttcccttt cgttcaacgg atacaacgtt gttctcgcag aagacggcat ccaagcacta | 180 |
| gagatgattg acaaggaaca gcctgctttg gtgatcctcg atgtcatgat gcctggtatg | 240 |
| gacggacttg aggtctgtcg ccaccttcgc agcgaaggcg atgatcggcc aattcttatt | 300 |
| cttactgccc gcgataatgt ttctgatcgt gttggtggcc tcgatgcagg cgcagatgac | 360 |
| tatttggcta aaccatttgc tcttgaagag ctgttggcgc gcgtccgttc actggtgcgt | 420 |
| cgctctgcag tggaatcaaa tcagagttcc agcattgaac aggctctatt atcttgtggc | 480 |
| gatttgacgc ttgacccaga aagtcgagat gtctaccgca acgacgcgc catcagcctt | 540 |
| actcgaacag agttcgcgct cctgcaattg ctcctcaaaa accaaaggaa agtgctcact | 600 |
| cgcgcccaga ttttggaaga ggtatggggc tgcgatttcc ccacttcagg caatgccctc | 660 |
| gaggtctaca ttgataccct cgacgcaag actgaattgg aaggagaaga ccgctgatc | 720 |
| catacagtac gaggagtcgg atacgtcctg cgagagaccg ctccgtga | 768 |
| | |
| SEQ ID No. 07 | |
| atggataact atcgtgatga aaacagaacg aaaggtaatg agaatgaggt ctttttaacg | 60 |
| aaagagaacg atcagagcgc ctcctactcg gcccgcaatg tcattcatga tcaggagaag | 120 |
| aaaaaacgag gattcggatg gttcagaccg ttgcttggcg gagtgatcgg cggcagtctt | 180 |
| gctcttggca tttacacgtt tacaccgctt ggtgaccatg attctcagga cactgcaaaa | 240 |
| caatcatcca gccagcagca aacgcaatct gttacagcaa caagcacctc ctctgaatct | 300 |
| aaaaaaagct caagcagctc atctgcattc aagagcgagg actcttctaa aatctcagat | 360 |
| atggtagaag accttttcacc agcagattgtc ggtattacaa atcttcaggc acaatcaaat | 420 |
| agctctttgt tcggctctag ttcttctgat tccagcgaag atacagaaag cggttcaggg | 480 |
| tcaggtgtca ttttcaaaaa agagaatggc aaggcttata tcattacaaa taaccacgtc | 540 |
| gtagaagggg catcatcact gaaggtatct ttatatgacg gcactgaggt tactgcaaag | 600 |
| ctggtaggca gtgactcgtt aactgattta gccgtcctcc aaatcagtga tgaccacgtc | 660 |
| acaaaagtgg caaacttcgg tgattcatct gatcttagaa caggcgagac cgttattgcg | 720 |
| attggggatc cgcttggaaa agacctgtcc cgcacagtaa cacaaggaat tgtaagcggc | 780 |
| gtggacagaa cggtttcaat gtctacatca gccggcgaaa cgagcattaa cgtcattcag | 840 |
| acagacgcag caattaatcc aggtaacagc ggcggtcctt tgttaaatac agacggcaaa | 900 |
| attgtcggca ttaacagtat gaaaatcagt gaggatgatg ttgagggtat cggattcgcc | 960 |
| attccaagca atgacgtaaa accgattgct gaagaattgc tgtctaaagg acaaattgaa | 1020 |
| cgtccatata tcggtgtcag catgcttgat ctagagcaaa caggcaaaaa ttaccaagaa | 1080 |
| ggcacactcg gcctgttcgg cagccagctg aataaaggcg tttacatccg tgaggtcgct | 1140 |
| tcaggctctc ctgctgaaaa ggccggatta aaagcggagg atattatcat cggcctaaaa | 1200 |
| ggtaaagaaa ttgatacagg cagtgaattg cgcaatatct tatataaga cgcaaagatc | 1260 |
| ggtgataccg ttgaagtgaa aattctccga aacggcaaag aaatgacgaa aaaaattaaa | 1320 |
| ctggatcaaa agaagagaa aacttcgtaa | 1350 |
| | |
| SEQ ID No. 08 | |
| ttgtcataca ccatttatct agttgaagat gaggataacc tgaatgaact gctgacgaag | 60 |
| tatttagaga atgagggctg gaacattaca tcttttacga aaggtgaaga cgccagaaag | 120 |
| aaaatgcac cgtctcccca cctatggatt ctcgatatca tgtgccgga taccgacggc | 180 |
| tatacattaa taaagaaat caaggcgaaa gatcctgacg tgccggtcat ttttatttcc | 240 |
| gcccgagatg cggatattga cagtgtgctt ggcttagagc ttggcagcaa tgactacatt | 300 |
| tcaaagccgt ttttgccgcg ggagctgatt atccgtgtgc aaaagctgct gcagctcgta | 360 |
| tataaggaag ctcctcctgt ccaaaaaaat gaaattgccg tctcctcgta tcgggtcgct | 420 |
| gaagacgccc gcgaggtcta tgacgaaaac gggaatatca tcaatttgac gtcaaaggaa | 480 |

-continued

| Sequences | |
|---|---|
| tttgatctgc tgctattatt tatccatcat aaagggcatc catactctcg tgaggatatc | 540 |
| ctcctaaaag tgtggggaca tgactacttc ggaacagacc gggtcgttga tgatctcgtc | 600 |
| cggagactgc gcagaaagat gcctgaattg aaggtggaga cgatttacgg tttcggctac | 660 |
| aggatgatgt catcatga | 678 |

SEQ ID No. 09

| | |
|---|---|
| tccggtgcga gatacgactc cggtcttata taaaaatcaa tctctgattc gttttgcata | 60 |
| tcttccaact tgtataagat gaagacaagg aaaacgaaag gaggatctgc atg | 113 |

SEQ ID No. 10

| | |
|---|---|
| gtgattcgag tattattgat tgatgatcat gaaatggtca gaatgggggct cgcggctttt | 60 |
| ttggaggcgc agcccgatat tgaagtcatc ggcgaagcat cggacgggcag cgaaggtgtt | 120 |
| cggcttgctg tggaactgtc gcctgatgtc attttaatgg accttgtcat ggagggcatg | 180 |
| gatggcattg aagctacaaa gcaaatttgc cgggagcttt ccgacccgaa aattattgtg | 240 |
| ctcactagct tcattgatga tgacaaagtg tacccggtta ttgaagctgg cgcgctcagc | 300 |
| tatctgttga aaacctcaaa agcggcagaa atcgccgatg ccatccgcgc gcaagcaag | 360 |
| ggagagccga agctggagtc aaaagtggcg ggaaaagtat tatccaggct gcgccactca | 420 |
| ggtgaaaacg cgctcccgca tgaatcgctt acaaaacggg agctcgaaat actctgcctg | 480 |
| atcgcagaag gaaagacaaa caaagaaata ggcgaggaac tgtttattac gattaaaaca | 540 |
| gtcaaaacac atattacgaa tattttatca aagctggatg tcagtgaccg gacgcaggcg | 600 |
| gcggtgtacg cacaccgaaa tcatctcgtg aattag | 636 |

SEQ ID No. 11

| | |
|---|---|
| atgacaaaaa aacagcttct cggattgatc attgctttat tcggcatcag tatgttttg | 60 |
| caaattatcg gaataggcga tctgctgttt tggccgctct tttttctgat tgccggctat | 120 |
| ttccttaaaa aatattcccg tgattggctt ggctccgtca tgtatatctt tgccgcgttt | 180 |
| ctattttga aaaacctctt cagcatcacc tttaattat tcggctatgc gtttgccgca | 240 |
| tttctgattt acgccggcta caggctatc aaagggaagc cgatatttga accgaatgag | 300 |
| aaacaggtca atctcaataa aaagaacat catgagccgc caaaagatgt aaaacatccc | 360 |
| gacatgcgca gcttttttat cggtgagctg caaatgatga agcagccgtt tgacctgaac | 420 |
| gatttaaatg tctctggttt tatcggtgat atcaaaatcg atttatctaa agcgatgatt | 480 |
| cccgagggag aaagtacaat cgtcattagc ggagtcattg gtaacgttga tatttatgta | 540 |
| ccatcggacc ttgaagtggc tgtcagctcg gctgttttta taggagacat taatctgatc | 600 |
| ggctcgaaga aaagcggatt aagcacgaag gtatatgccg cgtcaactga ttttagcgag | 660 |
| tcaaagcgcc gggtaaaagt gtccgtttcc ttatttatcg gtgatgtgga tgtgaagtac | 720 |
| gtatga | 726 |

SEQ ID No. 12

| | |
|---|---|
| atgagaaaaa aatgcttgc cagcctccaa tggcgcgcca tccgcatgac aacgggaatc | 60 |
| agcctgctcc ttttttgtttg cctgatttcc tttatgatgt tttactatcg gctcgatccg | 120 |
| cttgttttgc tgtcatcaag ctggttcgga attccgttta tcctgatttt gcttctgatc | 180 |
| agcgtgaccg tcggtttcgc ctcagggtat atgtacggca accggttgaa gacaaggatt | 240 |
| gatacattaa ttgaatccat tttaaccttt gaaaacggca atttcgctta tcggataccg | 300 |
| ccgctcggtg atgatgaaat cggcctggct gctgatcagc tgaacgaaat ggcgaagcgc | 360 |
| gtggagcttc aagtcgcatc cctccagaaa cttttccaatg aacgtgcgga atggcaggct | 420 |
| caaatgaaga agtcggttat ctcagaagaa cgccagcgat tggccagaga tcttcatgat | 480 |
| gcggtcagcc agcagctctt tgccatatcg atgatgacat cagccgtgct ggaacatgtc | 540 |
| aaggatgctg atgacaaaac agtcaagcgg atcaggatgg tcgagcatat ggcaggcgaa | 600 |
| gcccaaaatg agatgagggc gctgctgctc catttacggc ctgttaccct tgaaggaaaa | 660 |
| gggctgaagg agggccttac ggagcttttg gacgagttcc gaaaaaagca gccgattgat | 720 |
| attgagtggg atatacagga cacagcgata tccaagggtg ttgaagacca cttgttcaga | 780 |
| atcgtgcagg aggccctttc aaacgtattt agacattcaa aagcgtcaaa agtaaccgtg | 840 |
| attctgggca taaagaacag ccagtccgt ctgaaggtga ttgataatgg aaaaaggctttt | 900 |
| aaaatggacc aggtgaaagc ctcctcatac ggcttgaatt ctatgaaaga acgtgcaagt | 960 |
| gaaatcggcg gtgtcgccga agtgatttca gtagaaggaa aaggcactca aatcgaagtg | 1020 |
| aaggtcccga ttttttccgga agaaaaagga gagaacgaac gtgattcgag tattattgat | 1080 |
| tga | 1083 |

SEQ ID No. 13

| | |
|---|---|
| ggacatcgag aactctcggg gttcggcgaa cgttatctca gtggaatctc agtccacgcg | 60 |
| cgcaacctag ttgtgcagtt actgttgaaa gccacaccca tgccagtcca cgcatg | 116 |

SEQ ID No. 14

| | |
|---|---|
| atgtggtggt tccgccgccg agaccggcg ccgctgcgcg ccaccagctc attatccctg | 60 |
| cggtggcggt tcatgctgct ggcgatgtcc atggtcgcga tggtggttgt gctgatgtcg | 120 |
| ttcgccgtct atgcggtgat ctcggccgcg ctctacagcg acatcgacaa ccaactgcag | 180 |
| agccgggcgc aactgctcat gccagtggc tcgctgcgga ctgatccggg taaggcaatc | 240 |
| gagggtaccg cctattcgga tgtcaacgcg atgctggtca accccggcca gtccatctac | 300 |
| accgctcaac agccgggcca gacgctgccg gtcggtgctg ccgagaaggc ggtgatccgt | 360 |
| ggcgagttgt tcatgtcgcg gcgcaccacc gccgaccaac gggtgcttgc catccgtctg | 420 |
| accaacggta gttcgctgct gatctccaaa agtctcaagc ccaccgaagc agtcatgaac | 480 |
| aagctgcgtt gggtgctatt gatcgtgggt tggcggtgc tgccgtgggcc | 540 |
| gggggatgg tcacccgggc cgggctgagg ccgtggggcc gcctcaccga agcggccgag | 600 |
| cgggtgcgc gaaccgacga cctgcggccc atcccgtct tcggcagcga cgaattggcc | 660 |
| aggctgacag aggcattcaa tttaatgctg cgggcgctgg ccgagtcacg ggaacggcag | 720 |
| gcaaggctgg ttaccgacgc cggacatgaa ttgcgtaccc cgctaacgtc gctgcgcacc | 780 |
| aatgtcgaac tcttgatggc ctcgatggcc ccgggggctc cgcggctacc caagcaggag | 840 |

-continued

| Sequences | |
|---|---|
| atggtcgacc tgcgtgccga tgtgctggct caaatcgagg aattgtccac actggtaggc | 900 |
| gatttggtgg acctgtcccg aggcgacgcc ggagaagtgg tgcacgagcc ggtcgacatg | 960 |
| gctgacgtcg tcgaccgcag cctggagcgg gtcaggcggc ggcgcaacga tatccttttc | 1020 |
| gacgtcgagg tgattgggtg gcaggtttat ggcgataccg ctggattgtc gcggatggcc | 1080 |
| cttaacctga tggacaacgc cgcgaagtgg agcccgccgg gcggccacgt gggtgtcagg | 1140 |
| ctgagccagc tcgacgcgtc gcacgctgag ctggtggttt ccgaccgcgg cccgggcatt | 1200 |
| cccgtgcagg agcgccgtct ggtgtttgaa cggttttacc ggtcggcatc ggcacggggc | 1260 |
| ttgccgggtt cgggcctcgg gttggcgatc gtcaaacagg tggtgctcaa ccacggcgga | 1320 |
| ttgctgcgca tcgaagacac cgacccaggc ggccagcccc tggaacgtc gatttacgtg | 1380 |
| ctgctccccg gccgtcggat gccgattccg cagcttcccg gtgcgacggc tggcgctcgg | 1440 |
| agcacggaca tcgagaactc tcggggttcg gcgaacgtta tctcagtgga atctcagtcc | 1500 |
| acgcgcgcaa cctag | 1515 |
| SEQ ID No. 15 | |
| atggaactcc tcggcggacc ccgggttggg aatacggaat cgcaactttg cgttgccgac | 60 |
| ggtgacgact tgccaactta ttgcagtgca aattcggagg atctcaatat cacgaccatc | 120 |
| acgaccttga gtccgaccag catgtctcat ccccaacagg tccgcgatga ccagtgggtg | 180 |
| gagccgtctg accaattgca gggcaccgcc gtattcgacg ccaccgggga caaggccacc | 240 |
| atgccgtcct gggatgagct ggtccgtcag cacgccgatc gggtgtaccg gctggcttat | 300 |
| cggctctccg gcaaccagca cgatgccgaa gacctgaccg aggagacctt tatcagggtg | 360 |
| ttccggtcgg tccagaatta ccagccgggc accttcgaag gctggctaca ccgcatcacc | 420 |
| accaacttgt tcctggacat ggtccgccgc cgggctcgca tccggatgga ggcgttaccc | 480 |
| gaggactacg accgggtgcc cgccgatgag cccaacccg agcagatcta ccacgacgca | 540 |
| cggctgggac ctgacctgca ggctgccttg gcctcgctgc ggcccggagtt tcgtgccgcg | 600 |
| gtggtgctgt gtgacatcga gggtctgtcg tacgaggaga tcggcgccac actgggcgtg | 660 |
| aagctcggga cggtacgtag ccggatacac cgcggacgcc aggcactgcg ggactacctg | 720 |
| gcagcgcacc ccgaacatgg cgagtgcgca gttcacgtca acccagttcg ctga | 774 |
| SEQ ID No. 16 | |
| gtaaattacc gtcagattct cctgagtttc cgctatggga atattattac cgttgccgcc | 60 |
| tgctgcagga ttatatcagc ggtatgaccg acctctatgc gtgggatgaa taccgacgtc | 120 |
| tgatggccgt agaacaataa ccaggctttt gtaaagacga caataaatt tttaccttt | 180 |
| gcagaaactt tagttcggaa cttcaggcta taaaacgaat ctgaagaaca cagcaatttt | 240 |
| gcgttatctg ttaatcgaga ctgaaatacc tg | 272 |
| SEQ ID No. 17 | |
| atgaataaaa tcctgttagt tgatgatgac cgagagctga cttccctatt aaaggagctg | 60 |
| ctcgagatgg aaggcttcaa cgtgattgtt gcccacgatg gggaacaggc gcttgatctt | 120 |
| ctggacgaca gcattgattt acttttgctt gacgtaatga tgccgaagaa aaatggtatc | 180 |
| gacacattaa aagcacttcg ccagacacac cagacgcctg tcattatgtt gacggcgcgc | 240 |
| ggcagtgaac ttgatcgcgt tctcgccttt gagctgggca cagatgacta tctcccgaaa | 300 |
| ccgtttaatg atcgtgagct ggtggcacgt attcgcgcga tcctgcgccg ttcgcactgg | 360 |
| agcgagcaac agcaaaacaa cgacaacggt tcaccgacac tggaagttga tgccttagtg | 420 |
| ctgaatccag gccgtcagga agccagcttc gacgggcaaa cgctggagtt aaccggtact | 480 |
| gagtttaccc tgctctattt gctggcacag catctggatc aggtggttc ccgtgaacat | 540 |
| ttaagccagg aagtgttggg caaacgcctg acgcctttcg accgcgctat tgatatgcac | 600 |
| atttccaacc tgcgtcgtaa actgccggat cgtaaagatg gtcacccgtg gtttaaaacc | 660 |
| ttgcgtggtc gcggctatct gatggtttct gcttcatga | 699 |
| SEQ ID No. 18 | |
| gtgagcaagg gcgaggagct gttcaccggg gtggtgccca tcctggtcga gctggacggc | 60 |
| gacgtaaacg gccacaagtt cagcgtgtcc ggcgagggcg agggcgatgc cacctacggc | 120 |
| aagctgaccc tgaagttcat ctgcaccacc ggcaagctgc ccgtgccctg gcccaccctc | 180 |
| gtgaccacct tcggctacgg cctgcagtgc ttcgcccgct accccgacca catgaagcag | 240 |
| cacgacttct tcaagtccgc catgcccgaa ggctacgtcc aggagcgcac catcttcttc | 300 |
| aaggacgacg gcaactacaa gacccgcgcc gaggtgaagt tcgagggcga caccctggtg | 360 |
| aaccgcatcg agctgaaggg catcaacttc aaggaggacg gcaacatcct ggggcacaag | 420 |
| ctggagtaca actacaacag ccacaacgtc tatatcatgg ccgacaagca gaagaacggc | 480 |
| atcaaggtga acttcaagat ccgccacaac atcgagggcg acagcgtgca gctcgccgac | 540 |
| cactaccagc agaacacccc catcggcgac ggccccgtgc tgctgcccga caaccactac | 600 |
| ctgagctacc agtccgccct gagcaaagac cccaacgaga gcgcgatca catggtcctg | 660 |
| ctggagttcg tgaccgccgc cgggatcact ctcggcatgg acgagctgta caagtaataa | 720 |
| SEQ ID No. 19 | |
| VSKGEELFTG VVPILVELDG DVNGHKFSVS GEGEGDATYG KLTLKFICTT GKLPVPWPTL | 60 |
| VTTFGYGLQC FARYPDHMKQ HDFFKSAMPE GYVQERTIFF KDDGNYKTRA EVKFEGDTLV | 120 |
| NRIELKGINF KEDGNILGHK LEYNYNSHNV YIMADKQKNG IKVNFKIRHN IEGGSVQLAD | 180 |
| HYQQNTPIGD GPVLLPDNHY LSYQSALSKD PNEKRDHMVL LEFVTAAGIT LGMDELYK | 238 |
| SEQ ID No. 20 | |
| gcggtcgacg ggtaaacgtg ggatataaa | 29 |
| SEQ ID No. 21 | |
| gcgcatatga tatctccttc ttctagcggg tctgccacat ttgctg | 46 |
| SEQ ID No. 22 | |
| gcgccgcgga ctaataacgt aacgtgactg gcaagag | 37 |

-continued

| Sequences | |
|---|---|
| SEQ ID No. 23 | |
| gcgagatctt ctgcctcgtg aagaaggtgt tgctgac | 37 |
| | |
| SEQ ID No. 24 | |
| gtcgccgtcc agctcgacca ggatg | 25 |
| | |
| SEQ ID No. 25 | |
| cgggaagcta gagtaagtag ttcg | 24 |
| | |
| SEQ ID No. 26 | |
| gcggtcgacg agctgtaagg gtttacttg | 29 |
| | |
| SEQ ID No. 27 | |
| gcgcatatga tatctccttc ttctaaccag cgacgccgcc gatcc | 45 |
| | |
| SEQ ID No. 28 | |
| gaatttaaca agagccagtt atcttctctt aaaatgagga ggtaactggc ttctttatgc | 60 |
| ttaagaggtg ttagcataag tgaaatatgt tccaacgcgt ggacgtctta attgggagga | 120 |
| agtctgtcac ggactggaag acgaaaaggg tatcgatgaa aatttagtt gttgatgacg | 180 |
| agcaagctgt acgttaatct atcgcgccgt cagctcccgt tccatgccgg gatcgggatt | 240 |
| aggtcttgcc atcgtgaatc aggttgtgaa tcggcatggt ggccaactcg ttgtgggtga | 300 |
| atcagatgat ggcggaacga gaatcactat tgatttgcca ggggaaccca ttcgcagcgg | 360 |
| gttcgaaaat gtcgatgatt aaggtaccac cactaaagag ctcacaggaa gtgttcagac | 420 |
| tacttagagt gacgccccag ccacagggtt cataatcaaa tcatgacaaa tcaattcccc | 480 |
| acaaacaacg gtgagaaccc ggaccgtgca tcggaaactc catcagaaac caactccggt | 540 |
| acctgaactt aagaaggag atatcatatg | 570 |
| | |
| SEQ ID No. 29 | |
| caatttaaca agagccagtt atcttctctt aaaatgagga ggtaactggc ttctttatgc | 60 |
| ttaagaggtg ttagcataag tgaaatatgt tccaacgcgt ggacgtctta attgggagga | 120 |
| agtctgtcac ggactggaag acgaaaaggg tatcgatgaa aacccattcg cagcgggttc | 180 |
| gaaaatgtcg atgattaagg taccaccact aaagagctca caggaagtgt tcagactact | 240 |
| tagagtgacg ccccagccac agggttcata atcaaatcat g | 281 |
| | |
| SEQ ID No. 30 | |
| aatttaacaa gagccagtta tcttctctta aatgaggag gtaactggct tctttatgct | 60 |
| taagaggtgt tagcataagt gaaatatgtt ccaacgcgtg gacgtcttaa ttgggaggaa | 120 |
| gtctgtcacg gactggaaga cgaaaagggt atcgatgaaa atttagttg ttgatgacga | 180 |
| gcaagctgta cgtgactcct tgcgacgttc cctttcgttc aacggataca acgttgttct | 240 |
| cgcagaagac ggcatccaag cactagagat gattgacaag gaacagcctg ctttggtgat | 300 |
| cctcgatgtc atgatgcctg gtatggacgg acttgaggtc tgtcgccacc ttcgcagcga | 360 |
| aggcgatgat cggccaattc ttattcttac tgcccgcgat aatgtttcg atcgtgttgg | 420 |
| tggcctcgat gcaggcgcag atgactattt ggctaaacca tttgctcttg aagagctgtt | 480 |
| ggcgcgcgtc cgttcactgg tgcgtcgctc tgcagtggaa tcaaatcaga gttccagcat | 540 |
| tgaacaggct ctattatctt gtggcgattt gacgcttgac ccagaaagtc gagatgtcta | 600 |
| ccgcaacgga cgcgccatca gccttactcg aacagagttc gcgctcctgc aattgctcct | 660 |
| caaaaaccaa aggaaagtgc tcactcgcgc ccagattttg gaagaggtat ggggctgcaa | 720 |
| tttcccccact tcaggcaatg ccctcgaggt ctacattgga taccttcgac gcaagactga | 780 |
| attggaagga gaagaccgcc tgatccatac agtacgagga gtcggatacg tcctgcgaga | 840 |
| gaccgctccg tgacattaag gcgaatcggc gcagggaaa atgggcctgc ccctaccgaa | 900 |
| agtgatgact ccgacggttc aatgtcgttg cgttggcgct tggcttgct gagcgccact | 960 |
| ttggtagctt tcgccgttgg tgttattact gttgctgcat attggtctgt ctccagctat | 1020 |
| gtcaccaact caatcgatcg tgatctggaa aaacaagcgg atgcaatgct ggacgagcc | 1080 |
| agtgaagcgg gattctatgc aaccgcagaa accgaaattg ctctgttagg tgaatatgcc | 1140 |
| agtgacactc gaatcgcctt aatcccacct gggtgggaat acgtcatcgg tgaatccata | 1200 |
| tcactgcctg attcagattt ccttaagagt aaagaagcgg ggaaacagat cctcgtaaca | 1260 |
| agtgctgagc gcattctcat gaaacgagat agctcgggca cagtggtggt ttttgctaaa | 1320 |
| gatatggtgg ataccgatcg gcagctcacg gtgcttggcg tcattctctt gatcattggc | 1380 |
| ggcagtggtg ttttgcgtc gattctgctt ggtttcatca ttgcgaagga ggggctgaaa | 1440 |
| ccactgtcaa agctgcagcg tgccgtcgaa gagatcgaac gaactgatga gcttcgtgcg | 1500 |
| attcccgtgg tgggaaatga tgagttcgct aagttgactc gtagtttcaa tgacatgctc | 1560 |
| aaggcactgc gggagtctcg tacccggcaa tctcagttgg tggcagatgc aggacacgag | 1620 |
| ctgaaaactc cactgacctc aatgcggaca aatattgaat tgctgttgat ggcaaccaac | 1680 |
| agtggaggat cgggaatccc caaggaagaa ttggatggcc ttcagcgtga tgtattggcg | 1740 |
| cagatgaccg aaatgtctga tttgattggt gatcttgttg atcttgcgcg tgaagaaacc | 1800 |
| gccgaaacgt caagcattgt agatctcaac caagtgttgg aaattgcgct tgaccgaatg | 1860 |
| gaaagccgtc gcatgacggt gcggatagat gtttccgaga ctgtggattg gaactgctg | 1920 |
| ggcgatgatt ttccttaac cagggcatta gtaaatgttt tggataatgc cattaaatgg | 1980 |
| tcgcctgaga atggcattgt tcgagtgtcg atgtcacaga tcgacaaagc aacggtccgc | 2040 |
| attgttattg atgattcagg gcctggaatt gctgaaaaag aacgaggatt agttttggaa | 2100 |
| cggttctatc gcgccgtcag ctcccgttcc atgccggat cgggattagg tcttgccatc | 2160 |
| gtgaatcagg ttgtgaatcg gcatggtggc caactcgttg gggtgaatc agatgatggc | 2220 |
| ggaacgagaa tcactattga tttgccaggg gaacccattc gcagcgggtt cgaaaatgtc | 2280 |

-continued

| Sequences | |
|---|---|
| gatgattaaa ccactaaaga gctcacagga agtgttcaga ctacttagag tgacgcccca | 2340 |
| gccacagggt tcataatcaa atcatgacaa atcaattccc cacaaacaac ggtgagaacc | 2400 |
| cggaccgtgc atcggaaact ccatcagaaa ccaactccgg tacctgaact ttaagaagga | 2460 |
| gatatcatat g | 2471 |

SEQ ID No. 31
ctgaacttgt ggccgtttac                   20

SEQ ID No. 32
ttgttgccgg gaagctagag                   20

SEQ ID No. 33
gcgcgttaac cgaaggagat atagatatgt ttgc   34

SEQ ID No. 34
cagtgaattc gagctcctag tg                22

SEQ ID No. 35

| | |
|---|---|
| ggatccttat tacttgtaca gctcgtccat gccgagagtg atcccggcgg cggtcacgaa | 60 |
| ctccagcagg accatgtgat cgcgcttctc gttgggtct ttgctcaggg cggactggta | 120 |
| gctcaggtag tggttgtcgg gcagcagcac ggggccgtcg ccgatggggg tgttctgctg | 180 |
| gtagtggtcg gcgagctgca cgctgccgcc ctcgatgttg tggcggatct tgaagttcac | 240 |
| cttgatgccg ttcttctgct tgtcggccat gatatagacg ttgtggctgt tgtagttgta | 300 |
| ctccaggttg tgcccagga tgttgccgtc ctccttgaag ttgatgccct tcagctcgat | 360 |
| gcggttcacc agggtgtcgc cctcgaactt cacctcggcg cgggtcttgt agttgccgtc | 420 |
| gtccttgaag aagatggtgc gctcctggac gtagccttcg ggcatggcgg acttgaagaa | 480 |
| gtcgtgctgc ttcatgtggt cggggtagcg ggcgaagcac tgcaggccgt agccgaaggt | 540 |
| ggtcacgagg gtgggccagg gcacgggcag cttgccggtg gtgcagatga acttcagggt | 600 |
| cagcttgccg taggtggcat cgccctcgcc ctcgccggac acgctgaact tgtggccgtt | 660 |
| tacgtcgccg tccagctcga ccaggatggg caccaccccg gtgaacagct cctcgccctt | 720 |
| gctcaccata tgatatctcc ttcttctagc gggtctgcca catttgctga aaagtaccag | 780 |
| ttgcaaggtg tggtgttgga gcttcataac caggttgggc aaaagggatg aatccctggt | 840 |
| tgtgctgggg ctcctgaaaa gtactcatag actctattgt ggagtgttga ggctgataag | 900 |
| tgaatggggg aaagccctga aaaggtggcg ttcagggtct tccctgatgg tttggtgtcg | 960 |
| caggggcatg acatgatcga agatatgagt aacacacctg cgccttatac cccgcagcct | 1020 |
| gcggggcaag cggtgccttt atatcccacg tttacccgtc gacctgcagc aatggcaaca | 1080 |
| acgttgcgca aactattaac tggcgaacta cttactctag cttcccggca acaattaata | 1140 |
| gactggatgg aggcggataa agttgcagga ccacttctgc gctcggccct tccggctggc | 1200 |
| tggtttattg ctgataaatc tggagccggt gagcgtgggt ctcgcggtat cattgcagca | 1260 |
| ctggggccag atggtaagcc ctcccgtatc gtagttatct acacgacggg gagtcaggca | 1320 |
| actatggatg aacgaaatag acagatcgct gagataggtg cctcactgat taagcattgg | 1380 |
| taactgtcag accaagttta ctcatatata ctttagattg atttaaaact tcatttttaa | 1440 |
| tttaaaagga tctaggtgaa gatccttttt gataatctca tgaccaaaat cccttaacgt | 1500 |
| gagttttcgt tccactgagc gtcagacccc ttaataagat gatcttcttg agatcgtttt | 1560 |
| ggtctgcgcg taatctcttg ctctgaaaac gaaaaaaccg ccttgcaggg cggttttcg | 1620 |
| aaggttctct gagctaccaa ctctttgaac cgaggtaact ggcttggagg agcgcagtca | 1680 |
| ccaaaacttg tcctttcagt ttagccttaa ccggcgcatg acttcaagac taactcctct | 1740 |
| aaaatcaatta ccagtggctg ctgccagtgg tgcttttgca tgtctttccg ggttggactc | 1800 |
| aagacgatag ttaccggata aggcgcagcg gtcggactga acggggggtt cgtgcataca | 1860 |
| gtccagcttg gagcgaactg cctacccgga actgagtgtc aggcgtggaa tgagacaaac | 1920 |
| gcggccataa cagcggaatg acaccggtaa accgaaaggc aggaacagga gagcgcacga | 1980 |
| gggagccgcc aggggaaac gcctggtatc tttatagtcc tgtcgggttt cgccaccact | 2040 |
| gatttgagcg tcagatttcg tgatgcttgt caggggggcg gagcctatgg aaaaacggct | 2100 |
| ttgccgcggc cctctcactt ccctgttaag tatcttcctg gcatcttcca ggaaatctcc | 2160 |
| gccccgttcg taagccattt ccgctcgccg cagtcgaacg accgagcgta gcgagtcagt | 2220 |
| gagcgaggaa gcggaatata tcctgtatca catattctgc tgacgcaccg gtgcagcctt | 2280 |
| ttttctcctg ccacatgaag cacttcactg acacccctcat cagtgccaac atagtaagcc | 2340 |
| agtatacact ccgctagcgc tgaggtctgc ctcgtgaaga aggtgttgct gactcatacc | 2400 |
| aggcctgaat cgccccatca tccagccaga aagtgaggga gccacggttg atgagagctt | 2460 |
| tgttgtaggt ggaccagttg gtgattttga acttttgctt tgccacgaa cggtctgcgt | 2520 |
| tgtcgggaag atgcgtgatc tgatccttca actcagcaaa agttcgattt attcaacaaa | 2580 |
| gccacgttgt gtctcaaaat ctctgatgtt acattgcaca agataaaaat atatcatgat | 2640 |
| gaacaataaa actgtctgct tacataaaca gtaatacaag gggtgttatg agccatattc | 2700 |
| aacgggaaac gtcttgctcg aggccgcgat taaattccaa catggatgct gatttatatg | 2760 |
| ggtataaatg ggctcgcgat aatgtcgggc aatcaggtgc gacaatctat cgattgtatg | 2820 |
| ggaagcccga tgcgccagag ttgtttctga aacatggcaa aggtagcgtt gccaatgatg | 2880 |
| ttacagatga gatggtcaga ctaaactggc tgacggaatt tatgcctctt ccgaccatca | 2940 |
| agcatttat ccgtactcct gatgatgcat ggttactcac cactgcgatc cccgggaaaa | 3000 |
| cagcattcca ggtattagaa gaatatcctg attcaggtga aaatattgtt gatgcgctgg | 3060 |
| cagtgttcct gcgccggttg cattcgattc ctgtttgtaa ttgtccttt aacagcgatc | 3120 |
| gcgtatttcg tctcgctcag gcgcaatcac gaatgaataa cggtttggtt gatgcgagtg | 3180 |
| attttgatga cgagcgtaat ggctggcctg ttgaacaagt ctggaaagaa atgcataagc | 3240 |
| ttttgccatt ctcaccggat tcagtcgtca ctcatggtga tttctcactt gataaccta | 3300 |
| tttttgacga ggggaaatta ataggttgta ttgatgttgg acgagtcgga atcgcagacc | 3360 |
| gataccagga tcttgccatc ctatggaact gcctcggtga gttttctcct tcattacaga | 3420 |
| aacggctttt tcaaaaatat ggtattgata atcctgatat gaataaattg cagtttcatt | 3480 |
| tgatgctcga tgagttttc taatcagaat tggttaattg gttgtaacac tggcagagca | 3540 |

```
                              Sequences ttacgctgac ttgacgggac ggcggctttg ttgaataaat cgaacttttg ctgagttgaa    3600
ggatcagatc acgcatcttc ccgacaacgc agaccgttcc gtggcaaagc aaaagttcaa    3660
aatcaccaac tggtccacct acaacaaagc tctcatcaac cgtggctccc tcacttttctg   3720
gctgatgat ggggcgattc aggcctggta tgagtcagca acaccttctt cacgaggcag     3780
acctcagcgc tcaaagatgc aggggtaaaa gctaaccgca tctttaccga caaggcatcc    3840
ggcagttcaa cagatcggga agggctggat ttgctgagga tgaaggtgga ggaaggtgat    3900
gtcattctgg tgaagaagct cgaccgtctt ggccgcgaca ccgccgacat gatccaactg    3960
ataaaagagt ttgatgctca gggtgtagcg gttcggttta ttgacgacgg gatcagtacc    4020
gacggtgata tggggcaaat ggtggtcacc atcctgtcgg ctgtggcaca ggctgaacgc    4080
cggaggatca agtcggtcaa gccaagcgca accagcggca ccgccgcgag caacgtcgca    4140
agggcgatca ggggacgatt tttgcgaaga atttccacgg taagaatcca atctctcgaa    4200
tttagggtga aagaagcttg gcataggggt gtgcacgaac tcggtggagg aaatttccgc    4260
ggggcaaggc ttcgcgaagc ggagtcgcgg cagtggcttt gaagatcttt gggagcagtc    4320
cttgtgcgct tacgaggtga gccggtgggg aaccgttatc tgcctatggt gtgagccccc    4380
ctagagagct tcaagagcaa tcagcccgac ctagaaagga ggccaagaga gagacccta    4440
cgggggggaac cgttttctgc ctacgagatg gcacatttac tgggaagctt tacgcgtcc    4500
tcgtggaagt tcaatgcccg cagacttaag tgctctattc acgtctgac gtgcacgcgt    4560
aaattcagac atagcttcat tgattgtcgg ccacgagcca gtctctccct caacagtcat    4620
aaaccaacct gcaatggtca agcgatttcc tttagctttc ctagcttgtc gttgactgga    4680
cttagctagt ttttctcgct gtgctcgggc gtactcactg tttgggtctt tccagcgttc    4740
tgcggccttt ttaccgccac gtcttcccat agtggccaga gctttcgcc ctcggctgct     4800
ctgcgtctct gtctgacgag cagggacgac tggctggcct ttagcgacgt agccgcgcac    4860
acgtcgcgcc atcgtctggc ggtcacgcat cggcggcaga tcaggctcac ggccgtctgc    4920
tccgaccgcc tgagcgacgg tgtaggcacg ctcgtaggcg tcgatgatct tggtgtctt    4980
taggcgctca ccagccgctt taactggta tcccacagtc aaagcgtggc gaaaagccgt     5040
ctcatcacgg gcggcacgcc ctggagcagt ccagaggaca cggacgccgt cgatcagctc    5100
tccagacgct tcagcggcgc tcggcaggct tgcttcaagc gtggcaagtg ctttttgcttc   5160
cgcagtggct tttcttgccg cttcgatacg tgcccgtccg ctagaaaact cctgctcata    5220
gcgtttttta ggttttttctg tgcctgagat catgcgagca acctccataa gatcagctag   5280
gcgatccacg cgattgtgct gggcatgcca gcggtacgcg gtgggatcgt cggagacgtg    5340
cagtggccac cggctcagcc tatgtgaaaa agctggtca gcgccgaaaa cgcgggtcat     5400
ttcctcggtc gttgcagcca gcaggcgcat attcgggctg ctcatgcctg tcgcggcata    5460
caccggatca atgagccaga tgagctggca tttccccgctc agtggattca cgccgatcca   5520
agctggcgct ttttccaggc gtgcccagcg ctccaaaatc gcgtagacct cggggtttac    5580
gtgctcgatt ttcccgccgg cctggtggct cggcacatca atgtccagga caagcacggc    5640
tgcgtgctgc gcgtgcgtca gagcaacata ctggcaccgg gcaagcgatt ttgaaccaac    5700
tcggtataac ttcggctgtg tttctcccgt gtccggtctt tgatccaag cgctggcgaa     5760
gtcgcgggtc ttgctgccct ggaaattttc tctgcccagg tgagcgagga attcgcggcg    5820
gtcttcgctc gtccagccac gtgatcgcag cgcgagctcg ggatgggtgt cgaacagatc    5880
agcggaaaat ttccaggccg gtgtgtcaat gtctcgtgaa tccgctagag tcatttttga    5940
gcgcttttctc ccaggttttgg actggggggtt agccgacgcc ctgtgagtta ccgctcacgg   6000
ggcgttcaac atttttcagg tattcgtgca gcttatcgct tcttgccgcc tgtgcgcttt    6060
ttcgacgcgc gacgctgctg ccgattcggt gcaggtggtg gcggcgctga cacgtcctgg    6120
gcggccacgg ccacacgaaa cgcggcattt acgatgtttg tcatgcctgc gggcaccgcg    6180
ccacgatcgc ggataattct cgctgccgct tccagctctg tgacgaccat ggccaaaatt    6240
tcgctcgggg gacgcacttc cagcgccatt tgcgacctag ccgcctccag ctcctcggcg    6300
tggcgtttgt tggcgcgctc gcggctggct gcggcacgac acgcatctga gcaatatttt    6360
gcgcgccgtc ctcgcgggtc aggccgggga ggaatcaggc caccgcagta ggcgcaactg    6420
attcgatcct ccactactgt gcgtcctcct ggcgctgcgg agcacgcagc tcgtcagcca    6480
gctcctcaag atccgccacg agagtttcta ggtcgctcgc ggcactggcc cagtctcgtg   6540
atgctggcgc gtccgtcgta tcgagagctc ggaaaaatcc gatcaccgtt tttaaatcga    6600
cggcagcatc gagcgcgtcg gactccagcg cgacatcaga gagatccata gctgatgatt    6660
cgggccaatt ttggtacttc gtcgtgaagg tcatgcacc attataacga acgttcgtta    6720
aagtttttgg cggaaaatca cgcggcacga aaatttttcac gaagcgggac tttgcgcagc    6780
tcaggggtgc taaaaatttt gtatcgcact tgatttttcc gaaagacaga ttatctgcaa    6840
acggtgtgtc gtatttctgg cttggttttt aaaaaatctg gaatcgaaaa tttgcgggc    6900
gaccgagaag ttttttacaa aaggcaaaaa ctttttcggg atcgacagaa ataaaacgat    6960
cgacggtacg caacaaaaaa gcgtcaggat cgccgtgaaga ccgtcaacca                7020
aaggggaagc ctccaatcga cgcgacgcgc gctctacggc gatcctgacg cagatttta    7080
gctatctgtc gcagcgccct cagggacaag ccacccgcac aacgtcgcga gggcgatcag    7140
cgacgccgca ggg                                                        7153

SEQ ID No. 36
ggatccttat tacttgtaca gctcgtccat gccgagagtg atcccggcgg cggtcacgaa      60
ctccagcagg accatgtgat cgcgcttctc gttggggtct ttgctcaggg cggactggta    120
gctcaggtag tggttgtcgg gcagcagcac ggggccgtcg ccgatggggg tgttctgctg    180
gtagtggtcg gcgagctgca cgctgccgcc ctcgatgttg tgcggatct tgaagttcac     240
cttgatgccg ttcttctgct tgtcggccat gatatagacg ttgtggctgt tgtagttgta    300
ctccagcttg tgcccagga tgttgccgtc tccttgaag ttgatgccct tcagctcgat      360
gcggttcacc agggtgtcgc cctcgaactt cacctcggcg cgggtcttgt agttgccgtc    420
gtccttgaag aagatggtgc gctcctggac gtagccttcg ggcatggcgg acttgaagaa    480
gtcgtcgtgc ttcatgtggt cggggtagcg ggcgaagcac tgcaggcgt agccgaaggt    540
ggtcacgagg gtgggccagg gcacgggcag cttgccggtg gtgcagatga acttcaggt    600
cagcttgccg taggtggcat cgccctgcc ctcgccggac acgctgaact gtggccgtt     660
tacgtcgccc tccagctcga ccaggatggg caccaccccg gtgaacagct cctcgccctt    720
gctcaccata tgatatctcc ttcttctaac cagcgacgcc gccgatccat ttgtcggtgg    780
tgcttcgggc gagtcgtcga gattgtgctg ggaaagtcat cgggatcaag ctcctttatg    840
```

-continued

| Sequences | |
|---|---|
| gctgattgag tttttctttc ttcttcaatc atcgccaata agaacctaga gcacatcggg | 900 |
| gatttcccct ctcctaaccc ctaaaaaccc ctgagaaaac gctccaagta aacccttaca | 960 |
| gctcgtcgac ctgcagcaat ggcaacaacg ttgcgcaaaa tattaactgg gaactactt | 1020 |
| actctagctt cccggcaaca attaatagac tggatggagg cggataaagt tgcaggacca | 1080 |
| cttctgcgct cggccttcc ggctggctgg tttattgctg ataaatctgg agccggtgag | 1140 |
| cgtgggtctc gcggtatcat tgcagcactg gggccagatg gtaagccctc ccgtatcgta | 1200 |
| gttatctaca cgacggggag tcaggcaact atggatgaac gaaatagaca gatcgctgag | 1260 |
| ataggtgcct cactgattaa gcattggtaa ctgtcagacc aagtttactc atatatactt | 1320 |
| tagattgatt taaaacttca ttttttaattt aaaaggatct aggtgaagat ccttttgat | 1380 |
| aatctcatga ccaaaatccc ttaacgtgag ttttcgttcc actgagcgtc agacccctta | 1440 |
| ataagatgat cttcttgaga tcgtttttggt ctgcgcgtaa tctcttgctc tgaaaacgaa | 1500 |
| aaaaccgcct tgcagggcgg tttttcgaag gttctctgag ctaccaactc tttgaaccga | 1560 |
| ggtaactggc ttggaggagc gcagtcacca aaacttgtcc tttcagttta gccttaaccg | 1620 |
| gcgcatgact tcaagactaa ctcctctaaa tcaattacca gtggctgctg ccagtggtgc | 1680 |
| ttttgcatgt ctttccgggt tggactcaag acgatagtta ccggataagg cgcagcggtc | 1740 |
| ggactgaacg gggggttcgt gcatacagtc cagcttgagg cgaactgcct acccggaact | 1800 |
| gagtgtcagg cgtggaatga gacaaacgcg gccataacag cggaatgaca ccggtaaacc | 1860 |
| gaaaggcagg aacaggagag cgcacgaggg agccgccagg gggaaacgcc tggtatcttt | 1920 |
| atagtcctgt cgggtttcgc caccactgat ttgagcgtca gatttcgtga tgcttgtcag | 1980 |
| ggggcgggag cctatggaaa aacggcttg ccgcggccct ctcacttccc tgttaagtat | 2040 |
| cttcctggca tcttccagga aatctccgcc ccgttcgtaa gccatttccg ctcgccgcag | 2100 |
| tcgaacgacc gagcgtagcg agtcagtgag cgaggaagcg gaatatatcc tgtatcacat | 2160 |
| attctgctga cgcaccggtg cagccttttt tctcctgcca catgaagcac ttcactgaca | 2220 |
| ccctcatcag tgccaacata gtaagccagt atacactccg ctagcgctga ggtctgcctc | 2280 |
| gtgaagaagg tgttgctgac tcataccagg cctgaatcgc cccatcatcc agccagaaag | 2340 |
| tgagggagcc acgttgatg agagctttgt tgtaggtgga ccagttggtg atttgaact | 2400 |
| tttgctttgc cacggaacgg tctgcgttgt cgggaagatg cgtgatctga tccttcaact | 2460 |
| cagcaaaagt tcgatttatt caacaaagcc acgttgtgtc tcaaaatctc tgatgttaca | 2520 |
| ttgcacaaga taaaaatata tcatcatgaa caataaaact gtctgcttac ataaacagta | 2580 |
| atacaagggg tgttatgagc catattcaac gggaaacgtc ttgctcgagg ccgcgattaa | 2640 |
| attccaacat ggatgctgat ttatatgggg ataaatgggc tcgcgataat gtcgggcaat | 2700 |
| caggtgcgac aatctatcga ttgtatggga agcccgatgc gccagagttg tttctgaaac | 2760 |
| atggcaaagg tagcgttgcc aatgatgtta cagatgagt ggtcagacta aactggctga | 2820 |
| cggaatttat gcctcttccg accatcaagc atttttatccg tactcctgat gatgcatggt | 2880 |
| tactcaccac tgcgatcccc gggaaaacag cattccaggt attagaagaa tatcctgatt | 2940 |
| caggtgaaaa tattgttgat gcgctggcag tgttcctgcg ccggttgcat tcgattcctg | 3000 |
| tttgtaattg tccttttaac agcgatcgcg tatttcgtct cgctcaggcg caatcacgaa | 3060 |
| tgaataacgg tttggttgat gcgagtgatt ttgatgacga gcgtaatggc tggcctgttg | 3120 |
| aacaagtctg gaaagaaatg cataagcttt tgccattctc accggattca gtcgtcactc | 3180 |
| atggtgattt ctcacttgat aaccttattt ttgacgaggg gaaattaata ggttgtattg | 3240 |
| atgttgacg agtcggaatc gcagaccgat accaggatct tgccaactgc tggaactgcc | 3300 |
| tcggtgagtt ttctccttca ttacagaaac ggcttttttca aaaatatggt attgataatc | 3360 |
| ctgatatgaa taaattgcag tttcatttga tgctcgatga gttttctaa tcagaattgg | 3420 |
| ttaattggtt gtaacactgg cagagcatta cgctgacttg acgggacggc ggctttgttg | 3480 |
| aataaatcga acttttgctg agttgaagga tcagatcacg catcttcccg acaacgcaga | 3540 |
| ccgttccgtg gcaaagcaaa agttcaaaat caccaactgg tccacctaca acaaagctct | 3600 |
| catcaaccgt ggctccctca ctttctggct ggatgatggg gcgattcagg cctggtatga | 3660 |
| gtcagcaaca ccttcttcac gaggcagacc tcagcgctca aagatgcagg ggtaaaagct | 3720 |
| aaccgcatct ttaccgacaa ggcatccggc agttcaacag atcgggaagg gctggatttg | 3780 |
| ctgaggatga aggtggagga aggtgatgtc attctggtga agaagctcga ccgtcttggc | 3840 |
| cgcgacaccg ccgacatgat ccaactgata aaagagtttg atgctcaggg tgtagcggtt | 3900 |
| cggtttattg acgacgggat cagtaccgac ggtgatatgg ggcaaatggt ggtcaccatc | 3960 |
| ctgtcggctg tggcacaggc tgaacgccgg aggatcaagt cggtcaagcc aagcgcaacc | 4020 |
| agcggcaccg ccgcgagcaa cgtcgcaagg gcgatcaggg gacgatttt gcgaagaatt | 4080 |
| tccacggtaa gaatccaatc tctcgaattt agggtgaaag aagcttggca tagggtgtg | 4140 |
| cacgaactcg gtgaggaaa tttccgcggg gcaaggcttc gcgaagcgga gtcgcggcag | 4200 |
| tggctttgaa gatctttggg agcagtcctt gtgcgcttac gaggtgagcc ggtggggaac | 4260 |
| cgttatctgc ctatggtgtg agcccccta gagagcttca agagcaatca gcccgaccta | 4320 |
| gaaaggaggc caagagagag acccctacgg ggggaaccgt tttctgccta cgagatggca | 4380 |
| catttactgg gaagctttac ggcgtcctcg tggaagttca atgcccgcag acttaagtgc | 4440 |
| tctattcacg gtctgacgtg acacgctaaa ttcagacata gcttcattga ttgtcggcca | 4500 |
| cgagccagtc tctccctcaa cagtcataaa ccaacctgca atggtcaagc gatttccttt | 4560 |
| agcttttccta gcttgtcgtt gactggactt agctagtttt tctcgctgtg ctcgggcgta | 4620 |
| ctcactgttt gggtctttcc agcgttctgc ggcttttta ccgccacgtc ttcccatagt | 4680 |
| ggccagagct tttcgccctc ggctgctctg cgtctctgtc tgacgagcag ggacgactgg | 4740 |
| ctggcctta gcgacgtagc cgcgcacacg tcgcgccatc gtctggcggt cacgcatcgg | 4800 |
| cggcagatca ggctcacggc cgtctgctcc gaccgcctga gcgacggtgt aggcacgctc | 4860 |
| gtaggcgtcg atgatcttgg tgtcttttag gcgctcacca gccgcttta actggtatcc | 4920 |
| cacagtcaaa gcgtggcgaa aagccgtctc atcacgggcg gcacgccctg gagcagtcca | 4980 |
| gaggacacgg acgccgtcga tcagctcccc agacgcttca gcggcgctcg gcaggcttgc | 5040 |
| ttcaagcgtg gcaagtgctt tgcttccgc agtggctttt cttgccgctt cgatacgtgc | 5100 |
| ccgtccgcta gaaaactcct gctcatagcg ttttttaggt ttttctgtgc ctgagatcat | 5160 |
| gcgagcaacc tccataagat cagctaggcg atccacgtaa ttgtgctggg catgccagtc | 5220 |
| gtacgcggtg ggatcgtcgg agacgtgcag tggccaccgg ctcagcctat gtgaaaaagc | 5280 |
| ctggtcagcc ccgaaaacgc gggtcatttc ctcggtcgtt gcagcagca ggcgcatatt | 5340 |
| cgggctgctc atgcctgctg cggcatacac cggatcaatg agccagatga gctggcattt | 5400 |
| cccgctcagt ggattcacgc cgatccaagc tggcgctttt tccaggcgtg cccagcgctc | 5460 |

-continued

| Sequences | | | | | |
|---|---|---|---|---|---|
| caaaatcgcg | tagacctcgg | ggtttacgtg | ctcgattttc | ccgccggcct | ggtggctcgg | 5520 |
| cacatcaatg | tccaggacaa | gcacggctgc | gtgctgcgcg | tgcgtcagag | caacatactg | 5580 |
| gcaccgggca | agcgattttg | aaccaactcg | gtataacttc | ggctgtgttt | ctcccgtgtc | 5640 |
| cgggtctttg | atccaagcgc | tggcgaagtc | gcgggtcttg | ctgccctgga | aattttctct | 5700 |
| gcccaggtga | gcgaggaatt | cgcggcggtc | ttcgctcgtc | cagccacgtg | atcgcagcgc | 5760 |
| gagctcggga | tgggtgtcga | acagatcagc | ggaaaatttc | caggccggtg | tgtcaatgtc | 5820 |
| tcgtgaatcc | gctagagtca | ttttttgagcg | cttctcccca | ggtttggact | ggggggttagc | 5880 |
| cgacgccctg | tgagttaccg | ctcacggggc | gttcaacatt | tttcaggtat | tcgtgcagct | 5940 |
| tatcgcttct | tgccgcctgt | gcgctttttc | gacgcgcgac | gctgctgccg | attcggtgca | 6000 |
| ggtggtggcg | gcgctgacac | gtcctgggcg | gccacggcca | cacgaaacgc | ggcatttacg | 6060 |
| atgtttgtca | tgcctgcggg | caccgcgcca | cgatcgcgga | taattctcgc | tgccgcttcc | 6120 |
| agctctgtga | cgaccatggc | caaaatttcg | ctcgggggca | gcacttccag | cgccatttgc | 6180 |
| gacctagccg | cctccagctc | ctcggcgtgg | cgtttgttgg | cgcgctcgcg | gctggctgcg | 6240 |
| gcacgacacg | catctgagca | atattttgcg | cgccgtcctc | gcgggtcagg | ccggggagga | 6300 |
| atcaggccac | cgcagtaggc | gcaactgatt | cgatcctcca | ctactgtgcg | tcctcctggc | 6360 |
| gctgccgagc | acgcagctcg | tcagccagct | cctcaagatc | cgccacgaga | gtttctaggt | 6420 |
| cgctcgcggc | actgcccag | tctcgtgatg | ctggcgcgtc | cgtcgtatcg | agagctcgga | 6480 |
| aaaatccgat | caccgttttt | aaatcgacgg | cagcatcgag | cgcgtcggac | tccagcgcga | 6540 |
| catcagagag | atccatagct | gatgattcgg | gccaattttg | gtacttcgtc | gtgaaggtca | 6600 |
| tgcaccatt | ataacgaacg | ttcgttaaag | ttttttggcgg | aaaatcacgc | ggcacgaaaa | 6660 |
| ttttcacgaa | gcgggacttt | gcgcagctca | ggggtgctaa | aaattttgta | tcgcacttga | 6720 |
| tttttccgaa | agacagatta | tctgcaaacg | gtgtgtcgta | tttctggctt | ggttttttaaa | 6780 |
| aaatctggaa | tcgaaaattt | gcggggcgac | cgagaagttt | tttacaaaag | gcaaaaactt | 6840 |
| tttcgggatc | gacagaaata | aaacgatcga | cggtacgcaa | caaaaaagcg | tcaggatcgc | 6900 |
| cgtagagcga | ttgaagaccg | tcaaccaaag | gggaagcctc | caatcgacgc | gacgcgcgct | 6960 |
| ctacggcgat | cctgacgcag | atttttagct | atctgtcgca | gcgccctcag | ggacaagcca | 7020 |
| cccgcacaac | gtcgcgaggg | cgatcagcga | cgccgcaggg | | | 7060 |

SEQ ID No. 37
| | | | | | | |
|---|---|---|---|---|---|---|
| ccctgcggcg | tcgctgatcg | ccctcgcgac | gttgtgcggg | tggcttgtcc | ctgagggcgc | 60 |
| tgcgacagat | agctaaaaat | ctgcgtcagg | atcgccgtag | agcgcgcgtc | gcgtcgattg | 120 |
| gaggcttccc | ctttggttga | cggtcttcaa | tcgctctacg | gcgatcctga | cgcttttttg | 180 |
| ttgcgtaccg | tcgatcgttt | tatttctgtc | gatcccgaaa | aagttttttgc | cttttgtaaa | 240 |
| aaacttctcg | gtcgcccgc | aaattttcga | ttccagattt | tttaaaaacc | aagccagaaa | 300 |
| tacgacacac | cgtttgcaga | taatctgtct | ttcggaaaaa | tcaagtgcga | tacaaaattt | 360 |
| ttagcacccc | tgagctgcgc | aaagtcccgc | ttcgtgaaaa | ttttcgtgcc | gcgtgatttt | 420 |
| ccgccaaaaa | ctttaacgaa | cgttcgttat | aatggtgtca | tgaccttcac | gacgaagtac | 480 |
| caaaattggc | ccgaatcatc | agctatggat | ctctctgatg | tcgcgctgga | gtccgacgcg | 540 |
| ctcgatgctg | ccgtcgattt | aaaaacggtg | atcggatttt | tccgagctct | cgatacgacg | 600 |
| gacgcgccag | catcacgaga | ctgggccagt | gccgcgagcg | acctagaaac | tctcgtggcg | 660 |
| gatcttgagg | agctggctga | cgagctgcgt | gctcggcagc | gaggaggga | ggcacagtag | 720 |
| tggaggatcg | aatcagttgc | gcctactgcg | gtggcctgat | tcctccccgg | cctgaccccgg | 780 |
| gaggacggcg | cgcaaaatat | tgctcagatg | cgtgtcgtgc | cgcagccagc | cgcgagcgcg | 840 |
| ccaacaaacg | ccacgccgag | gagctggagg | cggctaggtc | gcaaatggcg | ctggaagtgc | 900 |
| gtccccgag | cgaaatttttg | gccatggtcg | tcacagagct | ggaagcggca | gcgagaatta | 960 |
| tccgcgatcg | tggcgcggtg | cccgcaggca | tgacaaacat | cgtaaatgcc | gcgtttcgtg | 1020 |
| tggccgtggc | cgcccaggac | gtgtcagcgc | cgccaccacc | tgcaccgaat | cggcagcagc | 1080 |
| gtcgcgcgtc | gaaaaagcgc | acaggcggca | agaagcgata | agctgcacga | atacctgaaa | 1140 |
| aatgttgaac | gccccgtgag | cggtaactca | cagggcgtcg | gctaacccc | agtccaaaca | 1200 |
| tgggagaaag | cgctcaaaaa | tgactctagc | ggattcacga | gacattgaca | caccggcctg | 1260 |
| gaaattttcc | gctgatctgt | tcgacaccca | tcccgagctc | gcgctgcgat | cacgtggctg | 1320 |
| gacgagcgaa | gaccgccgcg | aattcctcgc | tcacctgggc | agagaaaatt | tccagggcag | 1380 |
| caagaccccgc | gacttcgcca | gcgcttggat | caaagacccg | gacacgggag | aaacacagcc | 1440 |
| gaagttatac | cgagttggtt | caaaatcgct | tgcccggtgc | cagtatgttg | ctctgacgca | 1500 |
| cgcgcagcac | gcagccgtgc | ttgtcctgga | cattgatgtg | ccgagccacc | aggccggcgg | 1560 |
| gaaaatcgag | cacgtaaacc | ccgaggtcta | cgcgattttg | gagcgctggg | cacgcctgga | 1620 |
| aaaagcgcca | gcttggatcg | gcgtgaatcc | actgagcggg | aaatgccagc | tcatctggct | 1680 |
| cattgatccg | gtgtatgccg | cagcaggcat | gagcagcccg | aatatgcgcc | tgctggctgc | 1740 |
| aacgaccgag | gaaatgaccc | gcgttttcgg | cgctgaccag | gcttttttcac | ataggctgag | 1800 |
| ccggtggcca | ctgcacgtct | ccgacgatcc | caccgcgtac | cgctggcatg | cccagcacaa | 1860 |
| tcgcgtggat | cgcctagctg | atcttatgga | ggttgctcgc | atgatctcag | gcacagaaaa | 1920 |
| acctaaaaaa | cgctatgagc | aggagttttc | tagcggacgg | tggccgacaa | tcaatgaagc | 1980 |
| aaaagccact | gcggaagcaa | aagcacttgc | cacgcttgaa | gcaagcctgc | cgagcgccgc | 2040 |
| tgaagcgtct | ggagagctga | tcgacggcgt | ccgtgtcctc | tggactgctc | cagggcgtgc | 2100 |
| cgcccgtgat | gagacggctt | ttcgccacgc | tttgactgtg | gataccagt | taaaagcggc | 2160 |
| tggtgagcgc | ctaaaagaca | ccaagatcat | cgacgcctac | gagcgtgcct | acaccgtcga | 2220 |
| tcaggcggtc | ggagcagacg | gccgtgagcc | tgatcgccgg | ccgtgcgtg | accgccagac | 2280 |
| gatggcgcga | cgtgtgcgcg | gctacgtcgc | taaaggccag | ccagtcgtcc | ctgctcgtca | 2340 |
| gacagagacg | cagagcagcc | gagggcgaaa | agctctggcc | actatgggaa | gacgtggcgg | 2400 |
| taaaaaggcc | gcagaacgct | ggaaagaccc | aaacagtgag | tacgcccgag | cacagcgaga | 2460 |
| aaaactagct | aagtccagtc | aacgacaagc | taggaaagct | aaaggaaatc | gcttgaccat | 2520 |
| tgcaggttgg | tttatgctcg | ttgagggaga | gactggctcg | tggccgacaa | tcaatgaagc | 2580 |
| tatgtctgaa | tttagcgtgt | cacgtcagac | cgtgaataga | gcacttaagt | ctgcgggcat | 2640 |
| tgaacttcca | cgaggacgcc | gtaaagcttc | ccagtaaatg | tgccatctcg | taggcagaaa | 2700 |
| acggttcccc | ccgtaggggt | ctctctcttg | gcctcctttc | taggtcgggc | tgattgctct | 2760 |
| tgaagctctc | tagggggggct | cacaccatag | gcagataacg | gttccccacc | ggctcacctc | 2820 |
| gtaagcgcac | aaggactgct | cccaaagatc | ttcaaagcca | ctgccgcgac | tccgcttcgc | 2880 |

| | | | | | |
|---|---|---|---|---|---|
| gaagccttgc | cccgcggaaa | tttcctccac | cgagttcgtg | cacacccta | tgccaagctt | 2940 |
| ctttcacccct | aaattcgaga | gattggattc | ttaccgtgga | aattcttcgc | aaaaatcgtc | 3000 |
| ccctgatcgc | ccttgcgacg | ttgctcgcgg | cggtgccgct | ggttgcgctt | ggcttgaccg | 3060 |
| acttgatcct | ccggcgttca | gcctgtgcca | cagccgacag | gatggtgacc | accatttgcc | 3120 |
| ccatatcacc | gtcggtactg | atcccgtcgt | caataaaccg | aaccgctaca | ccctgagcat | 3180 |
| caaactctttt | tatcagttgg | atcatgtcgg | cggtgtcgcg | gccaagacgg | tcgagcttct | 3240 |
| tcaccagaat | gacatcacct | tcctccacct | tcatcctcag | caaatccagc | ccttcccgat | 3300 |
| ctgttgaact | gccggatgcc | ttgtcggtaa | agatgcggtt | agcttttacc | cctgcatctt | 3360 |
| tgagcgctga | ggtctgcctc | gtgaagaagg | tgttgctgac | tcataccagg | cctgaatcgc | 3420 |
| cccatcatcc | agccagaaag | tgagggagcc | acggttgatg | agagctttgt | tgtaggtgga | 3480 |
| ccagttggtg | atttttgaact | tttgctttgc | cacggaacgg | tctgcgttgt | cgggaagatg | 3540 |
| cgtgatctga | tccttcaact | cagcaaaagt | tcgatttatt | caacaaagcc | gccgtcccgt | 3600 |
| caagtcagcg | taatgctctg | ccagtgttac | aaccaattaa | ccaattctga | ttagaaaaac | 3660 |
| tcatcgagca | tcaaatgaaa | ctgcaattta | ttcatatcag | gattatcaat | accatatttt | 3720 |
| tgaaaaagcc | gtttctgtaa | tgaaggagaa | aactcaccga | ggcagttcca | taggatggca | 3780 |
| agatcctggt | atcggtctgc | gattccgact | cgtccaacat | caatacaacc | tattaatttc | 3840 |
| ccctcgtcaa | aaataaggtt | atcaagtgag | aaatccaccat | gagtgacgac | tgaatccggt | 3900 |
| gagaatggca | aaagcttatg | catttctttc | cagacttgtt | caacaggcca | gccattacgc | 3960 |
| tcgtcatcaa | aatcactcgc | atcaaccaaa | ccgttattca | ttcgtgattg | cgcctgagcg | 4020 |
| agacgaaata | cgcgatcgct | gttaaaagga | caattacaaa | caggaatcga | atgcaaccgg | 4080 |
| cgcaggaaca | ctgccagcgc | atcaacaata | ttttcacctg | aatcaggata | ttcttctaat | 4140 |
| acctggaatg | ctgttttccc | ggggatcgca | gtggtgagta | accatgcatc | atcaggagta | 4200 |
| cggataaaat | gcttgatggt | cggaagaggc | ataaattccg | tcagccagtt | tagtctgacc | 4260 |
| atctcatctg | taacatcatt | ggcaacgcta | cctttgccat | gtttcagaaa | caactcctga | 4320 |
| gcatcgggct | tcccatacaa | tcgatagatt | gtcgcacctg | attgcccgac | attatcgcga | 4380 |
| gcccatttat | acccatataa | atcagcatcc | atgttgaat | taatcgcgg | cctcgagcaa | 4440 |
| gacgtttccc | gttgaatatg | gctcataaca | cccccttgtat | tactgtttat | gtaagcagac | 4500 |
| agtttattg | ttcatgatga | tatatttta | tcttgtgtgca | tgtaacatca | gagattttga | 4560 |
| gacacaacgt | ggctttgttg | aataaaatcga | acttttgctg | agttgaagga | tcagatcacg | 4620 |
| catcttcccg | acaacgcaga | ccgttccgtg | gcaaagcaaa | agttcaaaat | caccaactgg | 4680 |
| tccacctaca | acaaagctct | catcaaccgt | ggctccctca | ctttctggct | ggatgatggg | 4740 |
| gcgattcagg | cctggtatga | gtcagcaaca | ccttcttcac | gaggcagacc | tcagcgctag | 4800 |
| cggagtgtat | actggcttac | tatgttggca | ctgatgaggg | tgtcagtgaa | gtgcttcatg | 4860 |
| tggcaggaga | aaaaaggctg | caccggtgcg | tcagcagaat | atgtgataca | ggatatattc | 4920 |
| cgcttcctcg | ctcactgact | cgctacgctc | ggtcgttcga | ctgcggcgag | cggaaatggc | 4980 |
| ttacgaacgg | ggcggagatt | tcctggaaga | tgccaggaag | atacttaaca | gggaagtgag | 5040 |
| agggccgcg | caaagccgtt | tttccatagg | ctccgccccc | ctgacaagca | tcacgaaatc | 5100 |
| tgacgctcaa | atcagtggtg | gcgaaacccg | acaggactat | aaagatacca | ggcgtttccc | 5160 |
| cctggcggct | ccctcgtgcg | ctctcctgtt | cctgcctttc | ggtttaccgg | tgtcattccg | 5220 |
| ctgttatggc | cgcgtttgtc | tcattccacg | cctgacactc | agttccgggt | aggcagttcg | 5280 |
| ctccaagctg | gactgtatgc | acgaaccccc | cgttcagtcc | gaccgctgcg | ccttatccgg | 5340 |
| taactatcgt | cttgagtcca | acccggaaag | acatgcaaaa | gcaccactgg | cagcagccac | 5400 |
| tggtaattga | tttagaggag | ttagtcttga | agtcatgcgc | cggttaaggc | taaactgaaa | 5460 |
| ggacaagttt | tggtgactgc | gctcctccaa | gccagttacc | tcggttcaaa | gagttggtag | 5520 |
| ctcagagaac | cttcgaaaaa | ccgccctgca | aggcggtttt | ttcgttttca | gagcaagaga | 5580 |
| ttacgcgcag | accaaaacga | tctcaagaag | atcatcttat | taaggggtct | gacgctcagt | 5640 |
| ggaacgaaaa | ctcacgttaa | gggattttgg | tcatgagatt | atcaaaaagg | atcttcacct | 5700 |
| agatcctttt | aaattaaaaa | tgaagtttta | aatcaatcta | aagtatatat | gagtaaactt | 5760 |
| ggtctgacag | ttaccaatgc | ttaatcagtg | aggcacctat | ctcagcgatc | tgtctatttc | 5820 |
| gttcatccat | agttgcctga | ctccccgtcg | tgtagataac | tacgatacgg | gagggcttac | 5880 |
| catctggccc | cagtgctgca | atgataccgc | gagacccacg | ctcaccggct | ccagatttat | 5940 |
| cagcaataaa | ccagccagcc | ggaagggccg | agcgcagaag | tggtcctgca | actttatccg | 6000 |
| cctccatcca | gtctattaat | tgttgccggg | aagctagagt | aagtagttcg | ccagttaata | 6060 |
| gtttgcgcaa | cgttgttgcc | attgctgcag | gtcgaccatg | cgccgttccc | agtggaaggc | 6120 |
| cgacaatgtc | gcccttcagg | aggtcaagat | cgacgtcag | accgttcgca | tcccacgccg | 6180 |
| tctggttaag | gcagcacagc | tcggtctcgt | ggacgtagag | cagttctaaa | ccttaaattc | 6240 |
| atcgcctaca | acctttttgta | ggtaagaatt | taacaagagc | cagttatctt | ctcttaaaat | 6300 |
| gaggaggtaa | ctggcttctt | tatgcttaag | aggtgttagc | ataagtgaaa | tatgttccaa | 6360 |
| cgcgtggacg | tcttaattgg | gaggaagtct | gtcacggact | ggaagacgaa | aagggtatcg | 6420 |
| atgaaaattt | tagttgttga | tgacgagcaa | gctgtacgtt | aatctatcgc | gccgtcagct | 6480 |
| cccgttccat | gccgggatcg | ggattaggtc | ttgccatcgt | gaatcaggtt | gtgaatcggc | 6540 |
| atggtggcca | actcgttgtg | ggtgaatcag | atgatgcgg | aacgagaatc | actattgatt | 6600 |
| tgccagggga | acccattcgc | agcggggtcg | aaaatgtcga | tgattaaggt | accaccacta | 6660 |
| aagagctcac | aggaagtgtt | cagactactt | agagtgacgc | cccagccaca | gggttcataa | 6720 |
| tcaaatcatg | acaaatcaat | tccccacaaa | caacggtacg | aacccggacc | gtgcatcgga | 6780 |
| aactccatca | gaaaccaact | ccggtacctg | aactttaaga | aggagatatc | atatggtgag | 6840 |
| caagggcgag | gagctgttca | ccggggtggt | gcccatcctg | gtcgagctgg | acggcgacgt | 6900 |
| aaacggccac | aagttcagcg | tgtccggcga | gggcgagggc | gatgccacct | acggcaagct | 6960 |
| gaccctgaag | ttcatctgca | ccaccggcaa | gctgcccgtg | ccctggccca | cctcgtgac | 7020 |
| caccttcggc | tacggcctgc | agtgcttcgc | ccgctacccc | gaccacatga | agcagcacga | 7080 |
| cttcttcaag | tccgccatgc | ccgaaggcta | cgtccaggag | cgcaccatct | tcttcaagga | 7140 |
| cgacggcaac | tacaagaccc | gcgccgaggt | gaagttcgag | ggcgacaccc | tggtgaaccg | 7200 |
| catcgagctg | aagggcatca | acttcaagga | ggacggcaac | atcctgggc | acaagctgga | 7260 |
| gtacaactac | aacagccaca | acgtctatat | catggccgac | aagcagaaga | acggcatcaa | 7320 |
| ggtgaacttc | aagatccgcc | acaacatcga | gggcggcagc | gtgcagctcg | ccgaccacta | 7380 |

|  |  |  |  |  |  |
|---|---|---|---|---|---|
| ccagcagaac | accccatcg | gcgacggccc | cgtgctgctg | cccgacaacc | actacctgag | 7440 |
| ctaccagtcc | gccctgagca | aagaccccaa | cgagaagcgc | gatcacatgg | tcctgctgga | 7500 |
| gttcgtgacc | gccgccggga | tcactctcgg | catggacgag | ctgtacaagt | aataaggatc | 7560 |
| c | | | | | | 7561 |

SEQ ID No. 38

|  |  |  |  |  |  |
|---|---|---|---|---|---|
| ccctgcggcg | tcgctgatcg | ccctcgcgac | gttgtgcggg | tggcttgtcc | ctgagggcgc | 60 |
| tgcgacagat | agctaaaaat | ctgcgtcagg | atcgccgtag | agcgcgcgtc | gcgtcgattg | 120 |
| gaggcttccc | ctttggttga | cggtcttcaa | tcgctctacg | gcgatcctga | cgcttttttg | 180 |
| ttgcgtaccg | tcgatcgttt | tatttctgtc | gatcccgaaa | aagttttttgc | cttttgtaaa | 240 |
| aaacttctcg | gtcgccccgc | aaattttcga | ttccagattt | tttaaaaacc | aagccagaaa | 300 |
| tacgacacac | cgtttgcaga | taatctgtct | ttccgaaaaa | tcaagtgcga | tacaaaattt | 360 |
| ttagcacccc | tgagctgcgc | aaagtcccgc | ttcgtgaaaa | ttttcgtgcc | gcgtgatttt | 420 |
| ccgccaaaaa | ctttaacgaa | cgttcgttat | aatggtgtca | tgaccttcac | gacgaagtac | 480 |
| caaaattggc | ccgaatcatc | agctatggat | ctctctgatg | tcgcgctgga | gtccgacgcg | 540 |
| ctcgatgctg | ccgtcgattt | aaaaacggtg | atcggatttt | tccgagctct | cgatacgacg | 600 |
| gacgcgccag | catcacgaga | ctgggccagt | gccgcgagcg | acctagaaac | tctcgtggcc | 660 |
| gatcttgagg | agctggctga | cgagctgcgt | gctcggcagc | gccaggagga | cgcacagtag | 720 |
| tggaggatcg | aatcagttgc | gcctactgcg | gtggcctgat | tcctcccgg | cctgaccccgc | 780 |
| gaggacggcg | cgcaaaatat | tgctcagatg | cgtgtcgtgc | gcagccgac | cgcgagcgcg | 840 |
| ccaacaaacg | ccacgccgag | gagctggagg | cggctaggtc | gcaaatggcg | ctggaagtgc | 900 |
| gtccccccgag | cgaaattttg | gccatggtcg | tcacagagct | ggaagcggca | gcgagaatta | 960 |
| tccgcgatcg | tggcgcggtg | cccgcaggca | tgacaaacat | cgtaaatgcc | gcgtttcgtg | 1020 |
| tggccgtggc | cgcccaggac | gtgtcagcgc | cgccaccacc | tgcaccgaat | cggcagcagc | 1080 |
| gtcgcgcgtc | gaaaaagcgc | acaggcggca | agaagcgata | agctgcacga | atacctgaaa | 1140 |
| aatgttgaac | gccccgtgag | cggtaactca | cagggcgtcg | gctaaccccc | agtccaaacc | 1200 |
| tgggagaaag | cgctcaaaaa | tgactctagc | ggattcacga | gacattgaca | caccggcctg | 1260 |
| gaaattttcc | gctgatctgt | tcgacaccca | tcccgagctc | gcgctgcgat | cacgtggctg | 1320 |
| gacgagcgaa | gaccgccgcg | aattcctcgc | tcacctgggc | agagaaaatt | tccagggcag | 1380 |
| caagacccgc | gacttcgcca | gcgcttggat | caaagacccg | gacacgggag | aaacacagcc | 1440 |
| gaagttatac | cgagttggtt | caaaatcgct | tgcccggtgc | cagtatgttg | ctctgacgca | 1500 |
| cgcgcagcac | gcagccgtgc | ttgtcctgga | cattgatgtg | ccgagccacc | aggccggcgg | 1560 |
| gaaaatcgag | cacgtaaacc | ccgaggtcta | cgcgattttg | gagcgctggg | cacgcctgga | 1620 |
| aaaagcgcca | gcttggatcg | gcgtgaatcc | actgagcggg | aaatgccagc | tcatctggct | 1680 |
| cattgatccg | gtgtatgccg | cagcaggcat | gagcagcccg | aatatgcgcc | tgctggctgc | 1740 |
| aacgaccgag | gaaatgaccc | gcgttttcgg | cgctgaccag | gcttttcac | ataggctgag | 1800 |
| ccggtggcca | ctgcacgtct | ccgacgatcc | caccgcgtac | cgctggcatg | cccagcacaa | 1860 |
| tcgcgtggat | cgcctagctg | atcttatgga | ggttgctcgc | atgatctcag | gcacagaaaa | 1920 |
| acctaaaaaa | cgctatgagc | aggagttttc | tagcggacgg | gcacgtatcg | aagcggcaag | 1980 |
| aaaagccact | gcggaagcaa | aagcacttgc | cacgcttgaa | gcaagcctgc | cgagcgccgc | 2040 |
| tgaagcgtct | ggagagctga | tcgacggcgt | ccgtgtcctc | tggactgctc | cagggcgtgc | 2100 |
| cgcccgtgat | gagacggctt | ttcgccacgc | tttgactgtg | gataccagt | taaagcggc | 2160 |
| tggtgagcgc | ctaaaagaca | ccaagatcat | cgacgcctac | gagcgtgcct | acaccgtcgc | 2220 |
| tcaggcggtc | ggagcagacg | gccgtgagcc | tgatctgccg | ccgatgcgtg | accgccagac | 2280 |
| gatggccgga | cgtgtgcgcg | gctacgtcgc | taaaggccag | ccagtcgtcc | ctgctcgtca | 2340 |
| gacagagacg | cagagcagcc | gagggcgaaa | agctctggcc | actatgggaa | gacgtggcgg | 2400 |
| taaaaaggcc | gcagaacgct | ggaaagaccc | aaacagtgag | tacgcccgag | cacagcgaga | 2460 |
| aaaactagct | aagtccagtc | aacgacaagc | taggaaagct | aaaggaaatc | gcttgaccat | 2520 |
| tgcaggttgg | tttatgactg | ttgagggaga | gactggctcg | tggccgacaa | tcaatgaagc | 2580 |
| tatgtctgaa | tttagcgtgt | cacgtcagac | cgtgaataga | gcacttaagt | ctgcgggcat | 2640 |
| tgaacttcca | cgaggacgcc | gtaaagcttc | ccagtaaatg | tgccatctcg | taggcagaaa | 2700 |
| acggttcccc | ccgtaggggt | ctctctcttg | gcctcctttc | taggtcgggc | tgattgctct | 2760 |
| tgaagctctc | taggggggct | cacaccatag | gcagataacg | gttccccacc | ggctcacctc | 2820 |
| gtaagcgcac | aaggactgct | cccaaagatc | ttcaaagcca | ctgccgcgac | tccgcttcgc | 2880 |
| gaagccttgc | cccgcggaaa | ttcctccac | cgagttcgtg | cacacccta | tgccaagctt | 2940 |
| cttcaccct | aaattcgaga | gattggattc | ttaccgtgga | aattcttcgc | aaaaatcgtc | 3000 |
| ccctgatcgc | ccttgcgacg | ttgctcgcgg | cggtgccgct | ggttgcgctt | ggctttgaccg | 3060 |
| acttgatcct | ccggcgttca | gcctgtgcca | cagccgacag | gatggtgacc | accatttgcc | 3120 |
| ccatatcacc | gtcggtactg | atcccgtcgt | caataaaccg | aaccgctaca | ccctgagcat | 3180 |
| caaactcttt | tatcagttgg | atcatgtcgg | cggtgtcgcg | gccaagacgg | tcgagcttct | 3240 |
| tcaccagaat | gacatcacct | tcctccacct | tcatcctcag | caaatccagc | ccttcccgat | 3300 |
| ctgttgaact | gccggatgcc | tgtcggtaa | agatgcggtt | agcttttacc | cctgcatctt | 3360 |
| tgagcgctga | ggtctgcctc | gtgaagaagg | tgttgctgac | tcataccagg | cctgaatcgc | 3420 |
| cccatcatcc | agccagaaag | tgagggagcc | acgttgatg | agagctttgt | tgtaggtgga | 3480 |
| ccagttggtg | attttgaact | tttgctttgc | cacggaacgg | tctgcgttgt | cggaagatg | 3540 |
| cgtgatctga | tccttaact | cagcaaaagt | tcgatttatt | caacaaagcc | gccgtcccgt | 3600 |
| caagtcagcg | taatgctctg | ccagtgttac | aaccaaattaa | ccaattctga | ttagaaaaac | 3660 |
| tcatcgagca | tcaaatgaaa | ctgcaattta | ttcatatcag | gattatcaat | accatatttt | 3720 |
| tgaaaaagcc | gtttctgtaa | tgaaggagaa | aactcaccga | ggcagttcca | taggatggca | 3780 |
| agatcctggt | atcggtctgc | gattccgact | cgtccaacat | caatacaacc | tattaatttc | 3840 |
| ccctcgtcaa | aaataaggtt | atcaagtgag | aaatcaccat | gagtgacgac | tgaatccggt | 3900 |
| gagaatggca | aaagcttatg | catttctttc | cagacttgtt | caacaggcca | gccattacgc | 3960 |
| tcgtcatcaa | aatcactcgc | atcaaccaaa | ccgttattca | ttcgtgattg | cgcctgagcg | 4020 |
| agacgaaata | cgcgatcgct | gttaaaagga | caattacaaa | caggaatcga | atgcaaccgg | 4080 |
| cgcaggaaca | ctgccagcgc | atcaacaata | ttttcacctg | aatcaggata | ttcttctaat | 4140 |
| acctggaatg | ctgttttccc | ggggatcgca | gtggtgagta | accatgcatc | atcaggagta | 4200 |
| cggataaaat | gcttgatggt | cggaagaggc | ataaattccg | tcagccagtt | tagtctgacc | 4260 |

| | | | | | |
|---|---|---|---|---|---|
| atctcatctg | taacatcatt | ggcaacgcta | cctttgccat | gtttcagaaa | caactctggc | 4320 |
| gcatcgggct | tcccatacaa | tcgatagatt | gtcgcacctg | attgcccgac | attatcgcga | 4380 |
| gcccatttat | acccatataa | atcagcatcc | atgttggaat | ttaatcgcgg | cctcgagcaa | 4440 |
| gacgtttccc | gttgaatatg | gctcataaca | cccttgtat | tactgtttat | gtaagcagac | 4500 |
| agttttattg | ttcatgatga | tatattttta | tcttgtgcaa | tgtaacatca | gagattttga | 4560 |
| gacacaacgt | ggctttgttg | aataaatcga | acttttgctg | agttgaagga | tcagatcacg | 4620 |
| catcttcccg | acaacgcaga | ccgttccgtg | gcaaagcaaa | agttcaaaat | caccaactgg | 4680 |
| tccacctaca | acaaagctct | catcaaccgt | ggctccctca | ctttctggct | ggatgatgag | 4740 |
| gcgattcagg | cctggtatga | gtcagcaaca | ccttcttcac | gaggcagacc | tcagcgctag | 4800 |
| cggagtgtat | actggcttac | tatgttggca | ctgatgaggg | tgtcagtgaa | gtgcttcatg | 4860 |
| tggcaggaga | aaaaaggctg | caccggtgcg | tcagcagaat | atgtgataca | ggatatattc | 4920 |
| cgcttcctcg | ctcactgact | cgctacgctc | ggtcgttcga | ctgcggcgag | cggaaatggc | 4980 |
| ttacgaacgg | ggcggagatt | tcctggaaga | tgccaggaaga | atacttaaca | gggaagtgag | 5040 |
| agggccgcgg | caaagccgtt | tttccatagg | ctccgccccc | ctgacaagca | tcacgaaatc | 5100 |
| tgacgctcaa | atcagtggtg | gcgaaacccg | acaggactat | aaagatacca | ggcgtttccc | 5160 |
| cctggcgccc | ccctcgtgcg | ctctcctgtt | cctgcctttc | ggtttaccgg | tgtcattccg | 5220 |
| ctgttatggc | cgcgtttgtc | tcattccacg | cctgacactc | agttccgggt | aggcagttcg | 5280 |
| ctccaagctg | gactgtatgc | acgaaccccc | cgttcagtcc | gaccgctgcg | ccttatccgg | 5340 |
| taactatcgt | cttgagtcca | acccggaaag | acatgcaaaa | gcaccactgg | cagcagccac | 5400 |
| tggtaattga | tttagaggag | ttagtcttga | agtcatgcgc | ggttaaggc | taaactgaaa | 5460 |
| ggacaagttt | tggtgactgc | gctcctccaa | gccagttacc | tcggttcaaa | gagttggtag | 5520 |
| ctcagagaac | cttcgaaaaa | ccgccctgca | aggcggtttt | ttcgttttca | gagcaagaga | 5580 |
| ttacgcgcag | accaaaacga | tctcaagaag | atcatcttat | taagggtct | gacgctcagt | 5640 |
| ggaacgaaaa | ctcacgttaa | gggatttttgg | tcatgagatt | atcaaaaagg | atcttcacct | 5700 |
| agatccttt | aaattaaaaa | tgaagttta | aatcaatcta | aagtatatat | gagtaaactt | 5760 |
| ggtctgacag | ttaccaatgc | ttaatcagtg | aggcacctat | ctcagcgatc | tgtctatttc | 5820 |
| gttcatccat | agttgcctga | ctccccgtcg | tgtagataac | tacgatacgg | gagggcttac | 5880 |
| catctggccc | cagtgctgca | atgataccgc | gagacccacg | ctcaccggct | ccagatttat | 5940 |
| cagcaataaa | ccagccagcc | ggaagggccg | agcgcagaag | tggtcctgca | acttatccgg | 6000 |
| cctccatcca | gtctattaat | tgttgccggg | aagctagagt | aagtagtcg | ccagttaata | 6060 |
| gtttgcgcaa | cgttgttgcc | attgctgcag | gtcgacaatt | taacaagagc | cagttatctt | 6120 |
| ctcttaaaat | gaggaggtaa | ctggcttctt | tatgcttaag | aggtgttagc | ataagtgaaa | 6180 |
| tatgttccaa | cgcgtggacg | tcttaattgg | gaggaagtct | gtcacggact | ggaagacgaa | 6240 |
| aagggtatcg | atgtgaaccc | attcgcagcg | ggttcgaaaa | tgtcgatgat | taaggtacca | 6300 |
| ccactaaaga | gctcacagga | agtgttcaga | ctacttagag | tgacgcccca | gccacagggt | 6360 |
| tcataatcaa | atcatggtga | gcaagggcga | ggagctgttc | accggggtgg | tgcccatcct | 6420 |
| ggtcgagctg | gacggcgacg | taaacggcca | caagttcagc | gtgtccggcg | agggcgaggg | 6480 |
| cgatgccacc | tacggcaagc | tgaccctgaa | gttcatctgc | accaccggca | agctgcccgt | 6540 |
| gccctggccc | accctcgtga | ccaccttcgg | ctacggcctg | cagtgcttcg | cccgctaccc | 6600 |
| cgaccacatg | aagcagcacg | acttcttcaa | gtccgccatg | cccgaaggct | acgtccagga | 6660 |
| gcgcaccatc | ttcttcaagg | acgacggcaa | ctacaagacc | cgcgccgagg | tgaagttcga | 6720 |
| gggcgacacc | ctggtgaacc | gcatcgagct | gaagggcatc | aacttcaagg | aggacggcaa | 6780 |
| catcctgggg | cacaagctgg | agtacaacta | caacagccac | aacgtctata | tcatggccga | 6840 |
| caagcagaag | aacggcatca | aggtgaactt | caagatccgc | cacaacatcg | agggcggcag | 6900 |
| cgtgcagctc | gccgaccact | accagcagaa | caccccagc | gccgacggcc | ccgtgctgct | 6960 |
| gcccgacaac | cactacctga | gctaccagtc | cgccctgagc | aaagacccca | acgagaagcg | 7020 |
| cgatcacatg | gtcctgctgg | agttcgtgac | cgccgccggg | atcactctcg | gcatggacga | 7080 |
| gctgtacaag | taataaggat | cc | | | | 7102 |

SEQ ID NO. 39

| | | | | | |
|---|---|---|---|---|---|
| ccctgcggcg | tcgctgatcg | ccctcgcgac | gttgtgcggg | tggcttgtcc | ctgagggcgc | 60 |
| tgcgacagat | agctaaaaat | ctgcgtcagg | atcgccgtag | agcgcgcgtc | gcgtcgattg | 120 |
| gaggcttccc | ctttggttga | cggtcttcaa | tcgctctacg | gcgatcctga | cgcttttttg | 180 |
| ttgcgtaccg | tcgatcgttt | tatttctgtc | gatcccgaaa | aagttttgc | cttttgtaaa | 240 |
| aaacttctcg | gtcgccccgc | aaattttcga | ttccagattt | tttaaaaacc | aagccagaaa | 300 |
| tacgacacac | cgtttgcaga | taatctgtct | ttcggaaaaa | tcaagtgcga | tacaaaattt | 360 |
| ttagcacccc | tgagctgcgc | aaagtcccgc | ttcgtgaaaa | ttttcgtgcc | gcgtgatttt | 420 |
| ccgccaaaaa | ctttaacgaa | cgttcgttat | aatggtgtca | tgaccctcac | gacgaagtac | 480 |
| caaaattggc | ccgaatcatc | agctatggat | ctctctgatg | tcgcgctgga | gtccgacgcg | 540 |
| ctcgatgctg | ccgtcgattt | aaaaacggtg | atcggatttt | tccgagctct | cgatacgacg | 600 |
| gacgcgccag | catcacgaga | ctgggccagt | gccgcgagcg | acctagaaac | tctcgtggcg | 660 |
| gatcttgagg | agctggctga | cgagctgcgt | gctcggcagc | gggaggagga | cgcacagtag | 720 |
| tggaggatcg | aatcagttgc | gcctactgcg | gtgcctgat | tcctcccgg | cctgacccgc | 780 |
| gaggacggcg | cgcaaaatat | tgctcagatg | cgtgtcgtgc | cgcagccagc | cgcgagcgcg | 840 |
| ccaacaaacg | ccacgccgag | gagctggagg | cggctaggtc | gcaaatggcg | ctggaagtgc | 900 |
| gtcccccgag | cgaaattttg | gccatggtcg | tcacagagct | ggaagcggca | gcgagaatta | 960 |
| tccgcgatcg | tggcgcggtg | cccgcaggca | tgacaaacat | cgtaaatgcc | gcgtttcgtg | 1020 |
| tggccgtggc | cgcccaggac | gtgtcagcgc | cgccaccacc | tgcaccgaat | cggcagcagc | 1080 |
| gtcgcgcgtc | gaaaaagcgc | acaggcggca | agaagcgata | agctgcacga | atacctgaaa | 1140 |
| aatgttgaac | gccccgtgag | cggtaactca | cagggcgtcg | gctaaccccc | agtccaaacc | 1200 |
| tgggagaaag | cgctcaaaaa | tgactctagc | ggattcacga | gacattgaca | caccggcctg | 1260 |
| gaaattttcc | gctgatctgt | tcgacaccca | tcccgactgc | gctgcgat | cacgtggctg | 1320 |
| gacgagcgaa | gaccgccgcg | aattcctcgc | tcacctgggc | agagaaaatt | tccgggcag | 1380 |
| caagacccgc | gacttcgcca | gcgcttggat | caaagacccg | gacacgggag | aaacacagcc | 1440 |
| gaagtttatac | cgagttggtt | caaaatcgct | tgcccggtgc | cagtatgttg | ctctgacgca | 1500 |
| cgcgcagcac | gcagccgtgc | ttgtcctgga | cattgatgtg | ccgagccacc | aggccggcgg | 1560 |
| gaaaatcgag | cacgtaaacc | ccgaggtcta | cgcgattttg | gagcgctggg | cacgcctgga | 1620 |

-continued

| Sequences | | | | | |
|---|---|---|---|---|---|
| aaaagcgcca | gcttggatcg | gcgtgaatcc | actgagcggg | aaatgccagc | tcatctggct | 1680 |
| cattgatccg | gtgtatgccg | cagcaggcat | gagcagcccg | aatatgcgcc | tgctggctgc | 1740 |
| aacgaccgag | gaaatgaccc | gcgttttcgg | cgctgaccag | gctttttcac | ataggctgag | 1800 |
| ccggtggcca | ctgcacgtct | ccgacgatcc | caccgcgtac | cgctggcatg | cccagcacaa | 1860 |
| tcgcgtggat | cgcctagctg | atcttatgga | ggttgctcgc | atgatctcag | gcacagaaaa | 1920 |
| acctaaaaaa | cgctatgagc | aggagttttc | tagcggacgg | gcacgtatcg | aagcggcaag | 1980 |
| aaaagccact | gcggaagcaa | aagcacttgc | cacgcttgaa | gcaagcctgc | cgagcgccgc | 2040 |
| tgaagcgtct | ggagagctga | tcgacggcgt | ccgtgtcctc | tggactgctc | cagggcgtgc | 2100 |
| cgcccgtgat | gagacggctt | ttcgccacgc | tttgactgtg | ggataccagt | aaaagcggc | 2160 |
| tggtgagcgc | ctaaaagaca | ccaagatcat | cgacgcctac | gagcgtgcct | acaccgtcgc | 2220 |
| tcaggcggtc | ggagcagacg | gccgtgagcc | tgatctgccg | ccgatgcgtg | accgccagac | 2280 |
| gatggcgcga | cgtgtgcgcg | gctacgtcgc | taaaggccag | ccagtcgtcc | ctgctcgtca | 2340 |
| gacagagacg | cagagcagcc | gagggcgaaa | agctctggcc | actatgggaa | gacgtggcgg | 2400 |
| taaaaaggcc | gcagaacgct | ggaaagaccc | aaacagtgag | tacgcccgag | cacagcgaga | 2460 |
| aaaactagct | aagtccagtc | aacgacaagc | taggaaagct | aaaggaaatc | gcttgaccat | 2520 |
| tgcaggttgg | tttatgactg | ttgagggaga | gactggctcg | tggccgacaa | tcaatgaagc | 2580 |
| tatgtctgaa | tttagcgtgt | cacgtcagac | cgtgaataga | gcacttaagt | ctgcgggcat | 2640 |
| tgaacttcca | cgaggacgcc | gtaaagcttc | ccagtaaatg | tgccatctcg | taggcagaaa | 2700 |
| acggttcccc | ccgtagggt | ctctctcttg | gcctcctttc | taggtcgggc | tgattgctct | 2760 |
| tgaagctctc | taggggggct | cacaccatag | gcagataacg | gttccccacc | ggctcacctc | 2820 |
| gtaagcgcac | aaggactgct | cccaaagatc | ttcaaagcca | ctgccgcgac | tccgcttcgc | 2880 |
| gaagccttgc | cccgcggaaa | tttcctccac | cgagttcgtg | cacacccta | tgccaagctt | 2940 |
| cttcaccct | aaattcgaga | gattggattc | ttaccgtgga | aattcttcgc | aaaaatcgtc | 3000 |
| ccctgatcgc | ccttgcgacg | ttgctcgcgg | cggtgccgct | ggttgcgctt | ggcttgaccg | 3060 |
| acttgatcct | ccggcgttca | gcctgtgcca | cagccgacag | gatggtgacc | accatttgcc | 3120 |
| ccatatcacc | gtcggtactg | atcccgtcgt | caataaaccg | aaccgctaca | ccctgagcat | 3180 |
| caaactcttt | tatcagttgg | atcatgtcgg | cggtgtcgcg | gccaagacgg | tcgagcttct | 3240 |
| tcaccagaat | gacatcacct | tcctccacct | tcatcctcac | caaatccagc | ccttcccgat | 3300 |
| ctgttgaact | gccggatgcc | ttgtcggtaa | agatgcggtt | agcttttacc | cctgcatctt | 3360 |
| tgagcgctga | ggtctgcctc | gtgaagaagg | tgttgctgac | tcataccagg | cctgaatcgc | 3420 |
| cccatcatcc | agccagaaag | tgagggagcc | acggttgatg | agagctttgt | tgtaggtgga | 3480 |
| ccagttggtg | atttttgaact | tttgctttgc | cacggaacgg | tctgcgttgt | cgggaagatg | 3540 |
| cgtgatctga | tccttcaact | cagcaaaagt | tcgatttatt | caacaaagcc | gccgtcccgt | 3600 |
| caagtcagcg | taatgctctg | ccagtgttac | aaccaattaa | ccaattctga | ttagaaaaac | 3660 |
| tcatcgagca | tcaaatgaaa | ctgcaattta | ttcatatcag | gattatcaat | accatatttt | 3720 |
| tgaaaaagcc | gtttctgtaa | tgaaggagaa | aactcaccga | ggcagttcca | taggatggca | 3780 |
| agatcctggt | atcggtctgc | gattccgact | cgtccaacat | caatacaacc | tattaattc | 3840 |
| ccctcgtcaa | aaataaggtt | atcaagtgag | aaatcaccat | gagtgacgac | tgaatccggt | 3900 |
| gagaatggca | aaagcttatg | catttctttc | cagacttgtt | caacaggcca | gccattacgc | 3960 |
| tcgtcatcaa | aatcactcgc | atcaaccaaa | ccgttattca | ttcgtgattg | cgcctgagcg | 4020 |
| agacgaaata | cgcgatcgct | gttaaaagga | caattacaaa | caggaatcga | atgcaaccgg | 4080 |
| cgcaggaaca | ctgccagcgc | atcaacaata | ttttcacctg | aatcaggata | ttcttctaat | 4140 |
| acctggaatg | ctgttttccc | ggggatcgca | gtggtgagta | accatgcatc | atcaggagta | 4200 |
| cggataaaat | gcttgatggt | cggaagaggc | ataaattccg | tcagccagtt | tagtctgacc | 4260 |
| atctcatctg | taacatcatt | ggcaacgcta | cctttgccat | gtttcagaaa | caactctggc | 4320 |
| gcatcgggct | tcccatacaa | tcgatagatt | gtcgcacctg | attgcccgac | attatcgcga | 4380 |
| gcccatttat | acccatataa | atcagcatcc | atgttggaat | ttaatcgcgg | cctcgagcaa | 4440 |
| gacgtttccc | gttgaatatg | gctcataaca | ccccttgtat | tactgtttat | gtaagcagac | 4500 |
| agttttattg | ttcatgatga | tatatttta | tcttgtgcaa | tgtaacatca | gagatttttg | 4560 |
| gacacaacgt | ggctttgttg | aataaatcga | acttttgctg | agttgaagga | tcagatcacg | 4620 |
| catcttcccg | acaacgcaga | ccgttccgtg | gcaaagcaaa | agttcaaaat | caccaactgg | 4680 |
| tccacctaca | acaaagctct | catcaaccgt | ggctccctca | ctttctggct | ggatgatggg | 4740 |
| gcgattcagg | cctggtatga | gtcagcaaca | ccttcttcac | gaggcagacc | tcagcgctag | 4800 |
| cggagtgtat | actggcttac | tatgttggca | ctgatgaggg | tgtcagtgaa | gtgcttcatg | 4860 |
| tggcaggaga | aaaaaggctg | caccggtgcg | tcagcagaat | atgtgataca | ggatatattc | 4920 |
| cgcttcctcg | ctcactgact | cgctacgctc | ggtcgttcga | ctgcggcgag | cggaaatggc | 4980 |
| ttacgaacgg | ggcggagatt | tcctggaaga | tgccaggaag | atacttaaca | gggaagtgag | 5040 |
| agggccgcgg | caaagccgtt | tttccatagg | ctccgccccc | ctgacaagca | tcacgaaatc | 5100 |
| tgacgctcaa | atcagtggtg | gcgaaacccg | acaggactat | aaagatacca | ggcgtttccc | 5160 |
| cctggcggct | ccctcgtgcg | ctctcctgtt | cctgcctttc | ggtttaccgg | tgtcattccg | 5220 |
| ctgttatggc | cgcgtttgtc | tcattccacg | cctgacactc | agttccgggt | aggcagttcg | 5280 |
| ctccaagctg | gactgtatgc | acgaaccccc | cgttcagtcc | gaccgctgcg | ccttatccgg | 5340 |
| taactatcgt | cttgagtcca | acccggaaag | acatgcaaaa | gcaccactgg | cagcagccac | 5400 |
| tggtaattga | tttagaggag | ttagtcttga | agtcatgcgc | cggttaaggc | taaactgaaa | 5460 |
| ggacaagttt | tggtgactgc | gctcctccaa | gccagttacc | tcggttcaaa | gagttggtag | 5520 |
| ctcagagaac | cttcgaaaaa | ccgccctgca | aggcggtttt | ttcgttttca | gagcaagaga | 5580 |
| ttacgcgcag | accaaaacga | tctcaagaag | atcatcttat | taagggggtct | gacgctcagt | 5640 |
| ggaacgaaaa | ctcacgttaa | gggattttgg | tcatgagatt | atcaaaaagg | atcttcacct | 5700 |
| agatcctttt | aaattaaaaa | tgaagtttta | aatcaatcta | agtatatat | gagtaaactt | 5760 |
| ggtctgacag | ttaccaatgc | ttaatcagtg | aggcacctat | ctcagcgatc | tgtctatttc | 5820 |
| gttcatccat | agttgcctga | ctccccgtcg | tgtagataac | tacgatacgg | gagggcttac | 5880 |
| catctggccc | cagtgctgca | atgataccgc | gagacccacg | ctcaccggct | ccagatttat | 5940 |
| cagcaataaa | ccagccagcc | ggaagggcc | agcgcagaag | tggtcctgca | actttatccg | 6000 |
| cctccatcca | gtctattaat | tgttgccggg | aagctagagt | aagtagtcg | ccagttaata | 6060 |
| gtttgcgcaa | cgttgttgcc | attgctgcag | gtcgaccatg | cgccgttccc | agtggaaggc | 6120 |
| cgacaatgtc | gcccttcagg | aggtcaagat | cgacggtcag | accgttcgca | tcccacgccg | 6180 |
| tctggttaag | gcagcacagc | tcggtctcgt | ggacgtagag | cagttctaaa | ccttaaattc | 6240 |

-continued

| Sequences | |
|---|---|
| atcgcctaca accttttgta ggtaagaatt taacaagagc cagttatctt ctcttaaaat | 6300 |
| gaggaggtaa ctggcttctt tatgcttaag aggtgttagc ataagtgaaa tatgttccaa | 6360 |
| cgcgtggacg tcttaattgg gaggaagtct gtcacggact ggaagacgaa aagggtatcg | 6420 |
| atgaaaattt tagttgttga tgacgagcaa gctgtacgtg actccttgcg acgttccctt | 6480 |
| tcgttcaacg gatacaacgt tgttctcgca gaagacggca tccaagcact agagatgatt | 6540 |
| gacaaggaac agcctgcttt ggtgatcctc gatgtcatga tgcctggtat ggacggactt | 6600 |
| gaggtctgtc gccaccttcg cagcgaaggc gatgatcggc caattcttat tcttactgcc | 6660 |
| cgcgataatg tttctgatcg tgttggtggc ctcgatgcag gcgcagatga ctatttggct | 6720 |
| aaaccatttg ctcttgaaga gctgttggcg cgcgtccgtt cactggtgcg tcgctctgca | 6780 |
| gtggaatcaa atcagagttc cagcattgaa caggctctat tatcttgtgg cgatttgacg | 6840 |
| cttgacccag aaagtcgaga tgtctaccgc aacgacgcg ccatcagcct tactcgaaca | 6900 |
| gagttcgcgc tcctgcaatt gctcctcaaa aaccaaagga aagtgctcac tcgcgcccag | 6960 |
| attttggaag aggtatgggg ctgcgatttc cccacttcag gcaatgccct cgaggtctac | 7020 |
| attggatacc ttcgacgcaa gactgaattg aaggagaag accgcctgat ccatacagta | 7080 |
| cgaggagtcg gatacgtcct gcgagagacc gctccgtgac attaaggcga atcggcgcag | 7140 |
| gggaaaatgg gcctgcccct accgaaagtg atgactccga cggttcaatg tcgttgcgtt | 7200 |
| ggcgcttggc tttgctgagc gccacttttg tagctttcgc cgttggtgtt attactgttg | 7260 |
| ctgcatattg gtctgtctcc agctatgtca ccaactcaat cgatcgtgat ctggaaaaac | 7320 |
| aagcggatgc aatgcttgga cgagccagtg aagcgggatt ctatgcaacc gcagaaaccg | 7380 |
| aaaattgctct gttaggtgaa tatgccagtg acactccagt cgccttaatc ccacctgggt | 7440 |
| gggaatacgt catcggtgaa tccatatcac tgcctgattc agatttcctt aagagtaaag | 7500 |
| aagcggggaa acagatcctc gtaacaagtg ctgagcgcat tctcatgaaa cgagatagct | 7560 |
| cgggcacagt ggtggttttt gctaaagata tggtggatac cgatcggcag ctcacgtgc | 7620 |
| ttggcgtcat tctcttgatc attggcggca gtggtgtttt ggctgcagtt ctgcttggtt | 7680 |
| tcatcattgc gaaggagggg ctgaaaccac tgtcaaagct gcagcgtgcc gtcgaagaga | 7740 |
| tcgaacgaac tgatgagctt cgtgcgattc ccgtggtggg aaatgatgag ttcgctaagt | 7800 |
| tgactcgtag tttcaatgac atgctcaagg cactgcggga gtctcgtacc cggcaatctc | 7860 |
| agttggtggc agatgcagga cacgagctga aaactccact gacctcaatg cggacaaata | 7920 |
| ttgaattgct gttgatggca accaacagtg gaggatcggg aatccccaag gaagaattga | 7980 |
| atggccttca gcgtgatgta ttggcgcaga tgaccgaaat gtctgatttg attggtgatc | 8040 |
| ttgttgatct tgcgcgtgaa gaaaccgccg aaacgtcaag cattgtagat ctcaaccaag | 8100 |
| tgttggaaat tgcgcttgac cgaatggaaa gccgtcgcat gacggtgcgg atagatgttt | 8160 |
| ccgagactgt ggattggaaa ctgctgaggcg atgattttc cttaaccagg gcattagtaa | 8220 |
| atgttttgga taatgccatt aaatggtcgc ctgagaatga cattgttcga gtgtcgatgt | 8280 |
| cacagatcga caaagcaacg gtccgcattg ttattgatga ttcagggcct ggaattgctg | 8340 |
| aaaaagaacg aggattagtt ttggaacggt tctatcgcgc cgtcagctcc cgttccatgc | 8400 |
| cgggatcggg attaggtctt gccatcgtga atcaggttgt gaatcggcat ggtggccaac | 8460 |
| tcgttgtggg tgaatcagat gatggcggaa cgagaatcac tattgatttg ccaggggaac | 8520 |
| ccattcgcag cgggttcgaa aatgtcgatg attaaaccac taaagagctc acaggaagtg | 8580 |
| ttcagactac ttagagtgac gccccagcca caggggttcat aatcaaatca tgacaaatca | 8640 |
| attccccaca aacaacggtg agaacccgga ccgtgcatcg gaaactccat cagaaaccaa | 8700 |
| ctccggtacc tgaactttaa gaaggagata tcatatggtg agcaagggcg aggagctgtt | 8760 |
| caccggggtg gtgcccatcc tggtcgagct ggacggcgac gtaaacggcc acaagttcag | 8820 |
| cgtgtccggc gagggcgagg gcgatgccac ctacggcaag ctgaccctga agttcatctg | 8880 |
| caccaccggc aagctgcccg tgccctggcc caccctcgtg accaccttcg gctacggcct | 8940 |
| gcagtgcttc gcccgctacc ccgaccacat gaagcagcac gacttcttca gtccgccat | 9000 |
| gcccgaaggc tacgtccagg agcgcaccat cttcttcaag gacgacggca actacaagac | 9060 |
| ccgcgccgag gtgaagttcg agggcgacac cctggtgaac cgcatcgagc tgaagggcat | 9120 |
| caacttcaag gaggacggca acatcctggg gcacaagctg gagtacaact acaacagcca | 9180 |
| caacgtctat atcatggccg acaagcagaa gaacggcatc aaggtgaact tcaagatccg | 9240 |
| ccacaacatc gagggcggca gcgtgcagct cgccgaccac taccagcaga acccccat | 9300 |
| cggcgacggc cccgtgctgc tgcccgacaa ccactacctg agctaccagt ccgcctgag | 9360 |
| caaagacccc aacgagaagc gcgatcacat ggtcctgctg gagttcgtga ccgccgccgg | 9420 |
| gatcactctc ggcatggacg agctgtacaa gtaataagga tcc | 9463 |

SEQ ID No. 40
cgcggatcca aggagaatga cgatgagaaa acgtaaaaat ggattaatc    49

SEQ ID No. 41
gcggagctct aattatttac ccatatagat acagacccac    40

SEQ ID No. 42
gaagaaaccg ccgaaacgtc aagc    24

SEQ ID No. 43
cgatgcacgg tccgggttct c    21

SEQ ID No. 44
gtttaaaaga gttaatctgc atctaatcaa gtagcc    36

SEQ ID No. 45
gccatcacga attgccgaac gag    23

SEQ ID No. 46
gagaacccgg accgtgcatc gtagaagaag gagatatcat atgg    44

-continued

Sequences

SEQ ID No. 47
gcagattaac tcttttaaac ttattacttg tacagctcgt ccatgccg            48

SEQ ID No. 48
attaggcacc ccaggcttta cactttatgc ttccggctcg tatgttgtgt ggaattgtga    60
gcggataaca atttcacaca ggaaacagct atgaccatga ttacgccaag cttgcatgcc   120
tgcaggtcga ctctagagga tccccgggta ccgagctcga attcactggc cgtcgtttta   180
caacgtcgtg actgggaaaa ccctggcgtt acccaactta atcgccttgc agcacatccc   240
cctttcgcca gctggcgtaa tagcgaagag gcccgcaccg atcgcccttc ccaacagttg   300
cgcagcctga atggcgaatg gcgcgataag ctagcttcac gctgccgcaa gcactcaggg   360
cgcaagggct gctaaaggaa gcggaacacg tagaaagcca acggtgctga   420
ccccggatga atgtcagcta ctgggctatc tggacaaggg aaaacgcaag cgcaaagaga   480
aagcaggtag cttgcagtgg gcttacatgg cgatagctag actgggcggt tttatggaca   540
gcaagcgaac cggaattgcc agctggggcg ccctctggta aggttgggaa gccctgcaaa   600
gtaaactgga tggctttctt gccgccaagg atctgatggc gcaggggatc aagatctgat   660
caagagacag gatgaggatc gtttcgcatg attgaacaag atggattgca cgcaggttct   720
ccggccgctt gggtggagag gctattcggc tatgactggg cacaacagac aatcggctgc   780
tctgatgccg ccgtgttccg gctgtcagcg caggggcgcc cggttctttt tgtcaagacc   840
gacctgtccg gtgccctgaa tgaactccaa gacgaggcag gtccgcatc gtggctggcc   900
acgacgggcg ttccttgcgc agctgtgctc gacgttgtca ctgaagcggg aagggactga   960
ctgctattgg gcgaagtgcc ggggcaggat ctcctgtcat ctcaccttgc tcctgccgag  1020
aaagtatcca tcatgctga tgcaatgcgg cggctgcata cgcttgatcc ggctacctgc  1080
ccattcgacc accaagcgaa acatcgcatc gagcgagcac gtactcggat ggaagccggt  1140
cttgtcgatc aggatgatct ggacgaagag catcaggggc tcgcgccagc cgaactgttc  1200
gccaggctca aggcgcggat gcccgacggc gaggatctcg tcgtgaccca tggcgatgcc  1260
tgcttgccga atatcatggt ggaaaatggc cgcttttctg gattcatcga ctgtggccgg  1320
ctgggtgtgg cggaccgcta tcaggacata gcgttggcta cccgtgatat tgctgaagag  1380
cttggcggcg aatgggctga ccgcttcctc gtgctttacg gtatcgccgc tcccgattcg  1440
cagcgcatcg ccttctatcg ccttcttgac gagttcttct gagcgggact ctggggttcg  1500
ctagaggatc gatccttttt aacccatcac atatacctgc cgttcactat tatttagtga  1560
aatgagatat tatgatattt tctgaattgt gattaaaaag gcaactttat gcccatgcaa  1620
cagaaactat aaaaaataca gagaatgaaa agaaacagat agattttta gttctttagg  1680
cccgtagtct gcaaatcctt ttatgatttt ctatcaaaca aaagaggaaa atagaccagt  1740
tgcaatccaa acgagagtct aatagaatga ggtcgaaaag taaatcgcgc gggtttgtta  1800
ctgataaagc aggcaagacc taaaatgtgt aaagggcaaa gtgtatactt tggcgtcacc  1860
ccttacatat tttaggtctt tttttattgt gcgtaactaa cttgccatct tcaaacagga  1920
gggctggaag aagcagaccg ctaacacagt acataaaaaa ggagacatga acgatgaaca  1980
tcaaaaagtt tgcaaaacaa gcaacagtat taacctttac taccgcactg ctggcaggag  2040
gcgcaactca agcgtttgcg aaagaaacga accaaaagcc atataaggaa acatacggca  2100
tttcccatat tacacgccat gatatgctgc aaatccctga acagcaaaaa aatgaaaaat  2160
atcaagtttc tgaatttgat tcgtccacaa ttaaaaatat ctcttctgca aaaggcctgg  2220
acgtttggga cagctggcca ttacaaaacg ctgacggcac tgtcgcaaac tatcacggct  2280
accacatcgt ctttgcatta gccggagatc ctaaaaatgc ggatgacaca tcgatttaca  2340
tgttctatca aaaagtcggc gaaacttcta ttgcagtcg gaaaaacgct ggccgcgtct  2400
ttaaagacag cgacaaattc gatgcaaatg attctatcct aaaagaccaa acacaagaat  2460
ggtcaggttc agccacattt acatctgacg gaaaaatccg tttattctac actgatttct  2520
ccggtaaaca ttacggcaaa caaacactga caactgcaca agttaacgta tcagcatcag  2580
acagctcttt gaacatcaac ggtgtagagg attataaatc aatctttgac ggtgacggaa  2640
aaacgtatca aaatgtacag cagttcatcg atgaaggcaa ctacagctca ggcgacaacc  2700
atacgctgag agatcctcac tacgtagaag ataaggcca caaatactta gtatttgaag  2760
caaacactgg aactgaagat ggctaccaag gcgaagaatc tttatttaac aaagcatact  2820
atggcaaaag cacatcattc ttccgtcaag aagtcaaaa acttctgcaa agcgataaaa  2880
aacgcacggc tgagttagca aacgcgctc tcggtatgat tgagctaaac gatgattaca  2940
cactgaaaaa agtgatgaaa ccgctgattg catctaacac agtaacagat gaaattgaac  3000
gcgcgaacgt ctttaaatg aacggcaaat ggtacctgtt cactgactcc cgcggatcaa  3060
aaatgacgat tgacggcatt acgtctaacg atatttcat gcttggttat gtttctaatt  3120
ctttaactgg cccatacaag ccgctgaaca aaactggcct tgtgttaaaa atggatcttg  3180
atcctaacga tgtaaccttt acttactcac acttcgctgt acctcaagcg aaaggaaaca  3240
atgtcgtgat tacaagctat atgacaaaca gaggattcta cgcagacaaa caatcaacgt  3300
ttgcgccgag cttcctgctg aacatcaaag gcaagaaaac atctgttgtc aaagacagca  3360
tccttgaaca aggacaatta acagttaaca ataaaaacg caaaagaaa tgccgatggg  3420
taccgagcga aatgaccgac caagcgacgc ccaacctgcc atcacgagat ttcgattcca  3480
ccgccgcctt ctatgaaagg ttgggcttcg aatcgttttt ccgggacgcc ctcgcggacg  3540
tgctcatagt ccacgacgcc cgtgattttg tagccctggc cgacgccag caggtaggc   3600
gacaggctca tgccggccgc cgccgccttt tcctcaatcg ctcttcgttc gtctggaagg  3660
cagtacacct tgataggtgg gctgcccttc ctggttggct tggtttcatc agccatccgc  3720
ttgccctcat ctgttacgcc ggcggtagcc ggccagcctc gcagagcagg attcccgttg  3780
agcaccgcca ggtgcgaata agggacagtg aagaaggaac cccgctcgc gggtgggcct  3840
acttcaccta tcctgcccg ctgacgccgt tggatacacc aaggaaagtc tacacgaacc  3900
ctttggcaaa atcctgtata tcgtgcgaaa aaggatggat ataccgaaaa aatcgctata  3960
atgaccgtaa agcagggtta tgcagcggaa aagcgctgt tccctgctgt tttgtggaat  4020
atctaccgac tggaaacagg caaatgcagg aaattactga actgagggga caggcgagag  4080
acgatgccaa agagctcctg aaaatctcga taactcaaaa atacgcccg gtagtgatct  4140
tatttcatta tggtgaaagt tggaacctct acgtgccga tcaacgtctc attttcgcca  4200
aaagttggcc cagggcttcc cggtatcaac agggacacca ggatttattt attctgcgaa  4260
gtgatcttcc gtcacaggta tttattcggc gcaaagtgcg tcgggtgatg ctgccaactt  4320

```
                              Sequences actgatttag tgtatgatgg tgtttttgag gtgctccagt ggcttctgtt tctatcagct    4380
cctgaaaatc tcgataactc aaaaaatacg cccggtagtg atcttatttc attatggtga    4440
aagttggaac ctcttacgtg ccgatcaacg tctcattttc gccaaaagtt ggcccagggc    4500
ttcccggtat caacagggac accaggattt atttattctg cgaagtgatc ttccgtcaca    4560
ggtatttatt cggcgcaaag tgcgtcgggt gatgctgcca acttactgat ttagtgtatg    4620
atggtgtttt tgaggtgctc cagtggcttc tgtttctatc agggctggat gatcctccag    4680
cgcggggatc tcatgctgga gttcttcgcc caccccaaaa ggatctaggt gaagatcctt    4740
tttgataatc tcatgaccaa aatcccttaa cgtgagtttt cgttccactg agcgtcagac    4800
cccgtagaaa agatcaaagg atcttcttga gatcctttt ttctgcgcgt aatctgctgc    4860
ttgcaaacaa aaaaccacc gctaccagcg gtggtttgtt tgccggatca agagctacca    4920
actcttttc cgaaggtaac tggcttcagc agagcgcaga taccaaatac tgtccttcta    4980
gtgtagccgt agttaggcca ccacttcaag aactctgtag caccgcctac ataccctcgct    5040
ctgctaatcc tgttaccagt ggctgctgcc agtggcgata agtcgtgtct taccgggttg    5100
gactcaagac gatagttacc ggataagcgc agcggtcgg gctgaacggg gggttcgtgc    5160
acacagccca gcttggagcg aacgacctac accgaactga gatacctaca gcgtgagcat    5220
tgagaaagcg ccacgcttcc cgaagggaga aaggcggaca ggtatccggt aagcggcagg    5280
gtcggaacag gagagcgcac gagggagctt ccaggggaa acgcctggta tctttatagt    5340
cctgtcgggt ttcgccacct ctgacttgag cgtcgatttt tgtgatgctc gtcagggggg    5400
cggagcctat ggaaaaacgc cagcaacgcg gcctttttac ggttcctggc cttttgctgg    5460
ccttttgctc acatgttctt tcctgcgtta tcccctgatt ctgtggataa ccgtattacc    5520
gcctttgagt gagctgatac cgctcgccgc agccgaacga ccgagcgcag cgagtcagtg    5580
agcgaggaag cggaagagcg cccaatacgc aaaccgcctc tccccgcgcg ttggccgatt    5640
cattaatgca gctggcacga caggtttccc gactggaaag cgggcagtga gcgcaacgca    5700
attaatgtga gttagctcac tc                                             5722

SEQ ID No. 49
agggttttcc cagtcacgac gtt                                              23

SEQ ID No. 50
gagcggataa caatttcaca cagg                                             24

SEQ ID No. 51
cgataagcta gcttcacgct gccgcaagca ctcagggcgc aagggctgct aaaggaagcg      60
gaacacgtag aaagccagtc cgcagaaacg tgctgaccc cggatgaatg tcagctactg     120
ggctatctgg acaagggaaa acgcaagcgc aaagagaaag caggtagctt gcagtgggct    180
tacatggcga tagctagact gggcggtttt atggacagca agcgaaccgg aattgccagc    240
tggggcgccc tctggtaagg ttgggaagcc ctgcaaagta aactgatgg cttttcttgcg    300
gccaaggatc tgatggcgca ggggatcaag atctgatcaa gagacaggat gaggatcgtt    360
tcgcatgatt gaacaagatg gattgcacgc aggttctccg gccgcttggg tggagaggct    420
attcggctat gactgggcac aacagacaat cggctgctct gatgccgccg tgttccggct    480
gtcagcgcag gggcgcccgg ttcttttttgt caagaccgac ctgtccggtg ccctgaatga    540
actccaagac gaggcagcgc ggctatcgtg gctggccacg acgggcgttc cttgcgcagc    600
tgtgctcgac gttgtcactg aagcgggaag ggactggctg ctattgggcg aagtgccggg    660
gcaggatctc ctgtcatctc accttgctcc tgccgagaaa gtatccatca tggctgatgc    720
aatgcggcgg ctgcatacgc ttgatccggc tacctgccca ttcgaccacc aagcgaaaca    780
tcgcatcgag cgagcacgta ctcggatgga agccggtctt gtcgatcagg atgatctgga    840
cgaagagcat caggggctcg cgccagccga actgttcgcc aggctcaagg cgcggatgcc    900
cgacggcgag gatctcgtcg tgacccatgg cgatgcctgc ttgccgaata tcatggtgga    960
aaatggccgc ttttctggat tcatcgactg tggccggctg ggtgtggcgg accgctatca   1020
ggacatagcg ttggctaccc gtgatattgc tgaagagctt ggcggcgaat gggctgaccg   1080
cttcctcgtg ctttacggta tcgccgctcc cgattcgcag cgcatcgcct tctatcgcct   1140
tcttgacgag ttcttctgag cgggactctg ggttcgcta gaggatcgat ccttttttaac   1200
ccatcacata tacctgccgt tcactattat ttagtgaaat tagatattat gatattttct   1260
gaattgtgat taaaaaggca actttatgcc catgcaacag aaactataaa aaatacagag   1320
aatgaaaaga aacagataga tttttagtt ctttaggccc gtagtctgca atccttttta   1380
tgatttcta tcaaacaaaa gaggaaaata gaccagttgc aatccaaacg agagtctaat   1440
agaatgaggt cgaaaagtaa atcgcgcggg tttgttactg ataaagcagg caagacctaa   1500
aatgtgtaaa gggcaaagtg tatctttgg cgtcaccct tacatatttt aggtctttt    1560
ttattgtgcg taactaactt gccatcttca aacaggaggg ctggaagaag cagaccgcta   1620
acacagtaca taaaaagga gacatgaacg atgaacatca aaaagtttgc aaaacaagca   1680
acagtattaa cctttactac cgcactgctg gcaggaggcg caactcaagc gtttgcgaaa   1740
gaaacgaacc aaaagccata taggaaaca tacggcattt cccatattac acgccatgat   1800
atgctgcaaa tccctgaaca gcaaaaaaat gaaaatatc aagttctga atttgattcg   1860
tccacaatta aaaatatctc ttctgcaaaa ggcctgacg tttgggacag ctggccatta   1920
caaaacgctg acggcactgt cgcaaactat cacggctacc atcgtcttt gcattagcc    1980
ggagatccta aaaatgcgga tgacacatcg atttacatgt tctatcaaaa agtcggcgaa   2040
acttctattg acagctggaa aaacgctggc cgcgtcttta agacagcga caaattcgat   2100
gcaaatgatt ctatcctaaa agaccaaaca caagaatggt caggttcagc cacatttaca   2160
tctgacggaa aaatccgttt attctacact gattttctcc gtaaacatta cggcaaacaa   2220
acactgacaa ctgcacaagt taacgtatca gcatcagaca gctctttgaa catcaacggt   2280
gtagaggatt ataaatcaat cttttgacggt gacggaaaaa cgtatcaaaa tgtacagcag   2340
ttcatcgata aggcaacata cagctcaggc gacaaccata cgtgagaga tcctcactac   2400
gtagaagata aaggccacaa atacttagta tttgaagcaa acactggaac tgaagatggc   2460
taccaagcg aagaatcttt atttaacaaa gcatactatg gcaaaagcac atcattcttc   2520
cgtcaagaaa gtcaaaaact tctgcaaagc gataaaaaac gcacggctga gttagcaaac   2580
ggcgctctcg gtatgattga gctaaacgat gattacacac tgaaaaagt gatgaaaccg   2640
ctgattgcat ctaacacagt aacagatgaa attgaacgcg cgaacgtctt taaaatgaac   2700
```

-continued

| Sequences | | | | | |
|---|---|---|---|---|---|
| ggcaaatggt | acctgttcac | tgactcccgc | ggatcaaaaa | tgacgattga | cggcattacg | 2760 |
| tctaacgata | tttacatgct | tggttatgtt | tctaattctt | taactgggcc | atacaagccg | 2820 |
| ctgaacaaaa | ctggccttgt | gttaaaaatg | gatcttgatc | ctaacgatgt | aacctttact | 2880 |
| tactcacact | tcgctgtacc | tcaagcgaaa | ggaaacaatg | tcgtgattac | aagctatatg | 2940 |
| acaaacagag | gattctacgc | agacaaacaa | tcaacgtttg | cgccgagctt | cctgctgaac | 3000 |
| atcaaaggca | agaaaacatc | tgttgtcaaa | gacagcatcc | ttgaacaagg | acaattaaca | 3060 |
| gttaacaaat | aaaaacgcaa | aagaaaatgc | cgatgggtac | cgagcgaaat | gaccgaccaa | 3120 |
| gcgacgccca | acctgccatc | acgagatttc | gattccaccg | ccgccttcta | tgaaaggttg | 3180 |
| ggcttcggaa | tcgttttccg | ggacgccctc | gcggacgtgc | tcatagtcca | cgacgcccgt | 3240 |
| gattttgtag | ccctggccga | cggccagcag | gtaggccgac | aggctcatgc | cggccgccgc | 3300 |
| cgccttttcc | tcaatcgctc | ttcgttcgtc | tggaaggcag | tacaccttga | taggtgggct | 3360 |
| gcccttcctg | gttggcttgg | tttcatcagc | catccgcttg | ccctcatctg | ttacgccggc | 3420 |
| ggtagccggc | cagcctcgca | gagcaggatt | cccgttgagc | accgccaggt | gcgaataagg | 3480 |
| gacagtgaag | aaggaacacc | cgctcgcggg | tgggcctact | tcacctatcc | tgccccgctg | 3540 |
| acgccgttgg | atacaccaag | gaaagtctac | acgaacccct | tggcaaaatc | ctgtatatcg | 3600 |
| tgccaaaaag | gatggatata | ccgaaaaaat | cgctataatg | accccgaagc | agggttatgc | 3660 |
| agcgaaaaag | cgctgcttcc | ctgctgtttt | gtggaatatc | taccgactgg | aaacaggcaa | 3720 |
| atgcaggaaa | ttactgaact | gaggggacag | gcgagagacg | atgccaaaga | gctcctgaaa | 3780 |
| atctcgataa | ctcaaaaaat | acgcccggta | gtgatcttat | ttcattatgg | tgaaagttgg | 3840 |
| aacctcttac | gtgccaatca | acgtctcatt | ttcgccaaaa | gttggcccag | ggcttcccgg | 3900 |
| tatcaacagg | gacaccagga | tttatttatt | ctgcgaagtg | atcttccgtc | acaggtattt | 3960 |
| attcggcgca | aagtgcgtcg | ggtgatgctg | ccaacttact | gatttagtgt | atgatggtgt | 4020 |
| ttttgaggtg | ctccagtggc | ttctgtttct | atcagctcct | gaaaatctcg | ataactcaaa | 4080 |
| aaatacgccc | ggtagtgatc | ttatttcatt | atggtgaaag | ttggaacctc | ttacgtgccg | 4140 |
| atcaacgtct | cattttcgcc | aaaagttggc | ccagggcttc | ccggtatcaa | cagggacacc | 4200 |
| aggatttatt | tattctgcga | agtgatcttc | cgtcacaggt | atttattcgg | cgcaaagtgc | 4260 |
| gtcgggtgat | gctgccaact | tactgattta | gtgtatgatg | tgtttttga | ggtgctccag | 4320 |
| tggcttctgt | ttctatcagg | gctggatgat | cctccagcgc | agggcttctc | tgctggagtt | 4380 |
| cttcgcccac | cccaaaagga | tctaggtgaa | gatcctttt | gataatctca | tgaccaaaat | 4440 |
| cccttaacgt | gagttttcgt | tccactgagc | gtcagacccc | gtagaaaaga | tcaaaggatc | 4500 |
| ttcttgagat | ccttttttc | tgcgcgtaat | ctgctgcttg | caaacaaaaa | aaccaccgct | 4560 |
| accagcggtg | gtttgtttgc | cggatcaaga | gctaccaact | cttttccga | aggtaactgg | 4620 |
| cttcagcaga | gcgcagatac | caaatactgt | ccttctagtg | tagccgtagt | taggccacca | 4680 |
| cttcaagaac | tctgtagcac | cgcctacata | cctcgctctg | ctaatcctgt | taccagtggc | 4740 |
| tgctgccagt | ggcgataagt | cgtgtcttac | cgggttggac | tcaagacgat | agttaccgga | 4800 |
| taaggcgcag | cggtcgggct | gaacgggggg | ttcgtgcaca | cagcccagct | tggagcgaac | 4860 |
| gacctacacc | gaactgagat | acctacagcg | tgagcattga | gaaagcgcca | cgcttcccga | 4920 |
| agggagaaag | gcggacaggt | atccggtaag | cggcagggtc | ggaacaggag | agcgcacgag | 4980 |
| ggagcttcca | gggggaaacg | cctggtatct | ttatagtcct | gtcgggtttc | gccacctctg | 5040 |
| acttgagcgt | cgatttttgt | gatgctcgtc | aggggggcgg | agcctatgga | aaaacgccag | 5100 |
| caacgcggcc | tttttacggt | tcctggcctt | ttgctggcct | tttgctcaca | tgttctttcc | 5160 |
| tgcgttatcc | cctgattctg | tggataaccg | tattaccgcc | tttgagtgag | ctgataccgc | 5220 |
| tcgccgcagc | cgaacgaccg | agcgcagcga | gtcagtgagc | gaggaagcgg | aagagcgccc | 5280 |
| aatacgcaaa | ccgcctctcc | ccgcgcgttg | gccgattcat | taatgcagct | ggcacgacag | 5340 |
| gtttcccgac | tggaaagcgg | gcagtgagcg | caacgcaatt | aatgtgagtt | agctcactca | 5400 |
| ttaggcaccc | caggctttac | actttatgct | tccggctcgt | atgttgtgtg | gaattgtgag | 5460 |
| cggataacaa | tttcacacag | gaaacagcta | tgaccatgat | tacgccaagc | ttgcatgcct | 5520 |
| gcaggtcgac | tctagaggat | ccccgaagaa | accgccgaaa | cgtcaagcat | gtagatctc | 5580 |
| aaccaagtgt | tggaaattgc | gcttgaccga | atggaaagcc | gtcgcatgac | ggtgcggata | 5640 |
| gatgtttccg | agactgtgga | ttggaaactg | ctggcgcatg | attttccttt | aaccaggcca | 5700 |
| ttagtaaatg | ttttggataa | tgccattaaa | tggtcgcctg | agaatggcat | tgttcgagtg | 5760 |
| tcgatgtcac | agatcgacaa | agcaacggtc | cgcattgtta | ttgatgattc | agggcctgga | 5820 |
| attgctgaaa | aagaacgagg | attagttttg | gaacgttgct | atcgcgcgt | cagctcccgt | 5880 |
| tccatgccgg | gatcgggatt | aggtcttgcc | atcgtgaatc | aggttgtgaa | tcggcatggt | 5940 |
| ggccaactcg | ttgtgggtga | atcagatgat | ggcggaacga | gaatcactat | tgatttgcca | 6000 |
| ggggaaccca | ttcgcagcgg | gttcgaaaat | gtcgatgatt | aaaccactaa | agagctcaca | 6060 |
| ggaagtgttc | agactactta | gagtgacgcc | ccagccacag | ggttcataat | caaatcatga | 6120 |
| caaatcaatt | ccccacaaac | aacggtagag | acccggaccg | tgcatcgtag | aagaaggaga | 6180 |
| tatcatatgg | tgagcaaggg | cgaggagctg | ttcaccgggg | tggtgcccat | cctggtcgag | 6240 |
| ctggacggcg | acgtaaacgg | ccacaagttc | agcgtgtccg | gcgagggcga | gggcgatgcc | 6300 |
| acctacggca | agctgaccct | gaagttcatc | tgcaccaccg | gcaagctgcc | cgtgccctgg | 6360 |
| cccaccctcg | tgaccacctt | cggctacggc | ctgcagtgct | tcgcccgcta | ccccgaccac | 6420 |
| atgaagcagc | acgacttctt | caagtccgcc | atgcccgaag | gctacgtcca | ggagcgcacc | 6480 |
| atcttcttca | aggacgacgg | caactacaag | acccgcgccg | aggtgaagtt | cgagggcgac | 6540 |
| accctggtga | accgcatcga | gctgaagggc | atcaacttca | aggaggacgg | caacatcctg | 6600 |
| gggcacaagc | tggagtacaa | ctacaacagc | cacaacgtct | atatcatggc | cgacaagcag | 6660 |
| aagaacggca | tcaaggtgaa | cttcaagatc | cgccacaaca | tcgaggcgg | cagcgtgcag | 6720 |
| ctcgccgacc | actaccagca | gaacacccc | atcggcgacg | gccccgtgct | gctgcccgac | 6780 |
| aaccactacc | tgagctacca | gtccgccctg | agcaaagacc | ccaacgagaa | gcgcgatcac | 6840 |
| atggtcctgc | tggagttcgt | gaccgccgcc | gggatcactc | tcggcatgga | cgagctgtac | 6900 |
| aagtaataag | tttaaagag | ttaatctgca | tctaatcaag | tagccaagta | tgagtgagga | 6960 |
| acaatggga | aggatccatt | gggaagtctt | accgatgtta | tagacacg | agttccgctt | 7020 |
| ccggatgttg | aaccggatcc | ggagttcctg | aaggctacgg | aaaaagaatt | ccacatggca | 7080 |
| tcccagaagc | gcgctcttgt | tgtcctggtg | ggcgatcatg | tcgctgaggc | agatgggact | 7140 |
| ggccgttttgg | ttacggagct | gctcttagag | tctggcttca | acgtgacgc | tgtggtcagc | 7200 |
| gtgaagtcta | agaagtctca | gattaggcaa | gctattgaaa | ccgcagttgt | tggcggcgct | 7260 |
| gaccttgtgc | tgaccatcgg | cggagtgggc | gttggtcctc | gggataaaac | tcctgaggca | 7320 |

| Sequences | |
|---|---|
| accagcgctg tgttggacca ggacgtccca ggaatcgcgc aggcgcttcg ttcctccggt | 7380 |
| ttggcctgtg gcgcggtgga tgcaagtgtt cccgaggcg tagcgggcgt atccggctca | 7440 |
| accgtggtgg tcaacctcgc tgagtctcgt tcggcaattc gtgatgcgg gtaccgagct | 7500 |
| cgaattcact ggccgtcgtt ttacaacgtc gtgactggga aaaccctggc gttacccaac | 7560 |
| ttaatcgcct tgcagcacat ccccctttcg ccagctggcg taatagcgaa gaggcccgca | 7620 |
| ccgatcgccc ttcccaacag ttgcgcagcc tgaatggcga atggcg | 7666 |

SEQ ID No. 52
MGLGKKLSVA VAASFMSLSI SLPGVQA                                       27

SEQ ID No. 53
MKKRFSLIMM TGLLFGLTSP AFA                                           23

SEQ ID No. 54
ctcgtataat gtgtggaatt g                                             21

SEQ ID No. 55
cagaccgctt ctgcgttc                                                 18

The invention claimed is:

1. A cell which is genetically modified with respect to its wild type and which comprises a gene sequence coding for a fluorescent protein, wherein expression of the fluorescent protein depends on the amount of protein that is secreted across a cytoplasmic membrane into an extracytosolic space,
   wherein the gene sequence coding for the fluorescent protein is under the control of at least one promoter,
   wherein the at least one promoter is selected from the group consisting of a cg0706-promoter having SEQ ID NO: 01, a cg0996-promoter having SEQ ID NO: 02, a cg0998-promoter having SEQ ID NO: 03, a cg1325-promoter having SEQ ID NO: 04, a lial-promoter having SEQ ID NO: 09, a mprA-promoter having SEQ ID NO: 13, and variants of any of the above promoters, wherein the variants comprise nucleic acids which are at least 98% identical to SEQ ID NO: 01-04, 09, or 13.

2. The cell according to claim 1, wherein the cell is a cell of genus *Corynebacterium, Escherichia, Bacillus* or *Mycobacterium*.

3. The cell according to claim 1, wherein the gene sequence coding for the fluorescent protein is under the control of a combination of the cg0996-promoter having SEQ ID NO: 02 or a variant thereof that is at least 98% identical to SEQ ID NO: 02 and (ii) the cg0998-promoter having SEQ ID NO: 03 or a variant thereof that is at least 98% identical to SEQ ID NO: 03, in which the cg0996-promoter or variant thereof is located upstream from the cg0998-promoter or variant thereof.

4. A method for identifying a cell that is characterized by an increased secretion of protein across a cytoplasmic membrane into an extracytosolic space in a cell suspension, comprising the method steps of:
   α1) genetically modifying cells to obtain a cell suspension in which the cells differ with respect to an amount of protein that is secreted across a cytoplasmic membrane into an extracytosolic space, wherein each cell is a cell according to claim 1;
   α2) identifying individual cells in the cell suspension having an increased secretion of protein across the cytoplasmic membrane into the extracytosolic space compared to other cells in the cell suspension.

5. The method according to claim 4, further comprising the method step of:
   α3) separating off of the identified cells from the cell suspension.

6. The method according to claim 5, wherein the separating off is carried out by means of flow cytometry.

7. A method for identifying a cell that is characterized by a high secretion of protein across a cytoplasmic membrane into an extracytosolic space in a cell suspension, comprising the method steps of:
   β1) cultivating different cells in a cell suspension, wherein each cell is a cell according to claim 1;
   β2) identifying individual cells in the cell suspension having a high secretion of protein across the cytoplasmic membrane into the extracytosolic space compared to other cells in the cell suspension.

8. A method for identifying a culture medium composition that is optimized for the recombinant production of a protein, comprising the method steps of:
   γ1) cultivating cells in different culture media, thereby obtaining a plurality of cell suspensions in which the cells of the cell suspensions, due to the difference in compositions of the culture media, differ from each other with respect to an amount of secretion of protein that is secreted across a cytoplasmic membrane into an extracytosolic space, wherein each cell is a cell according to claim 1;
   γ2) identifying cell suspensions that comprise cells having a high secretion of protein across the cytoplasmic membrane into the extracytosolic space compared to other cell suspensions.

9. A method for identifying culture conditions that are optimized for the recombinant production of a protein, comprising the method steps of:
   δ1) cultivating cells in a plurality of cell suspensions under different culture conditions such that the cells in the different cell suspensions, due to the difference in the culture conditions, differ from each other with respect to an amount of protein that is secreted across a cytoplasmic membrane into an extracytosolic space, wherein each cell is a cell according to claim 1;
   δ2) identifying cell suspensions that comprise cells having a high secretion of protein across the cytoplasmic membrane into the extracytosolic space compared to other cell suspensions.

10. A method for identifying a compound that is characterized by an antibiotic activity due to its property to damage the membrane of a bacterial cell or to analyze the effect of such a compound on a population of genetically different bacterial cells or genetically identical cells in different physiological states or different growths phases, comprising the method steps of:
   ε1) cultivating cells in a cell suspension in the presence of a compound, wherein each cell is a cell according to claim 1;

ε2) determining antibiotic activity and concentration-dependent antibiotic activity of the compound by detection of an intracellular fluorescence activity.

11. A method for producing a cell which is genetically modified with respect to its wild type with optimized secretion of protein across a cytoplasmic membrane into an extracytosolic space, comprising the method steps of:
   I) genetically modifying cells to obtain a cell suspension in which the cells differ with respect to the amount of protein that is secreted across a cytoplasmic membrane into an extracytosolic space, wherein each cell is a cell according to claim 1;
   II) identifying individual cells in the cell suspension having an increased secretion of protein across the cytoplasmic membrane into the extracytosolic space compared to other cells in the cell suspension;
   III) separating off of the identified cells from the cell suspension;
   IV) identifying genetically modified genes G1 to Gn or mutations M1 to Mm in the cells identified and separated off which are responsible for the increased secretion of protein across the cytoplasmic membrane into the extracytosolic space;
   V) producing a cell which is genetically modified with respect to its wild type with optimized secretion of protein across the cytoplasmic membrane into the extracytosolic space, of which a genome comprises at least one of the genes G1 to Gn and/or at least one of the mutations MI to Mm.

12. A cell obtained by a method according to claim 11.

13. A method for producing a protein, comprising the method steps of:
   (a) producing a cell which is genetically modified with respect to its wild type with optimized secretion of protein across a cytoplasmic membrane into an extracytosolic space by a method according to claim 11;
   (b) cultivating the cell in a culture medium comprising nutrients under conditions under which the cell produces protein from the nutrients.

14. A method for identifying a cell suspension comprising cells that are characterized by a high secretion of protein across a cytoplasmic membrane into an extracytosolic space, comprising the method steps of:
   ß1) cultivating different cells in a plurality of cell suspensions, wherein each cell is a cell according to claim 1, and wherein the cell suspensions differ from each other with respect to the amount of protein that is secreted by the cells across the cytoplasmic membrane into the extracytosolic space; and
   ß2) identifying individual cell suspensions comprising cells having a high secretion of protein across the cytoplasmic membrane into the extracytosolic space compared to other cell suspensions.

* * * * *